(12) United States Patent
Tadesse

(10) Patent No.: US 9,951,038 B2
(45) Date of Patent: Apr. 24, 2018

(54) QUINAZOLIN-4(3H)-ONE-TYPE PIPERIDINE COMPOUNDS AND USES THEREOF

(71) Applicant: Purdue Pharma L.P., Stamford, CT (US)

(72) Inventor: Dawit Tadesse, Parlin, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/758,138

(22) PCT Filed: Dec. 23, 2013

(86) PCT No.: PCT/IB2013/002874
§ 371 (c)(1),
(2) Date: Jun. 26, 2015

(87) PCT Pub. No.: WO2014/102589
PCT Pub. Date: Jul. 3, 2014

(65) Prior Publication Data
US 2016/0002203 A1   Jan. 7, 2016

Related U.S. Application Data

(60) Provisional application No. 61/746,434, filed on Dec. 27, 2012, provisional application No. 61/782,902, filed on Mar. 14, 2013.

(51) Int. Cl.
*C07D 401/04* (2006.01)
*C07D 451/14* (2006.01)

(52) U.S. Cl.
CPC ......... *C07D 401/04* (2013.01); *C07D 451/14* (2013.01)

(58) Field of Classification Search
USPC ................................... 514/266.21
See application file for complete search history.

(56) References Cited

U.S. PATENT DOCUMENTS

| | | |
|---|---|---|
| 6,410,536 B1 | 6/2002 | Dudley et al. |
| 6,686,370 B2 | 2/2004 | Kyle et al. |
| 6,828,440 B2 | 12/2004 | Goehring et al. |
| 6,861,421 B2 | 3/2005 | Goehring et al. |
| 6,872,733 B2 | 3/2005 | Goehring et al. |
| 7,414,062 B2 | 8/2008 | Chen et al. |
| 7,495,109 B2 | 2/2009 | Sun et al. |
| 7,563,809 B2 | 7/2009 | Goehring et al. |
| 7,678,809 B2 | 3/2010 | Kyle et al. |
| 8,080,557 B2 | 12/2011 | Kennis et al. |
| 8,829,027 B2 | 9/2014 | Eckhardt et al. |
| 2004/0132757 A1 | 7/2004 | Kyle et al. |
| 2004/0259775 A1 | 12/2004 | Kyle |
| 2005/0075355 A1 | 4/2005 | Hartog et al. |
| 2005/0182045 A1 | 4/2005 | Nagase et al. |
| 2005/0192307 A1 | 9/2005 | Goehring et al. |
| 2005/0256000 A1 | 11/2005 | Schaper et al. |
| 2005/0256103 A1 | 11/2005 | Suzuki et al. |
| 2006/0106114 A1 | 5/2006 | Kyle et al. |
| 2008/0214827 A1 | 9/2008 | Goehring et al. |
| 2011/0021426 A1 | 1/2011 | Toll et al. |
| 2011/0092704 A1 | 4/2011 | Gharagozloo et al. |
| 2014/0045830 A1 | 2/2014 | Tsuno et al. |
| 2014/0128346 A1 | 5/2014 | Tadesse et al. |

(Continued)

FOREIGN PATENT DOCUMENTS

| | | |
|---|---|---|
| FR | 2767827 A1 | 3/1999 |
| JP | 2008-007416 A | 1/2008 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
Baudy et al. "Prodrugs of Perzinfotel with Imporved Oral Bioavailability," J. Med. Chem. 52:771-778 (2009).
Henderson et al., "The Orphan Opioid Receptor and its Endogenous Ligand—Nociceptin/Orphanin FQ," Trends Pharmacol. Sci. 18(8):293-300 (1997).
International Search Report for International Patent Application No. PCT/IB2013/002874, dated Sep. 5, 2014, European Patent Office, Rijswijk, Netherlands.

*Primary Examiner* — Marcos L Sznaidman
(74) *Attorney, Agent, or Firm* — Purdue Pharma L.P.; Alan L. Koller; Weiying Yang

(57) ABSTRACT

The present disclosure relates to Quinazolin-4(3H)-one-Type Piperidine Compounds, such as those of Formule (I) and the pharmaceutically acceptable salts and solvates thereof, wherein $R^1$, $R^2$, $R^3$, Q, $Y^1$, Z, A, B, E, and a are as defined herein; compositions comprising an effective amount of a Quinazolin-4(3H)-one-Type Piperidine Compound, and methods to treat or prevent a condition, such as pain, comprising administering to an animal in need thereof an effective amount of a Quinazolin-4(3H)-one-Type Piperidine Compound.

17 Claims, No Drawings

(56) References Cited

U.S. PATENT DOCUMENTS

| | | |
|---|---|---|
| 2014/0187535 A1 | 7/2014 | Tanaka et al. |
| 2014/0187544 A1 | 7/2014 | Marra et al. |
| 2015/0315201 A1 | 11/2015 | Tafesse |
| 2015/0322066 A1 | 11/2015 | Tanaka et al. |
| 2016/0002203 A1 | 1/2016 | Tadesse |
| 2016/0272640 A1 | 9/2016 | Brown |

FOREIGN PATENT DOCUMENTS

| | | |
|---|---|---|
| WO | WO-1996/023784 A1 | 8/1996 |
| WO | WO-1998/028293 A1 | 7/1998 |
| WO | WO-1999/046260 A1 | 9/1999 |
| WO | WO-1999/050254 A1 | 10/1999 |
| WO | WO-2001/090102 A2 | 11/2001 |
| WO | WO-2003/062234 A1 | 7/2003 |
| WO | WO-2005/028451 A1 | 3/2005 |
| WO | WO-2005/032547 | 4/2005 |
| WO | WO-2009/02780 | 3/2009 |
| WO | WO-2010/116090 | 10/2010 |
| WO | WO-2012/103806 A1 | 8/2012 |
| WO | WO-2014/102589 A1 | 7/2014 |
| WO | WO-2014/102590 A1 | 7/2014 |

* cited by examiner

QUINAZOLIN-4(3H)-ONE-TYPE PIPERIDINE COMPOUNDS AND USES THEREOF

CROSS-REFERENCE TO RELATED APPLICATIONS

This application is the U.S. national phase, pursuant to 35 U.S.C. § 371, of PCT International Application Ser. No. PCT/IB2013/002874, filed Dec. 23, 2013, designating the United States and published in English on Jul. 3, 2014 as PCT Publication No. WO 2014/102589 A1, which claims priority to U.S. Provisional Application Ser. No. 61/746,434, filed Dec. 27, 2012, and U.S. Provisional Application Ser. No. 61/782,902, filed Mar. 14, 2013. The contents of the afore-mentioned patent applications are incorporated herein by their entirety.

1. FIELD

The disclosure relates to Quinazolin-4(3H)-one-Type Piperidine Compounds, compositions comprising an effective amount of a Quinazolin-4(3H)-one-Type Piperidine Compound and methods to treat or prevent a condition, such as pain, comprising administering to an animal in need thereof an effective amount of a Quinazolin-4(3H)-one-Type Piperidine Compound.

2. BACKGROUND

Chronic pain is a major contributor to disability and is the cause of much suffering. The successful treatment of severe and chronic pain is a primary goal of the physician, with opioid analgesics being preferred drugs for doing so.

Three major classes of opioid receptors in the central nervous system (CNS) have long been known, with each class having subtype receptors. These receptor classes are known as $\mu$, $\kappa$ and $\delta$. As opiates have a high affinity for these receptors while not being endogenous to the body, research followed in order to identify and isolate the endogenous ligands to these receptors. These ligands were identified as endorphins, dynorphins and enkephalins, respectively.

Experimentation eventually led to the identification of an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for $\mu$, $\kappa$ and $\delta$ receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand—nociceptin/orphanin FQ," *Trends Pharmacol. Sci.* 18(8):293-300 (1997).

Subsequent research led to the isolation and structure of the endogenous ligand of the ORL-1 receptor (i.e., nociceptin; also known as orphanin FQ (OFQ)). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

International PCT Publication Nos. WO 99/46260, WO 99/50254, WO 01/90102, WO 2005/028451, WO 2003/062234, and U.S. Pat. App. No. 2005/0256000, respectively, describe quinoxalines or derivatives thereof as (i) inhibitors of protein kinase C, (ii) serine protease inhibitors, (iii) herbicides, (iv) M2 acetylcholine receptor agonists, (v) medicaments for diseases involving poly(ADP-ribose) polymerase, and (vi) safeners for plants.

The publication of Baudy et al., "Prodrugs of Perzinfotel with Improved Oral Bioavailability," *J. Med. Chem.* 52:771-778 (2009), describes prodrug derivatives of perzinfotel for increasing low oral bioavailability.

Citation of any reference in Section 2 of this application is not to be construed as an admission that such reference is prior art to the present application.

3. SUMMARY

In one aspect of the disclosure, new compounds that exhibit affinity for the ORL-1 receptor are described.

In some embodiments, such new compounds exhibit agonist activity or partial agonist activity at the ORL-1 receptor. In other embodiments, such new compounds exhibit agonist activity at the ORL-1 receptor. In other embodiments, such new compounds exhibit partial agonist activity at the ORL-1 receptor. In yet other embodiments, such new compounds exhibit antagonist activity at the ORL-1 receptor.

In another embodiment of the disclosure, such new compounds exhibit affinity for the ORL-1 receptor, and also for one or more of the $\mu$, $\kappa$ or $\delta$ receptors. In some embodiments, a new compound of the disclosure exhibits affinity for both the ORL-1 receptor and the $\mu$ receptor. In other embodiments, a new compound of the disclosure acts as an ORL-1 receptor agonist or partial agonist and as a $\mu$ receptor agonist or partial agonist. In other embodiments, a new compound of the disclosure acts as an ORL-1 receptor agonist and as a $\mu$ receptor agonist or partial agonist. In other embodiments, a new compound of the disclosure acts as an ORL-1 receptor partial agonist and as a $\mu$ receptor agonist or partial agonist. In other embodiments, a new compound of the disclosure acts as an ORL-1 receptor agonist or partial agonist and as a $\mu$ receptor agonist. In other embodiments, a new compound of the disclosure acts as an ORL-1 receptor agonist or partial agonist and as a $\mu$ receptor partial agonist. In other embodiments, a new compound of the disclosure acts as an ORL-1 receptor agonist and as a $\mu$ receptor agonist. In other embodiments, a new compound of the disclosure acts as an ORL-1 receptor agonist and as a $\mu$ receptor partial agonist. In other embodiments, a new compound of the disclosure acts as an ORL-1 receptor partial agonist and as a $\mu$ receptor agonist. In other embodiments, a new compound of the disclosure acts as an ORL-1 receptor partial agonist and as a $\mu$ receptor partial agonist. In other embodiments, a new compound of the disclosure acts as an ORL-1 receptor agonist or partial agonist and as a $\mu$ receptor antagonist. In other embodiments, a new compound of the disclosure acts as an ORL-1 receptor agonist and as a $\mu$ receptor antagonist. In other embodiments, a new compound of the disclosure acts as an ORL-1 receptor partial agonist and as a $\mu$ receptor antagonist. In other embodiments, a new compound of the disclosure acts as an ORL-1 receptor antagonist and as a $\mu$ receptor agonist or partial agonist. In other embodiments, a new compound of the disclosure acts as an ORL-1 receptor antagonist and as a $\mu$ receptor agonist. In other embodiments, a new compound of the disclosure acts as an ORL-1 receptor antagonist and as a $\mu$ receptor partial agonist.

Certain new compounds of the disclosure can be used to treat an animal suffering from chronic or acute pain.

In another embodiment of the disclosure, methods for treating chronic or acute pain in an animal by administering one or more Quinazolin-4(3H)-one-Type Piperidine Compounds to an animal in need of such treatment are described. In certain embodiments, such new Quinazolin-4(3H)-one-Type Piperidine Compounds effectively treat chronic or acute pain in the animal, while producing fewer or reduced side effects compared to previously available compounds.

Compounds of the disclosure include those of Formula (I):

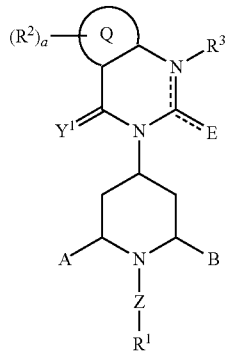

(I)

wherein:

Q is fused benzo or fused (5- or 6-membered)heteroaryl;

each $R^2$ is independently selected from:

(a) -halo, —C(halo)$_3$, —CH(halo)$_2$, —CH$_2$(halo), —CN, —NO$_2$, —N$_3$, —OT, —ST, —N(T)$_2$, —C(=Y)T, —C(=Y)YT, —YC(=Y)T, —YC(=Y)YT, —C(=Y)N(T)$_2$, —N(T)C(=Y)T, —N(T)C(=Y)N(T)$_2$, —YC(=Y)N(T)$_2$, —N(T)C(=Y)YT, —S(=O)$_p$T, —S(=O)$_p$OT, —OS(=O)$_p$T, —OS(=O)$_p$OT, —S(=O)$_p$N(T)$_2$, —N(T)S(=O)$_p$T, —N(T)S(=O)$_p$N(T)$_2$, —OS(=O)$_p$N(T)$_2$, and —N(T)S(=O)$_p$OT;

(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_7$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, —(C$_3$-C$_7$)cycloalkoxy, -(5- or 6-membered)heterocycle, and -(7- to 10-membered)bicycloheterocycle, each of which is unsubstituted or substituted with 1, 2, 3, or 4 independently selected $R^5$ groups; and (c) -phenyl, -benzyl, -naphthyl, —(C$_{14}$)aryl, and -(5- or 6-membered)heteroaryl, each of which is unsubstituted or substituted with 1, 2, 3, or 4 independently selected $R^6$ groups;

E is $Y^2$ or $R^4$;

$Y^1$, $Y^2$, and each Y are independently selected from O and S;

one --- denotes a double bond at its position, and the other --- denotes a single bond at its position, provided that:

(a) when the --- connected to E denotes a double bond, then $R^3$ is present, and E is $Y^2$; and (b) when the --- connected to $N(R^3)$ denotes a double bond, then $R^3$ is absent, and E is $R^4$; $R^3$, when present, is selected from:

(a) —H;

(b) —(CH$_2$)$_d$C(=Y)T, —(CH$_2$)$_d$C(=Y)YT, —(CH$_2$)$_e$YC(=Y)T, —(CH$_2$)$_e$YC(=Y)YT, —(CH$_2$)$_d$C(=Y)N(T)$_2$, —(CH$_2$)$_e$N(T)C(=Y)T, —(CH$_2$)$_e$N(T)C(=Y)N(T)$_2$, —(CH$_2$)$_e$YC(=Y)N(T)$_2$, —(CH$_2$)$_e$N(T)C(=Y)YT, —(CH$_2$)$_d$C(=Y)(CH$_2$)$_d$C(=Y)YT, —(CH$_2$)$_d$C(=Y)(CH$_2$)$_d$C(=Y)N(T)$_2$, —(CH$_2$)$_d$S(=O)$_p$T, —(CH$_2$)$_d$S(=O)$_p$OT, —(CH$_2$)$_e$OS(=O)$_p$T, —(CH$_2$)$_e$OS(=O)$_p$OT, —(CH$_2$)$_d$S(=O)$_p$N(T)$_2$, —(CH$_2$)$_e$N(T)S(=O)$_p$T, —(CH$_2$)$_e$N(T)S(=O)$_p$N(T)$_2$, —(CH$_2$)$_e$OS(=O)$_p$N(T)$_2$, —(CH$_2$)$_e$N(T)S(=O)$_p$OT, —P(=O)(OT)$_2$, and —YP(=O)(OT)$_2$;

(c) —(CH$_2$)$_e$N(T)$_2$ and —(CH$_2$)$_e$YT; and (d) an amino acid chain comprising 1, 2, 3, 4, or 5 amino acid residues, wherein the amino acid chain is bound to the 6-membered, nitrogen-containing ring that is fused to the Q ring via its N-terminal amino group or via its C-terminal carboxyl group;

$R^4$ is selected from:

(a) —H;

(b) —(CH$_2$)$_d$C(=Y)T, —(CH$_2$)$_d$C(=Y)YT, —(CH$_2$)$_d$YC(=Y)T, —(CH$_2$)$_d$YC(=Y)YT, —(CH$_2$)$_d$C(=Y)N(T)$_2$, —(CH$_2$)$_d$N(T)C(=Y)T, —(CH$_2$)$_d$N(T)C(=Y)N(T)$_2$, —(CH$_2$)$_d$YC(=Y)N(T)$_2$, —(CH$_2$)$_d$N(T)C(=Y)YT, —(CH$_2$)$_d$C(=Y)(CH$_2$)$_d$C(=Y)YT, —(CH$_2$)$_d$C(=Y)(CH$_2$)$_d$C(=Y)N(T)$_2$, —(CH$_2$)$_d$S(=O)$_p$T, —(CH$_2$)$_d$S(=O)$_p$OT, —(CH$_2$)$_d$OS(=O)$_p$T, —(CH$_2$)$_d$OS(=O)$_p$OT, —(CH$_2$)$_d$S(=O)$_p$N(T)$_2$, —(CH$_2$)$_d$N(T)S(=O)$_p$T, —(CH$_2$)$_d$N(T)S(=O)$_p$N(T)$_2$, —(CH$_2$)$_d$OS(=O)$_p$N(T)$_2$, and —(CH$_2$)$_d$N(T)S(=O)$_p$OT, —P(=O)(OT)$_2$, and —YP(=O)(OT)$_2$;

(c) —(CH$_2$)$_d$YT, —Y(CH$_2$)$_e$YT, —(CH$_2$)$_d$N(T)$_2$, —N(T)(CH$_2$)$_e$N(T)$_2$, —Y(CH$_2$)$_e$N(T)$_2$, and —N(T)(CH$_2$)$_e$YT;

(d) an amino acid chain comprising 1, 2, 3, 4, or 5 amino acid residues, wherein the amino acid chain is bound to the 6-membered, nitrogen-containing ring that is fused to the Q ring via its N-terminal amino group or via its C-terminal carboxyl group; and (e) -halo, —CN, and —NO$_2$;

A and B together form a (C$_2$-C$_6$) bridge, which is unsubstituted or substituted with 1, 2, 3, 4, 5, 6, 7, or 8 substituents independently selected from —OR$^7$, —(C$_1$-C$_6$)alkyl, -halo, —C(halo)$_3$, —CH(halo)$_2$, and —CH$_2$(halo) and which bridge optionally contains a carbon-carbon double bond, —O—, —S—, or —N(R$^7$)—, wherein the 6-membered, nitrogen-containing ring that is fused to the Q ring is in the endo- or exo-configuration with respect to the A-B bridge;

Z is selected from a direct bond, —(C$_1$-C$_{10}$)alkyl-, —(C$_2$-C$_{10}$)alkenyl-, —(C$_2$-C$_{10}$)alkynyl-, —(C$_2$-C$_{10}$)alkyl-Y—, —(C$_1$-C$_{10}$)alkyl-C(=Y)Y—, —(C$_2$-C$_{10}$)alkyl-YC(=Y)—, —(C$_2$-C$_{10}$)alkyl-N(R$^7$)—, —(C$_1$-C$_{10}$)alkyl-C(=Y)N(R$^7$)—, and —(C$_2$-C$_{10}$)alkyl-N(R$^7$)C(=Y)—, each of which is unsubstituted or substituted with 1, 2, or 3 independently selected $R^8$ groups;

$R^1$ is selected from —(C$_3$-C$_{14}$)cycloalkyl, —(C$_6$-C$_{14}$)bicycloalkyl, —(C$_7$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, —(C$_3$-C$_7$)cycloalkoxy, -(3- to 7-membered)heterocycle, and -(7- to 10-membered)bicycloheterocycle, each of which is unsubstituted or substituted with 1, 2, 3, or 4 independently selected $R^5$ groups;

each T is independently selected from (a) —H, —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_5$-C$_{10}$)cycloalkenyl, and -(5- or 6-membered)heterocycle, each of which is unsubstituted or substituted with 1, 2, 3, or 4 independently selected $R^5$ groups, and, optionally, in which 1, 2, or 3 —(C$_1$-C$_{10}$)alkyl carbon atoms except the carbon atom bonded directly to the atom to which T is attached is independently replaced by —O—, —S—, or —N(R$^7$)—; and (b) -phenyl, -benzyl, -naphthyl, and -(5- or 6-membered)heteroaryl, each of which is unsubstituted or substituted with 1, 2, 3, or 4 independently selected $R^6$ groups; or two occurrences of T attached to the same nitrogen atom together form a 4- to 8-membered ($C_2$-$C_7$)ring, wherein the number of atoms in the ring includes the nitrogen atom, which ring is unsubstituted or substituted with 1, 2, 3, or 4 independently selected $R^5$ groups, and wherein 1 or 2 of the ring carbon atoms is optionally and independently replaced by —O—, —S—, or —N($R^7$)—;

each $R^5$ is independently selected from —($C_1$-$C_6$)alkyl, —($C_2$-$C_6$)alkenyl, —($C_2$-$C_6$)alkynyl, -halo, —C(halo)$_3$, —CH(halo)$_2$, —CH$_2$(halo), —CN, —NO$_2$, —N$_3$, —OR$^7$, —SR$^7$, —N($R^7$)$_2$, =O, =S, —C(=O)R$^7$, —C(=O)OR$^7$, —OC(=O)R$^7$, —OC(=O)OR$^7$, —C(=O)N($R^7$)$_2$, —N($R^7$)C(=O)R$^7$, —N($R^7$)C(=O)N($R^7$)$_2$, —OC(=O)N($R^7$)$_2$, and —N($R^7$)C(=O)OR$^7$;

each $R^6$ is independently selected from —($C_1$-$C_6$)alkyl, —($C_2$-$C_6$)alkenyl, —($C_2$-$C_6$)alkynyl, -halo, —C(halo)$_3$, —CH(halo)$_2$, —CH$_2$(halo), —CN, —NO$_2$, —N$_3$, —OR$^7$, —SR$^7$, —N($R^7$)$_2$, —C(=O)R$^7$, —C(=O)OR$^7$, —OC(=O)R$^7$, —OC(=O)OR$^7$, —C(=O)N($R^7$)$_2$, —N($R^7$)C(=O)R$^7$, —N($R^7$)C(=O)N($R^7$)$_2$, —OC(=O)N($R^7$)$_2$, —N($R^7$)C(=O)OR$^7$, —S(=O)$_p$R$^7$, —S(=O)$_p$OR$^7$, —OS(=O)$_p$R$^7$, —OS(=O)$_p$OR$^7$, —S(=O)$_p$N($R^7$)$_2$, —N($R^7$)S(=O)$_p$R$^7$, —N($R^7$)S(=O)$_p$N($R^7$)$_2$, —OS(=O)$_p$N($R^7$)$_2$, and —N($R^7$)S(=O)$_p$OR$^7$;

each $R^7$ is independently selected from —H, —($C_1$-$C_6$) alkyl, or two occurrences of $R^7$ attached to the same nitrogen atom together form a 4- to 7-membered ($C_2$-$C_6$)ring, wherein the number of atoms in the ring includes the nitrogen atom, and wherein 1 or 2 of the ring carbon atoms is optionally and independently replaced by —O—, —S—, or —N($R^7$)—;

each $R^8$ is independently selected from -halo, —C(halo)$_3$, —CH(halo)$_2$, —CH$_2$(halo), —OR$^7$, —SR$^7$, —N($R^7$)$_2$, =O, =S, —($C_1$-$C_4$)alkyl, and —($C_1$-$C_4$)alkoxy;

a is an integer selected from 0, 1, 2, 3, and 4;

each d is an integer independently selected from 0, 1, 2, 3, 4, 5, and 6;

each e is an integer independently selected from 2, 3, 4, 5, and 6; and each p is an integer independently selected from 1 and 2; and pharmaceutically acceptable salts and solvates thereof.

A compound of Formula (I) or a pharmaceutically acceptable salt or solvate thereof (referred to hereinafter as a "Quinazolin-4(3H)-one-Type Piperidine Compound") is useful, e.g., as an analgesic, anti-inflammatory, diuretic, anesthetic agent, neuroprotective agent, anti-hypertensive, an anxiolytic agent, an agent for appetite control, hearing regulator, anti-tussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias, anti-epileptic, anti-convulsant, agent to treat withdrawal from alcohol, agent to treat withdrawal from drug(s) of addiction, agent to control water balance, agent to control sodium excretion, and/or agent to control arterial blood pressure disorder(s).

A Quinazolin-4(3H)-one-Type Piperidine Compound is useful for treating and/or preventing pain (see e.g.; Courteix, et al. (2004) "Evidence for an exclusive antinociceptive effect of nociceptin/orphanin FQ, an endogenous ligand for the ORL1 receptor, in two animal models of neuropathic pain." *Pain*, 110: 236-245; Reinscheid, et al. (1995). "Orphanin FQ: a neuropeptide that activates an opioid-like G protein-coupled receptor." *Science*, 270: 792-794; Bignan et al. (2005). "Recent advances towards the discovery of ORL-1 receptor agonists and antagonists." *Expert Opinion on Therapeutic Patents*, 15(4): 357-388; Meunier, et al. (1995). "Isolation and structure of the endogenous agonist of opioid receptor-like ORL1 receptor." *Nature*, 377: 532-535; Briscini, et al (2002). "Up-regulation of ORL-1 receptors in spinal tissue of allodynic rats after sciatic nerve injury." *Eur. J. Pharmacol.*, 447: 59-65; Li, et al. (2004). "Role of nociceptin in the modulation of nociception in the arcuate nucleus of rats." *Brain Res.*, 1025: 67-74), anxiety (see e.g., Jenck, et al. (1997). "Orphanin FQ acts as an anxiolytic to attenuate behavioral responses to stress." *Proc. Natl. Acad. Sci., U.S.A.*, 94: 14854-14858; Koster, et al. (1999). "Targeted disruption of the orphanin FQ/nociceptin gene increases stress susceptibility and impairs stress adaptation in mice." *Proc. Natl. Acad. Sci. U.S.A.*, 96: 10444-10449; Griebel, et al. (1999). "Orphanin FQ, a novel neuropeptide with anti-stress-like activity." *Brain Res.*, 836: 221-224; Jenck, et al. (2000). "A synthetic agonist at the orphanin FQ/nociceptin receptor ORL1: Anxiolytic profile in the rat." Proc. Natl. Acad. Sci., 97: 4938-4943), cough (see e.g., Fischer, et al. (1998). "Nociceptin-induced inhibition of tachykinergic neurotransmission in guinea pig bronchus." *J. Pharmacol. Ther.*, 285: 902-907; Rizzi, et al. (1999). "Nociceptin receptor activation inhibits tachykinergic non adrenergic non cholinergic contraction of guinea pig isolated bronchus." *Life Sci.*, 64: L157-L163; Shah, et al. (1998). "Nociceptin inhibits non-cholinergic contraction in guinea-pig airway." *Br. J. Pharmacol.*, 125: 510-516; Patel, et al., (1997). "Naloxone-insensitive inhibition of acetylcholine release from parasympathetic nerves innervating guinea-pig trachea by the novel opioid, nociceptin." *Br. J. Pharmacol.*, 120: 735-736; Helyes, et al. (1997). "Inhibition by nociceptin of neurogenic inflammation and the release of SP and CGRP from sensory nerve terminals." *Br. J. Pharmacol.*, 121: 613-615; Nemeth, et al., (1998). "Inhibition of nociceptin on sensory neuropeptide release and mast cell-mediated plasma extravasation in rats." *Eur. J Pharmacol.*, 347: 101-104; McLeod, et al. (2001). "Nociceptin inhibits cough in the guinea-pig by activation of ORL1 receptors." *Br. J. Pharmacol.*, 132: 1175-1178; Corboz, et al. (2000). "Nociceptin inhibits capsaicin-induced bronchoconstriction in isolated guinea pig lung." *Eur. J. Pharmacol.*, 402: 171-179), gut motility disorders (such as diarrhea and constipation) (see e.g., Wang, et al. (1994). "cDNA cloning of an orphan opiate receptor gene family member and its splice variant." *FEBS Lett.*, 348: 75-79; Calo', et al. (1996). "The mouse deferens: a pharmacological preparation sensitive to nociceptin." *Eur. J. Pharmacol.*, 311: R3-R5; Zhang, et al. (1997). "Orphanin FQ has an inhibitory effect on the guinea pig ileum and the mouse vas deferens." *Brain Res.*, 772: 102-106; Osinski, et al. (1999). "Cloning, expression and functional role of a nociceptin/orphanin FQ receptor in the porcine gastrointestinal tract." *Eur. J Pharmacol.*, 365: 281-289; Yasdani, et al. (1999). "Functional significance of a newly discovered neuropeptide, orphanin FQ, in rat gastrointestinal motility." *Gastroenterology*, 116: 108-117; Corbett, et al. (1998). "The pharmacological actions of nociceptin in the isolated colon of rat, mouse, and man." *Naunyn Schmiedebergs Arch. Pharmacol.*, 358(Suppl 1): P40.47; Osinski, et al. (1999). "Peripheral and central actions of orphanin FQ (nociceptin) on murine colon." *Am. J. Physiol.*, 276: G125-G131; Rizzi, et al. (1999). "[Nphe$^1$]nociceptin (1-13)NH$_2$ antagonizes nociceptin effects in the mouse colon." *Eur. J. Pharmacol.*, 285: R3-R5; Taniguchi, et al. (1998). "The effect of nociceptin an endogenous ligand for the ORL1 receptor, on rat colonic contraction and transit."*Eur. J. Pharmacol.*, 353: 265-271; Pheng, et al. (2000).

"[Nphe¹]nociceptin(1-13)NH$_2$ selectively antagonizes nociceptin effects in the rabbit isolated ileum." *Eur. J. Pharmacol.*, 397: 383-388), high blood pressure (see e.g., Champion & Kadowitz (1997). "Nociceptin, an endogenous ligand for the ORL1 receptor, has novel hypotensive activity in the rat." *Life Sci.*, 60: PL 241-245; Giuliani, et al. (1997). "Effect of nociceptin on heart rate and blood pressure in anaesthetized rats." *Eur. J. Pharmacol.*, 333: 177-179; Kapusta, et al. (1997). "Diuretic and antinatriuretic responses produced by the endogenous opioid-like peptide, noceptin (orphanin FQ)." Life Sci., 60: PL15-PL21; Kapusta, et al. (1999). "Central administration of [Phelpsi(CH$_2$—NH)Gly2]nociceptin(1-13)-NH$_2$ and orphanin FQ/nociceptin (OFQ/N) produce similar cardiovascular and renal responses in conscious rats." J. Pharmacol. Exp. Ther., 289: 173-180; Madeddu, et al. (1999). "Cardiovascular effects of nociceptin in unanesthetized mice." *Hypertension*, 33: 914-919; Bigoni, et al. (1999). "Characterization of nociceptin receptors in the periphery: in vitro and in vivo studies." *Naunyn Schmiedebergs Arch. Pharmacol.*, 359: 160-167; Chu, et al. (1999). "Inhibition of cardiovascular activity following microinjection of novel opioid-like neuropeptide nociceptin (orphanin FQ) into the rat rostral ventrolateral medulla." *Brain Res.*, 829: 134-142; Chu, et al. (1999). "The nociceptin receptor-mediated inhibition of the rat rostral ventrolateral medulla neurons in vitro." *Eur. J. Pharmacol.*, 364: 49-53; Arndt, et al. (1999). "Nociceptin/orphanin FQ increases blood pressure and heart rate via sympathetic activation in sheep." *Peptides*, 20: 465-470; Gumusel, et al. (1997). "Nociceptin: an endogenous agonist for central opioid-like1 (ORL1) receptors possesses systemic vasorelaxant properties." *Life Sci.*, 69: PL141-PL145; Champion et al. (1998). "Nociceptin, a novel endogenous ligand for the ORL1 receptor, dilates isolated resistance arteries from the rat." *Regul. Peptides*, 78: 69-74; Czapla, et al. (1997). "Decreases in systemic arterial and hindquarters perfusion pressure in response to nociceptin are not inhibited by naloxone in the rat." *Peptides*, 18: 1197-1200; Armstead (1999), "Nociceptin/orphanin FQ dilates pial arteries by K(ATP) and k(ca) channel activation." *Brain Res.*, 835: 315-323; Bucher (1998), "ORL1 receptor-mediated inhibition by nociceptin of noradrenaline release from perivascular sympathetic nerve endings of the rat tail artery." *Naunyn Schmiedebergs Arch. Pharmacol.*, 358: 682-685; Champion et al. (1997). "Nociceptin, a novel endogenous ligand for the ORL1 receptor, has potent erectile activity in the cat." *Am. J. Physiol.*, 73: E214-E219), epilepsy (see e.g., Nicol, et al. (1996), "Nociceptin induced inhibition of K+ evoked glutamate release from rat cerebrocortical slices." *Br. J. Pharmacol.*, 119: 1081-1083; Nicol, et al. (1998). "Nociceptin inhibits glutamate release from rat cerebellar slices." *Br. J. Pharmacol.*, 123: 217P; Allen, et al. (1999). "Orphanin-FQ/nociceptin (OFQ/N) modulates the activity of suprachiasmatic nucleus neurons." *J. Neurosci.*, 19: 2152-2160; Faber, et al. (1996). "Depression of glutamatergic transmission by nociceptin in the neonatal rat hemisected spinal cord preparation in vitro." *Br. J. Pharmacol.*, 119: 189-190; Vaughn, et al. (1997). "Actions of the ORL1 receptor ligand nociceptin on membrane properties of rat periaqueductal gray neurons in vitro." *J. Neurosci.*, 17: 996-1003; Wang, et al. (1996). "Nociceptin (orphanin FQ), and endogenous ligand for the ORL1 (opioid receptor-like1) receptor, modulates responses of trigeminal neurons evoked by excitatory amino acids and somatosensory stimuli." *J. Neurophysiol.*, 76: 3568-3572; Yu & Xie (1998). "Orphanin FQ/nociceptin inhibits synaptic transmission and long-term potentiation in rat dentate gyrus through postsynaptic mechanisms." *J. Neurophysiol.*, 80: 1277-1284; Bregola, et al. (1999). "Limbic seizures increase pronociceptin mRNA levels in the thalamic reticular nucleus." *Neuroreport*, 19: 541-546; Sieklucka-Dziuba, et al. (2002). "Nociceptin, OP4 receptor ligand in different models of experimental epilepsy." *Peptides*, 23: 497-505; Gutierrez, et al, (2001). "Orphanin FQ/nociceptin inhibits kindling epileptogenesis and enhances hippocampal feed-forward inhibition." *Neuroscience*, 105: 325-333; Tallent, et al. (2001). "Nociceptin reduces epileptiform events in CA3 hippocampus via presynaptic and postsynaptic mechanisms." *J. Neurosci.*, 21: 6940-6948), eating-related disorders (such as anorexia/cachexia and obesity) (see e.g., Pomonis, et al. (1996). "Orphanin FQ, agonist of orphan opioid receptor ORL1, stimulates feeding in rats." *Neuroreport*, 8: 369-371; Stratford et al. (1997). "Injections of nociceptin into nucleus accumbens shell of ventromedial hypothalamic nucleus increase food intake." *Neuroreport*, 8: 423-426; Lee, et al. (1997). "Nociceptin hyperpolarises neurones in the rat ventromedial hypothalamus." *Neurosci. Lett.*, 239: 37-40; Polidori, et al. (1999). "Sensitivity of brain sites to the orexigenic effect of nociceptin or of its analog [Phe]psi(CH$_2$—NH)Gly2]NC(1-13) NH$_2$." *Regul. Peptides*, 80:126; Polidori, et al. (2000). "Pharmacological characterization of the nociceptin receptor mediating hyperphagia: identification of a selective antagonist." *Psychopharmacology*, 148: 430-437; Rowland, et al. (1996). "The physiology and brain mechanisms of feeding." *Nutrition*, 12: 626-639), urinary incontinence (see e.g., Giuliani, et al. (1998). "The inhibitory effect of nociceptin on the micturition reflex in anaesthetized." *Br. J. Pharmacol.*, 24: 1566-1572; Giuliani, et al. (1999). "Nociceptin protects capsaicin-sensitive afferent fibers in the rat urinary bladder from desensitization." Nanyn Schmiedeberg's *Arch. Pharmacol.*, 360: 202-208; Lecci, et al. (2000). "Multiple sites of action in the inhibitory effect of nociceptin on the micturition reflex." *J. Urology*, 163: 638-645), renal function (see e.g., Kapusta, et al. (1997). "Diuretic and antinatriuretic responses produced by the endogenous opioid-like peptide, noceptin (orphanin FQ)." Life Sci., 60: PL15-PL21; Kapusta, et al. (1999). "Central administration of [Phe1psi(CH2-NH)Gly2]nociceptin(1-13)-NH2 and orphanin FQ/nociceptin (OFQ/N) produce similar cardiovascular and renal responses in conscious rats." *J. Pharmacol. Exp. Ther.*, 289: 173-180), drug abuse (see e.g., Devine et al. (1996). "The novel neuropeptide orphanin FQ fails to produce conditioned place preference or aversion." *Brain Res.*, 727: 225-229; Ciccocioppo, et al. (1999). "Effect of nociceptin on alcohol intake in alcohol-preferring rats." *Psychopharmacology*, 141: 220-224; Angeletti, et al., (1999). "Effect of nociceptin on morphine-induced conditioned place preference in rats." *Regulatory Peptides*, 80: 122; Murphy et al. (1999). "Orphanin FQ/nociceptin blocks acquisition of morphine place preference." *Brain Res.*, 832: 168-170; Pieretti & Di Giannuario (1999). "Orphanin FQ effects on morphine-induced dopamine release in the accumbens of rats." *Regulatory Peptides*, 80: 126; Walker et al. (1998). "Nociceptin fails to affect heroin self-administration in the rat." *Neuroreport*, 9: 2243-2247; Narayanan & Maidment (1999). "Orphanin FQ and behavioral sensitization to cocaine." *Pharmacol. Biochem. Behav.*, 63: 271-277), memory disorders (see e.g., Sandin, et al. (1997). "Nociceptin/orphanin FQ microinjected into hippocampus impairs spatial learning in rats." *Eur. J. Neurosci.*, 9: 194-197; Yu, et al. (1997). "Orphanin FQ inhibits synaptic transmission and long-term potentiation in rat hippocampus." *Hippocampus*, 7: 88-94; Yu & Xie (1998). "Orphanin FQ/nociceptin inhibits synaptic transmission and long-term potentiation in rat dentate gyrus through postsynaptic mechanisms." *J. Neurophysiol.*, 80: 1277-1284; Manabe, et al. (1998). "Facilitation of long-term potentiation and memory in mice lacking nociceptin receptors." *Nature*, 394: 577-581; Hiramatsu & Inoue (1999). "Effects of nocistatin on nociceptin-induced impairment of learning and memory in mice." *Eur. J. Pharmacol.*, 367: 151-155; Mamiya, et al. (1999). "Nociceptin system plays a role in the memory retention: involvement of naloxone benzoylhydrazone binding sites." *Neuroreport*, 10: 1171-1175; Hiramatsu & Inoue (2000). "Improvement by low doses of nociceptin on scopolamine-induced impairment of learning and/or memory." *Eur. J. Pharmacol.*, 395: 149-156), depression (see e.g. Rizzi, et al. (2011). "Nociceptin/orphanin FQ receptor knockout rats: in vitro and in vivo studies." *Neuropharmacology*, 60: 572-579; Goeldner, et al. (2010). "Endogenous nociceptin/orphanin-FQ in the dorsal hippocampus facilitates despair-related behavior." *Hippocampus*, 20: 911-916; Vitale, et al. (2009). "Chronic treatment with the selective NOP receptor antagonist [Nphe 1, Arg 14, Lys 15]N/OFQ-NH2 (UFP-101) reverses the behavioural and biochemical effects of unpredictable chronic mild stress in rats." *Psychopharmacology*, 207: 173-189; Zambello, et al. (2008). "Acute stress differentially affects corticotropin-releasing hormone mRNA expression in the central amygdala of the 'epressed' flinders sensitive line and the control flinders resistant line rats." *Progress in Neuro-Psychopharmacology & Biological Psychiatry*, 32: 651-661; Gavioli & Calo' (2006). "Antidepressant—an anxiolytic-like effects of nociceptin/orphanin FQ receptor ligands." *Naunyn-Schmiedebergs Arch. Pharmacol.*, 372: 319-330; Gavioli, et al. (2003). "Blockade of nociceptin/orphanin FQ-NOP receptor signalling produces antidepressant-like effects: pharmacological and genetic evidences from the mouse forced swimming test." *Eur. J. Neurosci.*, 17: 1987-1990), dementia, or locomotor disorders (such as Parkinsonism) (see e.g., Reinscheid, et al. (1995). "Orphanin FQ: a neuropeptide that activates an opioidlike G protein-coupled receptor." *Science*, 270: 792-794; Calo' et al. (1999). "Characterization of nociceptin receptors modulating locomotor activity in mice." *Fund. Clin. Pharmacol.*, 13-S1: S27.6; Devine, et al. (1996). "Rats rapidly develop tolerance to the locomotor-inhibiting effects of the novel neuropeptide orphanin FQ." *Neurochem. Res.*, 21: 1387-1396; Noble & Roques (1997). "Association of aminopeptidase N and endopeptidase 14.15 inhibitors potentiate behavioral effects mediated by nociceptin/orphanin FQ in mice." *FEBS Lett.*, 401: 227-229; Florin, et al. (1996). "Nociceptin stimulates locomotion and exploratory behaviour in mice." *Eur. J. Pharmacol.*, 317: 9-13) (each being a "Condition") in an animal. For a general discussion of ORL-1 receptors, see Calo' et al. (2000). "Pharmacology of nociceptin and its receptor: a novel therapeutic target." *Br. J. Pharmacol.* 129: 1261-1283.

The present disclosure further provides compositions comprising an effective amount of a Quinazolin-4(3H)-one-Type Piperidine Compound and a pharmaceutically acceptable carrier or excipient. The compositions are useful for treating or preventing a Condition in an animal.

The present disclosure further provides methods for treating or preventing a Condition, comprising administering to an animal in need thereof an effective amount of a Quinazolin-4(3H)-one-Type Piperidine Compound.

The present disclosure further provides Quinazolin-4(3H)-one-Type Piperidine Compounds for use in the manufacture of a medicament useful for treating a Condition or for preventing a Condition.

The present disclosure further provides methods for inhibiting ORL-1 receptor function in a cell, comprising contacting a cell capable of expressing the ORL-1 receptor with an ORL-1 receptor function-inhibiting amount of a Quinazolin-4(3H)-one-Type Piperidine Compound. The present disclosure further provides methods for activating ORL-1 receptor function in a cell, comprising contacting a cell capable of expressing the ORL-1 receptor with an ORL-1 receptor function-activating amount of a Quinazolin-4(3H)-one-Type Piperidine Compound.

The present disclosure further provides methods for preparing a composition, comprising the step of admixing a Quinazolin-4(3H)-one-Type Piperidine Compound and a pharmaceutically acceptable carrier or excipient.

The present disclosure further provides a kit comprising a sterile container containing an effective amount of a Quinazolin-4(3H)-one-Type Piperidine Compound.

The present disclosure further provides novel intermediates for use in making a Quinazolin-4(3H)-one-Type Piperidine Compound.

The disclosure can be understood more fully by reference to the following detailed description and illustrative examples, which are intended to exemplify non-limiting embodiments of the disclosure.

4. DETAILED DESCRIPTION

4.1 Numbered Embodiments of Quinazolin-4(3H)-one-Type Piperidine Compounds

In certain embodiments, Quinazolin-4(3H)-one-Type Piperidine Compounds include the following:

(1) Compounds of Formula (I):

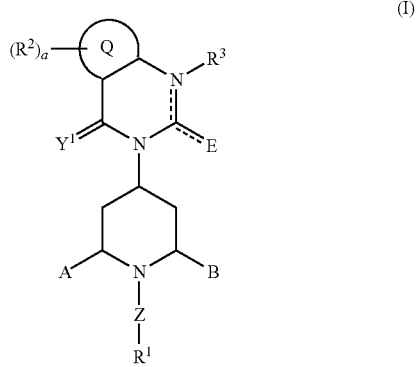

and the pharmaceutically acceptable salts and solvates thereof, as defined above (i.e., "Quinazolin-4(3H)-one-Type Piperidine Compounds").

(2) Quinazolin-4(3H)-one-Type Piperidine Compounds of (1), wherein Q is fused benzo.

(3) Quinazolin-4(3H)-one-Type Piperidine Compounds of (1), wherein Q is fused pyridyl.

(4) Quinazolin-4(3H)-one-Type Piperidine Compounds of (3), wherein the pyridyl nitrogen in the Q ring is in a 1,3-relationship with the carbon atom double bonded to $Y^1$.

(5) Quinazolin-4(3H)-one-Type Piperidine Compounds of any one of (1)-(4), wherein $Y^1$ is O.

(6) Quinazolin-4(3H)-one-Type Piperidine Compounds of any one of (1)-(5), wherein the --- connected to E denotes a double bond, $R^3$ is present, and E is $Y^2$.

(7) Quinazolin-4(3H)-one-Type Piperidine Compounds of (6), wherein $Y^2$ is O.

(8) Quinazolin-4(3H)-one-Type Piperidine Compounds of (6) or (7), wherein $R^3$ is selected from —$(CH_2)_dC(=Y)T$, —$(CH_2)_dC(=Y)YT$, —$(CH_2)_eYC(=Y)T$, —$(CH_2)_eYC(=Y)YT$, —$(CH_2)_dC(=Y)N(T)_2$, —$(CH_2)_eN(T)C(=Y)T$, —$(CH_2)_eN(T)C(=Y)N(T)_2$, —$(CH_2)_eYC(=Y)N(T)_2$, —$(CH_2)_eN(T)C(=Y)YT$, —$(CH_2)_dC(=Y)(CH_2)_dC(=Y)YT$, and —$(CH_2)_dC(=Y)(CH_2)_dC(=Y)N(T)_2$.

(9) Quinazolin-4(3H)-one-Type Piperidine Compounds of (8), wherein $R^3$ is —$(CH_2)_dC(=Y)YT$ wherein Y is O for each occurrence and d is 1 or 2.

(10) Quinazolin-4(3H)-one-Type Piperidine Compounds of (9), wherein in the —$(CH_2)_dC(=Y)YT$ of $R^3$, T is —H or unsubstituted —$(C_1-C_6)$alkyl.

(11) Quinazolin-4(3H)-one-Type Piperidine Compounds of (8), wherein $R^3$ is —$(CH_2)_dC(=Y)N(T)_2$ wherein Y is O and d is 1 or 2.

(12) Quinazolin-4(3H)-one-Type Piperidine Compounds of (1), wherein in the —$(CH_2)_dC(=Y)N(T)_2$ of $R^3$, one occurrence of T is —H, and the other occurrence of T is —$(C_1-C_6)$alkyl substituted with at least one $R^5$.

(13) Quinazolin-4(3H)-one-Type Piperidine Compounds of (12), wherein at least one $R^5$ in an occurrence of T of $R^3$ is —$C(=O)OR^7$.

(14) Quinazolin-4(3H)-one-Type Piperidine Compounds of (6) or (7), wherein $R^3$ is —H.

(15) Quinazolin-4(3H)-one-Type Piperidine Compounds of any one of (1)-(5), wherein the --- connected to $N(R^3)$ denotes a double bond, $R^3$ is absent, and E is $R^4$.

(16) Quinazolin-4(3H)-one-Type Piperidine Compounds of (15), wherein $R^4$ is selected from —$(CH_2)_dC(=Y)T$, —$(CH_2)_dC(=Y)YT$, —$(CH_2)_dYC(=Y)T$, —$(CH_2)_dYC(=Y)YT$, —$(CH_2)_dC(=Y)N(T)_2$, —$(CH_2)_dN(T)C(=Y)T$, —$(CH_2)_dN(T)C(=Y)N(T)_2$, —$(CH_2)_dYC(=Y)N(T)_2$, —$(CH_2)_dN(T)C(=Y)YT$, —$(CH_2)_dC(=Y)(CH_2)_dC(=Y)YT$, and —$(CH_2)_dC(=Y)(CH_2)_dC(=Y)N(T)_2$.

(17) Quinazolin-4(3H)-one-Type Piperidine Compounds of (16), wherein $R^4$ is —$(CH_2)_dC(=Y)YT$.

(18) Quinazolin-4(3H)-one-Type Piperidine Compounds of (17), wherein in the —$(CH_2)_dC(=Y)YT$ of $R^4$, Y is O for each occurrence and d is 0.

(19) Quinazolin-4(3H)-one-Type Piperidine Compounds of (17), wherein in the —$(CH_2)_dC(=Y)YT$ of $R^4$, T is —H or unsubstituted —$(C_1-C_6)$alkyl.

(20) Quinazolin-4(3H)-one-Type Piperidine Compounds of any one of (1)-(19), wherein a is 0.

(21) Quinazolin-4(3H)-one-Type Piperidine Compounds of (1), wherein the compounds are of Formula (Ia):

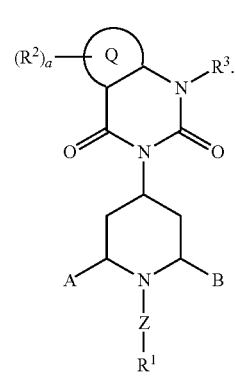

(Ia)

(22) Quinazolin-4(3H)-one-Type Piperidine Compounds of (21), wherein the compounds are of Formula (Ia'):

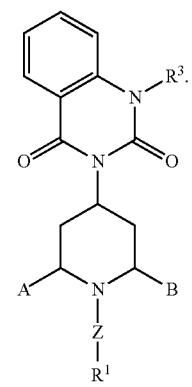

(Ia')

(23) Quinazolin-4(3H)-one-Type Piperidine Compounds of (21) or (22), wherein $R^1$ is selected from —$(CH_2)_dC(=Y)T$, —$(CH_2)_dC(=Y)YT$, —$(CH_2)_eYC(=Y)T$, —$(CH_2)_eYC(=Y)YT$, —$(CH_2)_dC(=Y)N(T)_2$, —$(CH_2)_eN(T)C(=Y)T$, —$(CH_2)_eN(T)C(=Y)N(T)_2$, —$(CH_2)_eYC(=Y)N(T)_2$, —$(CH_2)_eN(T)C(=Y)YT$, —$(CH_2)_dC(=Y)(CH_2)_dC(=Y)YT$, and —$(CH_2)_dC(=Y)(CH_2)_dC(=Y)N(T)_2$.

(24) Quinazolin-4(3H)-one-Type Piperidine Compounds of (23), wherein $R^3$ is —$(CH_2)_dC(=Y)YT$ wherein Y is O for each occurrence and d is 1 or 2.

(25) Quinazolin-4(3H)-one-Type Piperidine Compounds of (24), wherein in the —$(CH_2)_dC(=Y)YT$ of $R^3$, T is —H or unsubstituted —$(C_1-C_6)$alkyl.

(26) Quinazolin-4(3H)-one-Type Piperidine Compounds of (23), wherein $R^3$ is —$(CH_2)_dC(=Y)N(T)_2$ wherein Y is O and d is 1 or 2.

(27) Quinazolin-4(3H)-one-Type Piperidine Compounds of (26), wherein in the —$(CH_2)_dC(=Y)N(T)_2$ of $R^3$, one occurrence of T is —H, and the other occurrence of T is —$(C_1-C_6)$alkyl substituted with at least one $R^5$.

(28) Quinazolin-4(3H)-one-Type Piperidine Compounds of (27), wherein at least one $R^5$ in an occurrence of T of $R^3$ is —$C(=O)OR^7$.

(29) Quinazolin-4(3H)-one-Type Piperidine Compounds of (21) or (22), wherein $R^3$ is —H.

(30) Quinazolin-4(3H)-one-Type Piperidine Compounds of (1), wherein the compounds are of Formula (Ib):

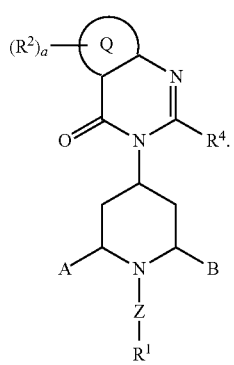

(Ib)

(31) Quinazolin-4(3H)-one-Type Piperidine Compounds of (30), wherein the compounds are of Formula (Ib'):

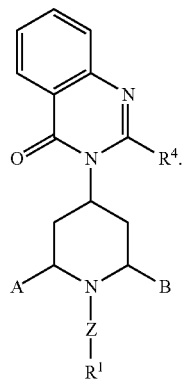

(Ib')

(32) Quinazolin-4(3H)-one-Type Piperidine Compounds of (30) or (31), wherein $R^4$ is selected from —$(CH_2)_dC(=Y)$T, —$(CH_2)_dC(=Y)$YT, —$(CH_2)_dYC(=Y)$T, —$(CH_2)_dYC(=Y)$YT, —$(CH_2)_dC(=Y)N(T)_2$, —$(CH_2)_dN(T)C(=Y)$T, —$(CH_2)_dN(T)C(=Y)N(T)_2$, —$(CH_2)_dYC(=Y)N(T)_2$, —$(CH_2)_dN(T)C(=Y)$YT, —$(CH_2)_dC(=Y)(CH_2)_dC(=Y)$YT, and —$(CH_2)_dC(=Y)(CH_2)_dC(=Y)N(T)_2$.

(33) Quinazolin-4(3H)-one-Type Piperidine Compounds of (32), wherein $R^4$ is —$(CH_2)_dC(=Y)$YT.

(34) Quinazolin-4(3H)-one-Type Piperidine Compounds of (33), wherein in the —$(CH_2)_dC(=Y)$YT of $R^4$, Y is O for each occurrence and d is 0.

(35) Quinazolin-4(3H)-one-Type Piperidine Compounds of (33), wherein in the —$(CH_2)_dC(=Y)$YT of $R^4$, T is —H or unsubstituted —$(C_1-C_6)$alkyl.

(36) Quinazolin-4(3H)-one-Type Piperidine Compounds of any one of (1)-(35), wherein Z is a direct bond or —$(C_1-C_{10})$alkyl-, which is unsubstituted or substituted with 1, 2, or 3 independently selected $R^8$ groups.

(37) Quinazolin-4(3H)-one-Type Piperidine Compounds of any one of (1)-(36), wherein $R^1$ is selected from —$(C_3-C_{14})$cycloalkyl, —$(C_6-C_{14})$bicycloalkyl, and —$(C_7-C_{20})$tricycloalkyl, each of which is unsubstituted or substituted with 1, 2, 3, or 4 independently selected $R^5$ groups.

(38) Quinazolin-4(3H)-one-Type Piperidine Compounds of any one of (1)-(37), wherein $R^1$ is —$(C_6-C_{14})$bicycloalkyl, which is unsubstituted or substituted with 1, 2, 3, or 4 independently selected $R^5$ groups.

(39) Quinazolin-4(3H)-one-Type Piperidine Compounds of any one of (1)-(38), wherein $R^1$ is —$(C_6-C_{14})$bicycloalkyl, which is unsubstituted or substituted with 1, 2, 3, or 4 independently selected $R^5$ groups, which are selected from —$(C_1-C_6)$alkyl, -halo, —$OR^7$, and =O.

(40) Quinazolin-4(3H)-one-Type Piperidine Compounds of any one of (1)-(39), wherein $R^1$ is —$(C_6-C_{14})$bicycloalkyl, which includes a bridging group in the bicyclic ring system.

(41) Quinazolin-4(3H)-one-Type Piperidine Compounds of any one of (1)-(40), wherein Z is a direct bond.

(42) Quinazolin-4(3H)-one-Type Piperidine Compounds of any one of (1)-(41), wherein —Z—$R^1$ is:

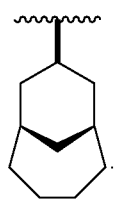 [SMILES: *[C@H]1C[C@H]2CCCC[C@@H](C1)C2]

(43) Quinazolin-4(3H)-one-Type Piperidine Compounds of any one of (1)-(41), wherein —Z—$R^1$ is:

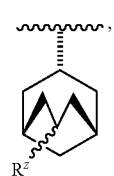

wherein $R^z$ is —H or —$(C_1-C_6)$alkyl.

(44) Quinazolin-4(3H)-one-Type Piperidine Compounds of any one of (1)-(37), wherein —Z—$R^1$ is selected from:

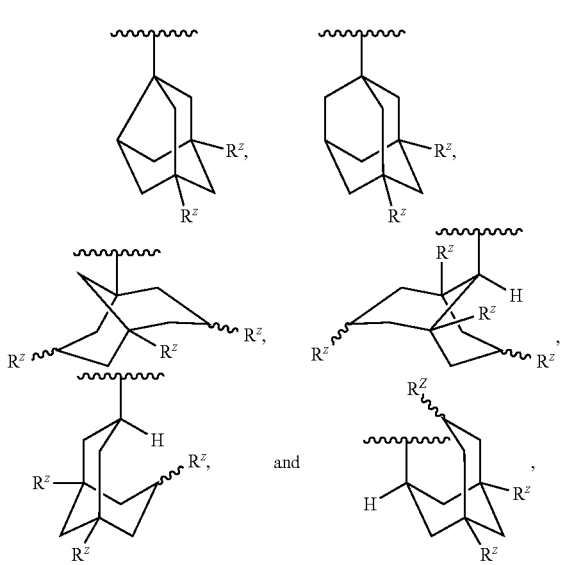

wherein each $R^z$ is independently —H or —$(C_1-C_6)$alkyl.

(45) Quinazolin-4(3H)-one-Type Piperidine Compounds of any one of (1)-(40), wherein Z is —$(C_1-C_{10})$alkyl-, which is unsubstituted or substituted with 1, 2, or 3 independently selected $R^5$ groups.

(46) Quinazolin-4(3H)-one-Type Piperidine Compounds of any one of (1)-(40) or (45), wherein Z is —($C_1$-$C_3$)alkyl-, which is unsubstituted or substituted with 1, 2, or 3 independently selected $R^8$ groups.

(47) Quinazolin-4(3H)-one-Type Piperidine Compounds of any one of (1)-(40) or (45)-(46), wherein Z is unsubstituted.

(48) Quinazolin-4(3H)-one-Type Piperidine Compounds of any one of (1)-(40) or (45)-(47), wherein Z is —$CH_2$—$CH_2$—.

(49) Quinazolin-4(3H)-one-Type Piperidine Compounds of any one of (1)-(40) or (45)-(48), wherein —Z—$R^1$ is:

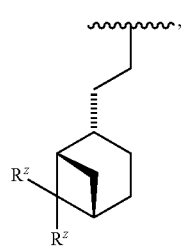

wherein each $R^z$ is independently selected from —H, —($C_1$-$C_6$)alkyl, and —OH.

(50) Quinazolin-4(3H)-one-Type Piperidine Compounds of any one of (1)-(49), wherein A and B together form a bridge such that the bridged-piperidine is:

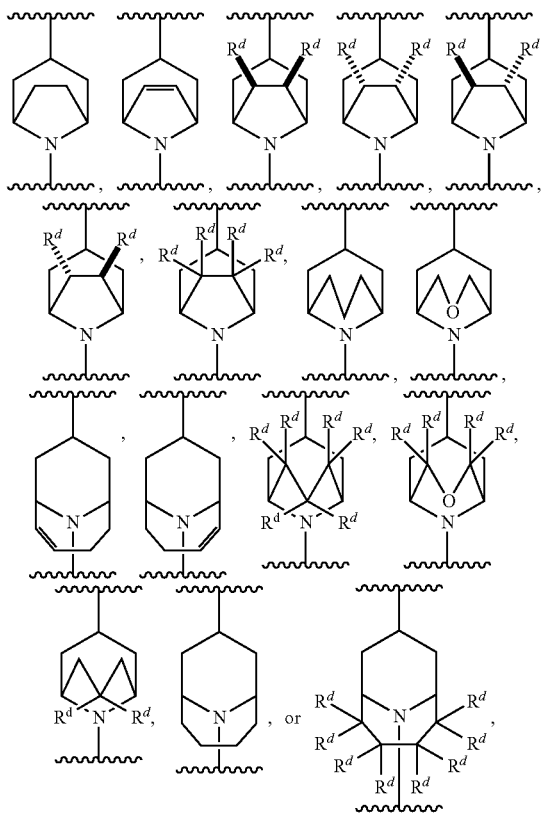

wherein each $R^d$ is independently selected from —H, —($C_1$-$C_6$)alkyl, -halo, —C(halo)$_3$, —CH(halo)$_2$, and —CH$_2$(halo), wherein the piperidine nitrogen is optionally in pharmaceutically acceptable salt form.

(51) Quinazolin-4(3H)-one-Type Piperidine Compounds of any one of (1)-(50), wherein A and B together form a bridge such that the bridged-piperidine is:

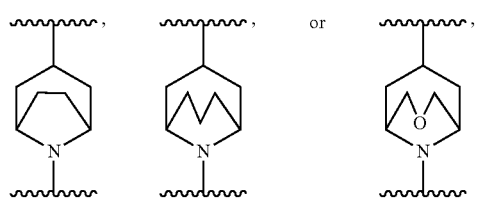 [SMILES: *C1CC2CCC(C1)N2* ; *C1CC2CCCC(C1)N2* ; *C1CC2COCC(C1)N2*]

wherein the piperidine nitrogen is optionally in pharmaceutically acceptable salt form.

(52) Quinazolin-4(3H)-one-Type Piperidine Compounds of any one of (1)-(5), wherein A and B together form a bridge such that the bridged-piperidine is:

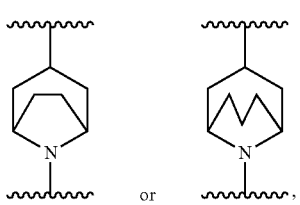 [SMILES: *C1CC2CCC(C1)N2* ; *C1CC2CCCC(C1)N2*]

wherein the piperidine nitrogen is optionally in pharmaceutically acceptable salt form.

(53) Quinazolin-4(3H)-one-Type Piperidine Compounds of any one of claims (1)-(52), wherein the 6-membered, nitrogen-containing ring that is fused to the Q ring is in the endo-configuration with respect to the A-B bridge.

(54) Quinazolin-4(3H)-one-Type Piperidine Compounds of (1), wherein the compounds have the structure:

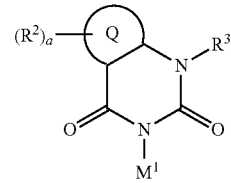

wherein $M^1$ is selected from:

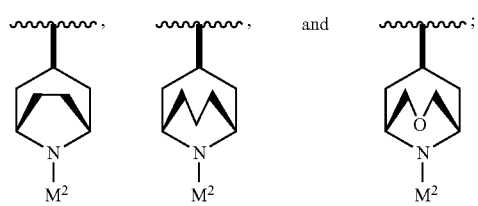

M² is selected from:

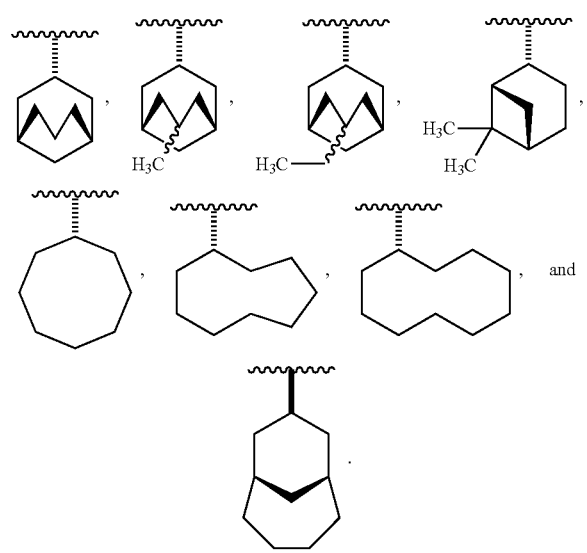

(55) Quinazolin-4(3H)-one-Type Piperidine Compounds of (54), wherein the compounds have the structure:

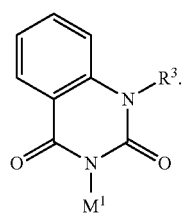

(56) Quinazolin-4(3H)-one-Type Piperidine Compounds of (54) or (55), wherein $R^3$ is selected from —$(CH_2)_d C(=Y)T$, —$(CH_2)_d C(=Y)YT$, —$(CH_2)_e YC(=Y)T$, —$(CH_2)_e YC(=Y)YT$, —$(CH_2)_d C(=Y)N(T)_2$, —$(CH_2)_e N(T)C(=Y)T$, —$(CH_2)_e N(T)C(=Y)N(T)_2$, —$(CH_2)_e YC(=Y)N(T)_2$, —$(CH_2)_e N(T)C(=Y)YT$, —$(CH_2)_d C(=Y)(CH_2)_d C(=Y)YT$, and —$(CH_2)_d C(=Y)(CH_2)_d C(=Y)N(T)_2$.

(57) Quinazolin-4(3H)-one-Type Piperidine Compounds of (56), wherein $R^3$ is —$(CH_2)_d C(=Y)YT$ wherein Y is O for each occurrence and d is 1 or 2.

(58) Quinazolin-4(3H)-one-Type Piperidine Compounds of (57), wherein in the —$(CH_2)_d C(=Y)YT$ of $R^3$, T is —H or unsubstituted —$(C_1-C_6)$alkyl.

(59) Quinazolin-4(3H)-one-Type Piperidine Compounds of (56), wherein $R^3$ is —$(CH_2)_d C(=Y)N(T)_2$ wherein Y is O and d is 1 or 2.

(60) Quinazolin-4(3H)-one-Type Piperidine Compounds of (59), wherein in the —$(CH_2)_d C(=Y)N(T)_2$ of $R^3$, one occurrence of T is —H, and the other occurrence of T is —$(C_1-C_6)$alkyl substituted with at least one $R^5$.

(61) Quinazolin-4(3H)-one-Type Piperidine Compounds of (60), wherein at least one $R^5$ in an occurrence of T of $R^3$ is —$C(=O)OR^7$.

(62) Quinazolin-4(3H)-one-Type Piperidine Compounds of (54) or (55), wherein $R^3$ is —H.

(63) Quinazolin-4(3H)-one-Type Piperidine Compounds of (1), wherein the compounds have the structure:

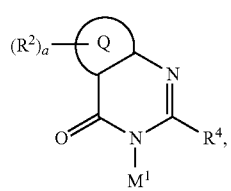

wherein $M^1$ is selected from:

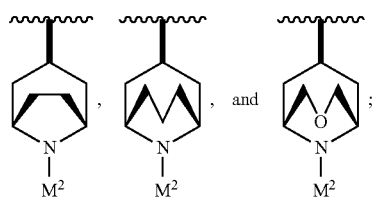

$M^2$ is selected from:

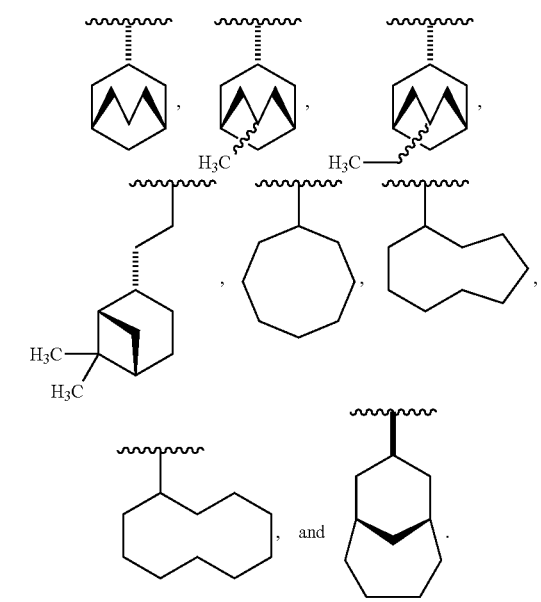

(64) Quinazolin-4(3H)-one-Type Piperidine Compounds of (63), wherein the compounds have the structure:

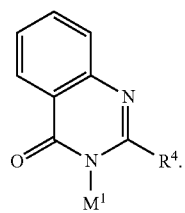

(65) Quinazolin-4(3H)-one-Type Piperidine Compounds of (63) or (64), wherein $R^4$ is selected from —$(CH_2)_d C(=Y)T$, —$(CH_2)_d C(=Y)YT$, —$(CH_2)_d YC(=Y)T$, —$(CH_2)_d YC(=Y)YT$, —$(CH_2)_d C(=Y)N(T)_2$, —$(CH_2)_d N(T)C(=Y)T$, —(CH$_2$)$_d$N(T)C(=Y)N(T)$_2$, —(CH$_2$)$_d$YC(=Y)N(T)$_2$, —(CH$_2$)$_d$N(T)C(=Y)YT, —(CH$_2$)$_d$C(=Y)(CH$_2$)$_d$C(=Y)YT, and —(CH$_2$)$_d$C(=Y)(CH$_2$)$_d$C(=Y)N(T)$_2$.

(66) Quinazolin-4(3H)-one-Type Piperidine Compounds of (65), wherein R$^4$ is —(CH$_2$)$_d$C(=Y)YT.

(67) Quinazolin-4(3H)-one-Type Piperidine Compounds of (66), wherein in the —(CH$_2$)$_d$C(=Y)YT of R$^4$, Y is O for each occurrence and d is 0.

(68) Quinazolin-4(3H)-one-Type Piperidine Compounds of (66), wherein in the —(CH$_2$)$_d$C(=Y)YT of R$^4$, T is —H or unsubstituted —(C$_1$-C$_6$)alkyl.

(69) A Quinazolin-4(3H)-one-Type Piperidine Compound selected from:

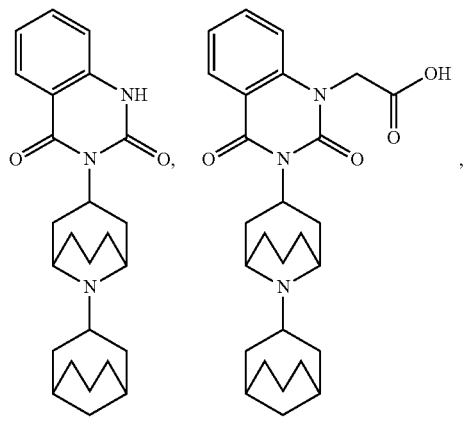

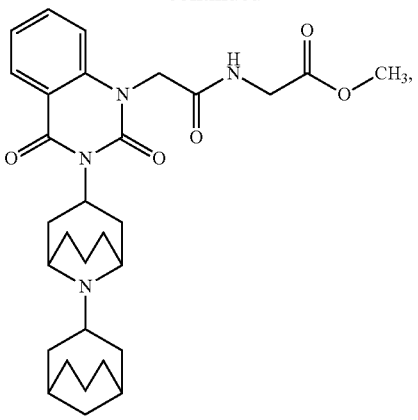

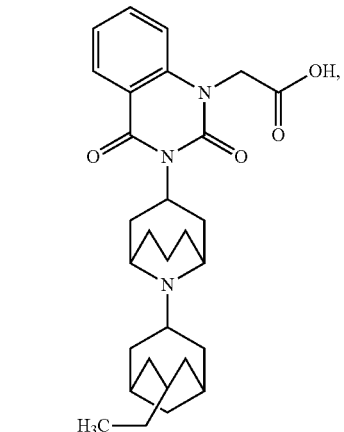

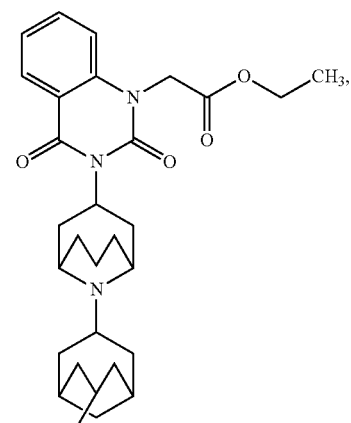

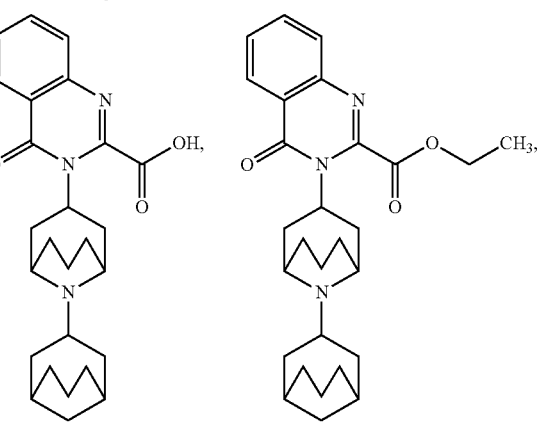

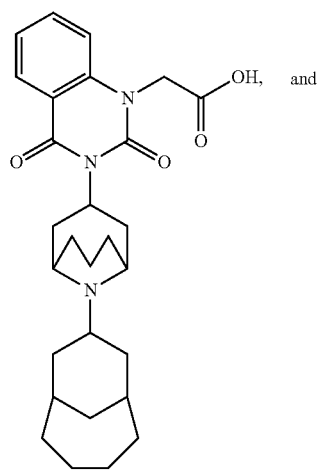
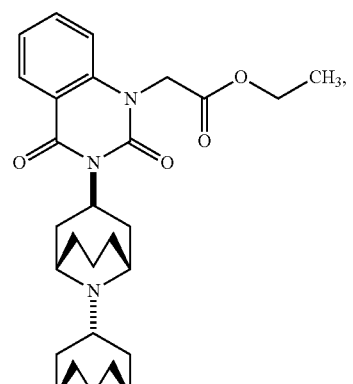
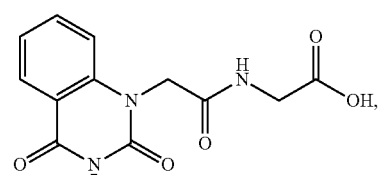
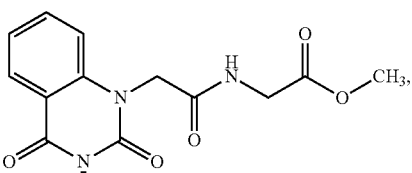
or a pharmaceutically acceptable salt or solvate.
(70) The Quinazolin-4(3H)-one-Type Piperidine Compound of (69) selected from:
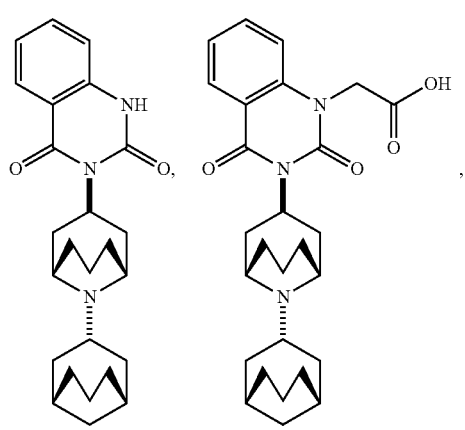
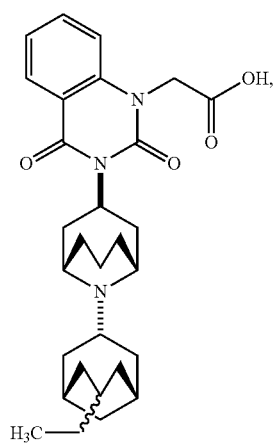

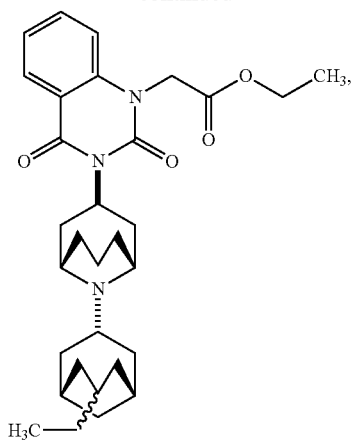
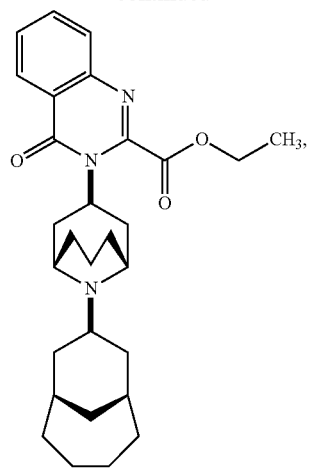
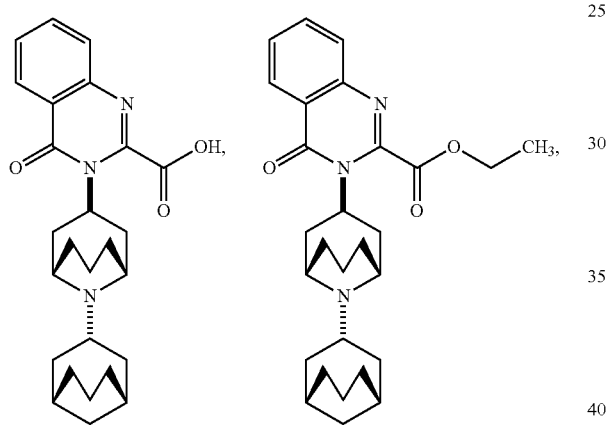
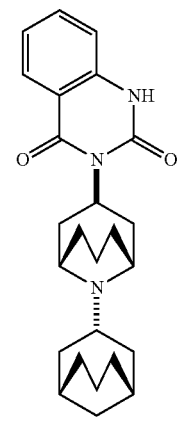
or a pharmaceutically acceptable salt or solvate thereof.
(71) The Quinazolin-4(3H)-one-Type Piperidine Compound of (70) having the formula:
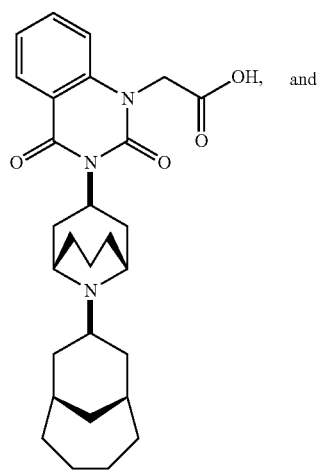
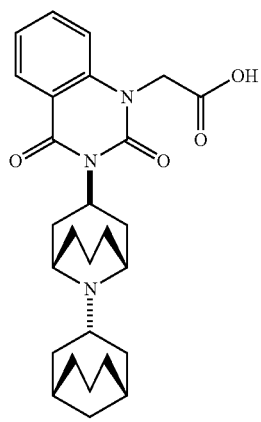
or a pharmaceutically acceptable salt or solvate thereof.
(72) The Quinazolin-4(3H)-one-Type Piperidine Compound of (70) having the formula:
or a pharmaceutically acceptable salt or solvate thereof.

(73) The Quinazolin-4(3H)-one-Type Piperidine Compound of (70) having the formula:

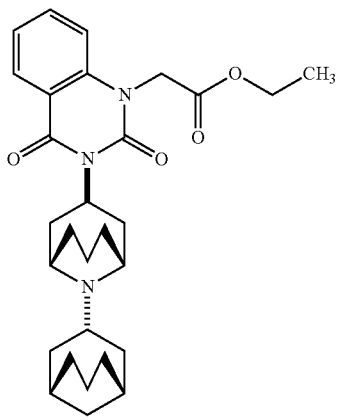

or a pharmaceutically acceptable salt or solvate thereof.

(74) The Quinazolin-4(3H)-one-Type Piperidine Compound of (70) having the formula:

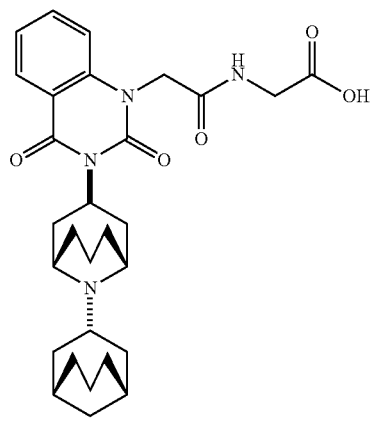

or a pharmaceutically acceptable salt or solvate thereof.

(75) The Quinazolin-4(3H)-one-Type Piperidine Compound of (70) having the formula:

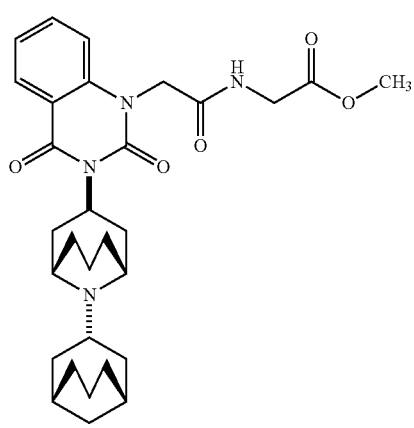

or a pharmaceutically acceptable salt or solvate thereof.

(76) The Quinazolin-4(3H)-one-Type Piperidine Compound of (70) having the formula:

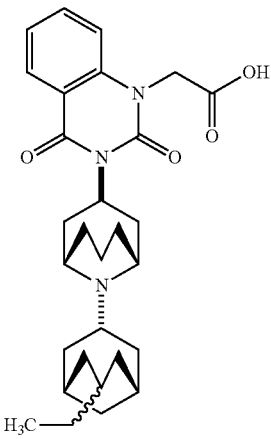

or a pharmaceutically acceptable salt or solvate thereof.

(77) The Quinazolin-4(3H)-one-Type Piperidine Compound of (70) having the formula:

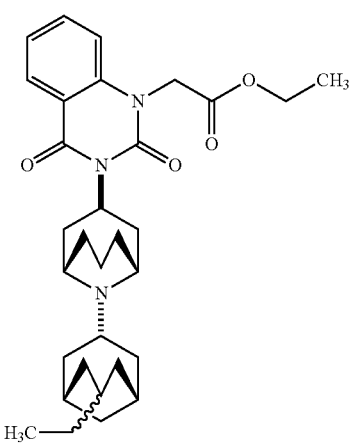

or a pharmaceutically acceptable salt or solvate thereof.

(78) The Quinazolin-4(3H)-one-Type Piperidine Compound of (70) having the formula:

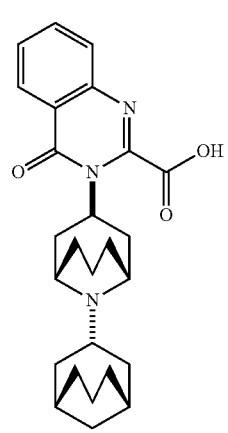

or a pharmaceutically acceptable salt or solvate thereof.

(79) The Quinazolin-4(3H)-one-Type Piperidine Compound of (70) having the formula:

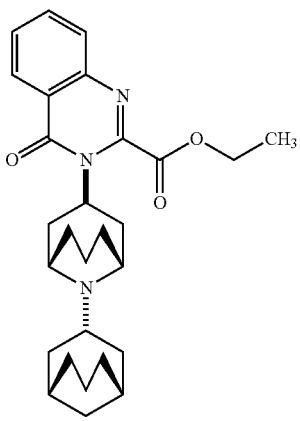

or a pharmaceutically acceptable salt or solvate thereof.

(80) The Quinazolin-4(3H)-one-Type Piperidine Compound of (70) having the formula:

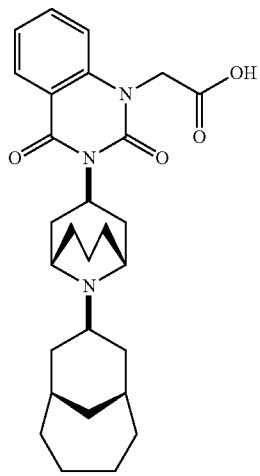

or a pharmaceutically acceptable salt or solvate thereof.

(81) The Quinazolin-4(3H)-one-Type Piperidine Compound of (70) having the formula:

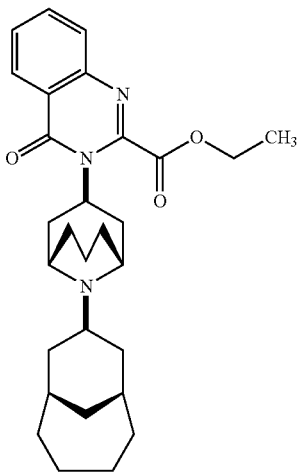

or a pharmaceutically acceptable salt or solvate thereof.

(82) Quinazolin-4(3H)-one-Type Piperidine Compounds of any one of (1)-(81), wherein the compounds are pharmaceutically acceptable salts.

(83) Quinazolin-4(3H)-one-Type Piperidine Compounds of (82), wherein the pharmaceutically acceptable salts are hydrochloride salts.

(84) Quinazolin-4(3H)-one-Type Piperidine Compounds of any one of (1)-(83), wherein the % de of the compounds are at least about 95%.

(85) Quinazolin-4(3H)-one-Type Piperidine Compounds of (84), wherein the % de of the compounds are at least about 99%.

(86) A composition comprising an effective amount of a Quinazolin-4(3H)-one-Type Piperidine Compound of any one of (1)-(85) and a pharmaceutically acceptable carrier or excipient.

(87) A method for preparing a composition, comprising the step of admixing a Quinazolin-4(3H)-one-Type Piperidine Compound of any one of (1)-(85) and a pharmaceutically acceptable carrier or excipient.

(88) A method for modulating ORL-1 receptor function in a cell, comprising contacting a cell capable of expressing the ORL-1 receptor with an effective amount of a Quinazolin-4(3H)-one-Type Piperidine Compound of any one of (1)-(85).

(89) The method of (88), wherein the Quinazolin-4(3H)-one-Type Piperidine Compound acts as an agonist at the ORL-1 receptor.

(90) The method of (88), wherein the Quinazolin-4(3H)-one-Type Piperidine Compound acts as a partial agonist at the ORL-1 receptor.

(91) The method of (88), wherein the Quinazolin-4(3H)-one-Type Piperidine Compound acts as an antagonist at the ORL-1 receptor.

(92) A method for treating pain in an animal, comprising administering to an animal in need thereof an effective amount of a Quinazolin-4(3H)-one-Type Piperidine Compound of any one of (1)-(85).

(93) A method for treating a memory disorder, obesity, constipation, depression, Parkinsonism, anxiety, cough, diarrhea, high blood pressure, epilepsy, anorexia/cachexia, urinary incontinence, drug abuse, a sleep disorder (see e.g., U.S. Pat. No. 8,003,669), a metabolic disorder (see e.g., Matsushita, et al. (2009). "Chronic intracerebroventricular infusion of nociceptin/orphanin FQ produces body weight gain by affecting both feeding and energy metabolism in mice." *Endocrinology*, 150: 2668-2673; Cifani, et al. (2009). "Nociceptin/orphanin FQ-induced food intake and cocaine amphetamine regulated transcript gene expression in strains derived from rats prone (WOKW) and resistant (Dark Agouti) to metabolic syndrome." *Peptides*, 30: 727-734; Hantos, et al. (2002). "Elevated plasma nociceptin level in patients with Wilson disease." *Brain Res. Bull.*, 58: 311-313), a renal disorder, or a cardiovascular disorder in an animal, comprising administering to an animal in need thereof an effective amount of a Quinazolin-4(3H)-one-Type Piperidine Compound of any one of (1)-(85).

(94) Use of a Quinazolin-4(3H)-one-Type Piperidine Compound of any one of (1)-(85) in the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, drug abuse, a sleep disorder, a metabolic disorder, a renal disorder, or a cardiovascular disorder.

(95) A Quinazolin-4(3H)-one-Type Piperidine Compound of any one of (1)-(85) for use in the treatment of pain, a memory disorder, obesity, constipation, depression, dementia, Parkinsonism, anxiety, cough, diarrhea, high blood pressure, epilepsy, anorexia/cachexia, urinary incontinence, drug abuse, a sleep disorder, a metabolic disorder, a renal disorder, or a cardiovascular disorder.

(96) A kit, comprising a sterile container containing an effective amount of a Quinazolin-4(3H)-one-Type Piperidine Compound of any one of (1)-(85).

4.2 General Embodiments of Quinazolin-4(3H)-one-Type Piperidine Compounds

As stated above, the present disclosure encompasses Quinazolin-4(3H)-one-Type Piperidine Compounds of Formula (I):

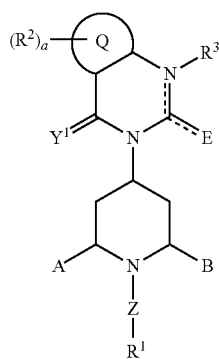

(I)

and the pharmaceutically acceptable salts and solvates thereof, wherein $R^1$, $R^2$, $R^3$, Q, $Y^1$, Z, A, B, E, and a are as defined herein.

In certain embodiments, Q is fused benzo. In other embodiments, Q is a fused (5- or 6-membered)heteroaryl, such as fused pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

In some embodiments, Q is fused pyridyl, such as wherein the pyridyl nitrogen in the Q ring is in a 1,3 or 1,4 or 1,5 or 1,6-relationship with the carbon atom double bonded to $Y^1$. In certain embodiments, the pyridyl nitrogen in the Q ring is in a 1,3-relationship with the carbon atom double bonded to $Y^1$.

In certain embodiments a is 0. In other embodiments, a is 1, 2, 3, or 4. For example, in some embodiments, a is 1, in other embodiments, a is 2, in other embodiments, a is 3, and in other embodiments, a is 4.

In some embodiments when a is 1, 2, 3, or 4, each $R^2$ is independently selected from -halo, —C(halo)$_3$, —CH(halo)$_2$, —CH$_2$(halo), —CN, —NO$_2$, —N$_3$, —OT, —ST, —N(T)$_2$, —C(=Y)T, —C(=Y)YT, —YC(=Y)T, —YC(=Y)YT, —C(=Y)N(T)$_2$, —N(T)C(=Y)T, —N(T)C(=Y)N(T)$_2$, —YC(=Y)N(T)$_2$, —N(T)C(=Y)YT, —S(=O)$_p$T, —S(=O)$_p$OT, —OS(=O)$_p$T, —OS(=O)$_p$OT, —S(=O)$_p$N(T)$_2$, —N(T)S(=O)$_p$T, —N(T)S(=O)$_p$N(T)$_2$, —OS(=O)$_p$N(T)$_2$, and —N(T)S(=O)$_p$OT, particularly -halo, —OT, —N(T)$_2$, —C(=Y)T, —C(=Y)YT, —YC(=Y)T, —C(=Y)N(T)$_2$, and —N(T)C(=Y)T, such as halo, —OH, —NH$_2$, —N(H)((C$_1$-C$_{10}$)alkyl)), and —N((C$_1$-C$_{10}$)alkyl)$_2$.

In other embodiments when a is 1, 2, 3, or 4, each $R^2$ is independently selected from —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_7$-C$_{20}$)tricycloalkyl, —(C$_5$-C$_{10}$)cycloalkenyl, —(C$_7$-C$_{14}$)bicycloalkenyl, —(C$_5$-C$_{20}$)tricycloalkenyl, —(C$_3$-C$_7$)cycloalkoxy, -(5- or 6-membered)heterocycle, and -(7- to 10-membered)bicycloheterocycle, each of which is unsubstituted or substituted with 1, 2, 3, or 4 independently selected $R^5$ groups. In certain embodiments, when a is 1, 2, 3, or 4, each $R^2$ is independently selected from —(C$_1$-C$_6$)alkyl and —(C$_1$-C$_6$)alkoxy unsubstituted or substituted with 1, 2, 3, or 4 independently selected $R^5$ groups.

In other embodiments when a is 1, 2, 3, or 4, each $R^2$ is independently selected from -phenyl, -benzyl, -naphthyl, —(C$_{14}$)aryl, and -(5- or 6-membered)heteroaryl, each of which is unsubstituted or substituted with 1, 2, 3, or 4 independently selected $R^6$ groups. In other embodiments when a is 1, 2, 3, or 4, each $R^2$ is independently selected from -phenyl or -benzyl, each of which is unsubstituted or substituted with 1, 2, 3, or 4 independently selected $R^6$ groups.

In certain embodiments, $Y^1$ is O. In other embodiments, $Y^1$ is S.

In some embodiments, the --- connected to E denotes a double bond, $R^3$ is present, and E is $Y^2$.

In some of such embodiments, $Y^2$ is O. In other such embodiments, $Y^2$ is S.

In certain embodiments when $R^3$ is present, $R^3$ is —H. In other embodiments when $R^3$ is present, $R^3$ is selected from —(CH$_2$)$_d$C(=Y)T, —(CH$_2$)$_d$C(=Y)YT, —(CH$_2$)$_e$YC(=Y)T, —(CH$_2$)$_e$YC(=Y)YT, —(CH$_2$)$_d$C(=Y)N(T)$_2$, —(CH$_2$)$_e$N(T)C(=Y)T, —(CH$_2$)$_e$N(T)C(=Y)N(T)$_2$, —(CH$_2$)$_e$YC(=Y)N(T)$_2$, —(CH$_2$)$_e$N(T)C(=Y)YT, —(CH$_2$)$_d$C(=Y)(CH$_2$)$_d$C(=Y)YT, —(CH$_2$)$_d$C(=Y)(CH$_2$)$_d$ C(=Y)N(T)$_2$, —(CH$_2$)$_d$S(=O)$_p$T, —(CH$_2$)$_d$S(=O)$_p$OT, —(CH$_2$)$_e$OS(=O)$_p$T, —(CH$_2$)$_e$OS(=O)$_p$OT, —(CH$_2$)$_d$S(=O)$_p$N(T)$_2$, —(CH$_2$)$_e$N(T)S(=O)$_p$T, —(CH$_2$)$_e$N(T)S(=O)$_p$N(T)$_2$, —(CH$_2$)$_e$OS(=O)$_p$N(T)$_2$, —(CH$_2$)$_e$N(T)S(=O)$_p$OT, —P(=O)(OT)$_2$, and —YP(=O)(OT)$_2$, particularly —(CH$_2$)$_d$C(=Y)T, —(CH$_2$)$_d$C(=Y)YT, —(CH$_2$)$_e$YC(=Y)T, —(CH$_2$)$_e$YC(=Y)YT, —(CH$_2$)$_d$C(=Y)N(T)$_2$, —(CH$_2$)$_e$N(T)C(=Y)T, —(CH$_2$)$_e$N(T)C(=Y)N(T)$_2$, —(CH$_2$)$_e$YC(=Y)N(T)$_2$, —(CH$_2$)$_e$N(T)C(=Y)YT, —(CH$_2$)$_d$C(=Y)(CH$_2$)$_d$C(=Y)YT, and —(CH$_2$)$_d$C(=Y)(CH$_2$)$_d$C(=Y)N(T)$_2$. In certain embodiments, when $R^3$ is present, $R^3$ is selected from —(CH$_2$)$_d$C(=Y)YT, —(CH$_2$)$_e$YC(=Y)T, —(CH$_2$)$_d$C(=Y)N(T)$_2$, and —(CH$_2$)$_e$N(T)C(=Y)T, particularly —(CH$_2$)$_d$C(=Y)YT and —(CH$_2$)$_d$C(=Y)N(T)$_2$.

In some of these embodiments of $R^3$, each d independently is 0, 1, 2, 3, or 4. In some embodiments, one or more occurrences of d are 0. In certain embodiments, each d independently is 1 or 2. In some of these embodiments of $R^3$, each e independently is 2, 3, or 4; such as 2 or 3, particularly 2.

In some of these embodiments of $R^3$, each T is independently selected from —H, —(C$_1$-C$_{10}$)alkyl, —(C$_2$-C$_{10}$)alkenyl, —(C₂-C₁₀)alkynyl, —(C₃-C₁₀)cycloalkyl, —(C₅-C₁₀)cycloalkenyl, and -(5- or 6-membered)heterocycle, each of which is unsubstituted or substituted with 1, 2, 3, or 4 independently selected $R^5$ groups. For example, in some embodiments, occurrences of —YT in $R^1$ are independently selected from —YH, such as —OH, and —Y—(C₁-C₁₀)alkyl, such as —O—(C₁-C₁₀)alkyl, wherein (C₁-C₁₀)alkyl is unsubstituted (for example, methyl, ethyl, propyl, or butyl including all structural isomers of any of these) or substituted with 1, 2, 3, or 4 independently selected $R^5$ groups. In another example, in some embodiments, occurrences of —N(T)₂ in $R^3$ are independently selected from —NH₂, —N(H)((C₁-C₁₀)alkyl), and —N((C₁-C₁₀)alkyl)₂, wherein (C₁-C₁₀)alkyl is unsubstituted (for example, methyl, ethyl, propyl, or butyl including all structural isomers of any of these, i.e., —N(H)(CH₃), —N(CH₃)₂, —N(H)(CH₂CH₃), —N(CH₂CH₃)₂, —N(CH₃)(CH₂CH₃), etc.) or substituted with 1, 2, 3, or 4 independently selected $R^5$ groups.

In other embodiments, each T in $R^3$ is independently selected from -phenyl, -benzyl, -naphthyl, and -(5- or 6-membered)heteroaryl, each of which is unsubstituted or substituted with 1, 2, 3, or 4 independently selected $R^6$ groups.

In particular embodiments, R is —(CH₂)_dC(=Y)YT wherein Y is O for each occurrence and d is 1, 2, 3, or 4; such as 1 or 2; particularly 1. In some instances of these embodiments, T is —H or —(C₁-C₆)alkyl unsubstituted (such as methyl, ethyl, propyl, or butyl including all structural isomers of any of these) or substituted with 1, 2, 3, or 4 independently selected $R^5$ groups. In another particular embodiment, $R^3$ is —(CH₂)_dC(=Y)N(T)₂ wherein Y is O and d is 1, 2, 3, or 4; such as 1 or 2; particularly 1. In some instances of these embodiments, one occurrence of T is —H, and the other occurrence of T is —(C₁-C₆)alkyl substituted with at least one $R^5$. For example, in some embodiments, at least one $R^5$ in an occurrence of T of $R^3$ is —C(=O)OR⁷. In some instances, T of R is selected from —CH₂C(=O)OR⁷, —CH₂CH₂C(=O)OR⁷, and —CH₂CH₂CH₂C(=O)OR⁷. In some of such examples, $R^7$ is —H.

In some embodiments $R^3$ has a structure selected from:

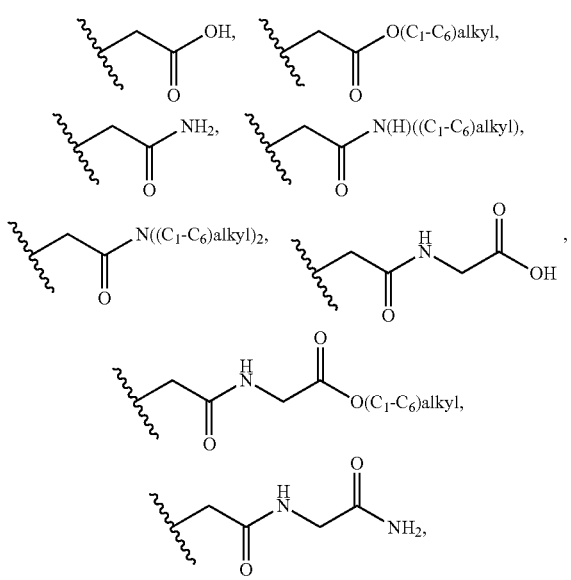

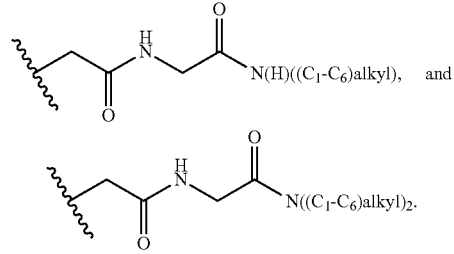

In other embodiments, $R^3$ has a structure selected from:

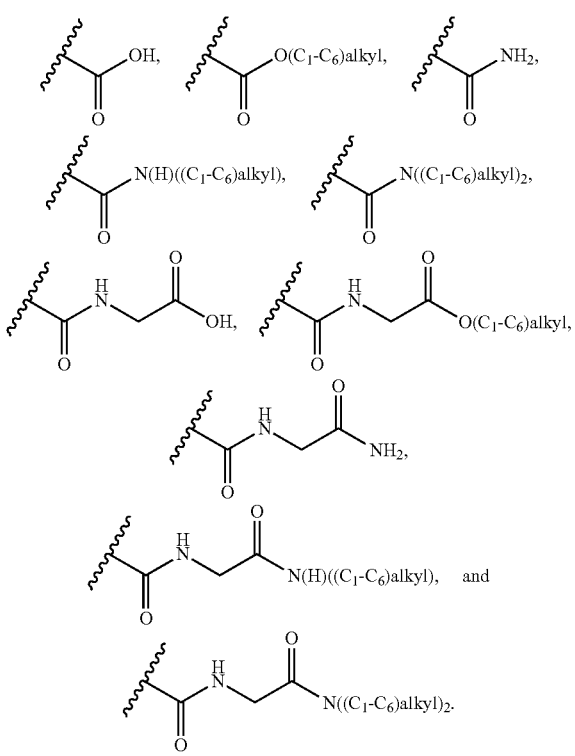

In other embodiments, $R^3$ is selected from —(CH₂)_eN(T)₂ and —(CH₂)_eYT, such as —(CH₂)_eOT, for example, —(CH₂)_eNH₂, —(CH₂)_eN(H)((C₁-C₁₀)alkyl), —(CH₂)_eN((C₁-C₁₀)alkyl)₂, —(CH₂)_eOH, and —(CH₂)_eO(C₁-C₁₀)alkyl, wherein (C₁-C₁₀)alkyl is unsubstituted (for example, methyl, ethyl, propyl, or butyl including all structural isomers of any of these) or substituted with 1, 2, 3, or 4 independently selected $R^5$ groups. In some of these embodiments of $R^4$, each e independently is 2, 3, or 4; such as 2 or 3, particularly 2.

In other embodiments, $R^3$ is an amino acid chain comprising 1, 2, 3, 4, or 5 amino acid residues, wherein the amino acid chain is bound to the 6-membered, nitrogen-containing ring that is fused to the Q ring via its N-terminal amino group or via its C-terminal carboxyl group. In some embodiments, the amino acid chain is directly bound to the 6-membered, nitrogen-containing ring that is fused to the Q ring via its N-terminal amino group, i.e., the nitrogen atom bearing $R^1$ is the N-terminal amino group of the amino acid chain. In other embodiments, the amino acid chain is indirectly bound to the 6-membered, nitrogen-containing ring that is fused to the Q ring via its N-terminal amino group, i.e., the N-terminal amino group of the amino acid chain is linked to the nitrogen atom bearing $R^3$ via a linking group, such as —$(C_1-C_6)$alkyl-, —$(C_1-C_6)$alkyl-C(=O)—, —C(=O)$(C_1-C_6)$alkyl or —C(=O)$(C_1-C_6)$alkyl-C(=O)—. In other embodiments, the amino acid chain is directly bound to the 6-membered, nitrogen-containing ring that is fused to the Q ring via its C-terminal carboxyl group, i.e., the C-terminal carboxyl group of the amino acid chain forms an amide with the nitrogen atom bearing $R^3$. In another embodiment, the amino acid chain is indirectly bound to the 6-membered, nitrogen-containing ring that is fused to the Q ring via its C-terminal carboxyl group, i.e., the C-terminal carboxyl group of the amino acid chain is linked to the nitrogen atom bearing $R^3$ via a linking group, such as a 1 to 6 atom linking group. The amino acid chain may include naturally occurring amino acids, non-naturally occurring amino acids, or a combination of these.

In some embodiments, one or more or all occurrences of Y in $R^1$ are O. In other embodiments, one or more or all occurrences of Y in $R^3$ are S. In certain embodiments, at least one occurrence of Y in $R^3$ is O and at least one occurrence is S.

In certain embodiments, $R^3$ includes one or more functional groups capable of forming a pharmaceutically acceptable salt, such as a pharmaceutically acceptable acid addition salt or a pharmaceutically acceptable base addition salt. For example, in some embodiments, $R^3$ includes one or more carboxylic acid groups, and in some embodiments, one or more of such carboxylic acid groups forms a pharmaceutically acceptable base addition salt, such as a sodium salt. Similarly, in some embodiments, $R^3$ includes one or more substituted or unsubstituted amine groups, and in some embodiments, one or more of such amine groups forms a pharmaceutically acceptable acid addition salt, such as a HCl salt.

In certain embodiments, the --- connected to N($R^3$) denotes a double bond, $R^3$ is absent, and E is $R^4$.

In some of such embodiments, $R^4$ is —H. In other embodiments, $R^4$ is selected from —$(CH_2)_dC(=Y)T$, —$(CH_2)_dC(=Y)YT$, —$(CH_2)_dYC(=Y)T$, —$(CH_2)_dYC(=Y)YT$, —$(CH_2)_dC(=Y)N(T)_2$, —$(CH_2)_dN(T)C(=Y)T$, —$(CH_2)_dN(T)C(=Y)N(T)_2$, —$(CH_2)_dYC(=Y)N(T)_2$, —$(CH_2)_dN(T)C(=Y)YT$, —$(CH_2)_dC(=Y)(CH_2)_dC(=Y)YT$, —$(CH_2)_dC(=Y)(CH_2)_dC(=Y)N(T)_2$, —$(CH_2)_dS(=O)T$, —$(CH_2)_dS(=O)_pOT$, —$(CH_2)_dOS(=O)_pT$, —$(CH_2)_dOS(=O)_pOT$, —$(CH_2)_dS(=O)_pN(T)_2$, —$(CH_2)_dN(T)S(=O)_pT$, —$(CH_2)_dN(T)S(=O)_pN(T)_2$, —$(CH_2)_dOS(=O)_pN(T)_2$, and —$(CH_2)_dN(T)S(=O)_pOT$, —P(=O)(OT)_2, and —YP(=O)(OT)_2, particularly —$(CH_2)_dC(=Y)T$, —$(CH_2)_dC(=Y)YT$, —$(CH_2)_dYC(=Y)T$, —$(CH_2)_dYC(=Y)YT$, —$(CH_2)_dC(=Y)N(T)_2$, —$(CH_2)_dN(T)C(=Y)T$, —$(CH_2)_dN(T)C(=Y)N(T)_2$, —$(CH_2)_dYC(=Y)N(T)_2$, —$(CH_2)_dN(T)C(=Y)YT$, —$(CH_2)_dC(=Y)(CH_2)_dC(=Y)YT$, and —$(CH_2)_dC(=Y)(CH_2)_dC(=Y)N(T)_2$. In certain embodiments when E is $R^4$, $R^4$ is selected from —$(CH_2)_dC(=Y)YT$, —$(CH_2)_dYC(=Y)T$, —$(CH_2)_dC(=Y)N(T)_2$, and —$(CH_2)_dN(T)C(=Y)T$, particularly —$(CH_2)_dC(=Y)YT$ and —$(CH_2)_dC(=Y)N(T)_2$.

In some of these embodiments of $R^4$, each d independently is 0, 1, 2, 3, or 4. In some embodiments, one or more occurrences of d are 0. In certain embodiments, each d independently is 1 or 2. In some of these embodiments of $R^4$, each e independently is 2, 3, or 4; such as 2 or 3, particularly 2.

In some of these embodiments of $R^4$, each T is independently selected from —H, —$(C_1-C_{10})$alkyl, —$(C_2-C_{10})$alkenyl, —$(C_2-C_{10})$alkynyl, —$(C_3-C_{10})$cycloalkyl, —$(C_5-C_{10})$cycloalkenyl, and -(5- or 6-membered)heterocycle, each of which is unsubstituted or substituted with 1, 2, 3, or 4 independently selected $R^5$ groups. For example, in some embodiments, occurrences of —YT in $R^4$ are independently selected from —YH, such as —OH, and —Y—$(C_1-C_{10})$alkyl, such as —O—$(C_1-C_{10})$alkyl, wherein $(C_1-C_{10})$alkyl is unsubstituted (for example, methyl, ethyl, propyl, or butyl including all structural isomers of any of these) or substituted with 1, 2, 3, or 4 independently selected $R^5$ groups. In another example, in some embodiments, occurrences of —N(T)_2 in $R^4$ are independently selected from —NH_2, —N(H)(($C_1-C_{10}$)alkyl), and —N(($C_1-C_{10}$)alkyl)_2, wherein $(C_1-C_{10})$alkyl is unsubstituted (for example, methyl, ethyl, propyl, or butyl including all structural isomers of any of these, i.e., —N(H)(CH_3), —N(CH_3)_2, —N(H)(CH_2CH_3), —N(CH_2CH_3)_2, —N(CH_3)(CH_2CH_3), etc.) or substituted with 1, 2, 3, or 4 independently selected $R^5$ groups.

In other embodiments, each T in $R^4$ is independently selected from -phenyl, -benzyl, -naphthyl, and -(5- or 6-membered)heteroaryl, each of which is unsubstituted or substituted with 1, 2, 3, or 4 independently selected $R^6$ groups.

In particular embodiments, $R^4$ is —$(CH_2)_dC(=Y)YT$ wherein Y is O for each occurrence and d is 0, 1, 2, 3, or 4; such as 0, 1, or 2; particularly 0. In some instances of these embodiments, T is —H or —$(C_1-C_6)$alkyl unsubstituted (such as methyl, ethyl, propyl, or butyl including all structural isomers of any of these) or substituted with 1, 2, 3, or 4 independently selected $R^5$ groups. In another particular embodiment, $R^4$ is —$(CH_2)_dC(=Y)N(T)_2$ wherein Y is O and d is 0, 1, 2, 3, or 4; such as 0, 1, or 2; particularly 0. In some instances of these embodiments, one occurrence of T is —H, and the other occurrence of T is —$(C_1-C_6)$alkyl substituted with at least one $R^5$. For example, in some embodiments, at least one $R^5$ in an occurrence of T of $R^4$ is —C(=O)OR^7. In some instances, T of $R^4$ is selected from —CH_2C(=O)OR^7, —CH_2CH_2C(=O)OR^7, and —CH_2CH_2CH_2C(=O)OR. In some of such examples, $R^7$ is —H.

In some embodiments, $R^4$ has a structure selected from:

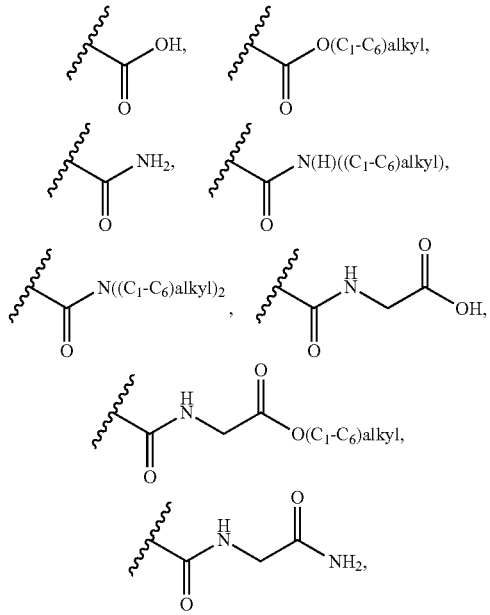

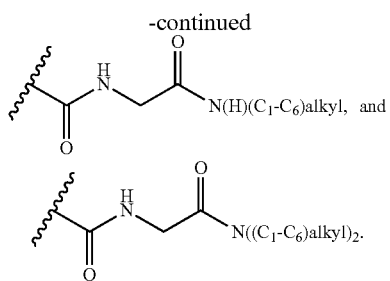

In other embodiments, $R^4$ has a structure selected from:

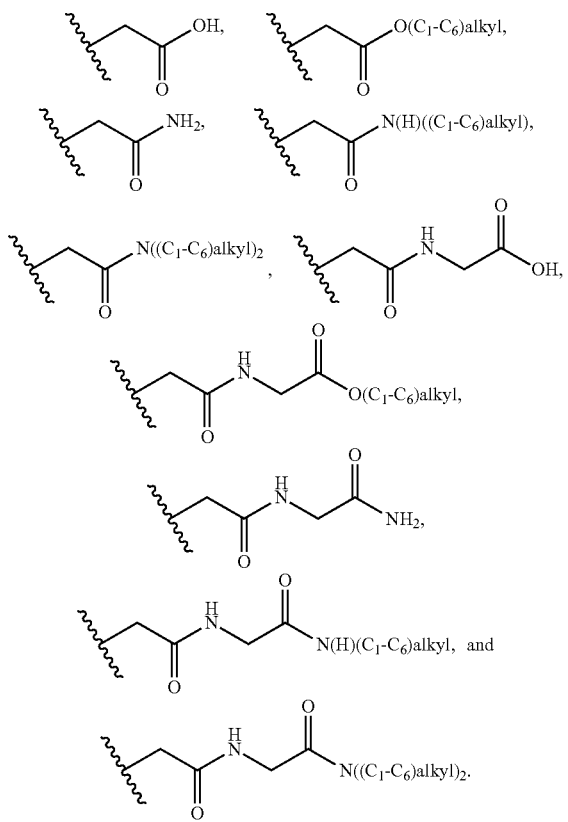

In other embodiments, $R^4$ is selected from $-(CH_2)_dYT$, $-Y(CH_2)_eYT$, $-(CH_2)_dN(T)_2$, $-N(T)(CH_2)_eN(T)_2$, $-Y(CH_2)_eN(T)_2$, and $-N(T)(CH_2)_eYT$, particularly $-(CH_2)_dYT$ and $-(CH_2)_dN(T)_2$, such as $-(CH_2)_dOT$, for example, $-(CH_2)_dNH_2$, $-(CH_2)_dN(H)((C_1-C_{10})alkyl)$, $-(CH_2)_dN((C_1-C_{10})alkyl)_2$, $-(CH_2)_dOH$, and $-(CH_2)_dO(C_1-C_{10})alkyl$, wherein $(C_1-C_{10})alkyl$ is unsubstituted (for example, methyl, ethyl, propyl, or butyl including all structural isomers of any of these) or substituted with 1, 2, 3, or 4 independently selected $R^5$ groups. In some of these embodiments of $R^4$, each d independently is 0, 1, 2, 3, or 4. In some embodiments, one or more occurrences of d are 0. In certain embodiments, each d independently is 1 or 2. In some of these embodiments of $R^4$, each e independently is 2, 3, or 4; such as 2 or 3, particularly 2.

In other embodiments, $R^4$ is an amino acid chain comprising 1, 2, 3, 4, or 5 amino acid residues, wherein the amino acid chain is bound to the 6-membered, nitrogen-containing ring that is fused to the Q ring via its N-terminal amino group or via its C-terminal carboxyl group. In some embodiments, the amino acid chain is directly bound to the 6-membered, nitrogen-containing ring that is fused to the Q ring via its N-terminal amino group, i.e., the N-terminal amino group of the amino acid chain is bonded to the carbon atom bearing $R^4$. In another embodiment, the amino acid chain is indirectly bound to the 6-membered, nitrogen-containing ring that is fused to the Q ring via its N-terminal amino group, i.e., the N-terminal amino group of the amino acid chain is linked to the carbon atom bearing $R^4$ via a linking group, such as a 1 to 6 atom linking group. In other embodiments, the amino acid chain is directly bound to the 6-membered, nitrogen-containing ring that is fused to the Q ring via its C-terminal carboxyl group, i.e., the carbonyl of the C-terminal carboxyl group of the amino acid chain is bound to the carbon atom bearing $R^4$, the non-carbonyl oxygen atom of the C-terminal carboxyl group of the amino acid chain is bound to the carbon atom bearing $R^4$, or the carbonyl of the C-terminal carboxyl group of the amino acid chain is bound to a $-N(R^7)-$ group which is then bound to the carbon atom bearing $R^4$. In a further embodiment, the amino acid chain is indirectly bound to the 6-membered, nitrogen-containing ring that is fused to the Q ring via its C-terminal carboxyl group, i.e., the C-terminal carboxyl group of the amino acid chain is linked to the carbon atom bearing $R^4$ via a linking group, such as a 1 to 6 atom linking group. The amino acid chain may include naturally occurring amino acids, non-naturally occurring amino acids, or a combination of these.

In other embodiments, $R^4$ is selected from -halo, $-CN$, and $-NO_2$. Such embodiments may be used as starting materials or intermediates to prepare additional compounds of Formula (I).

In some embodiments, one or more or all occurrences of Y in $R^4$ are O. In other embodiments, one or more or all occurrences of Y in $R^4$ are S. In certain embodiments, at least one occurrence of Y in $R^4$ is O and at least one occurrence is S.

In certain embodiments, $R^4$ includes one or more functional groups capable of forming a pharmaceutically acceptable salt, such as a pharmaceutically acceptable acid addition salt or a pharmaceutically acceptable base addition salt. For example, in some embodiments, $R^4$ includes one or more carboxylic acid groups, and in some embodiments, one or more of such carboxylic acid groups forms a pharmaceutically acceptable base addition salt, such as a sodium salt. Similarly, in some embodiments, $R^4$ includes one or more substituted or unsubstituted amine groups, and in some embodiments, one or more of such amine groups forms a pharmaceutically acceptable acid addition salt, such as a HCl salt.

In certain embodiments, A and B together form a $(C_2-C_6)$ bridge, which is unsubstituted or substituted with 1, 2, 3, 4, 5, 6, 7, or 8 substituents independently selected from $-OR^7$, $-(C_1-C_6)alkyl$, -halo, $-C(halo)_3$, $-CH(halo)_2$, and $-CH_2(halo)$ and which bridge optionally contains a carbon-carbon double bond, $-O-$, $-S-$, or $-N(R^7)-$. In some embodiments, the A-B bridge is unsubstituted. In other embodiments, the A-B bridge is substituted with 1, 2, 3, 4, 5, 6, 7, or 8 substituents independently selected from $-OR^7$ (e.g., $-OH$), $-(C_1-C_4)alkyl$, -halo, $-C(halo)_3$, $-CH(halo)_2$, and $-CH_2(halo)$, particularly $-(C_1-C_4)alkyl$, such as methyl, ethyl, propyl, or butyl including all structural isomers of any of these, particularly methyl. In some embodiments, the A-B bridge contains a carbon-carbon double bond, such as a cis-carbon-carbon double bond. In certain embodiments, the A-B bridge contains a $-Y-$ group, such as —O—. In some embodiments, the A-B bridge contains a —N(R$^7$)— group.

In another embodiment, A-B together form a (C$_2$)bridge which bridge is substituted or unsubstituted. In another embodiment, A-B together form a (C$_2$)bridge which bridge is unsubstituted. In another embodiment, A-B together form a (C$_2$)bridge which bridge is substituted by one or two methyl groups. In another embodiment, A-B together form a (C$_3$)bridge which bridge is substituted or unsubstituted. In another embodiment, A-B together form a (C$_3$)bridge which bridge is unsubstituted. In another embodiment, A-B together form a (C$_3$)bridge which bridge is substituted by one or two methyl groups. In another embodiment, A-B together form a (C$_4$)bridge which bridge is substituted or unsubstituted. In another embodiment, A-B together form a (C$_4$)bridge which bridge is unsubstituted. In another embodiment, A-B together form a (C$_4$)bridge which bridge is substituted by one or two methyl groups. In another embodiment, A-B together form a (C$_5$)bridge which bridge is substituted or unsubstituted. In another embodiment, A-B together form a (C$_5$)bridge which bridge is unsubstituted. In another embodiment, A-B together form a (C$_5$)bridge which bridge is substituted by one or two methyl groups. In another embodiment, A-B together form a (C$_6$)bridge which bridge is substituted or unsubstituted. In another embodiment, A-B together form a (C$_6$)bridge which bridge is unsubstituted. In another embodiment, A-B together form a (C$_6$)bridge which bridge is substituted by one or two methyl groups.

In some embodiments, A-B together form a substituted or unsubstituted alkylene bridge, such as a substituted or unsubstituted (C$_1$-C$_6$)alkylene bridge, such as a substituted or unsubstituted methylene, ethylene, n-propylene, or n-butylene bridge, particularly a substituted or unsubstituted ethylene or n-propylene bridge.

In certain embodiments, A-B together form a substituted or unsubstituted (C$_3$)bridge, for example a (C$_3$)bridge which bridge is unsubstituted, such as —CH$_2$—CH$_2$—CH$_2$—.

In another embodiment, A-B together form a (C$_2$)bridge which bridge is —HC=CH— and is substituted or unsubstituted. In another embodiment, A-B together form a (C$_2$) bridge which bridge is —HC=CH— and is unsubstituted. In another embodiment, A-B together form a (C$_2$)bridge which is —HC=CH— and is substituted by one or two methyl groups. In another embodiment, A-B together form a (C$_3$)bridge which is —CH$_2$—HC=CH— or —HC=CH—CH$_2$— and is substituted or unsubstituted. In another embodiment, A-B together form a (C$_3$)bridge which is —CH$_2$—HC=CH— or —HC=CH—CH$_2$— and is unsubstituted. In another embodiment, A-B together form a (C$_3$)bridge which is —CH$_2$—HC=CH— or —HC=CH—CH$_2$— and is substituted by one or two methyl groups. In another embodiment, A-B together form a (C$_4$)bridge which is —CH$_2$—CH$_2$—HC=CH—, —CH$_2$—HC=CH—CH$_2$—, or —HC=CH—CH$_2$—CH$_2$— and is substituted or unsubstituted. In another embodiment, A-B together form a (C$_4$)bridge which is —CH$_2$—CH$_2$—HC=CH—, —CH$_2$—HC=CH—CH$_2$—, or —HC=CH—CH$_2$—CH$_2$— and is unsubstituted. In another embodiment, A-B together form a (C$_4$)bridge which is —CH$_2$—CH$_2$—HC=CH—, —CH$_2$—HC=CH—CH$_2$—, or —HC=CH—CH$_2$—CH$_2$— and is substituted by one or two methyl groups.

In another embodiment, A-B together form a (C$_2$)bridge which is —CH$_2$—O—CH$_2$— and is substituted or unsubstituted. In another embodiment, A-B together form a (C$_2$) bridge which is —CH$_2$—O—CH$_2$— and is unsubstituted. In another embodiment, A-B together form a (C$_2$)bridge which is —CH$_2$—O—CH$_2$— and is substituted by one or two methyl groups. In another embodiment, A-B together form a (C$_3$)bridge which is —CH$_2$—O—CH$_2$—CH$_2$— or —CH$_2$—CH$_2$—O—CH$_2$— and is substituted or unsubstituted. In another embodiment, A-B together form a (C$_3$) bridge which is —CH$_2$—O—CH$_2$—CH$_2$— or —CH$_2$—CH$_2$—O—CH$_2$— and is unsubstituted.

In another embodiment, A-B together form a (C$_3$)bridge which is —CH$_2$—O—CH$_2$—CH$_2$— or —CH$_2$—CH$_2$—O—CH$_2$— and is substituted by one or two methyl groups. In another embodiment, A-B together form a (C$_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted or unsubstituted. In another embodiment, A-B together form a (C$_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is unsubstituted. In another embodiment, A-B together form a (C$_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted by one or two methyl groups.

In another embodiment, A-B together form a —CH$_2$—NH—CH$_2$— bridge. In another embodiment, A-B together form a —CH$_2$—N(CH$_3$)—CH$_2$— bridge. In another embodiment, A-B together form a —CH$_2$—N(CH$_2$CH$_3$)—CH$_2$— bridge.

In another embodiment, A and B together form a bridge such that the bridged-piperidine is:

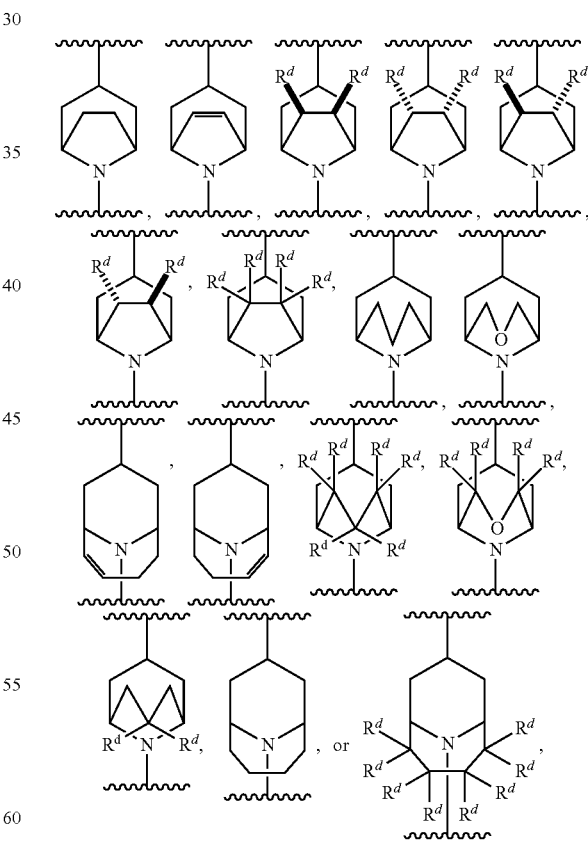

wherein each R$^d$ is independently selected from —H, —(C$_1$-C$_4$)alkyl (such as methyl, ethyl, propyl, or butyl including all structural isomers of any of these), -halo, —C(halo)$_3$, —CH (halo)$_2$, and —CH$_2$(halo), wherein the piperidine nitrogen is optionally in pharmaceutically acceptable salt form. In another embodiment, A and B together form a bridge such that the bridged-piperidine is:

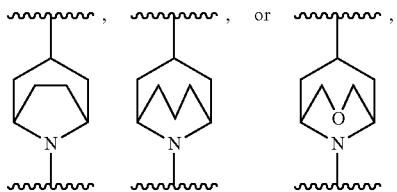

wherein the piperidine nitrogen is optionally in pharmaceutically acceptable salt form.

In another embodiment, A and B together form a bridge such that the bridged-piperidine is:

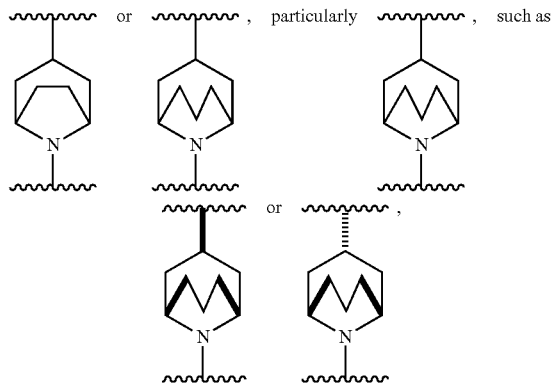

wherein the piperidine nitrogen is optionally in pharmaceutically acceptable salt form.

In certain embodiments, the 6-membered, nitrogen-containing ring that is fused to the Q ring is in the endo-configuration with respect to the A-B bridge, i.e., the 6-membered, nitrogen-containing ring that is fused to the Q ring and the A-B bridge are on the same side of the piperidine ring. In other embodiments, the 6-membered, nitrogen-containing ring that is fused to the Q ring is in the exo-configuration with respect to the A-B bridge, i.e., the 6-membered, nitrogen-containing ring that is fused to the Q ring and the A-B bridge are on opposite sides of the piperidine ring.

In some embodiments, Z is a direct bond. In other embodiments, Z is selected from —$(C_1-C_{10})$alkyl-, —$(C_2-C_{10})$alkenyl-, —$(C_2-C_{10})$alkynyl-, —$(C_2-C_{10})$alkyl-Y—, —$(C_1-C_{10})$alkyl-C(=Y)Y—, —$(C_2-C_{10})$alkyl-YC(=Y)—, —$(C_2-C_{10})$alkyl-N($R^7$)—, —$(C_1-C_{10})$alkyl-C(=Y)N($R^7$)—, and —$(C_2-C_{10})$alkyl-N($R^7$)C(=Y)—, each of which is unsubstituted or substituted with 1, 2, or 3 independently selected $R^8$ groups. In certain embodiments, Z is selected from —$(C_1-C_{10})$alkyl-, —$(C_2-C_{10})$alkyl-Y—, —$(C_1-C_{10})$alkyl-C(=Y)Y—, —$(C_2-C_{10})$alkyl-YC(=Y)—, —$(C_2-C_{10})$alkyl-N($R^7$)—, —$(C_1-C_{10})$alkyl-C(=Y)N($R^7$)—, and —$(C_2-C_{10})$alkyl-N($R^7$)C(=Y)—, each of which is unsubstituted or substituted with 1, 2, or 3 independently selected $R^8$ groups. In certain embodiments, Z is selected from —$(C_1-C_6)$alkyl-, —$(C_2-C_6)$alkyl-Y—, —$(C_1-C_6)$alkyl-C(=Y)Y—, —$(C_2-C_6)$alkyl-YC(=Y)—, —$(C_2-C_6)$alkyl-N($R^7$)—, —$(C_1-C_6)$alkyl-C(=Y)N($R^7$)—, and —$(C_2-C_6)$alkyl-N($R^7$)C(=Y)—, particularly —$(C_1-C_6)$alkyl-, each of which is unsubstituted or substituted with 1, 2, or 3 independently selected $R^8$ groups.

In some embodiments, Z is —$(C_2-C_{10})$alkenyl-. In another embodiment, Z is —$(C_2-C_6)$alkenyl-. In another embodiment, Z is —$CH_2$—CH=CH—. In another embodiment, Z is —$CH_2$—CH=CH—$CH_2$—. In another embodiment, Z is a —$(C_3)$alkenyl-.

In another embodiment, Z is —$CH_2$—$CH_2$—NH—C(=O)—. In another embodiment, Z is —$CH_2$—$CH_2$—NH—C(=S)—. In another embodiment, Z is —$CH_2$—$CH_2$—N($CH_3$)—C(=O)—. In another embodiment, Z is —$CH_2$—$CH_2$—N($CH_3$)—C(=S)—.

In another embodiment, Z is —$(C_1-C_3)$alkyl- unsubstituted or substituted with 1, 2, or 3 independently selected $R^8$ groups. In another embodiment, Z is —$CH_2$—. In another embodiment, Z is —$CH_2$—$CH_2$—. In another embodiment, Z is —$CH_2$—$CH_2$—$CH_2$—. In another embodiment, Z is —$(C_1-C_3)$alkyl-substituted by —$CF_3$. In another embodiment, Z is —$CH_2$—CH($CF_3$)—$CH_2$—.

In certain embodiments, $R^1$ is selected from —$(C_3-C_{14})$cycloalkyl, —$(C_6-C_{14})$bicycloalkyl, and —$(C_7-C_{20})$tricycloalkyl, particularly, —$(C_6-C_{14})$bicycloalkyl, each of which is unsubstituted or substituted with 1, 2, 3, or 4 independently selected $R^5$ groups. In some embodiments, $R^1$ is selected from —$(C_5-C_{10})$cycloalkenyl, —$(C_7-C_{14})$bicycloalkenyl, and —$(C_5-C_{20})$tricycloalkenyl, each of which is unsubstituted or substituted with 1, 2, 3, or 4 independently selected $R^5$ groups. In some embodiments, $R^1$ is selected from —$(C_3-C_7)$cycloalkoxy, -(3- to 7-membered)heterocycle, and -(7- to 10-membered)bicycloheterocycle, each of which is unsubstituted or substituted with 1, 2, 3, or 4 independently selected $R^5$ groups.

In another embodiment, $R^1$ is cyclooctyl unsubstituted or substituted with 1, 2, 3, or 4 independently selected $R^5$ groups. In another embodiment, $R^1$ is cycloundecyl unsubstituted or substituted with 1, 2, 3, or 4 independently selected $R^5$ groups. In another embodiment, $R^1$ is cyclooctenyl unsubstituted or substituted with 1, 2, 3, or 4 independently selected $R^5$ groups. In another embodiment, $R^1$ is —$(C_6-C_{14})$bicycloalkyl unsubstituted or substituted with 1, 2, 3, or 4 independently selected $R^5$ groups. In another embodiment, $R^1$ is bicyclo[3.3.1]nonyl unsubstituted or substituted with 1, 2, 3, or 4 independently selected $R^5$ groups. In another embodiment, $R^1$ is bicyclo[2.2.1]heptyl unsubstituted or substituted with 1, 2, 3, or 4 independently selected $R^5$ groups. In another embodiment, $R^1$ is —$(C_5-C_{10})$tricycloalkyl unsubstituted or substituted with 1, 2, 3, or 4 independently selected $R^5$ groups. In another embodiment, $R^1$ is adamantyl unsubstituted or substituted with 1, 2, 3, or 4 independently selected $R^5$ groups. In another embodiment, $R^1$ is noradamantyl unsubstituted or substituted with 1, 2, 3, or 4 independently selected $R^5$ groups.

In another embodiment, Z—$R^1$ is selected from

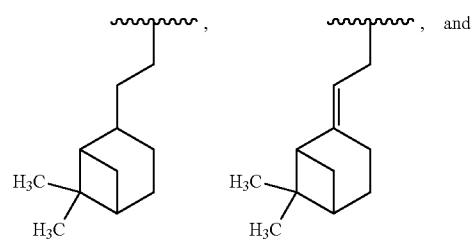

-continued

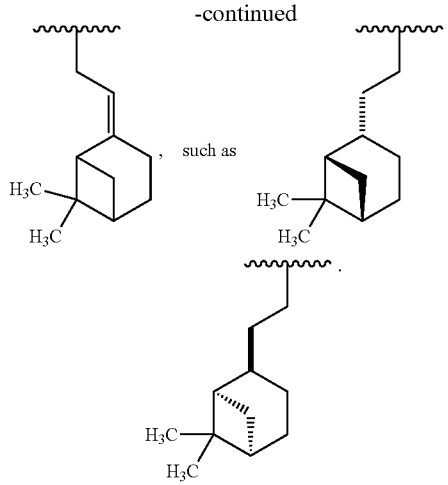

In another embodiment, Z—R¹ is selected from

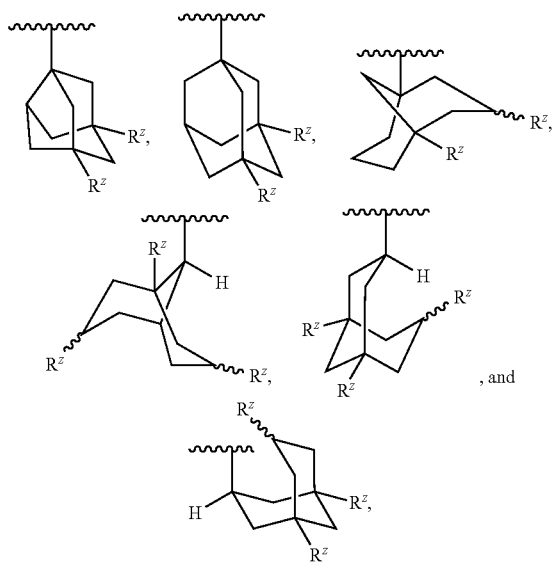

wherein each $R^z$ is independently —H or —($C_1$-$C_6$)alkyl, for example, each $R^z$ is independently —H, methyl, ethyl, propyl, or butyl including all structural isomers of any of these, particularly methyl or ethyl.

In certain embodiments, —Z—R¹ is selected from:

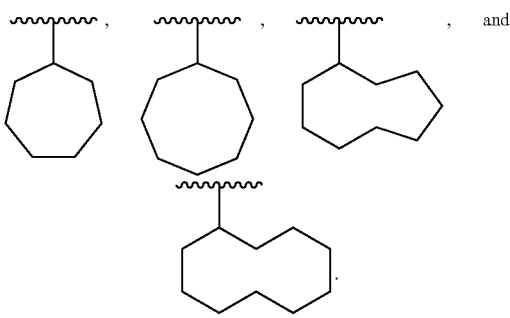

In another embodiment, —Z—R¹ is selected from:

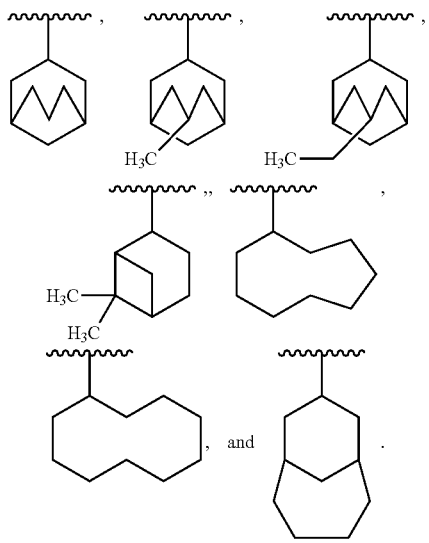

For example, in certain embodiments, —Z—R¹ is selected from:

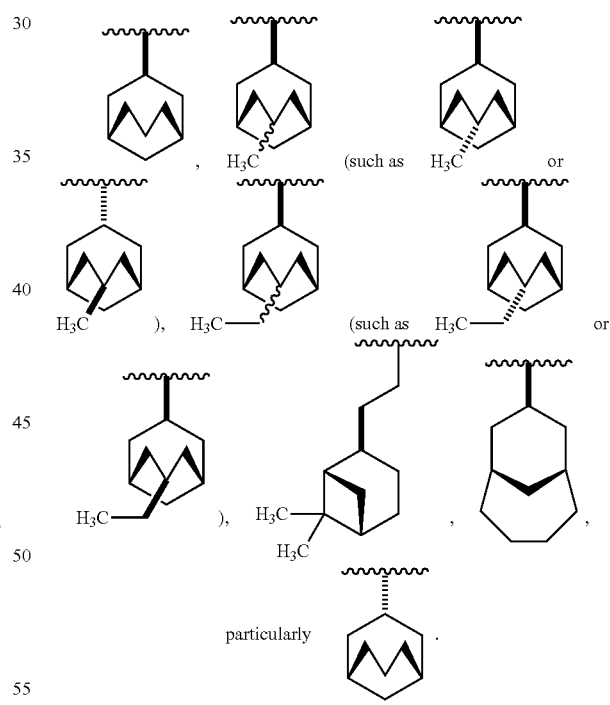

In another embodiment, —Z—R¹ is selected from:

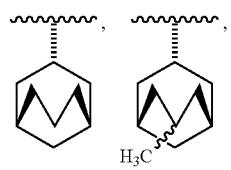

-continued

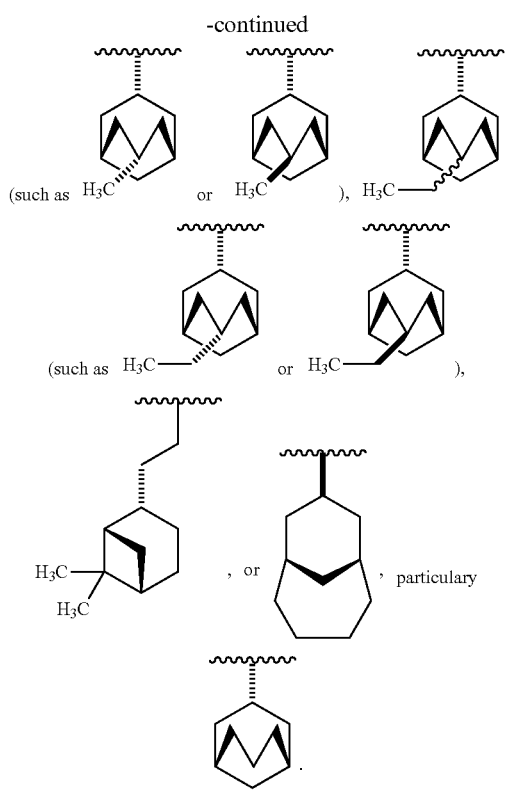

In another embodiment —Z—R¹ is selected from:

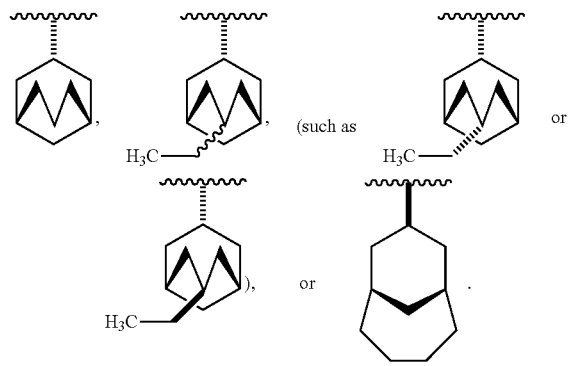

In another embodiment, —Z—R¹ is:

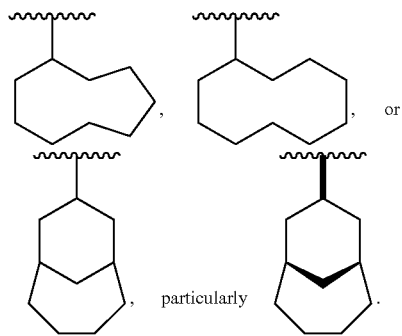

In another embodiment, —Z—R¹ is:

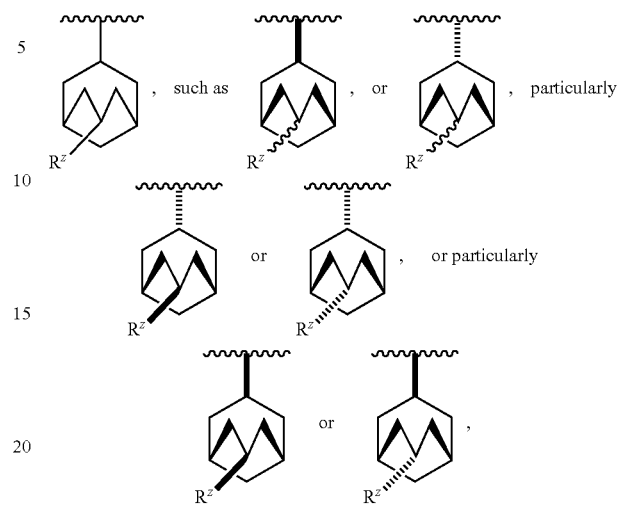

wherein $R^z$ is —H or —$(C_1$-$C_6)$alkyl, such as methyl, ethyl, propyl, or butyl including all structural isomers of any of these, particularly methyl or ethyl.

In some embodiments, one or more occurrences of d are 0. In other embodiments, one or more occurrences of d are 1, 2, 3, or 4. For example, in some embodiments, one or more occurrences of d are 1; in some embodiments, one or more occurrences of d are 2; in some embodiments, one or more occurrences of d are 3; and in some embodiments, one or more occurrences of d are 4.

In some embodiments, one or more occurrences of e are 2. In other embodiments, one or more occurrences of e are 3. In other embodiments, one or more occurrences of e are 4.

In some embodiments, one or more occurrences of p are 1. In other embodiments, one or more occurrences of p are 2.

In certain embodiments, the Quinazolin-4(3H)-one-Type Piperidine Compound has the formula:

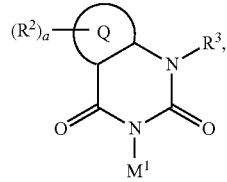

such as

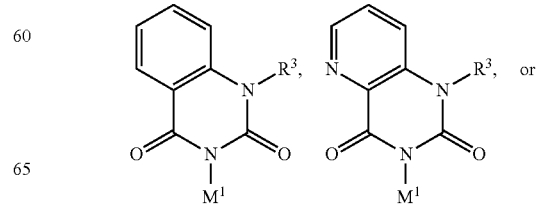

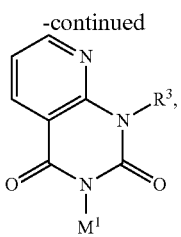

or a pharmaceutically acceptable salt or solvate thereof, wherein $M^1$, $R^2$, $R^3$, and a are as defined herein.

In certain embodiments, the Quinazolin-4(3H)-one-Type Piperidine Compound has the formula:

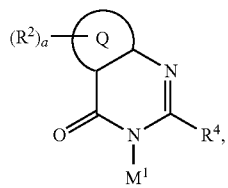

such as

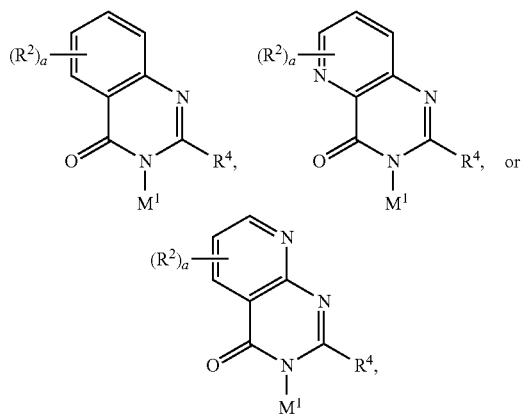

for example

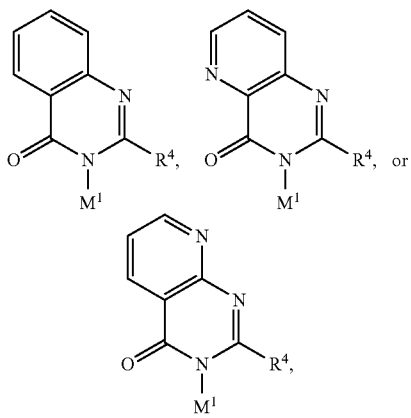

or a pharmaceutically acceptable salt or solvate thereof, wherein $M^1$, $R^2$, $R^4$, and a are as defined herein. In certain embodiments a is 0, 1, 2, or 3; such as 0, 1, or 2; such as 0 or 1. In some embodiments, a is 0. In certain embodiments, a is 1. In certain embodiments, a is 2. In certain embodiments, a is 3. In certain embodiments, a is 4.

In certain embodiments, $M^1$ is selected from

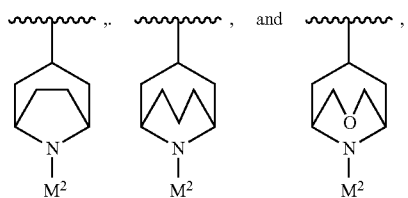

wherein the piperidine nitrogen is optionally in pharmaceutically acceptable salt form. For example, in some embodiments, $M^1$ is selected from

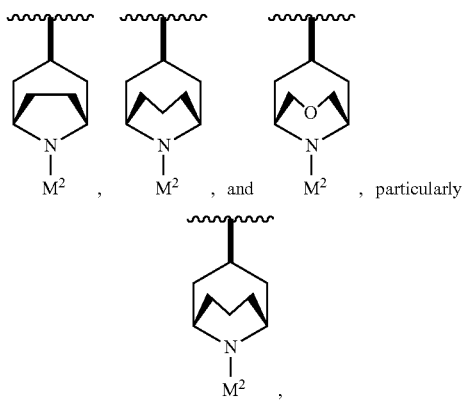

wherein the piperidine nitrogen is optionally in pharmaceutically acceptable salt form. In other embodiments, $M^1$ is selected from

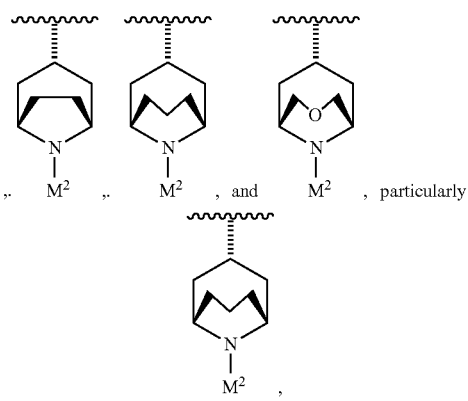

wherein the piperidine nitrogen is optionally in pharmaceutically acceptable salt form. In the above embodiments, $M^2$ is selected from

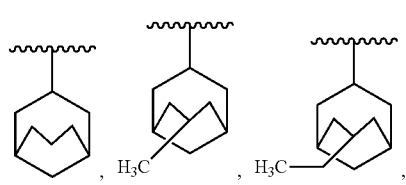

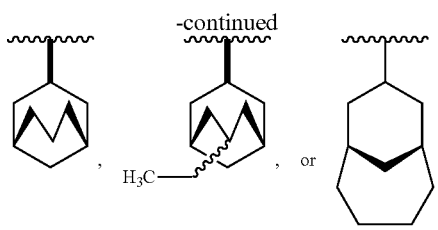

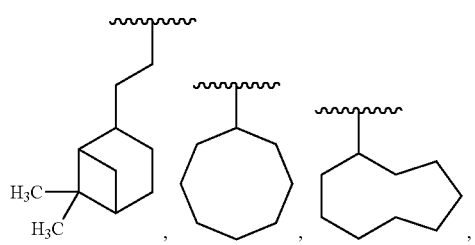

In other embodiments, M² is selected from

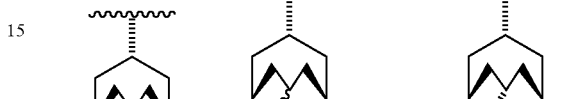

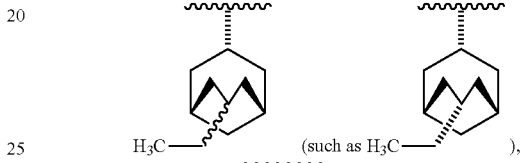

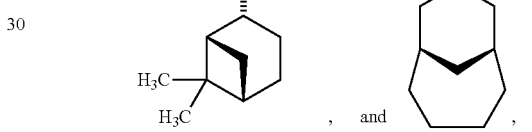

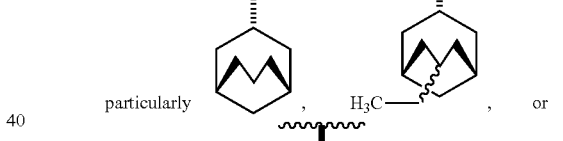

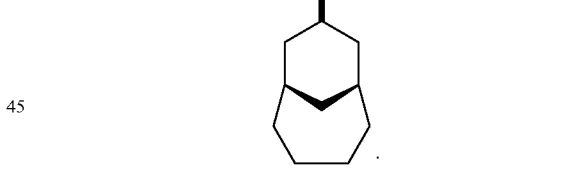

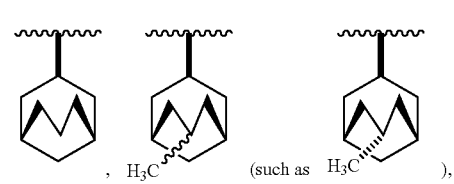

For example, in some embodiments, M² is selected from

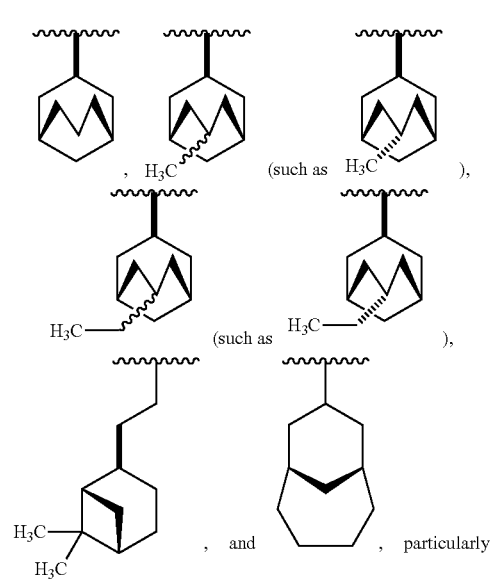

In certain embodiments, the Quinazolin-4(3H)-one-Type Piperidine Compound includes a carboxylic acid group. For example, in some embodiments a carboxylic acid group is at the terminal end of the $R^3$ group. In other embodiments, a carboxylic acid group is at the terminal end of the $R^4$ group. In some embodiments, a carboxylic acid group is at the terminal end of both the $R^3$ and $R^4$ groups.

In some embodiments, the Quinazolin-4(3H)-one-Type Piperidine Compound includes an ester group or an amide group or both. For example, in some embodiments an ester group or an amide group is at the terminal end of the $R^3$ group. In other embodiments, an ester group or an amide group is at the terminal end of the $R^4$ group. In some embodiments, an ester group or an amide group is at the terminal end of both the $R^3$ and $R^4$ groups. In certain embodiments, the Quinazolin-4(3H)-one-Type Piperidine Compound includes an ester group or an amide group or both and is a prodrug that is converted in vivo to an active species, such as a carboxylic acid.

In some embodiments, the Quinazolin-4(3H)-one-Type Piperidine Compound is selected from:
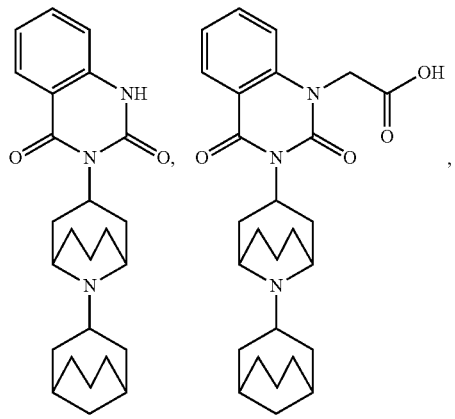
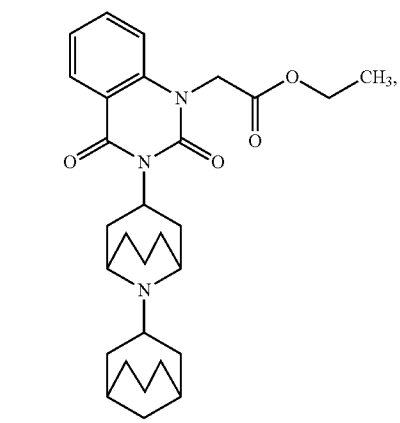
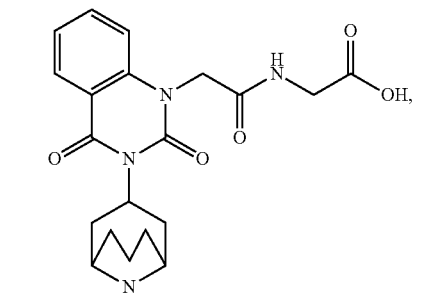
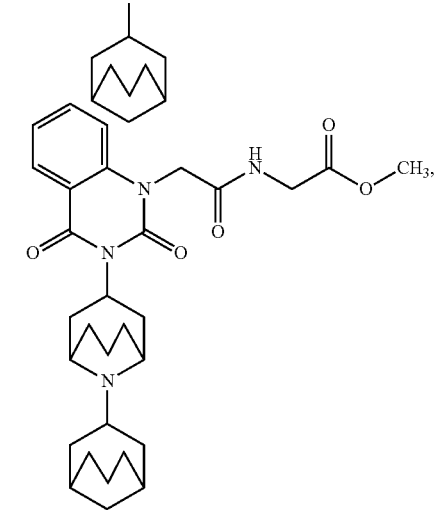
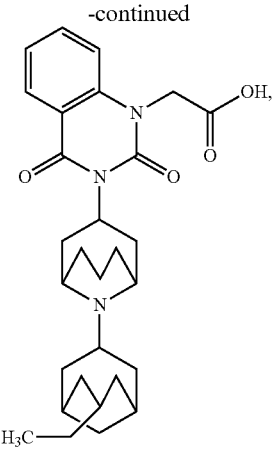
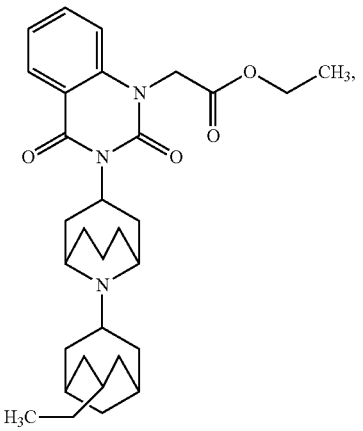
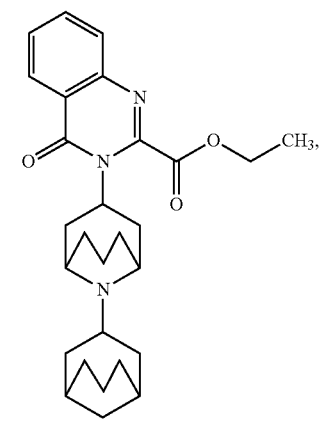

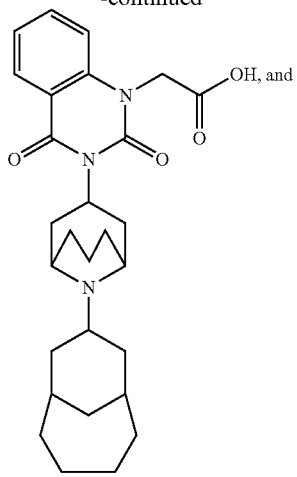
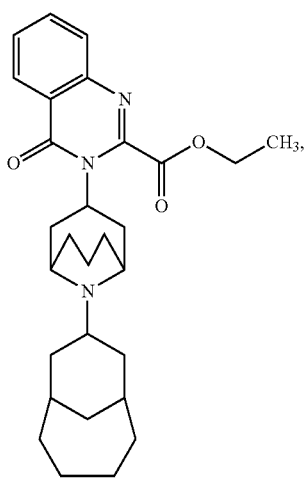 [SMILES: CCOC(=O)c1nc2ccccc2c(=O)n1C1CC2CCCC(C1)N2C1CC2CCCCC(C2)C1]
and the pharmaceutically acceptable salts and solvates thereof.
For example, in certain embodiments, the Quinazolin-4(3H)-one-Type Piperidine Compound is selected from:
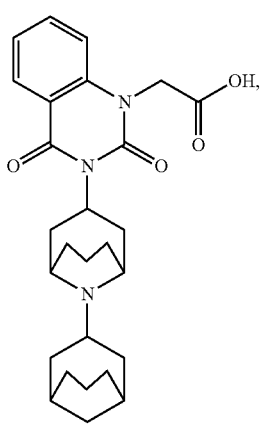
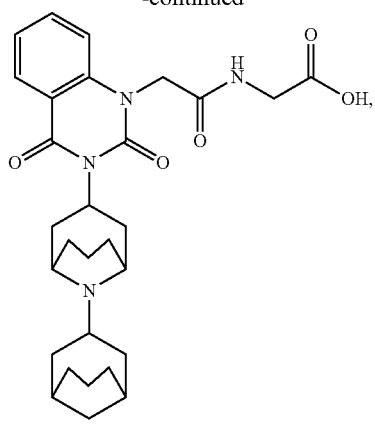
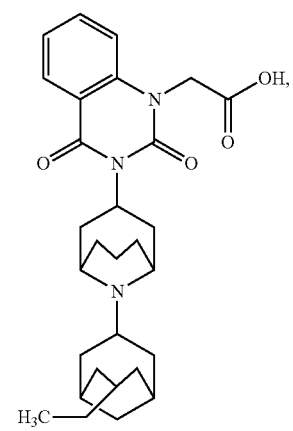
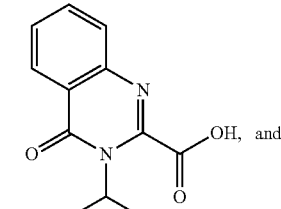
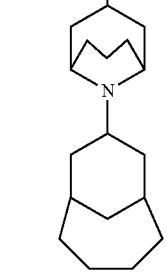
and the pharmaceutically acceptable salts and solvates thereof.

In other embodiments, the Quinazolin-4(3H)-one-Type Piperidine Compound is selected from:
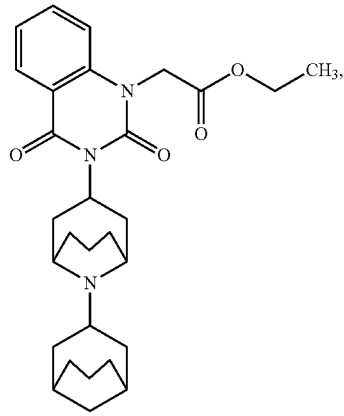
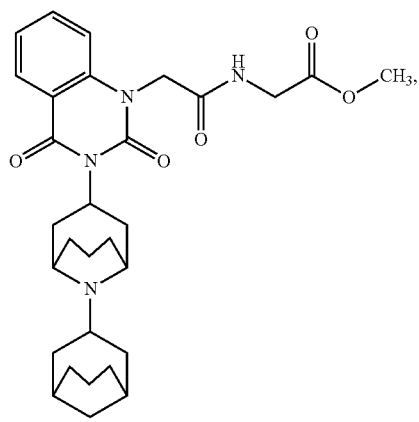
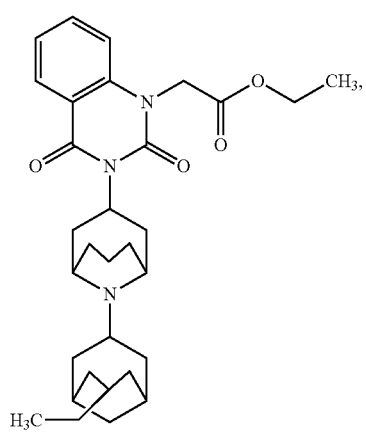
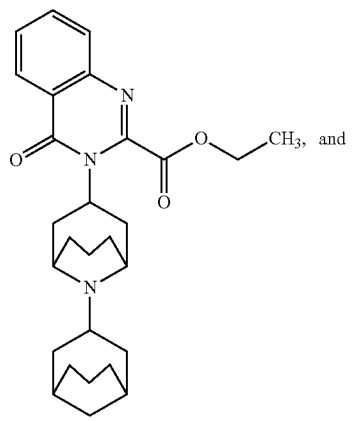
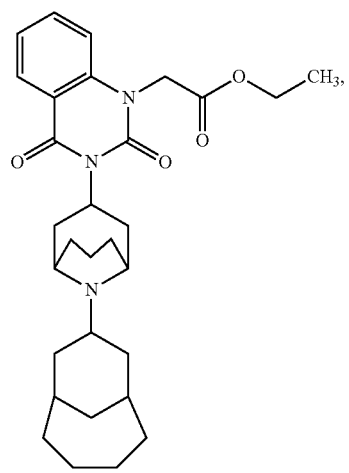
and the pharmaceutically acceptable salts and solvates thereof.
In some embodiments, the Quinazolin-4(3H)-one-Type Piperidine Compound is selected from:
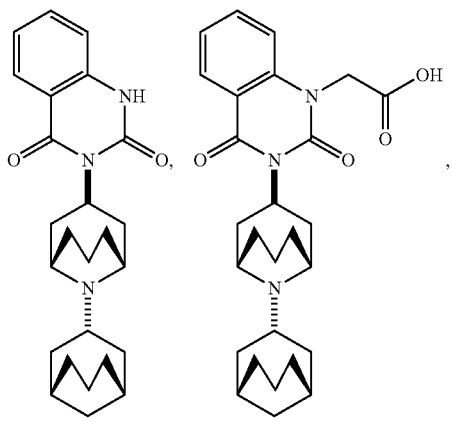

55
-continued
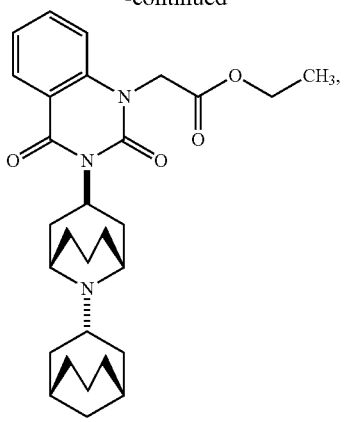
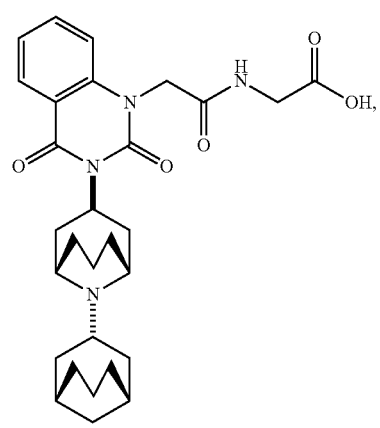
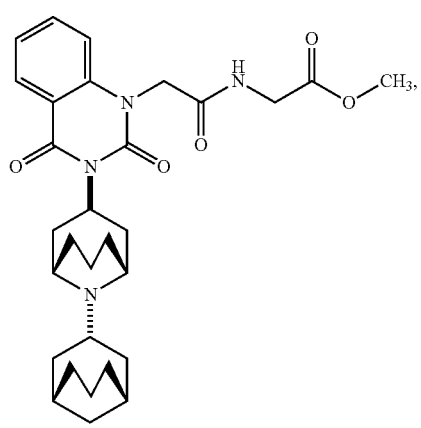
56
-continued
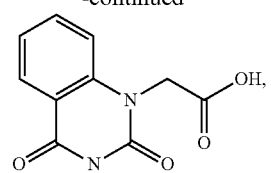
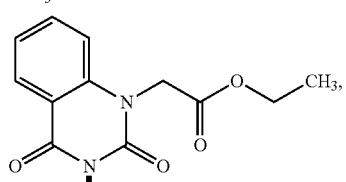
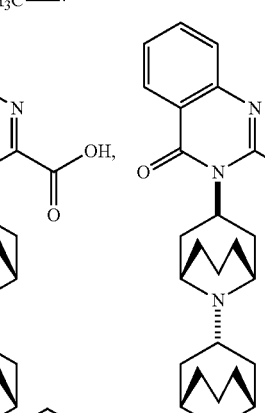
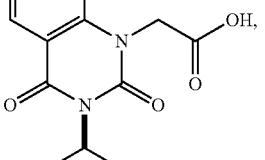 

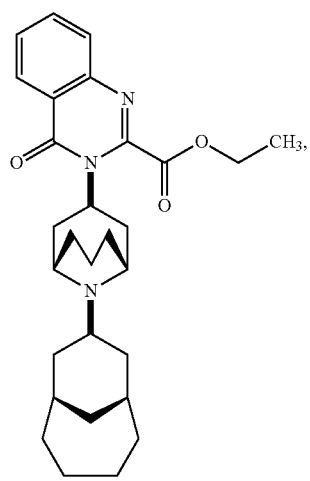 [SMILES: CCOC(=O)c1nc2ccccc2c(=O)n1[C@H]1C[C@H]2CCC[C@@H](C1)N2[C@@H]1C[C@@H]2CCCC[C@@H](C2)C1]
and the pharmaceutically acceptable salts and solvates thereof.
For example, in certain embodiments, the Quinazolin-4 (3H)-one-Type Piperidine Compound is selected from:
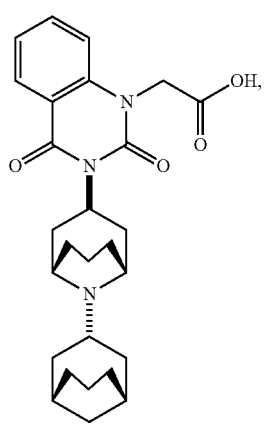
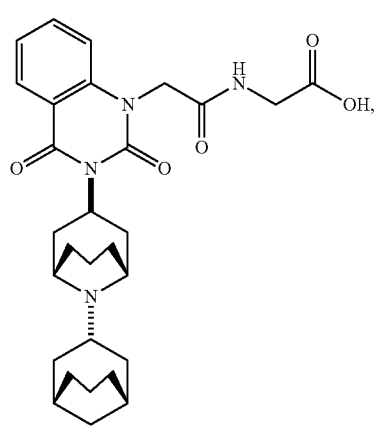
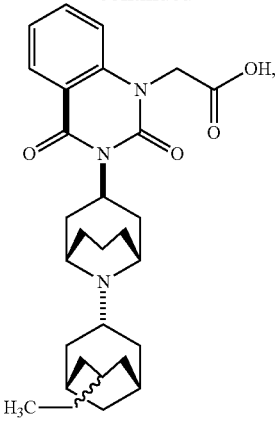
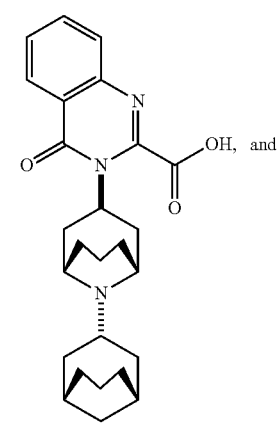
and the pharmaceutically acceptable salts and solvates thereof.

In other embodiments, the Quinazolin-4(3H)-one-Type Piperidine Compound is selected from:

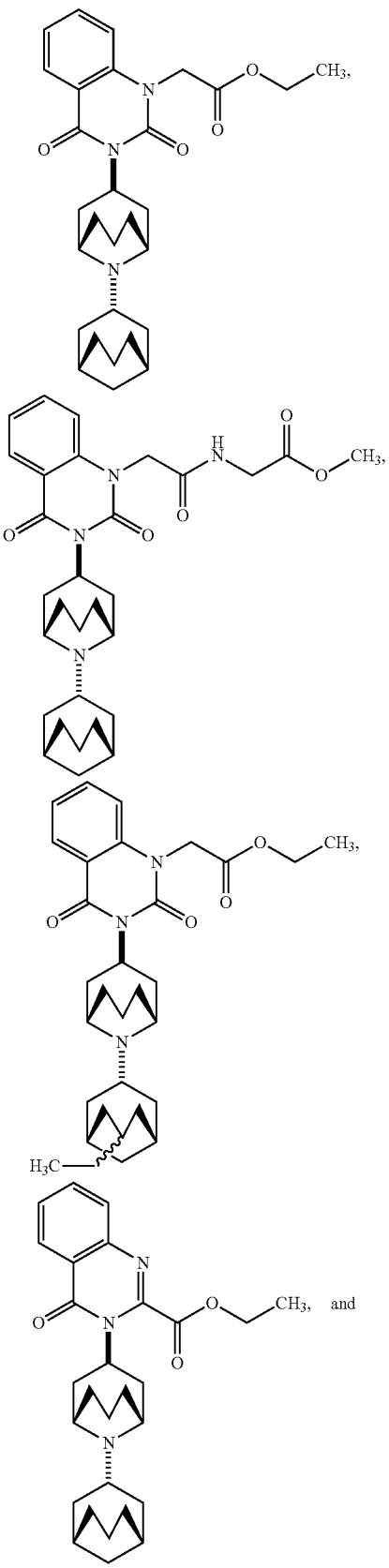

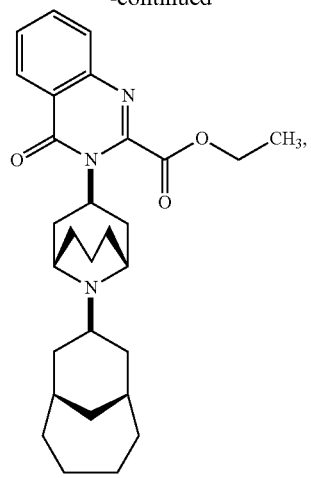

and the pharmaceutically acceptable salts and solvates thereof.

In another embodiment, the Quinazolin-4(3H)-one-Type Piperidine Compound is in the form of a pharmaceutically acceptable salt. In some embodiments, the pharmaceutically acceptable salt is a halide salt, such as a hydrochloride or hydrobromide salt, particularly a hydrochloride salt. In another embodiment, the pharmaceutically acceptable salt is a sodium salt. In another embodiment, the pharmaceutically acceptable salt is a potassium salt. In another embodiment, the pharmaceutically acceptable salt is apara-toluenesulfonic acid salt. In certain embodiments, the pharmaceutically acceptable salt includes two or more salt groups, such as two halide salt groups, and/or a combination of salt types, such as a chloride salt group and a bromide salt group. For example, in some embodiments, the pharmaceutically acceptable salt includes both a base addition salt group and an acid addition salt group. In certain embodiments, the pharmaceutically acceptable salt is a zwitterion.

In some embodiments, the Quinazolin-4(3H)-one-Type Piperidine Compound is a compound of Formula (Ia):

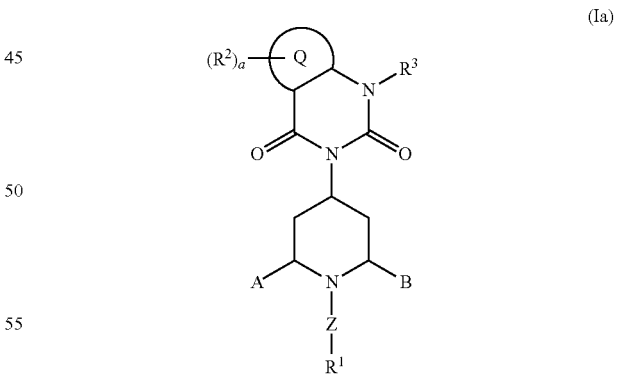

(Ia)

or a pharmaceutically acceptable salt or solvate thereof, wherein $R^1$, $R^2$, $R^3$, Q, Z, A, B, and a are as defined herein. In some of such embodiments, Q is fused benzo. In other such embodiments, Q is fused pyridyl, for example, wherein the pyridyl nitrogen in the Q ring is in a 1,3-relationship with the amide carbonyl carbon and in a 1,5-relationship with the urea carbonyl carbon, or wherein the pyridyl nitrogen in the Q ring is in a 1,3-relationship with the nitrogen directly bonded to $R^3$.

In certain embodiments, the Quinazolin-4(3H)-one-Type Piperidine Compound is a compound of Formula (Ia'), Formula (Ia''), or Formula (Ia'''):

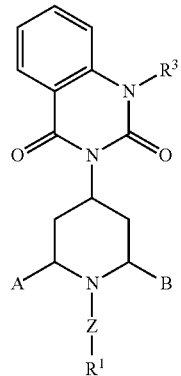
(Ia')

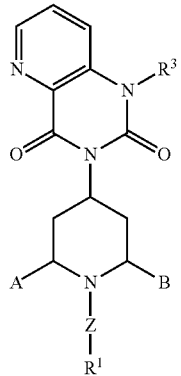
(Ia'')

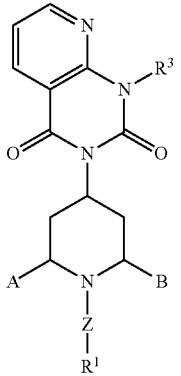
(Ia''')

or a pharmaceutically acceptable salt or solvate thereof, wherein $R^1$, $R^3$, Z, A, and B are as defined herein.

In other embodiments, the Quinazolin-4(3H)-one-Type Piperidine Compound is a compound of Formula (Ib):

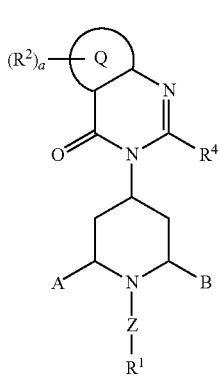
(Ib)

or a pharmaceutically acceptable salt or solvate thereof, wherein $R^1$, $R^2$, $R^4$, Q, Z, A, B, and a are as defined herein. In some of such embodiments, Q is fused benzo. In other such embodiments, Q is fused pyridyl, for example, wherein the pyridyl nitrogen in the Q ring is in a 1,3-relationship with the amide carbonyl carbon, or wherein the pyridyl nitrogen in the Q ring is in a 1,4-relationship with the carbon directly bonded to $R^4$.

In certain embodiments, the Quinazolin-4(3H)-one-Type Piperidine Compound is a compound of Formula (Ib'), Formula (Ib''), or Formula (Ib'''):

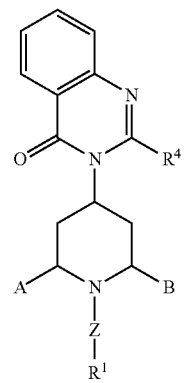
(Ib')

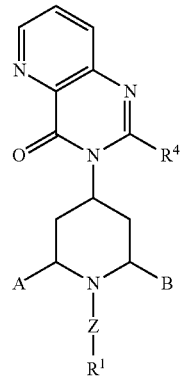
(Ib'')

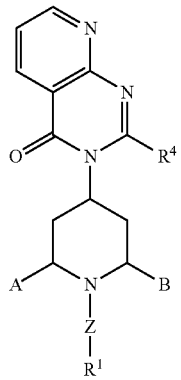
(Ib''')

or a pharmaceutically acceptable salt or solvate thereof, wherein $R^1$, $R^4$, Z, A, and B are as defined herein.

4.3 Tabulated Embodiments of Quinazolin-4(3H)-One-Type Piperidine Compounds
In some embodiments, the Quinazolin-4(3H)-one-Type Piperidine Compound has a structure according to one of the formulas of Table 1, or a pharmaceutically acceptable salt or solvate thereof, wherein $R^1$, $R^2$, $R^3$, Z, and a are as defined herein:
TABLE 1
| Formula | Compound |
|---|---|
| Ia-A | 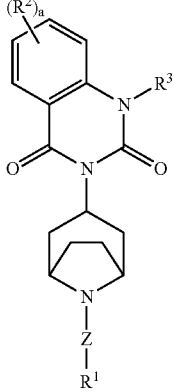 |
| Ia-B | 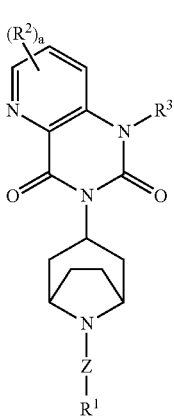 |
| Ia-C | 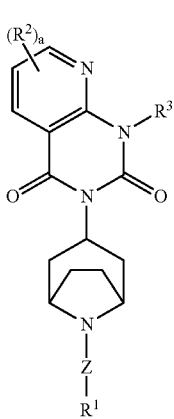 |
| Ia-D† | 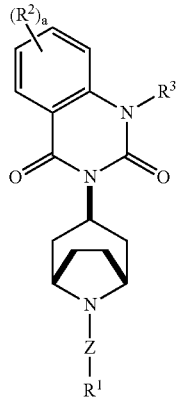 |
| Ia-E† | 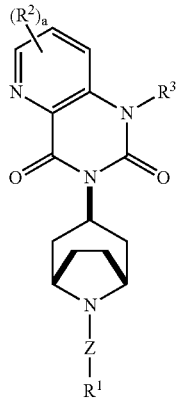 |
| Ia-F† | 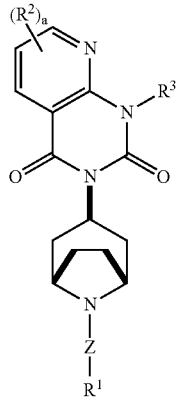 |
| Ia-G‡ | 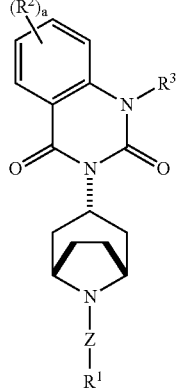 |

TABLE 1-continued

| Formula | Compound |
|---|---|
| Ia-H‡ | (structure) |
| Ia-I‡ | (structure) |
| Ia-J | (structure) |
| Ia-K | (structure) |
| Ia-L | (structure) |
| Ia-M† | (structure) |
| Ia-N† | (structure) |

TABLE 1-continued
| Formula | Compound |
|---|---|
| Ia-O† | 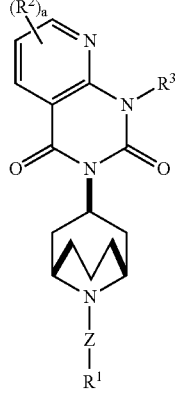 |
| Ia-P‡ | 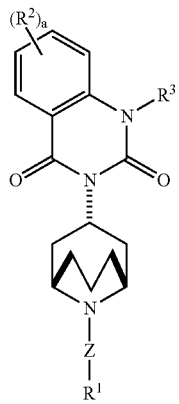 |
| Ia-Q‡ |  |
| Ia-R‡ | 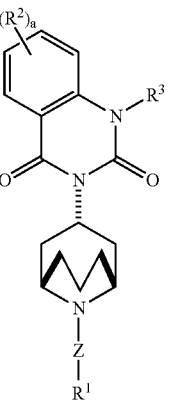 |
| Ia-S | 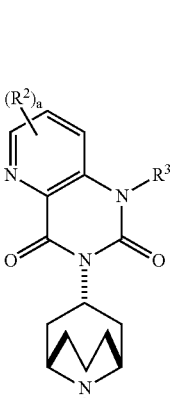 |
| Ia-T | 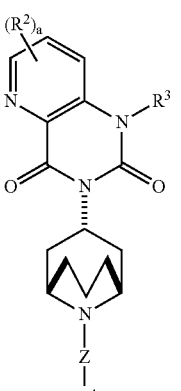 |
| Ia-U | 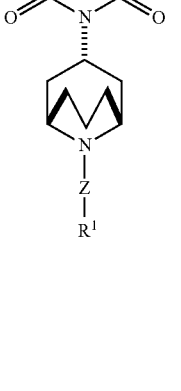 |

TABLE 1-continued

| Formula | Compound |
|---|---|
| Ia-V[†] | 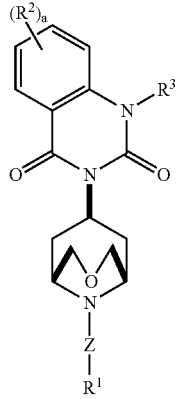 |
| Ia-W[†] | 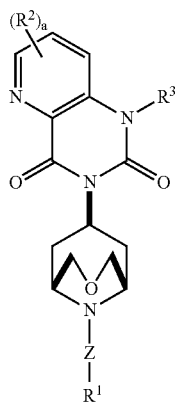 |
| Ia-X[†] | 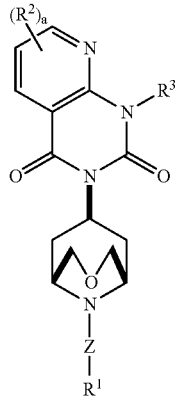 |

TABLE 1-continued

| Formula | Compound |
|---|---|
| Ia-Y[‡] | 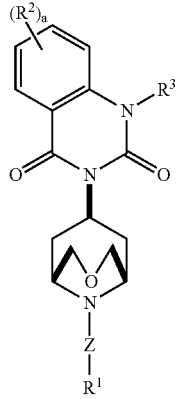 |
| Ia-Z[‡] | 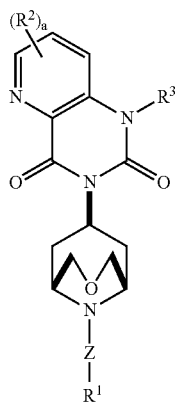 |
| Ia-AA[‡] | 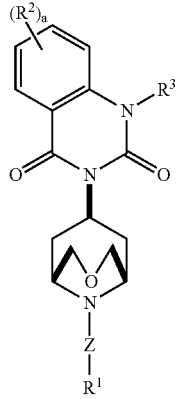 |

[†]indicates the 6-membered, nitrogen-containing ring that is fused to the Q ring (i.e., fused to the benzo or pyridyl ring) is in the endo-configuration with respect to the A—B bridge (i.e., the ethylenyl, propylenyl, or —CH$_2$—O—CH$_2$— bridge).

[‡]indicates the 6-membered, nitrogen-containing ring that is fused to the Q ring (i.e., fused to the benzo or pyridyl ring) is in the exo-configuration with respect to the A—B bridge (i.e., the ethylenyl, propylenyl, or —CH$_2$—O—CH$_2$— bridge).

In some embodiments, the Quinazolin-4(3H)-one-Type Piperidine Compound has a structure according to one of the formulas of Table 2, or a pharmaceutically acceptable salt or solvate thereof, where $R^1$, $R^2$, $R^4$, Z, and a are as defined herein:

TABLE 2

| Formula | Compound |
|---|---|
| Ib-A | (structure) |
| Ib-B | (structure) |
| Ib-C | (structure) |
| Ib-D† | (structure) |

TABLE 2-continued

| Formula | Compound |
|---|---|
| Ib-E† | (structure) |
| Ib-F† | (structure) |
| Ib-G‡ | (structure) |

TABLE 2-continued

| Formula | Compound |
| --- | --- |
| Ib-H‡ | (structure) |
| Ib-I‡ | (structure) |
| Ib-J | (structure) |
| Ib-K | (structure) |
| Ib-L | (structure) |
| Ib-M† | (structure) |
| Ib-N† | (structure) |

TABLE 2-continued
| Formula | Compound |
|---|---|
| Ib-O† | 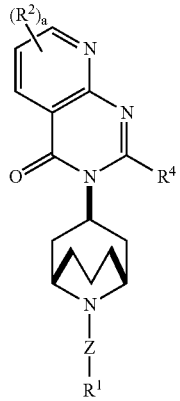 |
| Ib-P‡ | 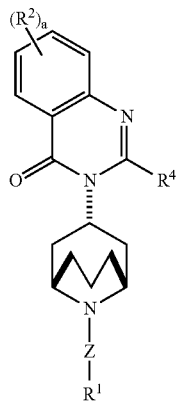 |
| Ib-Q‡ | 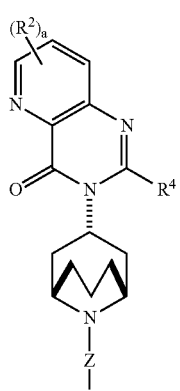 |
| Ib-R‡ | 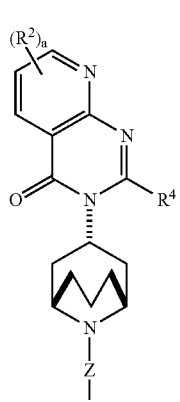 |
| Ib-S | 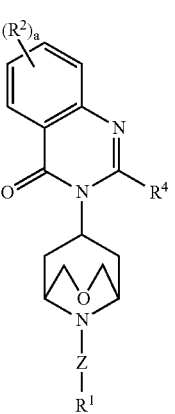 |
| Ib-T | 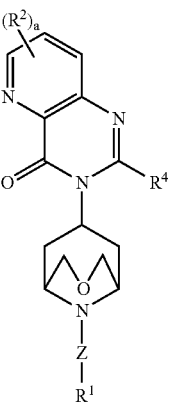 |
| Ib-U | 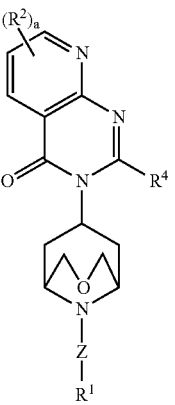 |

TABLE 2-continued

| Formula | Compound |
|---|---|
| Ib-V[†] | 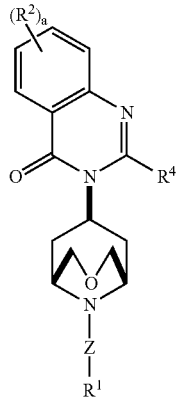 |
| Ib-W[†] | 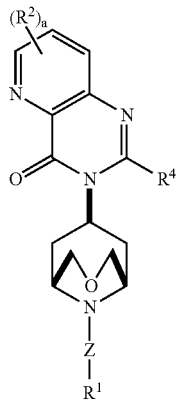 |
| Ib-X[†] | 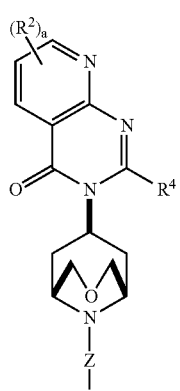 |
| Ib-Y[‡] | 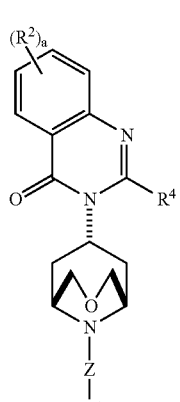 |
| Ib-Z[‡] | 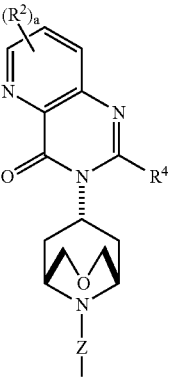 |
| Ib-AA[‡] | 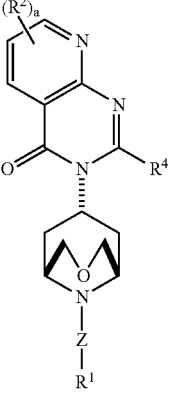 |

[†]indicates the 6-membered, nitrogen-containing ring that is fused to the Q ring (i.e., fused to the benzo or pyridyl ring) is in the endo-configuration with respect to the A—B bridge (i.e., the ethylenyl, propylenyl, or —CH$_2$—O—CH$_2$— bridge).

[‡]indicates the 6-membered, nitrogen-containing ring that is fused to the Q ring (i.e., fused to the benzo or pyridyl ring) is in the exo-configuration with respect to the A—B bridge (i.e., the ethylenyl, propylenyl, or —CH$_2$—O—CH$_2$— bridge).

Illustrative Compounds of Formula (I) are listed below in Tables 3-4 (including their Legends).

TABLE 3

Legend

Series A: 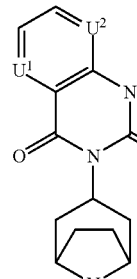 (a) 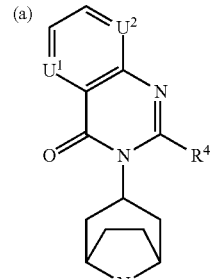 (b)

TABLE 3-continued
Legend
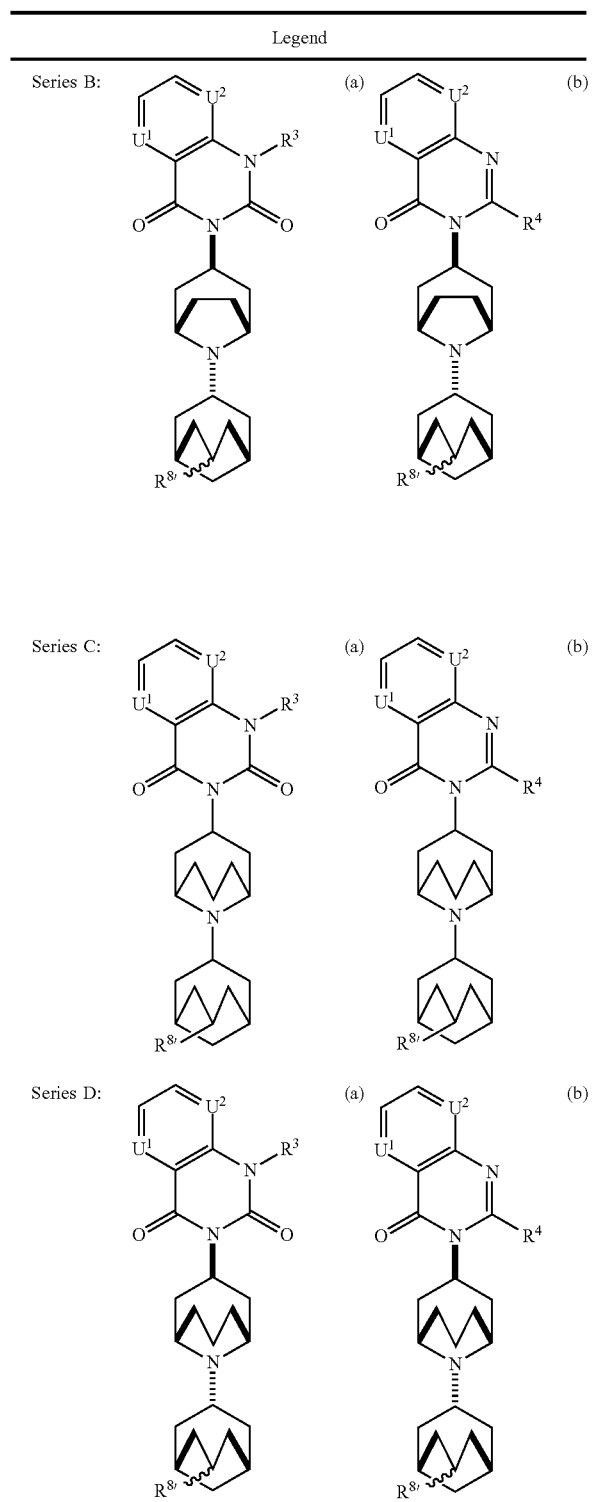
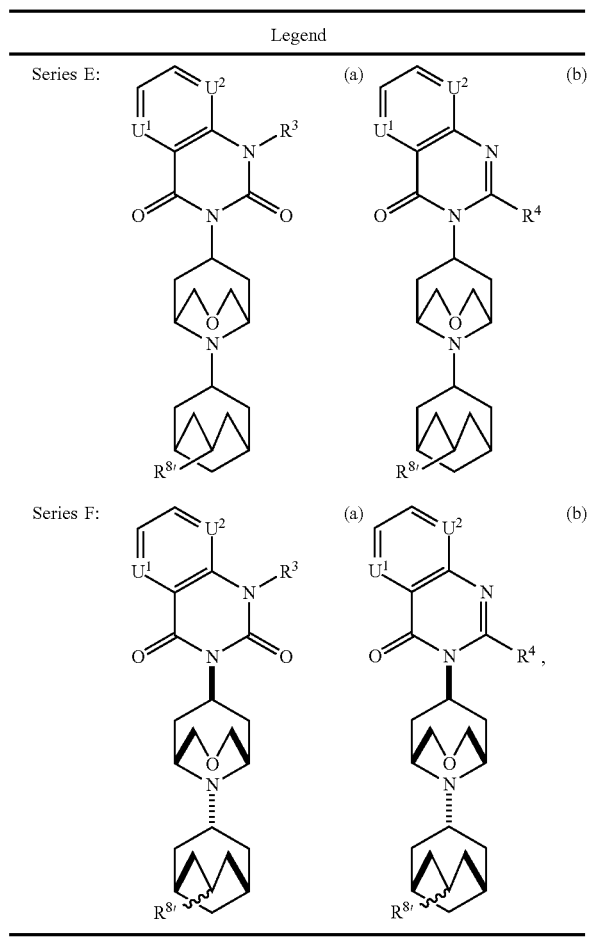
and the pharmaceutically acceptable salts and solvates thereof, where X refers to a compound of a formula of Series A, B, C, D, E, or F. For example, Compound D3a is:
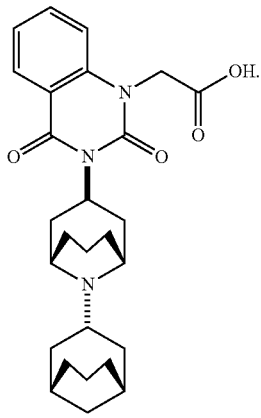
TABLE 3
| Compound | U¹ | U² | R³ (for a series) or R⁴ (for b series) | R⁸' |
|---|---|---|---|---|
| X1 a or b | C | C | H | H |
| X2 a or b | C | C | —C(=O)OH | H |
| X3 a or b | C | C | —CH₂—C(=O)OH | H |

TABLE 3-continued

| Compound | U$^1$ | U$^2$ | R$^3$ (for a series) or R$^4$ (for b series) | R$^{8'}$ |
|---|---|---|---|---|
| X4 a or b | C | C | —(CH$_2$)$_2$—C(=O)OH | H |
| X5 a or b | C | C | —(CH$_2$)$_3$—C(=O)OH | H |
| X6 a or b | C | C | —(CH$_2$)$_4$—C(=O)OH | H |
| X7 a or b | C | C | —C(=O)O—CH$_3$ | H |
| X8 a or b | C | C | —CH$_2$—C(=O)O—CH$_3$ | H |
| X9 a or b | C | C | —(CH$_2$)$_2$—C(=O)O—CH$_3$ | H |
| X10 a or b | C | C | —(CH$_2$)$_3$—C(=O)O—CH$_3$ | H |
| X11 a or b | C | C | —(CH$_2$)$_4$—C(=O)O—CH$_3$ | H |
| X12 a or b | C | C | —C(=O)O—CH$_2$—CH$_3$ | H |
| X13 a or b | C | C | —CH$_2$—C(=O)O—CH$_2$—CH$_3$ | H |
| X14 a or b | C | C | —(CH$_2$)$_2$—C(=O)O—CH$_2$—CH$_3$ | H |
| X15 a or b | C | C | —(CH$_2$)$_3$—C(=O)O—CH$_2$—CH$_3$ | H |
| X16 a or b | C | C | —(CH$_2$)$_4$—C(=O)O—CH$_2$—CH$_3$ | H |
| X17 a or b | C | C | —C(=O)NH$_2$ | H |
| X18 a or b | C | C | —CH$_2$—C(=O)NH$_2$ | H |
| X19 a or b | C | C | —(CH$_2$)$_2$—C(=O)NH$_2$ | H |
| X20 a or b | C | C | —(CH$_2$)$_3$—C(=O)NH$_2$ | H |
| X21 a or b | C | C | —(CH$_2$)$_4$—C(=O)NH$_2$ | H |
| X22 a or b | C | C | —C(=O)N(H)—CH$_3$ | H |
| X23 a or b | C | C | —CH$_2$—C(=O)N(H)—CH$_3$ | H |
| X24 a or b | C | C | —(CH$_2$)$_2$—C(=O)N(H)—CH$_3$ | H |
| X25 a or b | C | C | —(CH$_2$)$_3$—C(=O)N(H)—CH$_3$ | H |
| X26 a or b | C | C | —(CH$_2$)$_4$—C(=O)N(H)—CH$_3$ | H |
| X27 a or b | C | C | —C(=O)N(H)—CH$_2$—C(=O)OH | H |
| X28 a or b | C | C | —CH$_2$—C(=O)N(H)—CH$_2$—C(=O)OH | H |
| X29 a or b | C | C | —(CH$_2$)$_2$—C(=O)N(H)—CH$_2$—C(=O)OH | H |
| X30 a or b | C | C | —(CH$_2$)$_3$—C(=O)N(H)—CH$_2$—C(=O)OH | H |
| X31 a or b | C | C | —(CH$_2$)$_4$—C(=O)N(H)—CH$_2$—C(=O)OH | H |
| X32 a or b | C | C | —C(=O)N(H)—(CH$_2$)$_2$—C(=O)OH | H |
| X33 a or b | C | C | —CH$_2$—C(=O)N(H)—(CH$_2$)$_2$—C(=O)OH | H |
| X34 a or b | C | C | —(CH$_2$)$_2$—C(=O)N(H)—(CH$_2$)$_2$—C(=O)OH | H |
| X35 a or b | C | C | —(CH$_2$)$_3$—C(=O)N(H)—(CH$_2$)$_2$—C(=O)OH | H |
| X36 a or b | C | C | —(CH$_2$)$_4$—C(=O)N(H)—(CH$_2$)$_2$—C(=O)OH | H |
| X37 a or b | C | C | —C(=O)N(H)—(CH$_2$)$_3$—C(=O)OH | H |
| X38 a or b | C | C | —CH$_2$—C(=O)N(H)—(CH$_2$)$_3$—C(=O)OH | H |
| X39 a or b | C | C | —(CH$_2$)$_2$—C(=O)N(H)—(CH$_2$)$_3$—C(=O)OH | H |
| X40 a or b | C | C | —(CH$_2$)$_3$—C(=O)N(H)—(CH$_2$)$_3$—C(=O)OH | H |
| X41 a or b | C | C | —(CH$_2$)$_4$—C(=O)N(H)—(CH$_2$)$_3$—C(=O)OH | H |
| X42 a or b | C | C | —C(=O)N(H)—CH$_2$—C(=O)O—CH$_3$ | H |
| X43 a or b | C | C | —CH$_2$—C(=O)N(H)—CH$_2$—C(=O)O—CH$_3$ | H |
| X44 a or b | C | C | —(CH$_2$)$_2$—C(=O)N(H)—CH$_2$—C(=O)O—CH$_3$ | H |
| X45 a or b | C | C | —(CH$_2$)$_3$—C(=O)N(H)—CH$_2$—C(=O)O—CH$_3$ | H |
| X46 a or b | C | C | —(CH$_2$)$_4$—C(=O)N(H)—CH$_2$—C(=O)O—CH$_3$ | H |
| X47 a or b | C | C | —C(=O)N(H)—(CH$_2$)$_2$—C(=O)O—CH$_3$ | H |
| X48 a or b | C | C | —CH$_2$—C(=O)N(H)—(CH$_2$)$_2$—C(=O)O—CH$_3$ | H |
| X49 a or b | C | C | —(CH$_2$)$_2$—C(=O)N(H)—(CH$_2$)$_2$—C(=O)O—CH$_3$ | H |
| X50 a or b | C | C | —(CH$_2$)$_3$—C(=O)N(H)—(CH$_2$)$_2$—C(=O)O—CH$_3$ | H |
| X51 a or b | C | C | —(CH$_2$)$_4$—C(=O)N(H)—(CH$_2$)$_2$—C(=O)O—CH$_3$ | H |
| X52 a or b | C | C | —C(=O)N(H)—(CH$_2$)$_3$—C(=O)O—CH$_3$ | H |
| X53 a or b | C | C | —CH$_2$—C(=O)N(H)—(CH$_2$)$_3$—C(=O)O—CH$_3$ | H |
| X54 a or b | C | C | —(CH$_2$)$_2$—C(=O)N(H)—(CH$_2$)$_3$—C(=O)O—CH$_3$ | H |
| X55 a or b | C | C | —(CH$_2$)$_3$—C(=O)N(H)—(CH$_2$)$_3$—C(=O)O—CH$_3$ | H |
| X56 a or b | C | C | —(CH$_2$)$_4$—C(=O)N(H)—(CH$_2$)$_3$—C(=O)O—CH$_3$ | H |
| X57 a or b | C | C | —C(=O)N(H)—CH$_2$—C(=O)O—CH$_2$—CH$_3$ | H |
| X58 a or b | C | C | —CH$_2$—C(=O)N(H)—CH$_2$—C(=O)O—CH$_2$—CH$_3$ | H |
| X59 a or b | C | C | —(CH$_2$)$_2$—C(=O)N(H)—CH$_2$—C(=O)O—CH$_2$—CH$_3$ | H |
| X60 a or b | C | C | —(CH$_2$)$_3$—C(=O)N(H)—CH$_2$—C(=O)O—CH$_2$—CH$_3$ | H |
| X61 a or b | C | C | —(CH$_2$)$_4$—C(=O)N(H)—CH$_2$—C(=O)O—CH$_2$—CH$_3$ | H |
| X62 a or b | C | C | —C(=O)N(H)—(CH$_2$)$_2$—C(=O)O—CH$_2$—CH$_3$ | H |
| X63 a or b | C | C | —CH$_2$—C(=O)N(H)—(CH$_2$)$_2$—C(=O)O—CH$_2$—CH$_3$ | H |
| X64 a or b | C | C | —(CH$_2$)$_2$—C(=O)N(H)—(CH$_2$)$_2$—C(=O)O—CH$_2$—CH$_3$ | H |
| X65 a or b | C | C | —(CH$_2$)$_3$—C(=O)N(H)—(CH$_2$)$_2$—C(=O)O—CH$_2$—CH$_3$ | H |
| X66 a or b | C | C | —(CH$_2$)$_4$—C(=O)N(H)—(CH$_2$)$_2$—C(=O)O—CH$_2$—CH$_3$ | H |
| X67 a or b | C | C | —C(=O)N(H)—(CH$_2$)$_3$—C(=O)O—CH$_2$—CH$_3$ | H |
| X68 a or b | C | C | —CH$_2$—C(=O)N(H)—(CH$_2$)$_3$—C(=O)O—CH$_2$—CH$_3$ | H |
| X69 a or b | C | C | —(CH$_2$)$_2$—C(=O)N(H)—(CH$_2$)$_3$—C(=O)O—CH$_2$—CH$_3$ | H |
| X70 a or b | C | C | —(CH$_2$)$_3$—C(=O)N(H)—(CH$_2$)$_3$—C(=O)O—CH$_2$—CH$_3$ | H |
| X71 a or b | C | C | —(CH$_2$)$_4$—C(=O)N(H)—(CH$_2$)$_3$—C(=O)O—CH$_2$—CH$_3$ | H |
| X72 a or b | C | C | —C(=O)N(CH$_3$)$_2$ | H |
| X73 a or b | C | C | —CH$_2$—C(=O)N(CH$_3$)$_2$ | H |
| X74 a or b | C | C | —(CH$_2$)$_2$—C(=O)N(CH$_3$)$_2$ | H |
| X75 a or b | C | C | —(CH$_2$)$_3$—C(=O)N(CH$_3$)$_2$ | H |
| X76 a or b | C | C | —(CH$_2$)$_4$—C(=O)N(CH$_3$)$_2$ | H |
| X77 a or b | N | C | H | H |
| X78 a or b | N | C | —C(=O)OH | H |
| X79 a or b | N | C | —CH$_2$—C(=O)OH | H |
| X80 a or b | N | C | —(CH$_2$)$_2$—C(=O)OH | H |
| X81 a or b | N | C | —(CH$_2$)$_3$—C(=O)OH | H |

TABLE 3-continued

| Compound | U¹ | U² | R³ (for a series) or R⁴ (for b series) | R⁸' |
|---|---|---|---|---|
| X82 a or b | N | C | —(CH₂)₄—C(=O)OH | H |
| X83 a or b | N | C | —C(=O)O—CH₃ | H |
| X84 a or b | N | C | —CH₂—C(=O)O—CH₃ | H |
| X85 a or b | N | C | —(CH₂)₂—C(=O)O—CH₃ | H |
| X86 a or b | N | C | —(CH₂)₃—C(=O)O—CH₃ | H |
| X87 a or b | N | C | —(CH₂)₄—C(=O)O—CH₃ | H |
| X88 a or b | N | C | —C(=O)O—CH₂—CH₃ | H |
| X89 a or b | N | C | —CH₂—C(=O)O—CH₂—CH₃ | H |
| X90 a or b | N | C | —(CH₂)₂—C(=O)O—CH₂—CH₃ | H |
| X91 a or b | N | C | —(CH₂)₃—C(=O)O—CH₂—CH₃ | H |
| X92 a or b | N | C | —(CH₂)₄—C(=O)O—CH₂—CH₃ | H |
| X93 a or b | N | C | —C(=O)NH₂ | H |
| X94 a or b | N | C | —CH₂—C(=O)NH₂ | H |
| X95 a or b | N | C | —(CH₂)₂—C(=O)NH₂ | H |
| X96 a or b | N | C | —(CH₂)₃—C(=O)NH₂ | H |
| X97 a or b | N | C | —(CH₂)₄—C(=O)NH₂ | H |
| X98 a or b | N | C | —C(=O)N(H)—CH₃ | H |
| X99 a or b | N | C | —CH₂—C(=O)N(H)—CH₃ | H |
| X100 a or b | N | C | —(CH₂)₂—C(=O)N(H)—CH₃ | H |
| X101 a or b | N | C | —(CH₂)₃—C(=O)N(H)—CH₃ | H |
| X102 a or b | N | C | —(CH₂)₄—C(=O)N(H)—CH₃ | H |
| X103 a or b | N | C | —C(=O)N(H)—CH₂—C(=O)OH | H |
| X104 a or b | N | C | —CH₂—C(=O)N(H)—CH₂—C(=O)OH | H |
| X105 a or b | N | C | —(CH₂)₂—C(=O)N(H)—CH₂—C(=O)OH | H |
| X106 a or b | N | C | —(CH₂)₃—C(=O)N(H)—CH₂—C(=O)OH | H |
| X107 a or b | N | C | —(CH₂)₄—C(=O)N(H)—CH₂—C(=O)OH | H |
| X108 a or b | N | C | —C(=O)N(H)—(CH₂)₂—C(=O)OH | H |
| X109 a or b | N | C | —CH₂—C(=O)N(H)—(CH₂)₂—C(=O)OH | H |
| X110 a or b | N | C | —(CH₂)₂—C(=O)N(H)—(CH₂)₂—C(=O)OH | H |
| X111 a or b | N | C | —(CH₂)₃—C(=O)N(H)—(CH₂)₂—C(=O)OH | H |
| X112 a or b | N | C | —(CH₂)₄—C(=O)N(H)—(CH₂)₂—C(=O)OH | H |
| X113 a or b | N | C | —C(=O)N(H)—(CH₂)₃—C(=O)OH | H |
| X114 a or b | N | C | —CH₂—C(=O)N(H)—(CH₂)₃—C(=O)OH | H |
| X115 a or b | N | C | —(CH₂)₂—C(=O)N(H)—(CH₂)₃—C(=O)OH | H |
| X116 a or b | N | C | —(CH₂)₃—C(=O)N(H)—(CH₂)₃—C(=O)OH | H |
| X117 a or b | N | C | —(CH₂)₄—C(=O)N(H)—(CH₂)₃—C(=O)OH | H |
| X118 a or b | N | C | —C(=O)N(H)—CH₂—C(=O)O—CH₃ | H |
| X119 a or b | N | C | —CH₂—C(=O)N(H)—CH₂—C(=O)O—CH₃ | H |
| X120 a or b | N | C | —(CH₂)₂—C(=O)N(H)—CH₂—C(=O)O—CH₃ | H |
| X121 a or b | N | C | —(CH₂)₃—C(=O)N(H)—CH₂—C(=O)O—CH₃ | H |
| X122 a or b | N | C | —(CH₂)₄—C(=O)N(H)—CH₂—C(=O)O—CH₃ | H |
| X123 a or b | N | C | —C(=O)N(H)—(CH₂)₂—C(=O)O—CH₃ | H |
| X124 a or b | N | C | —CH₂—C(=O)N(H)—(CH₂)₂—C(=O)O—CH₃ | H |
| X125 a or b | N | C | —(CH₂)₂—C(=O)N(H)—(CH₂)₂—C(=O)O—CH₃ | H |
| X126 a or b | N | C | —(CH₂)₃—C(=O)N(H)—(CH₂)₂—C(=O)O—CH₃ | H |
| X127 a or b | N | C | —(CH₂)₄—C(=O)N(H)—(CH₂)₂—C(=O)O—CH₃ | H |
| X128 a or b | N | C | —C(=O)N(H)—(CH₂)₃—C(=O)O—CH₃ | H |
| X129 a or b | N | C | —CH₂—C(=O)N(H)—(CH₂)₃—C(=O)O—CH₃ | H |
| X130 a or b | N | C | —(CH₂)₂—C(=O)N(H)—(CH₂)₃—C(=O)O—CH₃ | H |
| X131 a or b | N | C | —(CH₂)₃—C(=O)N(H)—(CH₂)₃—C(=O)O—CH₃ | H |
| X132 a or b | N | C | —(CH₂)₄—C(=O)N(H)—(CH₂)₃—C(=O)O—CH₃ | H |
| X133 a or b | N | C | —C(=O)N(H)—CH₂—C(=O)O—CH₂—CH₃ | H |
| X134 a or b | N | C | —CH₂—C(=O)N(H)—CH₂—C(=O)O—CH₂—CH₃ | H |
| X135 a or b | N | C | —(CH₂)₂—C(=O)N(H)—CH₂—C(=O)O—CH₂—CH₃ | H |
| X136 a or b | N | C | —(CH₂)₃—C(=O)N(H)—CH₂—C(=O)O—CH₂—CH₃ | H |
| X137 a or b | N | C | —(CH₂)₄—C(=O)N(H)—CH₂—C(=O)O—CH₂—CH₃ | H |
| X138 a or b | N | C | —C(=O)N(H)—(CH₂)₂—C(=O)O—CH₂—CH₃ | H |
| X139 a or b | N | C | —CH₂—C(=O)N(H)—(CH₂)₂—C(=O)O—CH₂—CH₃ | H |
| X140 a or b | N | C | —(CH₂)₂—C(=O)N(H)—(CH₂)₂—C(=O)O—CH₂—CH₃ | H |
| X141 a or b | N | C | —(CH₂)₃—C(=O)N(H)—(CH₂)₂—C(=O)O—CH₂—CH₃ | H |
| X142 a or b | N | C | —(CH₂)₄—C(=O)N(H)—(CH₂)₂—C(=O)O—CH₂—CH₃ | H |
| X143 a or b | N | C | —C(=O)N(H)—(CH₂)₃—C(=O)O—CH₂—CH₃ | H |
| X144 a or b | N | C | —CH₂—C(=O)N(H)—(CH₂)₃—C(=O)O—CH₂—CH₃ | H |
| X145 a or b | N | C | —(CH₂)₂—C(=O)N(H)—(CH₂)₃—C(=O)O—CH₂—CH₃ | H |
| X146 a or b | N | C | —(CH₂)₃—C(=O)N(H)—(CH₂)₃—C(=O)O—CH₂—CH₃ | H |
| X147 a or b | N | C | —(CH₂)₄—C(=O)N(H)—(CH₂)₃—C(=O)O—CH₂—CH₃ | H |
| X148 a or b | N | C | —C(=O)N(CH₃)₂ | H |
| X149 a or b | N | C | —CH₂—C(=O)N(CH₃)₂ | H |
| X150 a or b | N | C | —(CH₂)₂—C(=O)N(CH₃)₂ | H |
| X151 a or b | N | C | —(CH₂)₃—C(=O)N(CH₃)₂ | H |
| X152 a or b | N | C | —(CH₂)₄—C(=O)N(CH₃)₂ | H |
| X153 a or b | C | N | H | H |
| X154 a or b | C | N | —C(=O)OH | H |
| X155 a or b | C | N | —CH₂—C(=O)OH | H |
| X156 a or b | C | N | —(CH₂)₂—C(=O)OH | H |
| X157 a or b | C | N | —(CH₂)₃—C(=O)OH | H |
| X158 a or b | C | N | —(CH₂)₄—C(=O)OH | H |
| X159 a or b | C | N | —C(=O)O—CH₃ | H |

TABLE 3-continued

| Compound | U$^1$ | U$^2$ | R$^3$ (for a series) or R$^4$ (for b series) | R$^{8'}$ |
|---|---|---|---|---|
| X160 a or b | C | N | —CH$_2$—C(=O)O—CH$_3$ | H |
| X161 a or b | C | N | —(CH$_2$)$_2$—C(=O)O—CH$_3$ | H |
| X162 a or b | C | N | —(CH$_2$)$_3$—C(=O)O—CH$_3$ | H |
| X163 a or b | C | N | —(CH$_2$)$_4$—C(=O)O—CH$_3$ | H |
| X164 a or b | C | N | —C(=O)O—CH$_2$—CH$_3$ | H |
| X165 a or b | C | N | —CH$_2$—C(=O)O—CH$_2$—CH$_3$ | H |
| X166 a or b | C | N | —(CH$_2$)$_2$—C(=O)O—CH$_2$—CH$_3$ | H |
| X167 a or b | C | N | —(CH$_2$)$_3$—C(=O)O—CH$_2$—CH$_3$ | H |
| X168 a or b | C | N | —(CH$_2$)$_4$—C(=O)O—CH$_2$—CH$_3$ | H |
| X169 a or b | C | N | —C(=O)NH$_2$ | H |
| X170 a or b | C | N | —CH$_2$—C(=O)NH$_2$ | H |
| X171 a or b | C | N | —(CH$_2$)$_2$—C(=O)NH$_2$ | H |
| X172 a or b | C | N | —(CH$_2$)$_3$—C(=O)NH$_2$ | H |
| X173 a or b | C | N | —(CH$_2$)$_4$—C(=O)NH$_2$ | H |
| X174 a or b | C | N | —C(=O)N(H)—CH$_3$ | H |
| X175 a or b | C | N | —CH$_2$—C(=O)N(H)—CH$_3$ | H |
| X176 a or b | C | N | —(CH$_2$)$_2$—C(=O)N(H)—CH$_3$ | H |
| X177 a or b | C | N | —(CH$_2$)$_3$—C(=O)N(H)—CH$_3$ | H |
| X178 a or b | C | N | —(CH$_2$)$_4$—C(=O)N(H)—CH$_3$ | H |
| X179 a or b | C | N | —C(=O)N(H)—CH$_2$—C(=O)OH | H |
| X180 a or b | C | N | —CH$_2$—C(=O)N(H)—CH$_2$—C(=O)OH | H |
| X181 a or b | C | N | —(CH$_2$)$_2$—C(=O)N(H)—CH$_2$—C(=O)OH | H |
| X182 a or b | C | N | —(CH$_2$)$_3$—C(=O)N(H)—CH$_2$—C(=O)OH | H |
| X183 a or b | C | N | —(CH$_2$)$_4$—C(=O)N(H)—CH$_2$—C(=O)OH | H |
| X184 a or b | C | N | —C(=O)N(H)—(CH$_2$)$_2$—C(=O)OH | H |
| X185 a or b | C | N | —CH$_2$—C(=O)N(H)—(CH$_2$)$_2$—C(=O)OH | H |
| X186 a or b | C | N | —(CH$_2$)$_2$—C(=O)N(H)—(CH$_2$)$_2$—C(=O)OH | H |
| X187 a or b | C | N | —(CH$_2$)$_3$—C(=O)N(H)—(CH$_2$)$_2$—C(=O)OH | H |
| X188 a or b | C | N | —(CH$_2$)$_4$—C(=O)N(H)—(CH$_2$)$_2$—C(=O)OH | H |
| X189 a or b | C | N | —C(=O)N(H)—(CH$_2$)$_3$—C(=O)OH | H |
| X190 a or b | C | N | —CH$_2$—C(=O)N(H)—(CH$_2$)$_3$—C(=O)OH | H |
| X191 a or b | C | N | —(CH$_2$)$_2$—C(=O)N(H)—(CH$_2$)$_3$—C(=O)OH | H |
| X192 a or b | C | N | —(CH$_2$)$_3$—C(=O)N(H)—(CH$_2$)$_3$—C(=O)OH | H |
| X193 a or b | C | N | —(CH$_2$)$_4$—C(=O)N(H)—(CH$_2$)$_3$—C(=O)OH | H |
| X194 a or b | C | N | —C(=O)N(H)—CH$_2$—C(=O)O—CH$_3$ | H |
| X195 a or b | C | N | —CH$_2$—C(=O)N(H)—CH$_2$—C(=O)O—CH$_3$ | H |
| X196 a or b | C | N | —(CH$_2$)$_2$—C(=O)N(H)—CH$_2$—C(=O)O—CH$_3$ | H |
| X197 a or b | C | N | —(CH$_2$)$_3$—C(=O)N(H)—CH$_2$—C(=O)O—CH$_3$ | H |
| X198 a or b | C | N | —(CH$_2$)$_4$—C(=O)N(H)—CH$_2$—C(=O)O—CH$_3$ | H |
| X199 a or b | C | N | —C(=O)N(H)—(CH$_2$)$_2$—C(=O)O—CH$_3$ | H |
| X200 a or b | C | N | —CH$_2$—C(=O)N(H)—(CH$_2$)$_2$—C(=O)O—CH$_3$ | H |
| X201 a or b | C | N | —(CH$_2$)$_2$—C(=O)N(H)—(CH$_2$)$_2$—C(=O)O—CH$_3$ | H |
| X202 a or b | C | N | —(CH$_2$)$_3$—C(=O)N(H)—(CH$_2$)$_2$—C(=O)O—CH$_3$ | H |
| X203 a or b | C | N | —(CH$_2$)$_4$—C(=O)N(H)—(CH$_2$)$_2$—C(=O)O—CH$_3$ | H |
| X204 a or b | C | N | —C(=O)N(H)—(CH$_2$)$_3$—C(=O)O—CH$_3$ | H |
| X205 a or b | C | N | —CH$_2$—C(=O)N(H)—(CH$_2$)$_3$—C(=O)O—CH$_3$ | H |
| X206 a or b | C | N | —(CH$_2$)$_2$—C(=O)N(H)—(CH$_2$)$_3$—C(=O)O—CH$_3$ | H |
| X207 a or b | C | N | —(CH$_2$)$_3$—C(=O)N(H)—(CH$_2$)$_3$—C(=O)O—CH$_3$ | H |
| X208 a or b | C | N | —(CH$_2$)$_4$—C(=O)N(H)—(CH$_2$)$_3$—C(=O)O—CH$_3$ | H |
| X209 a or b | C | N | —C(=O)N(H)—CH$_2$—C(=O)O—CH$_2$—CH$_3$ | H |
| X210 a or b | C | N | —CH$_2$—C(=O)N(H)—CH$_2$—C(=O)O—CH$_2$—CH$_3$ | H |
| X211 a or b | C | N | —(CH$_2$)$_2$—C(=O)N(H)—CH$_2$—C(=O)O—CH$_2$—CH$_3$ | H |
| X212 a or b | C | N | —(CH$_2$)$_3$—C(=O)N(H)—CH$_2$—C(=O)O—CH$_2$—CH$_3$ | H |
| X213 a or b | C | N | —(CH$_2$)$_4$—C(=O)N(H)—CH$_2$—C(=O)O—CH$_2$—CH$_3$ | H |
| X214 a or b | C | N | —C(=O)N(H)—(CH$_2$)$_2$—C(=O)O—CH$_2$—CH$_3$ | H |
| X215 a or b | C | N | —CH$_2$—C(=O)N(H)—(CH$_2$)$_2$—C(=O)O—CH$_2$—CH$_3$ | H |
| X216 a or b | C | N | —(CH$_2$)$_2$—C(=O)N(H)—(CH$_2$)$_2$—C(=O)O—CH$_2$—CH$_3$ | H |
| X217 a or b | C | N | —(CH$_2$)$_3$—C(=O)N(H)—(CH$_2$)$_2$—C(=O)O—CH$_2$—CH$_3$ | H |
| X218 a or b | C | N | —(CH$_2$)$_4$—C(=O)N(H)—(CH$_2$)$_2$—C(=O)O—CH$_2$—CH$_3$ | H |
| X219 a or b | C | N | —C(=O)N(H)—(CH$_2$)$_3$—C(=O)O—CH$_2$—CH$_3$ | H |
| X220 a or b | C | N | —CH$_2$—C(=O)N(H)—(CH$_2$)$_3$—C(=O)O—CH$_2$—CH$_3$ | H |
| X221 a or b | C | N | —(CH$_2$)$_2$—C(=O)N(H)—(CH$_2$)$_3$—C(=O)O—CH$_2$—CH$_3$ | H |
| X222 a or b | C | N | —(CH$_2$)$_3$—C(=O)N(H)—(CH$_2$)$_3$—C(=O)O—CH$_2$—CH$_3$ | H |
| X223 a or b | C | N | —(CH$_2$)$_4$—C(=O)N(H)—(CH$_2$)$_3$—C(=O)O—CH$_2$—CH$_3$ | H |
| X224 a or b | C | N | —C(=O)N(CH$_3$)$_2$ | H |
| X225 a or b | C | N | —CH$_2$—C(=O)N(CH$_3$)$_2$ | H |
| X226 a or b | C | N | —(CH$_2$)$_2$—C(=O)N(CH$_3$)$_2$ | H |
| X227 a or b | C | N | —(CH$_2$)$_3$—C(=O)N(CH$_3$)$_2$ | H |
| X228 a or b | C | N | —(CH$_2$)$_4$—C(=O)N(CH$_3$)$_2$ | H |
| X229 a or b | C | C | H | CH$_3$ |
| X230 a or b | C | C | —C(=O)OH | CH$_3$ |
| X231 a or b | C | C | —CH$_2$—C(=O)OH | CH$_3$ |
| X232 a or b | C | C | —(CH$_2$)$_2$—C(=O)OH | CH$_3$ |
| X233 a or b | C | C | —(CH$_2$)$_3$—C(=O)OH | CH$_3$ |
| X234 a or b | C | C | —(CH$_2$)$_4$—C(=O)OH | CH$_3$ |
| X235 a or b | C | C | —C(=O)O—CH$_3$ | CH$_3$ |
| X236 a or b | C | C | —CH$_2$—C(=O)O—CH$_3$ | CH$_3$ |
| X237 a or b | C | C | —(CH$_2$)$_2$—C(=O)O—CH$_3$ | CH$_3$ |

TABLE 3-continued

| Compound | U$^1$ | U$^2$ | R$^3$ (for a series) or R$^4$ (for b series) | R$^{8'}$ |
|---|---|---|---|---|
| X238 a or b | C | C | —(CH$_2$)$_3$—C(=O)O—CH$_3$ | CH$_3$ |
| X239 a or b | C | C | —(CH$_2$)$_4$—C(=O)O—CH$_3$ | CH$_3$ |
| X240 a or b | C | C | —C(=O)O—CH$_2$—CH$_3$ | CH$_3$ |
| X241 a or b | C | C | —CH$_2$—C(=O)O—CH$_2$—CH$_3$ | CH$_3$ |
| X242 a or b | C | C | —(CH$_2$)$_2$—C(=O)O—CH$_2$—CH$_3$ | CH$_3$ |
| X243 a or b | C | C | —(CH$_2$)$_3$—C(=O)O—CH$_2$—CH$_3$ | CH$_3$ |
| X244 a or b | C | C | —(CH$_2$)$_4$—C(=O)O—CH$_2$—CH$_3$ | CH$_3$ |
| X245 a or b | C | C | —C(=O)NH$_2$ | CH$_3$ |
| X246 a or b | C | C | —CH$_2$—C(=O)NH$_2$ | CH$_3$ |
| X247 a or b | C | C | —(CH$_2$)$_2$—C(=O)NH$_2$ | CH$_3$ |
| X248 a or b | C | C | —(CH$_2$)$_3$—C(=O)NH$_2$ | CH$_3$ |
| X249 a or b | C | C | —(CH$_2$)$_4$—C(=O)NH$_2$ | CH$_3$ |
| X250 a or b | C | C | —C(=O)N(H)—CH$_3$ | CH$_3$ |
| X251 a or b | C | C | —CH$_2$—C(=O)N(H)—CH$_3$ | CH$_3$ |
| X252 a or b | C | C | —(CH$_2$)$_2$—C(=O)N(H)—CH$_3$ | CH$_3$ |
| X253 a or b | C | C | —(CH$_2$)$_3$—C(=O)N(H)—CH$_3$ | CH$_3$ |
| X254 a or b | C | C | —(CH$_2$)$_4$—C(=O)N(H)—CH$_3$ | CH$_3$ |
| X255 a or b | C | C | —C(=O)N(H)—CH$_2$—C(=O)OH | CH$_3$ |
| X256 a or b | C | C | —CH$_2$—C(=O)N(H)—CH$_2$—C(=O)OH | CH$_3$ |
| X257 a or b | C | C | —(CH$_2$)$_2$—C(=O)N(H)—CH$_2$—C(=O)OH | CH$_3$ |
| X258 a or b | C | C | —(CH$_2$)$_3$—C(=O)N(H)—CH$_2$—C(=O)OH | CH$_3$ |
| X259 a or b | C | C | —(CH$_2$)$_4$—C(=O)N(H)—CH$_2$—C(=O)OH | CH$_3$ |
| X260 a or b | C | C | —C(=O)N(H)—(CH$_2$)$_2$—C(=O)OH | CH$_3$ |
| X261 a or b | C | C | —CH$_2$—C(=O)N(H)—(CH$_2$)$_2$—C(=O)OH | CH$_3$ |
| X262 a or b | C | C | —(CH$_2$)$_2$—C(=O)N(H)—(CH$_2$)$_2$—C(=O)OH | CH$_3$ |
| X263 a or b | C | C | —(CH$_2$)$_3$—C(=O)N(H)—(CH$_2$)$_2$—C(=O)OH | CH$_3$ |
| X264 a or b | C | C | —(CH$_2$)$_4$—C(=O)N(H)—(CH$_2$)$_2$—C(=O)OH | CH$_3$ |
| X265 a or b | C | C | —C(=O)N(H)—(CH$_2$)$_3$—C(=O)OH | CH$_3$ |
| X266 a or b | C | C | —CH$_2$—C(=O)N(H)—(CH$_2$)$_3$—C(=O)OH | CH$_3$ |
| X267 a or b | C | C | —(CH$_2$)$_2$—C(=O)N(H)—(CH$_2$)$_3$—C(=O)OH | CH$_3$ |
| X268 a or b | C | C | —(CH$_2$)$_3$—C(=O)N(H)—(CH$_2$)$_3$—C(=O)OH | CH$_3$ |
| X269 a or b | C | C | —(CH$_2$)$_4$—C(=O)N(H)—(CH$_2$)$_3$—C(=O)OH | CH$_3$ |
| X270 a or b | C | C | —C(=O)N(H)—CH$_2$—C(=O)O—CH$_3$ | CH$_3$ |
| X271 a or b | C | C | —CH$_2$—C(=O)N(H)—CH$_2$—C(=O)O—CH$_3$ | CH$_3$ |
| X272 a or b | C | C | —(CH$_2$)$_2$—C(=O)N(H)—CH$_2$—C(=O)O—CH$_3$ | CH$_3$ |
| X273 a or b | C | C | —(CH$_2$)$_3$—C(=O)N(H)—CH$_2$—C(=O)O—CH$_3$ | CH$_3$ |
| X274 a or b | C | C | —(CH$_2$)$_4$—C(=O)N(H)—CH$_2$—C(=O)O—CH$_3$ | CH$_3$ |
| X275 a or b | C | C | —C(=O)N(H)—(CH$_2$)$_2$—C(=O)O—CH$_3$ | CH$_3$ |
| X276 a or b | C | C | —CH$_2$—C(=O)N(H)—(CH$_2$)$_2$—C(=O)O—CH$_3$ | CH$_3$ |
| X277 a or b | C | C | —(CH$_2$)$_2$—C(=O)N(H)—(CH$_2$)$_2$—C(=O)O—CH$_3$ | CH$_3$ |
| X278 a or b | C | C | —(CH$_2$)$_3$—C(=O)N(H)—(CH$_2$)$_2$—C(=O)O—CH$_3$ | CH$_3$ |
| X279 a or b | C | C | —(CH$_2$)$_4$—C(=O)N(H)—(CH$_2$)$_2$—C(=O)O—CH$_3$ | CH$_3$ |
| X280 a or b | C | C | —C(=O)N(H)—(CH$_2$)$_3$—C(=O)O—CH$_3$ | CH$_3$ |
| X281 a or b | C | C | —CH$_2$—C(=O)N(H)—(CH$_2$)$_3$—C(=O)O—CH$_3$ | CH$_3$ |
| X282 a or b | C | C | —(CH$_2$)$_2$—C(=O)N(H)—(CH$_2$)$_3$—C(=O)O—CH$_3$ | CH$_3$ |
| X283 a or b | C | C | —(CH$_2$)$_3$—C(=O)N(H)—(CH$_2$)$_3$—C(=O)O—CH$_3$ | CH$_3$ |
| X284 a or b | C | C | —(CH$_2$)$_4$—C(=O)N(H)—(CH$_2$)$_3$—C(=O)O—CH$_3$ | CH$_3$ |
| X285 a or b | C | C | —C(=O)N(H)—CH$_2$—C(=O)O—CH$_2$—CH$_3$ | CH$_3$ |
| X286 a or b | C | C | —CH$_2$—C(=O)N(H)—CH$_2$—C(=O)O—CH$_2$—CH$_3$ | CH$_3$ |
| X287 a or b | C | C | —(CH$_2$)$_2$—C(=O)N(H)—CH$_2$—C(=O)O—CH$_2$—CH$_3$ | CH$_3$ |
| X288 a or b | C | C | —(CH$_2$)$_3$—C(=O)N(H)—CH$_2$—C(=O)O—CH$_2$—CH$_3$ | CH$_3$ |
| X289 a or b | C | C | —(CH$_2$)$_4$—C(=O)N(H)—CH$_2$—C(=O)O—CH$_2$—CH$_3$ | CH$_3$ |
| X290 a or b | C | C | —C(=O)N(H)—(CH$_2$)$_2$—C(=O)O—CH$_2$—CH$_3$ | CH$_3$ |
| X291 a or b | C | C | —CH$_2$—C(=O)N(H)—(CH$_2$)$_2$—C(=O)O—CH$_2$—CH$_3$ | CH$_3$ |
| X292 a or b | C | C | —(CH$_2$)$_2$—C(=O)N(H)—(CH$_2$)$_2$—C(=O)O—CH$_2$—CH$_3$ | CH$_3$ |
| X293 a or b | C | C | —(CH$_2$)$_3$—C(=O)N(H)—(CH$_2$)$_2$—C(=O)O—CH$_2$—CH$_3$ | CH$_3$ |
| X294 a or b | C | C | —(CH$_2$)$_4$—C(=O)N(H)—(CH$_2$)$_2$—C(=O)O—CH$_2$—CH$_3$ | CH$_3$ |
| X295 a or b | C | C | —C(=O)N(H)—(CH$_2$)$_3$—C(=O)O—CH$_2$—CH$_3$ | CH$_3$ |
| X296 a or b | C | C | —CH$_2$—C(=O)N(H)—(CH$_2$)$_3$—C(=O)O—CH$_2$—CH$_3$ | CH$_3$ |
| X297 a or b | C | C | —(CH$_2$)$_2$—C(=O)N(H)—(CH$_2$)$_3$—C(=O)O—CH$_2$—CH$_3$ | CH$_3$ |
| X298 a or b | C | C | —(CH$_2$)$_3$—C(=O)N(H)—(CH$_2$)$_3$—C(=O)O—CH$_2$—CH$_3$ | CH$_3$ |
| X299 a or b | C | C | —(CH$_2$)$_4$—C(=O)N(H)—(CH$_2$)$_3$—C(=O)O—CH$_2$—CH$_3$ | CH$_3$ |
| X300 a or b | C | C | —C(=O)N(CH$_3$)$_2$ | CH$_3$ |
| X301 a or b | C | C | —CH$_2$—C(=O)N(CH$_3$)$_2$ | CH$_3$ |
| X302 a or b | C | C | —(CH$_2$)$_2$—C(=O)N(CH$_3$)$_2$ | CH$_3$ |
| X303 a or b | C | C | —(CH$_2$)$_3$—C(=O)N(CH$_3$)$_2$ | CH$_3$ |
| X304 a or b | C | C | —(CH$_2$)$_4$—C(=O)N(CH$_3$)$_2$ | CH$_3$ |
| X305 a or b | N | C | H | CH$_3$ |
| X306 a or b | N | C | —C(=O)OH | CH$_3$ |
| X307 a or b | N | C | —CH$_2$—C(=O)OH | CH$_3$ |
| X308 a or b | N | C | —(CH$_2$)$_2$—C(=O)OH | CH$_3$ |
| X309 a or b | N | C | —(CH$_2$)$_3$—C(=O)OH | CH$_3$ |
| X310 a or b | N | C | —(CH$_2$)$_4$—C(=O)OH | CH$_3$ |
| X311 a or b | N | C | —C(=O)O—CH$_3$ | CH$_3$ |
| X312 a or b | N | C | —CH$_2$—C(=O)O—CH$_3$ | CH$_3$ |
| X313 a or b | N | C | —(CH$_2$)$_2$—C(=O)O—CH$_3$ | CH$_3$ |
| X314 a or b | N | C | —(CH$_2$)$_3$—C(=O)O—CH$_3$ | CH$_3$ |
| X315 a or b | N | C | —(CH$_2$)$_4$—C(=O)O—CH$_3$ | CH$_3$ |

TABLE 3-continued

| Compound | U¹ | U² | R³ (for a series) or R⁴ (for b series) | R⁸' |
|---|---|---|---|---|
| X316 a or b | N | C | —C(=O)O—CH₂—CH₃ | CH₃ |
| X317 a or b | N | C | —CH₂—C(=O)O—CH₂—CH₃ | CH₃ |
| X318 a or b | N | C | —(CH₂)₂—C(=O)O—CH₂—CH₃ | CH₃ |
| X319 a or b | N | C | —(CH₂)₃—C(=O)O—CH₂—CH₃ | CH₃ |
| X320 a or b | N | C | —(CH₂)₄—C(=O)O—CH₂—CH₃ | CH₃ |
| X321 a or b | N | C | —C(=O)NH₂ | CH₃ |
| X322 a or b | N | C | —CH₂—C(=O)NH₂ | CH₃ |
| X323 a or b | N | C | —(CH₂)₂—C(=O)NH₂ | CH₃ |
| X324 a or b | N | C | —(CH₂)₃—C(=O)NH₂ | CH₃ |
| X325 a or b | N | C | —(CH₂)₄—C(=O)NH₂ | CH₃ |
| X326 a or b | N | C | —C(=O)N(H)—CH₃ | CH₃ |
| X327 a or b | N | C | —CH₂—C(=O)N(H)—CH₃ | CH₃ |
| X328 a or b | N | C | —(CH₂)₂—C(=O)N(H)—CH₃ | CH₃ |
| X329 a or b | N | C | —(CH₂)₃—C(=O)N(H)—CH₃ | CH₃ |
| X330 a or b | N | C | —(CH₂)₄—C(=O)N(H)—CH₃ | CH₃ |
| X331 a or b | N | C | —C(=O)N(H)—CH₂—C(=O)OH | CH₃ |
| X332 a or b | N | C | —CH₂—C(=O)N(H)—CH₂—C(=O)OH | CH₃ |
| X333 a or b | N | C | —(CH₂)₂—C(=O)N(H)—CH₂—C(=O)OH | CH₃ |
| X334 a or b | N | C | —(CH₂)₃—C(=O)N(H)—CH₂—C(=O)OH | CH₃ |
| X335 a or b | N | C | —(CH₂)₄—C(=O)N(H)—CH₂—C(=O)OH | CH₃ |
| X336 a or b | N | C | —C(=O)N(H)—(CH₂)₂—C(=O)OH | CH₃ |
| X337 a or b | N | C | —CH₂—C(=O)N(H)—(CH₂)₂—C(=O)OH | CH₃ |
| X338 a or b | N | C | —(CH₂)₂—C(=O)N(H)—(CH₂)₂—C(=O)OH | CH₃ |
| X339 a or b | N | C | —(CH₂)₃—C(=O)N(H)—(CH₂)₂—C(=O)OH | CH₃ |
| X340 a or b | N | C | —(CH₂)₄—C(=O)N(H)—(CH₂)₂—C(=O)OH | CH₃ |
| X341 a or b | N | C | —C(=O)N(H)—(CH₂)₃—C(=O)OH | CH₃ |
| X342 a or b | N | C | —CH₂—C(=O)N(H)—(CH₂)₃—C(=O)OH | CH₃ |
| X343 a or b | N | C | —(CH₂)₂—C(=O)N(H)—(CH₂)₃—C(=O)OH | CH₃ |
| X344 a or b | N | C | —(CH₂)₃—C(=O)N(H)—(CH₂)₃—C(=O)OH | CH₃ |
| X345 a or b | N | C | —(CH₂)₄—C(=O)N(H)—(CH₂)₃—C(=O)OH | CH₃ |
| X346 a or b | N | C | —C(=O)N(H)—CH₂—C(=O)O—CH₃ | CH₃ |
| X347 a or b | N | C | —CH₂—C(=O)N(H)—CH₂—C(=O)O—CH₃ | CH₃ |
| X348 a or b | N | C | —(CH₂)₂—C(=O)N(H)—CH₂—C(=O)O—CH₃ | CH₃ |
| X349 a or b | N | C | —(CH₂)₃—C(=O)N(H)—CH₂—C(=O)O—CH₃ | CH₃ |
| X350 a or b | N | C | —(CH₂)₄—C(=O)N(H)—CH₂—C(=O)O—CH₃ | CH₃ |
| X351 a or b | N | C | —C(=O)N(H)—(CH₂)₂—C(=O)O—CH₃ | CH₃ |
| X352 a or b | N | C | —CH₂—C(=O)N(H)—(CH₂)₂—C(=O)O—CH₃ | CH₃ |
| X353 a or b | N | C | —(CH₂)₂—C(=O)N(H)—(CH₂)₂—C(=O)O—CH₃ | CH₃ |
| X354 a or b | N | C | —(CH₂)₃—C(=O)N(H)—(CH₂)₂—C(=O)O—CH₃ | CH₃ |
| X355 a or b | N | C | —(CH₂)₄—C(=O)N(H)—(CH₂)₂—C(=O)O—CH₃ | CH₃ |
| X356 a or b | N | C | —C(=O)N(H)—(CH₂)₃—C(=O)O—CH₃ | CH₃ |
| X357 a or b | N | C | —CH₂—C(=O)N(H)—(CH₂)₃—C(=O)O—CH₃ | CH₃ |
| X358 a or b | N | C | —(CH₂)₂—C(=O)N(H)—(CH₂)₃—C(=O)O—CH₃ | CH₃ |
| X359 a or b | N | C | —(CH₂)₃—C(=O)N(H)—(CH₂)₃—C(=O)O—CH₃ | CH₃ |
| X360 a or b | N | C | —(CH₂)₄—C(=O)N(H)—(CH₂)₃—C(=O)O—CH₃ | CH₃ |
| X361 a or b | N | C | —C(=O)N(H)—CH₂—C(=O)O—CH₂—CH₃ | CH₃ |
| X362 a or b | N | C | —CH₂—C(=O)N(H)—CH₂—C(=O)O—CH₂—CH₃ | CH₃ |
| X363 a or b | N | C | —(CH₂)₂—C(=O)N(H)—CH₂—C(=O)O—CH₂—CH₃ | CH₃ |
| X364 a or b | N | C | —(CH₂)₃—C(=O)N(H)—CH₂—C(=O)O—CH₂—CH₃ | CH₃ |
| X365 a or b | N | C | —(CH₂)₄—C(=O)N(H)—CH₂—C(=O)O—CH₂—CH₃ | CH₃ |
| X366 a or b | N | C | —C(=O)N(H)—(CH₂)₂—C(=O)O—CH₂—CH₃ | CH₃ |
| X367 a or b | N | C | —CH₂—C(=O)N(H)—(CH₂)₂—C(=O)O—CH₂—CH₃ | CH₃ |
| X368 a or b | N | C | —(CH₂)₂—C(=O)N(H)—(CH₂)₂—C(=O)O—CH₂—CH₃ | CH₃ |
| X369 a or b | N | C | —(CH₂)₃—C(=O)N(H)—(CH₂)₂—C(=O)O—CH₂—CH₃ | CH₃ |
| X370 a or b | N | C | —(CH₂)₄—C(=O)N(H)—(CH₂)₂—C(=O)O—CH₂—CH₃ | CH₃ |
| X371 a or b | N | C | —C(=O)N(H)—(CH₂)₃—C(=O)O—CH₃ | CH₃ |
| X372 a or b | N | C | —CH₂—C(=O)N(H)—(CH₂)₃—C(=O)O—CH₂—CH₃ | CH₃ |
| X373 a or b | N | C | —(CH₂)₂—C(=O)N(H)—(CH₂)₃—C(=O)O—CH₂—CH₃ | CH₃ |
| X374 a or b | N | C | —(CH₂)₃—C(=O)N(H)—(CH₂)₃—C(=O)O—CH₂—CH₃ | CH₃ |
| X375 a or b | N | C | —(CH₂)₄—C(=O)N(H)—(CH₂)₃—C(=O)O—CH₂—CH₃ | CH₃ |
| X376 a or b | N | C | —C(=O)N(CH₃)₂ | CH₃ |
| X377 a or b | N | C | —CH₂—C(=O)N(CH₃)₂ | CH₃ |
| X378 a or b | N | C | —(CH₂)₂—C(=O)N(CH₃)₂ | CH₃ |
| X379 a or b | N | C | —(CH₂)₃—C(=O)N(CH₃)₂ | CH₃ |
| X380 a or b | N | C | —(CH₂)₄—C(=O)N(CH₃)₂ | CH₃ |
| X381 a or b | C | N | H | CH₃ |
| X382 a or b | C | N | —C(=O)OH | CH₃ |
| X383 a or b | C | N | —CH₂—C(=O)OH | CH₃ |
| X384 a or b | C | N | —(CH₂)₂—C(=O)OH | CH₃ |
| X385 a or b | C | N | —(CH₂)₃—C(=O)OH | CH₃ |
| X386 a or b | C | N | —(CH₂)₄—C(=O)OH | CH₃ |
| X387 a or b | C | N | —C(=O)O—CH₃ | CH₃ |
| X388 a or b | C | N | —CH₂—C(=O)O—CH₃ | CH₃ |
| X389 a or b | C | N | —(CH₂)₂—C(=O)O—CH₃ | CH₃ |
| X390 a or b | C | N | —(CH₂)₃—C(=O)O—CH₃ | CH₃ |
| X391 a or b | C | N | —(CH₂)₄—C(=O)O—CH₃ | CH₃ |
| X392 a or b | C | N | —C(=O)O—CH₂—CH₃ | CH₃ |
| X393 a or b | C | N | —CH₂—C(=O)O—CH₂—CH₃ | CH₃ |

TABLE 3-continued

| Compound | $U^1$ | $U^2$ | $R^3$ (for a series) or $R^4$ (for b series) | $R^{8'}$ |
|---|---|---|---|---|
| X394 a or b | C | N | —(CH$_2$)$_2$—C(=O)O—CH$_2$—CH$_3$ | CH$_3$ |
| X395 a or b | C | N | —(CH$_2$)$_3$—C(=O)O—CH$_2$—CH$_3$ | CH$_3$ |
| X396 a or b | C | N | —(CH$_2$)$_4$—C(=O)O—CH$_2$—CH$_3$ | CH$_3$ |
| X397 a or b | C | N | —C(=O)NH$_2$ | CH$_3$ |
| X398 a or b | C | N | —CH$_2$—C(=O)NH$_2$ | CH$_3$ |
| X399 a or b | C | N | —(CH$_2$)$_2$—C(=O)NH$_2$ | CH$_3$ |
| X400 a or b | C | N | —(CH$_2$)$_3$—C(=O)NH$_2$ | CH$_3$ |
| X401 a or b | C | N | —(CH$_2$)$_4$—C(=O)NH$_2$ | CH$_3$ |
| X402 a or b | C | N | —C(=O)N(H)—CH$_3$ | CH$_3$ |
| X403 a or b | C | N | —CH$_2$—C(=O)N(H)—CH$_3$ | CH$_3$ |
| X404 a or b | C | N | —(CH$_2$)$_2$—C(=O)N(H)—CH$_3$ | CH$_3$ |
| X405 a or b | C | N | —(CH$_2$)$_3$—C(=O)N(H)—CH$_3$ | CH$_3$ |
| X406 a or b | C | N | —(CH$_2$)$_4$—C(=O)N(H)—CH$_3$ | CH$_3$ |
| X407 a or b | C | N | —C(=O)N(H)—CH$_2$—C(=O)OH | CH$_3$ |
| X408 a or b | C | N | —CH$_2$—C(=O)N(H)—CH$_2$—C(=O)OH | CH$_3$ |
| X409 a or b | C | N | —(CH$_2$)$_2$—C(=O)N(H)—CH$_2$—C(=O)OH | CH$_3$ |
| X410 a or b | C | N | —(CH$_2$)$_3$—C(=O)N(H)—CH$_2$—C(=O)OH | CH$_3$ |
| X411 a or b | C | N | —(CH$_2$)$_4$—C(=O)N(H)—CH$_2$—C(=O)OH | CH$_3$ |
| X412 a or b | C | N | —C(=O)N(H)—(CH$_2$)$_2$—C(=O)OH | CH$_3$ |
| X413 a or b | C | N | —CH$_2$—C(=O)N(H)—(CH$_2$)$_2$—C(=O)OH | CH$_3$ |
| X414 a or b | C | N | —(CH$_2$)$_2$—C(=O)N(H)—(CH$_2$)$_2$—C(=O)OH | CH$_3$ |
| X415 a or b | C | N | —(CH$_2$)$_3$—C(=O)N(H)—(CH$_2$)$_2$—C(=O)OH | CH$_3$ |
| X416 a or b | C | N | —(CH$_2$)$_4$—C(=O)N(H)—(CH$_2$)$_2$—C(=O)OH | CH$_3$ |
| X417 a or b | C | N | —C(=O)N(H)—(CH$_2$)$_3$—C(=O)OH | CH$_3$ |
| X418 a or b | C | N | —CH$_2$—C(=O)N(H)—(CH$_2$)$_3$—C(=O)OH | CH$_3$ |
| X419 a or b | C | N | —(CH$_2$)$_2$—C(=O)N(H)—(CH$_2$)$_3$—C(=O)OH | CH$_3$ |
| X420 a or b | C | N | —(CH$_2$)$_3$—C(=O)N(H)—(CH$_2$)$_3$—C(=O)OH | CH$_3$ |
| X421 a or b | C | N | —(CH$_2$)$_4$—C(=O)N(H)—(CH$_2$)$_3$—C(=O)OH | CH$_3$ |
| X422 a or b | C | N | —C(=O)N(H)—CH$_2$—C(=O)O—CH$_3$ | CH$_3$ |
| X423 a or b | C | N | —CH$_2$—C(=O)N(H)—CH$_2$—C(=O)O—CH$_3$ | CH$_3$ |
| X424 a or b | C | N | —(CH$_2$)$_2$—C(=O)N(H)—CH$_2$—C(=O)O—CH$_3$ | CH$_3$ |
| X425 a or b | C | N | —(CH$_2$)$_3$—C(=O)N(H)—CH$_2$—C(=O)O—CH$_3$ | CH$_3$ |
| X426 a or b | C | N | —(CH$_2$)$_4$—C(=O)N(H)—CH$_2$—C(=O)O—CH$_3$ | CH$_3$ |
| X427 a or b | C | N | —C(=O)N(H)—(CH$_2$)$_2$—C(=O)O—CH$_3$ | CH$_3$ |
| X428 a or b | C | N | —CH$_2$—C(=O)N(H)—(CH$_2$)$_2$—C(=O)O—CH$_3$ | CH$_3$ |
| X429 a or b | C | N | —(CH$_2$)$_2$—C(=O)N(H)—(CH$_2$)$_2$—C(=O)O—CH$_3$ | CH$_3$ |
| X430 a or b | C | N | —(CH$_2$)$_3$—C(=O)N(H)—(CH$_2$)$_2$—C(=O)O—CH$_3$ | CH$_3$ |
| X431 a or b | C | N | —(CH$_2$)$_4$—C(=O)N(H)—(CH$_2$)$_2$—C(=O)O—CH$_3$ | CH$_3$ |
| X432 a or b | C | N | —C(=O)N(H)—(CH$_2$)$_3$—C(=O)O—CH$_3$ | CH$_3$ |
| X433 a or b | C | N | —CH$_2$—C(=O)N(H)—(CH$_2$)$_3$—C(=O)O—CH$_3$ | CH$_3$ |
| X434 a or b | C | N | —(CH$_2$)$_2$—C(=O)N(H)—(CH$_2$)$_3$—C(=O)O—CH$_3$ | CH$_3$ |
| X435 a or b | C | N | —(CH$_2$)$_3$—C(=O)N(H)—(CH$_2$)$_3$—C(=O)O—CH$_3$ | CH$_3$ |
| X436 a or b | C | N | —(CH$_2$)$_4$—C(=O)N(H)—(CH$_2$)$_3$—C(=O)O—CH$_3$ | CH$_3$ |
| X437 a or b | C | N | —C(=O)N(H)—CH$_2$—C(=O)O—CH$_2$—CH$_3$ | CH$_3$ |
| X438 a or b | C | N | —CH$_2$—C(=O)N(H)—CH$_2$—C(=O)O—CH$_2$—CH$_3$ | CH$_3$ |
| X439 a or b | C | N | —(CH$_2$)$_2$—C(=O)N(H)—CH$_2$—C(=O)O—CH$_2$—CH$_3$ | CH$_3$ |
| X440 a or b | C | N | —(CH$_2$)$_3$—C(=O)N(H)—CH$_2$—C(=O)O—CH$_2$—CH$_3$ | CH$_3$ |
| X441 a or b | C | N | —(CH$_2$)$_4$—C(=O)N(H)—CH$_2$—C(=O)O—CH$_2$—CH$_3$ | CH$_3$ |
| X442 a or b | C | N | —C(=O)N(H)—(CH$_2$)$_2$—C(=O)O—CH$_2$—CH$_3$ | CH$_3$ |
| X443 a or b | C | N | —CH$_2$—C(=O)N(H)—(CH$_2$)$_2$—C(=O)O—CH$_2$—CH$_3$ | CH$_3$ |
| X444 a or b | C | N | —(CH$_2$)$_2$—C(=O)N(H)—(CH$_2$)$_2$—C(=O)O—CH$_2$—CH$_3$ | CH$_3$ |
| X445 a or b | C | N | —(CH$_2$)$_3$—C(=O)N(H)—(CH$_2$)$_2$—C(=O)O—CH$_2$—CH$_3$ | CH$_3$ |
| X446 a or b | C | N | —(CH$_2$)$_4$—C(=O)N(H)—(CH$_2$)$_2$—C(=O)O—CH$_2$—CH$_3$ | CH$_3$ |
| X447 a or b | C | N | —C(=O)N(H)—(CH$_2$)$_3$—C(=O)O—CH$_2$—CH$_3$ | CH$_3$ |
| X448 a or b | C | N | —CH$_2$—C(=O)N(H)—(CH$_2$)$_3$—C(=O)O—CH$_2$—CH$_3$ | CH$_3$ |
| X449 a or b | C | N | —(CH$_2$)$_2$—C(=O)N(H)—(CH$_2$)$_3$—C(=O)O—CH$_2$—CH$_3$ | CH$_3$ |
| X450 a or b | C | N | —(CH$_2$)$_3$—C(=O)N(H)—(CH$_2$)$_3$—C(=O)O—CH$_2$—CH$_3$ | CH$_3$ |
| X451 a or b | C | N | —(CH$_2$)$_4$—C(=O)N(H)—(CH$_2$)$_3$—C(=O)O—CH$_2$—CH$_3$ | CH$_3$ |
| X452 a or b | C | N | —C(=O)N(CH$_3$)$_2$ | CH$_3$ |
| X453 a or b | C | N | —CH$_2$—C(=O)N(CH$_3$)$_2$ | CH$_3$ |
| X454 a or b | C | N | —(CH$_2$)$_2$—C(=O)N(CH$_3$)$_2$ | CH$_3$ |
| X455 a or b | C | N | —(CH$_2$)$_3$—C(=O)N(CH$_3$)$_2$ | CH$_3$ |
| X456 a or b | C | N | —(CH$_2$)$_4$—C(=O)N(CH$_3$)$_2$ | CH$_3$ |
| X457 a or b | C | C | H | CH$_2$CH$_3$ |
| X458 a or b | C | C | —C(=O)OH | CH$_2$CH$_3$ |
| X459 a or b | C | C | —CH$_2$—C(=O)OH | CH$_2$CH$_3$ |
| X460 a or b | C | C | —(CH$_2$)$_2$—C(=O)OH | CH$_2$CH$_3$ |
| X461 a or b | C | C | —(CH$_2$)$_3$—C(=O)OH | CH$_2$CH$_3$ |
| X462 a or b | C | C | —(CH$_2$)$_4$—C(=O)OH | CH$_2$CH$_3$ |
| X463 a or b | C | C | —C(=O)O—CH$_3$ | CH$_2$CH$_3$ |
| X464 a or b | C | C | —CH$_2$—C(=O)O—CH$_3$ | CH$_2$CH$_3$ |
| X465 a or b | C | C | —(CH$_2$)$_2$—C(=O)O—CH$_3$ | CH$_2$CH$_3$ |
| X466 a or b | C | C | —(CH$_2$)$_3$—C(=O)O—CH$_3$ | CH$_2$CH$_3$ |
| X467 a or b | C | C | —(CH$_2$)$_4$—C(=O)O—CH$_3$ | CH$_2$CH$_3$ |
| X468 a or b | C | C | —C(=O)O—CH$_2$—CH$_3$ | CH$_2$CH$_3$ |
| X469 a or b | C | C | —CH$_2$—C(=O)O—CH$_2$—CH$_3$ | CH$_2$CH$_3$ |
| X470 a or b | C | C | —(CH$_2$)$_2$—C(=O)O—CH$_2$—CH$_3$ | CH$_2$CH$_3$ |
| X471 a or b | C | C | —(CH$_2$)$_3$—C(=O)O—CH$_2$—CH$_3$ | CH$_2$CH$_3$ |

TABLE 3-continued

| Compound | U$^1$ | U$^2$ | R$^3$ (for a series) or R$^4$ (for b series) | R$^{8'}$ |
|---|---|---|---|---|
| X472 a or b | C | C | —(CH$_2$)$_4$—C(=O)O—CH$_2$—CH$_3$ | CH$_2$CH$_3$ |
| X473 a or b | C | C | —C(=O)NH$_2$ | CH$_2$CH$_3$ |
| X474 a or b | C | C | —CH$_2$—C(=O)NH$_2$ | CH$_2$CH$_3$ |
| X475 a or b | C | C | —(CH$_2$)$_2$—C(=O)NH$_2$ | CH$_2$CH$_3$ |
| X476 a or b | C | C | —(CH$_2$)$_3$—C(=O)NH$_2$ | CH$_2$CH$_3$ |
| X477 a or b | C | C | —(CH$_2$)$_4$—C(=O)NH$_2$ | CH$_2$CH$_3$ |
| X478 a or b | C | C | —C(=O)N(H)—CH$_3$ | CH$_2$CH$_3$ |
| X479 a or b | C | C | —CH$_2$—C(=O)N(H)—CH$_3$ | CH$_2$CH$_3$ |
| X480 a or b | C | C | —(CH$_2$)$_2$—C(=O)N(H)—CH$_3$ | CH$_2$CH$_3$ |
| X481 a or b | C | C | —(CH$_2$)$_3$—C(=O)N(H)—CH$_3$ | CH$_2$CH$_3$ |
| X482 a or b | C | C | —(CH$_2$)$_4$—C(=O)N(H)—CH$_3$ | CH$_2$CH$_3$ |
| X483 a or b | C | C | —C(=O)N(H)—CH$_2$—C(=O)OH | CH$_2$CH$_3$ |
| X484 a or b | C | C | —CH$_2$—C(=O)N(H)—CH$_2$—C(=O)OH | CH$_2$CH$_3$ |
| X485 a or b | C | C | —(CH$_2$)$_2$—C(=O)N(H)—CH$_2$—C(=O)OH | CH$_2$CH$_3$ |
| X486 a or b | C | C | —(CH$_2$)$_3$—C(=O)N(H)—CH$_2$—C(=O)OH | CH$_2$CH$_3$ |
| X487 a or b | C | C | —(CH$_2$)$_4$—C(=O)N(H)—CH$_2$—C(=O)OH | CH$_2$CH$_3$ |
| X488 a or b | C | C | —C(=O)N(H)—(CH$_2$)$_2$—C(=O)OH | CH$_2$CH$_3$ |
| X489 a or b | C | C | —CH$_2$—C(=O)N(H)—(CH$_2$)$_2$—C(=O)OH | CH$_2$CH$_3$ |
| X490 a or b | C | C | —(CH$_2$)$_2$—C(=O)N(H)—(CH$_2$)$_2$—C(=O)OH | CH$_2$CH$_3$ |
| X491 a or b | C | C | —(CH$_2$)$_3$—C(=O)N(H)—(CH$_2$)$_2$—C(=O)OH | CH$_2$CH$_3$ |
| X492 a or b | C | C | —(CH$_2$)$_4$—C(=O)N(H)—(CH$_2$)$_2$—C(=O)OH | CH$_2$CH$_3$ |
| X493 a or b | C | C | —C(=O)N(H)—(CH$_2$)$_3$—C(=O)OH | CH$_2$CH$_3$ |
| X494 a or b | C | C | —CH$_2$—C(=O)N(H)—(CH$_2$)$_3$—C(=O)OH | CH$_2$CH$_3$ |
| X495 a or b | C | C | —(CH$_2$)$_2$—C(=O)N(H)—(CH$_2$)$_3$—C(=O)OH | CH$_2$CH$_3$ |
| X496 a or b | C | C | —(CH$_2$)$_3$—C(=O)N(H)—(CH$_2$)$_3$—C(=O)OH | CH$_2$CH$_3$ |
| X497 a or b | C | C | —(CH$_2$)$_4$—C(=O)N(H)—(CH$_2$)$_3$—C(=O)OH | CH$_2$CH$_3$ |
| X498 a or b | C | C | —C(=O)N(H)—CH$_2$—C(=O)O—CH$_3$ | CH$_2$CH$_3$ |
| X499 a or b | C | C | —CH$_2$—C(=O)N(H)—CH$_2$—C(=O)O—CH$_3$ | CH$_2$CH$_3$ |
| X500 a or b | C | C | —(CH$_2$)$_2$—C(=O)N(H)—CH$_2$—C(=O)O—CH$_3$ | CH$_2$CH$_3$ |
| X501 a or b | C | C | —(CH$_2$)$_3$—C(=O)N(H)—CH$_2$—C(=O)O—CH$_3$ | CH$_2$CH$_3$ |
| X502 a or b | C | C | —(CH$_2$)$_4$—C(=O)N(H)—CH$_2$—C(=O)O—CH$_3$ | CH$_2$CH$_3$ |
| X503 a or b | C | C | —C(=O)N(H)—(CH$_2$)$_2$—C(=O)O—CH$_3$ | CH$_2$CH$_3$ |
| X504 a or b | C | C | —CH$_2$—C(=O)N(H)—(CH$_2$)$_2$—C(=O)O—CH$_3$ | CH$_2$CH$_3$ |
| X505 a or b | C | C | —(CH$_2$)$_2$—C(=O)N(H)—(CH$_2$)$_2$—C(=O)O—CH$_3$ | CH$_2$CH$_3$ |
| X506 a or b | C | C | —(CH$_2$)$_3$—C(=O)N(H)—(CH$_2$)$_2$—C(=O)O—CH$_3$ | CH$_2$CH$_3$ |
| X507 a or b | C | C | —(CH$_2$)$_4$—C(=O)N(H)—(CH$_2$)$_2$—C(=O)O—CH$_3$ | CH$_2$CH$_3$ |
| X508 a or b | C | C | —C(=O)N(H)—(CH$_2$)$_3$—C(=O)O—CH$_3$ | CH$_2$CH$_3$ |
| X509 a or b | C | C | —CH$_2$—C(=O)N(H)—(CH$_2$)$_3$—C(=O)O—CH$_3$ | CH$_2$CH$_3$ |
| X510 a or b | C | C | —(CH$_2$)$_2$—C(=O)N(H)—(CH$_2$)$_3$—C(=O)O—CH$_3$ | CH$_2$CH$_3$ |
| X511 a or b | C | C | —(CH$_2$)$_3$—C(=O)N(H)—(CH$_2$)$_3$—C(=O)O—CH$_3$ | CH$_2$CH$_3$ |
| X512 a or b | C | C | —(CH$_2$)$_4$—C(=O)N(H)—(CH$_2$)$_3$—C(=O)O—CH$_3$ | CH$_2$CH$_3$ |
| X513 a or b | C | C | —C(=O)N(H)—CH$_2$—C(=O)O—CH$_2$—CH$_3$ | CH$_2$CH$_3$ |
| X514 a or b | C | C | —CH$_2$—C(=O)N(H)—CH$_2$—C(=O)O—CH$_2$—CH$_3$ | CH$_2$CH$_3$ |
| X515 a or b | C | C | —(CH$_2$)$_2$—C(=O)N(H)—CH$_2$—C(=O)O—CH$_2$—CH$_3$ | CH$_2$CH$_3$ |
| X516 a or b | C | C | —(CH$_2$)$_3$—C(=O)N(H)—CH$_2$—C(=O)O—CH$_2$—CH$_3$ | CH$_2$CH$_3$ |
| X517 a or b | C | C | —(CH$_2$)$_4$—C(=O)N(H)—CH$_2$—C(=O)O—CH$_2$—CH$_3$ | CH$_2$CH$_3$ |
| X518 a or b | C | C | —C(=O)N(H)—(CH$_2$)$_2$—C(=O)O—CH$_2$—CH$_3$ | CH$_2$CH$_3$ |
| X519 a or b | C | C | —CH$_2$—C(=O)N(H)—(CH$_2$)$_2$—C(=O)O—CH$_2$—CH$_3$ | CH$_2$CH$_3$ |
| X520 a or b | C | C | —(CH$_2$)$_2$—C(=O)N(H)—(CH$_2$)$_2$—C(=O)O—CH$_2$—CH$_3$ | CH$_2$CH$_3$ |
| X521 a or b | C | C | —(CH$_2$)$_3$—C(=O)N(H)—(CH$_2$)$_2$—C(=O)O—CH$_2$—CH$_3$ | CH$_2$CH$_3$ |
| X522 a or b | C | C | —(CH$_2$)$_4$—C(=O)N(H)—(CH$_2$)$_2$—C(=O)O—CH$_2$—CH$_3$ | CH$_2$CH$_3$ |
| X523 a or b | C | C | —C(=O)N(H)—(CH$_2$)$_3$—C(=O)O—CH$_2$—CH$_3$ | CH$_2$CH$_3$ |
| X524 a or b | C | C | —CH$_2$—C(=O)N(H)—(CH$_2$)$_3$—C(=O)O—CH$_2$—CH$_3$ | CH$_2$CH$_3$ |
| X525 a or b | C | C | —(CH$_2$)$_2$—C(=O)N(H)—(CH$_2$)$_3$—C(=O)O—CH$_2$—CH$_3$ | CH$_2$CH$_3$ |
| X526 a or b | C | C | —(CH$_2$)$_3$—C(=O)N(H)—(CH$_2$)$_3$—C(=O)O—CH$_2$—CH$_3$ | CH$_2$CH$_3$ |
| X527 a or b | C | C | —(CH$_2$)$_4$—C(=O)N(H)—(CH$_2$)$_3$—C(=O)O—CH$_2$—CH$_3$ | CH$_2$CH$_3$ |
| X528 a or b | C | C | —C(=O)N(CH$_3$)$_2$ | CH$_2$CH$_3$ |
| X529 a or b | C | C | —CH$_2$—C(=O)N(CH$_3$)$_2$ | CH$_2$CH$_3$ |
| X530 a or b | C | C | —(CH$_2$)$_2$—C(=O)N(CH$_3$)$_2$ | CH$_2$CH$_3$ |
| X531 a or b | C | C | —(CH$_2$)$_3$—C(=O)N(CH$_3$)$_2$ | CH$_2$CH$_3$ |
| X532 a or b | C | C | —(CH$_2$)$_4$—C(=O)N(CH$_3$)$_2$ | CH$_2$CH$_3$ |
| X533 a or b | N | C | H | CH$_2$CH$_3$ |
| X534 a or b | N | C | —C(=O)OH | CH$_2$CH$_3$ |
| X535 a or b | N | C | —CH$_2$—C(=O)OH | CH$_2$CH$_3$ |
| X536 a or b | N | C | —(CH$_2$)$_2$—C(=O)OH | CH$_2$CH$_3$ |
| X537 a or b | N | C | —(CH$_2$)$_3$—C(=O)OH | CH$_2$CH$_3$ |
| X538 a or b | N | C | —(CH$_2$)$_4$—C(=O)OH | CH$_2$CH$_3$ |
| X539 a or b | N | C | —C(=O)O—CH$_3$ | CH$_2$CH$_3$ |
| X540 a or b | N | C | —CH$_2$—C(=O)O—CH$_3$ | CH$_2$CH$_3$ |
| X541 a or b | N | C | —(CH$_2$)$_2$—C(=O)O—CH$_3$ | CH$_2$CH$_3$ |
| X542 a or b | N | C | —(CH$_2$)$_3$—C(=O)O—CH$_3$ | CH$_2$CH$_3$ |
| X543 a or b | N | C | —(CH$_2$)$_4$—C(=O)O—CH$_3$ | CH$_2$CH$_3$ |
| X544 a or b | N | C | —C(=O)O—CH$_2$—CH$_3$ | CH$_2$CH$_3$ |
| X545 a or b | N | C | —CH$_2$—C(=O)O—CH$_2$—CH$_3$ | CH$_2$CH$_3$ |
| X546 a or b | N | C | —(CH$_2$)$_2$—C(=O)O—CH$_2$—CH$_3$ | CH$_2$CH$_3$ |
| X547 a or b | N | C | —(CH$_2$)$_3$—C(=O)O—CH$_2$—CH$_3$ | CH$_2$CH$_3$ |
| X548 a or b | N | C | —(CH$_2$)$_4$—C(=O)O—CH$_2$—CH$_3$ | CH$_2$CH$_3$ |
| X549 a or b | N | C | —C(=O)NH$_2$ | CH$_2$CH$_3$ |

TABLE 3-continued

| Compound | U$^1$ | U$^2$ | R$^3$ (for a series) or R$^4$ (for b series) | R$^{8'}$ |
|---|---|---|---|---|
| X550 a or b | N | C | —CH$_2$—C(═O)NH$_2$ | CH$_2$CH$_3$ |
| X551 a or b | N | C | —(CH$_2$)$_2$—C(═O)NH$_2$ | CH$_2$CH$_3$ |
| X552 a or b | N | C | —(CH$_2$)$_3$—C(═O)NH$_2$ | CH$_2$CH$_3$ |
| X553 a or b | N | C | —(CH$_2$)$_4$—C(═O)NH$_2$ | CH$_2$CH$_3$ |
| X554 a or b | N | C | —C(═O)N(H)—CH$_3$ | CH$_2$CH$_3$ |
| X555 a or b | N | C | —CH$_2$—C(═O)N(H)—CH$_3$ | CH$_2$CH$_3$ |
| X556 a or b | N | C | —(CH$_2$)$_2$—C(═O)N(H)—CH$_3$ | CH$_2$CH$_3$ |
| X557 a or b | N | C | —(CH$_2$)$_3$—C(═O)N(H)—CH$_3$ | CH$_2$CH$_3$ |
| X558 a or b | N | C | —(CH$_2$)$_4$—C(═O)N(H)—CH$_3$ | CH$_2$CH$_3$ |
| X559 a or b | N | C | —C(═O)N(H)—CH$_2$—C(═O)OH | CH$_2$CH$_3$ |
| X560 a or b | N | C | —CH$_2$—C(═O)N(H)—CH$_2$—C(═O)OH | CH$_2$CH$_3$ |
| X561 a or b | N | C | —(CH$_2$)$_2$—C(═O)N(H)—CH$_2$—C(═O)OH | CH$_2$CH$_3$ |
| X562 a or b | N | C | —(CH$_2$)$_3$—C(═O)N(H)—CH$_2$—C(═O)OH | CH$_2$CH$_3$ |
| X563 a or b | N | C | —(CH$_2$)$_4$—C(═O)N(H)—CH$_2$—C(═O)OH | CH$_2$CH$_3$ |
| X564 a or b | N | C | —C(═O)N(H)—(CH$_2$)$_2$—C(═O)OH | CH$_2$CH$_3$ |
| X565 a or b | N | C | —CH$_2$—C(═O)N(H)—(CH$_2$)$_2$—C(═O)OH | CH$_2$CH$_3$ |
| X566 a or b | N | C | —(CH$_2$)$_2$—C(═O)N(H)—(CH$_2$)$_2$—C(═O)OH | CH$_2$CH$_3$ |
| X567 a or b | N | C | —(CH$_2$)$_3$—C(═O)N(H)—(CH$_2$)$_2$—C(═O)OH | CH$_2$CH$_3$ |
| X568 a or b | N | C | —(CH$_2$)$_4$—C(═O)N(H)—(CH$_2$)$_2$—C(═O)OH | CH$_2$CH$_3$ |
| X569 a or b | N | C | —C(═O)N(H)—(CH$_2$)$_3$—C(═O)OH | CH$_2$CH$_3$ |
| X570 a or b | N | C | —CH$_2$—C(═O)N(H)—(CH$_2$)$_3$—C(═O)OH | CH$_2$CH$_3$ |
| X571 a or b | N | C | —(CH$_2$)$_2$—C(═O)N(H)—(CH$_2$)$_3$—C(═O)OH | CH$_2$CH$_3$ |
| X572 a or b | N | C | —(CH$_2$)$_3$—C(═O)N(H)—(CH$_2$)$_3$—C(═O)OH | CH$_2$CH$_3$ |
| X573 a or b | N | C | —(CH$_2$)$_4$—C(═O)N(H)—(CH$_2$)$_3$—C(═O)OH | CH$_2$CH$_3$ |
| X574 a or b | N | C | —C(═O)N(H)—CH$_2$—C(═O)O—CH$_3$ | CH$_2$CH$_3$ |
| X575 a or b | N | C | —CH$_2$—C(═O)N(H)—CH$_2$—C(═O)O—CH$_3$ | CH$_2$CH$_3$ |
| X576 a or b | N | C | —(CH$_2$)$_2$—C(═O)N(H)—CH$_2$—C(═O)O—CH$_3$ | CH$_2$CH$_3$ |
| X577 a or b | N | C | —(CH$_2$)$_3$—C(═O)N(H)—CH$_2$—C(═O)O—CH$_3$ | CH$_2$CH$_3$ |
| X578 a or b | N | C | —(CH$_2$)$_4$—C(═O)N(H)—CH$_2$—C(═O)O—CH$_3$ | CH$_2$CH$_3$ |
| X579 a or b | N | C | —C(═O)N(H)—(CH$_2$)$_2$—C(═O)O—CH$_3$ | CH$_2$CH$_3$ |
| X580 a or b | N | C | —CH$_2$—C(═O)N(H)—(CH$_2$)$_2$—C(═O)O—CH$_3$ | CH$_2$CH$_3$ |
| X581 a or b | N | C | —(CH$_2$)$_2$—C(═O)N(H)—(CH$_2$)$_2$—C(═O)O—CH$_3$ | CH$_2$CH$_3$ |
| X582 a or b | N | C | —(CH$_2$)$_3$—C(═O)N(H)—(CH$_2$)$_2$—C(═O)O—CH$_3$ | CH$_2$CH$_3$ |
| X583 a or b | N | C | —(CH$_2$)$_4$—C(═O)N(H)—(CH$_2$)$_2$—C(═O)O—CH$_3$ | CH$_2$CH$_3$ |
| X584 a or b | N | C | —C(═O)N(H)—(CH$_2$)$_3$—C(═O)O—CH$_3$ | CH$_2$CH$_3$ |
| X585 a or b | N | C | —CH$_2$—C(═O)N(H)—(CH$_2$)$_3$—C(═O)O—CH$_3$ | CH$_2$CH$_3$ |
| X586 a or b | N | C | —(CH$_2$)$_2$—C(═O)N(H)—(CH$_2$)$_3$—C(═O)O—CH$_3$ | CH$_2$CH$_3$ |
| X587 a or b | N | C | —(CH$_2$)$_3$—C(═O)N(H)—(CH$_2$)$_3$—C(═O)O—CH$_3$ | CH$_2$CH$_3$ |
| X588 a or b | N | C | —(CH$_2$)$_4$—C(═O)N(H)—(CH$_2$)$_3$—C(═O)O—CH$_3$ | CH$_2$CH$_3$ |
| X589 a or b | N | C | —C(═O)N(H)—CH$_2$—C(═O)O—CH$_2$—CH$_3$ | CH$_2$CH$_3$ |
| X590 a or b | N | C | —CH$_2$—C(═O)N(H)—CH$_2$—C(═O)O—CH$_2$—CH$_3$ | CH$_2$CH$_3$ |
| X591 a or b | N | C | —(CH$_2$)$_2$—C(═O)N(H)—CH$_2$—C(═O)O—CH$_2$—CH$_3$ | CH$_2$CH$_3$ |
| X592 a or b | N | C | —(CH$_2$)$_3$—C(═O)N(H)—CH$_2$—C(═O)O—CH$_2$—CH$_3$ | CH$_2$CH$_3$ |
| X593 a or b | N | C | —(CH$_2$)$_4$—C(═O)N(H)—CH$_2$—C(═O)O—CH$_2$—CH$_3$ | CH$_2$CH$_3$ |
| X594 a or b | N | C | —C(═O)N(H)—(CH$_2$)$_2$—C(═O)O—CH$_2$—CH$_3$ | CH$_2$CH$_3$ |
| X595 a or b | N | C | —CH$_2$—C(═O)N(H)—(CH$_2$)$_2$—C(═O)O—CH$_2$—CH$_3$ | CH$_2$CH$_3$ |
| X596 a or b | N | C | —(CH$_2$)$_2$—C(═O)N(H)—(CH$_2$)$_2$—C(═O)O—CH$_2$—CH$_3$ | CH$_2$CH$_3$ |
| X597 a or b | N | C | —(CH$_2$)$_3$—C(═O)N(H)—(CH$_2$)$_2$—C(═O)O—CH$_2$—CH$_3$ | CH$_2$CH$_3$ |
| X598 a or b | N | C | —(CH$_2$)$_4$—C(═O)N(H)—(CH$_2$)$_2$—C(═O)O—CH$_2$—CH$_3$ | CH$_2$CH$_3$ |
| X599 a or b | N | C | —C(═O)N(H)—(CH$_2$)$_3$—C(═O)O—CH$_2$—CH$_3$ | CH$_2$CH$_3$ |
| X600 a or b | N | C | —CH$_2$—C(═O)N(H)—(CH$_2$)$_3$—C(═O)O—CH$_2$—CH$_3$ | CH$_2$CH$_3$ |
| X601 a or b | N | C | —(CH$_2$)$_2$—C(═O)N(H)—(CH$_2$)$_3$—C(═O)O—CH$_2$—CH$_3$ | CH$_2$CH$_3$ |
| X602 a or b | N | C | —(CH$_2$)$_3$—C(═O)N(H)—(CH$_2$)$_3$—C(═O)O—CH$_2$—CH$_3$ | CH$_2$CH$_3$ |
| X603 a or b | N | C | —(CH$_2$)$_4$—C(═O)N(H)—(CH$_2$)$_3$—C(═O)O—CH$_2$—CH$_3$ | CH$_2$CH$_3$ |
| X604 a or b | N | C | —C(═O)N(CH$_3$)$_2$ | CH$_2$CH$_3$ |
| X605 a or b | N | C | —CH$_2$—C(═O)N(CH$_3$)$_2$ | CH$_2$CH$_3$ |
| X606 a or b | N | C | —(CH$_2$)$_2$—C(═O)N(CH$_3$)$_2$ | CH$_2$CH$_3$ |
| X607 a or b | N | C | —(CH$_2$)$_3$—C(═O)N(CH$_3$)$_2$ | CH$_2$CH$_3$ |
| X608 a or b | N | C | —(CH$_2$)$_4$—C(═O)N(CH$_3$)$_2$ | CH$_2$CH$_3$ |
| X609 a or b | C | N | H | CH$_2$CH$_3$ |
| X610 a or b | C | N | —C(═O)OH | CH$_2$CH$_3$ |
| X611 a or b | C | N | —CH$_2$—C(═O)OH | CH$_2$CH$_3$ |
| X612 a or b | C | N | —(CH$_2$)$_2$—C(═O)OH | CH$_2$CH$_3$ |
| X613 a or b | C | N | —(CH$_2$)$_3$—C(═O)OH | CH$_2$CH$_3$ |
| X614 a or b | C | N | —(CH$_2$)$_4$—C(═O)OH | CH$_2$CH$_3$ |
| X615 a or b | C | N | —C(═O)O—CH$_3$ | CH$_2$CH$_3$ |
| X616 a or b | C | N | —CH$_2$—C(═O)O—CH$_3$ | CH$_2$CH$_3$ |
| X617 a or b | C | N | —(CH$_2$)$_2$—C(═O)O—CH$_3$ | CH$_2$CH$_3$ |
| X618 a or b | C | N | —(CH$_2$)$_3$—C(═O)O—CH$_3$ | CH$_2$CH$_3$ |
| X619 a or b | C | N | —(CH$_2$)$_4$—C(═O)O—CH$_3$ | CH$_2$CH$_3$ |
| X620 a or b | C | N | —C(═O)O—CH$_2$—CH$_3$ | CH$_2$CH$_3$ |
| X621 a or b | C | N | —CH$_2$—C(═O)O—CH$_2$—CH$_3$ | CH$_2$CH$_3$ |
| X622 a or b | C | N | —(CH$_2$)$_2$—C(═O)O—CH$_2$—CH$_3$ | CH$_2$CH$_3$ |
| X623 a or b | C | N | —(CH$_2$)$_3$—C(═O)O—CH$_2$—CH$_3$ | CH$_2$CH$_3$ |
| X624 a or b | C | N | —(CH$_2$)$_4$—C(═O)O—CH$_2$—CH$_3$ | CH$_2$CH$_3$ |
| X625 a or b | C | N | —C(═O)NH$_2$ | CH$_2$CH$_3$ |
| X626 a or b | C | N | —CH$_2$—C(═O)NH$_2$ | CH$_2$CH$_3$ |
| X627 a or b | C | N | —(CH$_2$)$_2$—C(═O)NH$_2$ | CH$_2$CH$_3$ |

TABLE 3-continued

| Compound | U¹ | U² | R³ (for a series) or R⁴ (for b series) | R⁸' |
|---|---|---|---|---|
| X628 a or b | C | N | —(CH$_2$)$_3$—C(=O)NH$_2$ | CH$_2$CH$_3$ |
| X629 a or b | C | N | —(CH$_2$)$_4$—C(=O)NH$_2$ | CH$_2$CH$_3$ |
| X630 a or b | C | N | —C(=O)N(H)—CH$_3$ | CH$_2$CH$_3$ |
| X631 a or b | C | N | —CH$_2$—C(=O)N(H)—CH$_3$ | CH$_2$CH$_3$ |
| X632 a or b | C | N | —(CH$_2$)$_2$—C(=O)N(H)—CH$_3$ | CH$_2$CH$_3$ |
| X633 a or b | C | N | —(CH$_2$)$_3$—C(=O)N(H)—CH$_3$ | CH$_2$CH$_3$ |
| X634 a or b | C | N | —(CH$_2$)$_4$—C(=O)N(H)—CH$_3$ | CH$_2$CH$_3$ |
| X635 a or b | C | N | —C(=O)N(H)—CH$_2$—C(=O)OH | CH$_2$CH$_3$ |
| X636 a or b | C | N | —CH$_2$—C(=O)N(H)—CH$_2$—C(=O)OH | CH$_2$CH$_3$ |
| X637 a or b | C | N | —(CH$_2$)$_2$—C(=O)N(H)—CH$_2$—C(=O)OH | CH$_2$CH$_3$ |
| X638 a or b | C | N | —(CH$_2$)$_3$—C(=O)N(H)—CH$_2$—C(=O)OH | CH$_2$CH$_3$ |
| X639 a or b | C | N | —(CH$_2$)$_4$—C(=O)N(H)—CH$_2$—C(=O)OH | CH$_2$CH$_3$ |
| X640 a or b | C | N | —C(=O)N(H)—(CH$_2$)$_2$—C(=O)OH | CH$_2$CH$_3$ |
| X641 a or b | C | N | —CH$_2$—C(=O)N(H)—(CH$_2$)$_2$—C(=O)OH | CH$_2$CH$_3$ |
| X642 a or b | C | N | —(CH$_2$)$_2$—C(=O)N(H)—(CH$_2$)$_2$—C(=O)OH | CH$_2$CH$_3$ |
| X643 a or b | C | N | —(CH$_2$)$_3$—C(=O)N(H)—(CH$_2$)$_2$—C(=O)OH | CH$_2$CH$_3$ |
| X644 a or b | C | N | —(CH$_2$)$_4$—C(=O)N(H)—(CH$_2$)$_2$—C(=O)OH | CH$_2$CH$_3$ |
| X645 a or b | C | N | —C(=O)N(H)—(CH$_2$)$_3$—C(=O)OH | CH$_2$CH$_3$ |
| X646 a or b | C | N | —CH$_2$—C(=O)N(H)—(CH$_2$)$_3$—C(=O)OH | CH$_2$CH$_3$ |
| X647 a or b | C | N | —(CH$_2$)$_2$—C(=O)N(H)—(CH$_2$)$_3$—C(=O)OH | CH$_2$CH$_3$ |
| X648 a or b | C | N | —(CH$_2$)$_3$—C(=O)N(H)—(CH$_2$)$_3$—C(=O)OH | CH$_2$CH$_3$ |
| X649 a or b | C | N | —(CH$_2$)$_4$—C(=O)N(H)—(CH$_2$)$_3$—C(=O)OH | CH$_2$CH$_3$ |
| X650 a or b | C | N | —C(=O)N(H)—CH$_2$—C(=O)O—CH$_3$ | CH$_2$CH$_3$ |
| X651 a or b | C | N | —CH$_2$—C(=O)N(H)—CH$_2$—C(=O)O—CH$_3$ | CH$_2$CH$_3$ |
| X652 a or b | C | N | —(CH$_2$)$_2$—C(=O)N(H)—CH$_2$—C(=O)O—CH$_3$ | CH$_2$CH$_3$ |
| X653 a or b | C | N | —(CH$_2$)$_3$—C(=O)N(H)—CH$_2$—C(=O)O—CH$_3$ | CH$_2$CH$_3$ |
| X654 a or b | C | N | —(CH$_2$)$_4$—C(=O)N(H)—CH$_2$—C(=O)O—CH$_3$ | CH$_2$CH$_3$ |
| X655 a or b | C | N | —C(=O)N(H)—(CH$_2$)$_2$—C(=O)O—CH$_3$ | CH$_2$CH$_3$ |
| X656 a or b | C | N | —CH$_2$—C(=O)N(H)—(CH$_2$)$_2$—C(=O)O—CH$_3$ | CH$_2$CH$_3$ |
| X657 a or b | C | N | —(CH$_2$)$_2$—C(=O)N(H)—(CH$_2$)$_2$—C(=O)O—CH$_3$ | CH$_2$CH$_3$ |
| X658 a or b | C | N | —(CH$_2$)$_3$—C(=O)N(H)—(CH$_2$)$_2$—C(=O)O—CH$_3$ | CH$_2$CH$_3$ |
| X659 a or b | C | N | —(CH$_2$)$_4$—C(=O)N(H)—(CH$_2$)$_2$—C(=O)O—CH$_3$ | CH$_2$CH$_3$ |
| X660 a or b | C | N | —C(=O)N(H)—(CH$_2$)$_3$—C(=O)O—CH$_3$ | CH$_2$CH$_3$ |
| X661 a or b | C | N | —CH$_2$—C(=O)N(H)—(CH$_2$)$_3$—C(=O)O—CH$_3$ | CH$_2$CH$_3$ |
| X662 a or b | C | N | —(CH$_2$)$_2$—C(=O)N(H)—(CH$_2$)$_3$—C(=O)O—CH$_3$ | CH$_2$CH$_3$ |
| X663 a or b | C | N | —(CH$_2$)$_3$—C(=O)N(H)—(CH$_2$)$_3$—C(=O)O—CH$_3$ | CH$_2$CH$_3$ |
| X664 a or b | C | N | —(CH$_2$)$_4$—C(=O)N(H)—(CH$_2$)$_3$—C(=O)O—CH$_3$ | CH$_2$CH$_3$ |
| X665 a or b | C | N | —C(=O)N(H)—CH$_2$—C(=O)O—CH$_2$—CH$_3$ | CH$_2$CH$_3$ |
| X666 a or b | C | N | —CH$_2$—C(=O)N(H)—CH$_2$—C(=O)O—CH$_2$—CH$_3$ | CH$_2$CH$_3$ |
| X667 a or b | C | N | —(CH$_2$)$_2$—C(=O)N(H)—CH$_2$—C(=O)O—CH$_2$—CH$_3$ | CH$_2$CH$_3$ |
| X668 a or b | C | N | —(CH$_2$)$_3$—C(=O)N(H)—CH$_2$—C(=O)O—CH$_2$—CH$_3$ | CH$_2$CH$_3$ |
| X669 a or b | C | N | —(CH$_2$)$_4$—C(=O)N(H)—CH$_2$—C(=O)O—CH$_2$—CH$_3$ | CH$_2$CH$_3$ |
| X670 a or b | C | N | —C(=O)N(H)—(CH$_2$)$_2$—C(=O)O—CH$_2$—CH$_3$ | CH$_2$CH$_3$ |
| X671 a or b | C | N | —CH$_2$—C(=O)N(H)—(CH$_2$)$_2$—C(=O)O—CH$_2$—CH$_3$ | CH$_2$CH$_3$ |
| X672 a or b | C | N | —(CH$_2$)$_2$—C(=O)N(H)—(CH$_2$)$_2$—C(=O)O—CH$_2$—CH$_3$ | CH$_2$CH$_3$ |
| X673 a or b | C | N | —(CH$_2$)$_3$—C(=O)N(H)—(CH$_2$)$_2$—C(=O)O—CH$_2$—CH$_3$ | CH$_2$CH$_3$ |
| X674 a or b | C | N | —(CH$_2$)$_4$—C(=O)N(H)—(CH$_2$)$_2$—C(=O)O—CH$_2$—CH$_3$ | CH$_2$CH$_3$ |
| X675 a or b | C | N | —C(=O)N(H)—(CH$_2$)$_3$—C(=O)O—CH$_2$—CH$_3$ | CH$_2$CH$_3$ |
| X676 a or b | C | N | —CH$_2$—C(=O)N(H)—(CH$_2$)$_3$—C(=O)O—CH$_2$—CH$_3$ | CH$_2$CH$_3$ |
| X677 a or b | C | N | —(CH$_2$)$_2$—C(=O)N(H)—(CH$_2$)$_3$—C(=O)O—CH$_2$—CH$_3$ | CH$_2$CH$_3$ |
| X678 a or b | C | N | —(CH$_2$)$_3$—C(=O)N(H)—(CH$_2$)$_3$—C(=O)O—CH$_2$—CH$_3$ | CH$_2$CH$_3$ |
| X679 a or b | C | N | —(CH$_2$)$_4$—C(=O)N(H)—(CH$_2$)$_3$—C(=O)O—CH$_2$—CH$_3$ | CH$_2$CH$_3$ |
| X680 a or b | C | N | —C(=O)N(CH$_3$)$_2$ | CH$_2$CH$_3$ |
| X681 a or b | C | N | —CH$_2$—C(=O)N(CH$_3$)$_2$ | CH$_2$CH$_3$ |
| X682 a or b | C | N | —(CH$_2$)$_2$—C(=O)N(CH$_3$)$_2$ | CH$_2$CH$_3$ |
| X683 a or b | C | N | —(CH$_2$)$_3$—C(=O)N(CH$_3$)$_2$ | CH$_2$CH$_3$ |
| X684 a or b | C | N | —(CH$_2$)$_4$—C(=O)N(CH$_3$)$_2$ | CH$_2$CH$_3$ |

TABLE 4
Legend
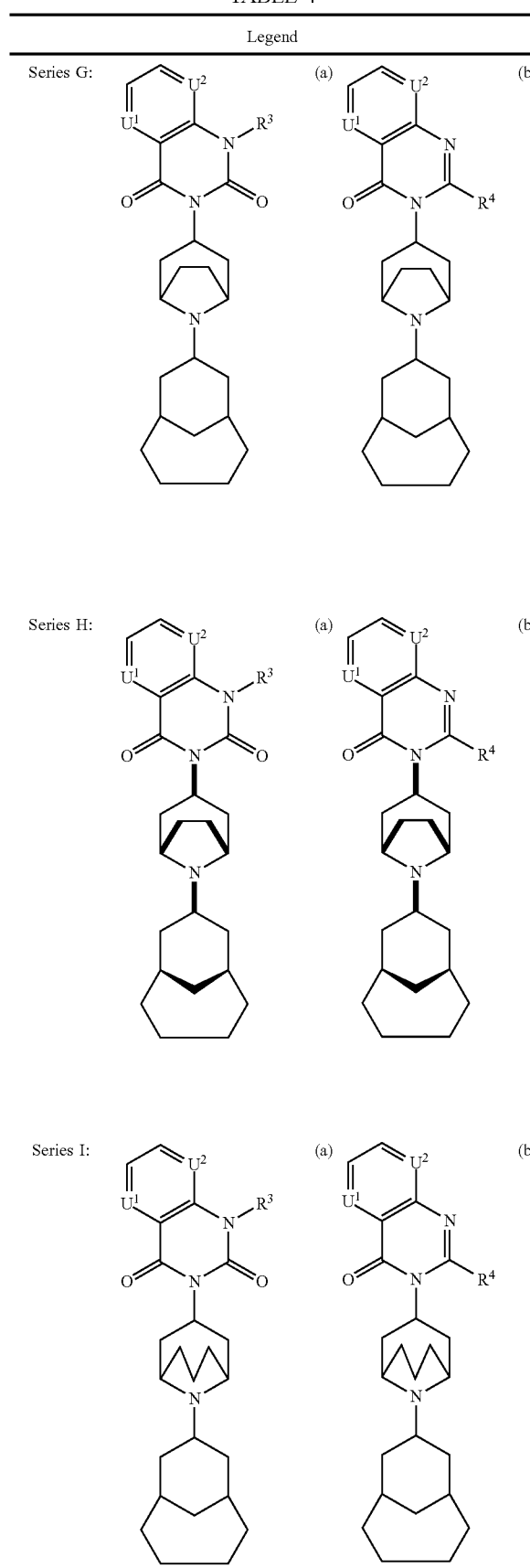
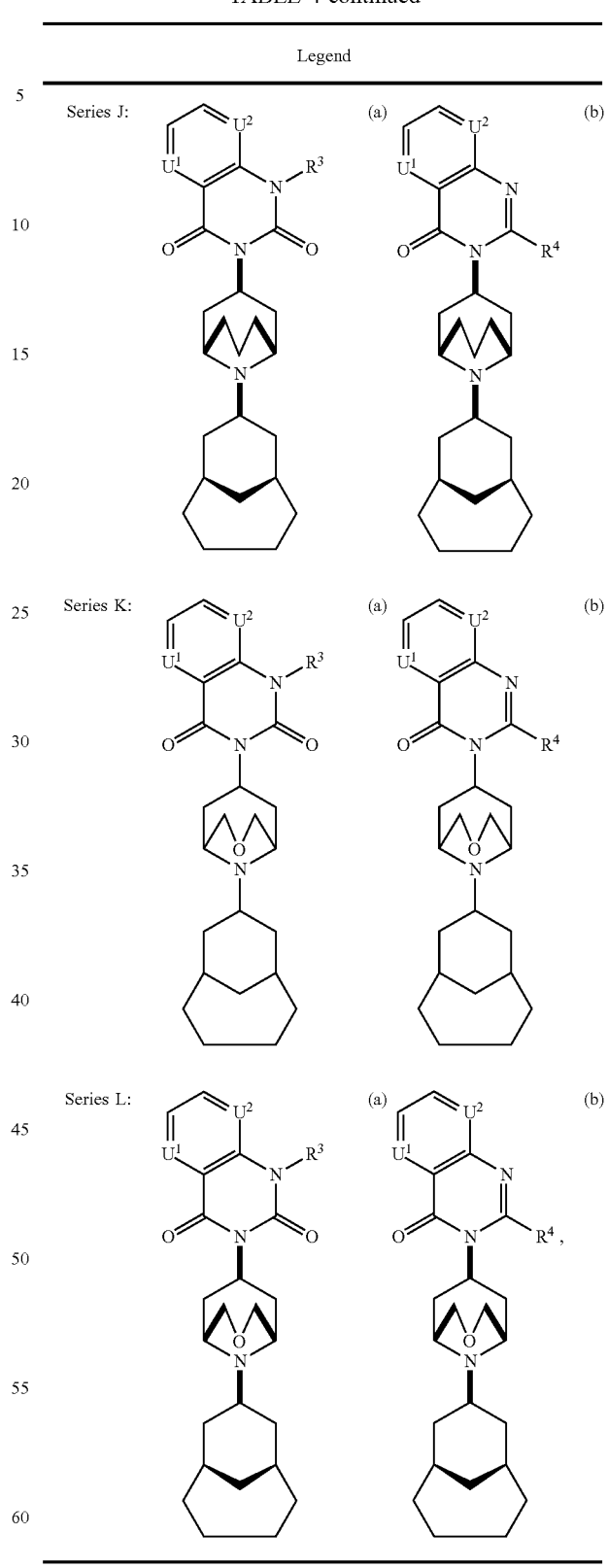
and the pharmaceutically acceptable salts and solvates thereof, where X refers to a compound of a formula of Series G, H, I, J, K, or L. For example, Compound J12b is:

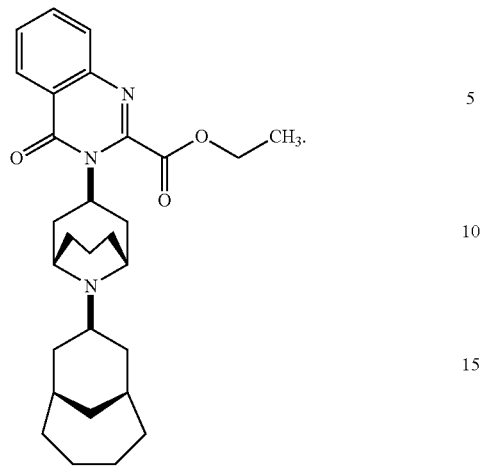

TABLE 4

| Compound | U¹ | U² | R³ (for a series) or R⁴ (for b series) |
|---|---|---|---|
| X1 a or b | C | C | H |
| X2 a or b | C | C | —C(=O)OH |
| X3 a or b | C | C | —CH₂—C(=O)OH |
| X4 a or b | C | C | —(CH₂)₂—C(=O)OH |
| X5 a or b | C | C | —(CH₂)₃—C(=O)OH |
| X6 a or b | C | C | —(CH₂)₄—C(=O)OH |
| X7 a or b | C | C | —C(=O)O—CH₃ |
| X8 a or b | C | C | —CH₂—C(=O)O—CH₃ |
| X9 a or b | C | C | —(CH₂)₂—C(=O)O—CH₃ |
| X10 a or b | C | C | —(CH₂)₃—C(=O)O—CH₃ |
| X11 a or b | C | C | —(CH₂)₄—C(=O)O—CH₃ |
| X12 a or b | C | C | —C(=O)O—CH₂—CH₃ |
| X13 a or b | C | C | —CH₂—C(=O)O—CH₂—CH₃ |
| X14 a or b | C | C | —(CH₂)₂—C(=O)O—CH₂—CH₃ |
| X15 a or b | C | C | —(CH₂)₃—C(=O)O—CH₂—CH₃ |
| X16 a or b | C | C | —(CH₂)₄—C(=O)O—CH₂—CH₃ |
| X17 a or b | C | C | —C(=O)NH₂ |
| X18 a or b | C | C | —CH₂—C(=O)NH₂ |
| X19 a or b | C | C | —(CH₂)₂—C(=O)NH₂ |
| X20 a or b | C | C | —(CH₂)₃—C(=O)NH₂ |
| X21 a or b | C | C | —(CH₂)₄—C(=O)NH₂ |
| X22 a or b | C | C | —C(=O)N(H)—CH₃ |
| X23 a or b | C | C | —CH₂—C(=O)N(H)—CH₃ |
| X24 a or b | C | C | —(CH₂)₂—C(=O)N(H)—CH₃ |
| X25 a or b | C | C | —(CH₂)₃—C(=O)N(H)—CH₃ |
| X26 a or b | C | C | —(CH₂)₄—C(=O)N(H)—CH₃ |
| X27 a or b | C | C | —C(=O)N(H)—CH₂—C(=O)OH |
| X28 a or b | C | C | —CH₂—C(=O)N(H)—CH₂—C(=O)OH |
| X29 a or b | C | C | —(CH₂)₂—C(=O)N(H)—CH₂—C(=O)OH |
| X30 a or b | C | C | —(CH₂)₃—C(=O)N(H)—CH₂—C(=O)OH |
| X31 a or b | C | C | —(CH₂)₄—C(=O)N(H)—CH₂—C(=O)OH |
| X32 a or b | C | C | —C(=O)N(H)—(CH₂)₂—C(=O)OH |
| X33 a or b | C | C | —CH₂—C(=O)N(H)—(CH₂)₂—C(=O)OH |
| X34 a or b | C | C | —(CH₂)₂—C(=O)N(H)—(CH₂)₂—C(=O)OH |
| X35 a or b | C | C | —(CH₂)₃—C(=O)N(H)—(CH₂)₂—C(=O)OH |
| X36 a or b | C | C | —(CH₂)₄—C(=O)N(H)—(CH₂)₂—C(=O)OH |
| X37 a or b | C | C | —C(=O)N(H)—(CH₂)₃—C(=O)OH |
| X38 a or b | C | C | —CH₂—C(=O)N(H)—(CH₂)₃—C(=O)OH |
| X39 a or b | C | C | —(CH₂)₂—C(=O)N(H)—(CH₂)₃—C(=O)OH |
| X40 a or b | C | C | —(CH₂)₃—C(=O)N(H)—(CH₂)₃—C(=O)OH |
| X41 a or b | C | C | —(CH₂)₄—C(=O)N(H)—(CH₂)₃—C(=O)OH |
| X42 a or b | C | C | —C(=O)N(H)—CH₂—C(=O)O—CH₃ |
| X43 a or b | C | C | —CH₂—C(=O)N(H)—CH₂—C(=O)O—CH₃ |
| X44 a or b | C | C | —(CH₂)₂—C(=O)N(H)—CH₂—C(=O)O—CH₃ |
| X45 a or b | C | C | —(CH₂)₃—C(=O)N(H)—CH₂—C(=O)O—CH₃ |
| X46 a or b | C | C | —(CH₂)₄—C(=O)N(H)—CH₂—C(=O)O—CH₃ |
| X47 a or b | C | C | —C(=O)N(H)—(CH₂)₂—C(=O)O—CH₃ |
| X48 a or b | C | C | —CH₂—C(=O)N(H)—(CH₂)₂—C(=O)O—CH₃ |
| X49 a or b | C | C | —(CH₂)₂—C(=O)N(H)—(CH₂)₂—C(=O)O—CH₃ |
| X50 a or b | C | C | —(CH₂)₃—C(=O)N(H)—(CH₂)₂—C(=O)O—CH₃ |
| X51 a or b | C | C | —(CH₂)₄—C(=O)N(H)—(CH₂)₂—C(=O)O—CH₃ |
| X52 a or b | C | C | —C(=O)N(H)—(CH₂)₃—C(=O)O—CH₃ |

TABLE 4-continued

| Compound | $U^1$ | $U^2$ | $R^3$ (for a series) or $R^4$ (for b series) |
|---|---|---|---|
| X53 a or b | C | C | —CH$_2$—C(=O)N(H)—(CH$_2$)$_3$—C(=O)O—CH$_3$ |
| X54 a or b | C | C | —(CH$_2$)$_2$—C(=O)N(H)—(CH$_2$)$_3$—C(=O)O—CH$_3$ |
| X55 a or b | C | C | —(CH$_2$)$_3$—C(=O)N(H)—(CH$_2$)$_3$—C(=O)O—CH$_3$ |
| X56 a or b | C | C | —(CH$_2$)$_4$—C(=O)N(H)—(CH$_2$)$_3$—C(=O)O—CH$_3$ |
| X57 a or b | C | C | —C(=O)N(H)—CH$_2$—C(=O)O—CH$_2$—CH$_3$ |
| X58 a or b | C | C | —CH$_2$—C(=O)N(H)—CH$_2$—C(=O)O—CH$_2$—CH$_3$ |
| X59 a or b | C | C | —(CH$_2$)$_2$—C(=O)N(H)—CH$_2$—C(=O)O—CH$_2$—CH$_3$ |
| X60 a or b | C | C | —(CH$_2$)$_3$—C(=O)N(H)—CH$_2$—C(=O)O—CH$_2$—CH$_3$ |
| X61 a or b | C | C | —(CH$_2$)$_4$—C(=O)N(H)—CH$_2$—C(=O)O—CH$_2$—CH$_3$ |
| X62 a or b | C | C | —C(=O)N(H)—(CH$_2$)$_2$—C(=O)O—CH$_2$—CH$_3$ |
| X63 a or b | C | C | —CH$_2$—C(=O)N(H)—(CH$_2$)$_2$—C(=O)O—CH$_2$—CH$_3$ |
| X64 a or b | C | C | —(CH$_2$)$_2$—C(=O)N(H)—(CH$_2$)$_2$—C(=O)O—CH$_2$—CH$_3$ |
| X65 a or b | C | C | —(CH$_2$)$_3$—C(=O)N(H)—(CH$_2$)$_2$—C(=O)O—CH$_2$—CH$_3$ |
| X66 a or b | C | C | —(CH$_2$)$_4$—C(=O)N(H)—(CH$_2$)$_2$—C(=O)O—CH$_2$—CH$_3$ |
| X67 a or b | C | C | —C(=O)N(H)—(CH$_2$)$_3$—C(=O)O—CH$_2$—CH$_3$ |
| X68 a or b | C | C | —CH$_2$—C(=O)N(H)—(CH$_2$)$_3$—C(=O)O—CH$_2$—CH$_3$ |
| X69 a or b | C | C | —(CH$_2$)$_2$—C(=O)N(H)—(CH$_2$)$_3$—C(=O)O—CH$_2$—CH$_3$ |
| X70 a or b | C | C | —(CH$_2$)$_3$—C(=O)N(H)—(CH$_2$)$_3$—C(=O)O—CH$_2$—CH$_3$ |
| X71 a or b | C | C | —(CH$_2$)$_4$—C(=O)N(H)—(CH$_2$)$_3$—C(=O)O—CH$_2$—CH$_3$ |
| X72 a or b | C | C | —C(=O)N(CH$_3$)$_2$ |
| X73 a or b | C | C | —CH$_2$—C(=O)N(CH$_3$)$_2$ |
| X74 a or b | C | C | —(CH$_2$)$_2$—C(=O)N(CH$_3$)$_2$ |
| X75 a or b | C | C | —(CH$_2$)$_3$—C(=O)N(CH$_3$)$_2$ |
| X76 a or b | C | C | —(CH$_2$)$_4$—C(=O)N(CH$_3$)$_2$ |
| X77 a or b | N | C | H |
| X78 a or b | N | C | —C(=O)OH |
| X79 a or b | N | C | —CH$_2$—C(=O)OH |
| X80 a or b | N | C | —(CH$_2$)$_2$—C(=O)OH |
| X81 a or b | N | C | —(CH$_2$)$_3$—C(=O)OH |
| X82 a or b | N | C | —(CH$_2$)$_4$—C(=O)OH |
| X83 a or b | N | C | —C(=O)O—CH$_3$ |
| X84 a or b | N | C | —CH$_2$—C(=O)O—CH$_3$ |
| X85 a or b | N | C | —(CH$_2$)$_2$—C(=O)O—CH$_3$ |
| X86 a or b | N | C | —(CH$_2$)$_3$—C(=O)O—CH$_3$ |
| X87 a or b | N | C | —(CH$_2$)$_4$—C(=O)O—CH$_3$ |
| X88 a or b | N | C | —C(=O)O—CH$_2$—CH$_3$ |
| X89 a or b | N | C | —CH$_2$—C(=O)O—CH$_2$—CH$_3$ |
| X90 a or b | N | C | —(CH$_2$)$_2$—C(=O)O—CH$_2$—CH$_3$ |
| X91 a or b | N | C | —(CH$_2$)$_3$—C(=O)O—CH$_2$—CH$_3$ |
| X92 a or b | N | C | —(CH$_2$)$_4$—C(=O)O—CH$_2$—CH$_3$ |
| X93 a or b | N | C | —C(=O)NH$_2$ |
| X94 a or b | N | C | —CH$_2$—C(=O)NH$_2$ |
| X95 a or b | N | C | —(CH$_2$)$_2$—C(=O)NH$_2$ |
| X96 a or b | N | C | —(CH$_2$)$_3$—C(=O)NH$_2$ |
| X97 a or b | N | C | —(CH$_2$)$_4$—C(=O)NH$_2$ |
| X98 a or b | N | C | —C(=O)N(H)—CH$_3$ |
| X99 a or b | N | C | —CH$_2$—C(=O)N(H)—CH$_3$ |
| X100 a or b | N | C | —(CH$_2$)$_2$—C(=O)N(H)—CH$_3$ |
| X101 a or b | N | C | —(CH$_2$)$_3$—C(=O)N(H)—CH$_3$ |
| X102 a or b | N | C | —(CH$_2$)$_4$—C(=O)N(H)—CH$_3$ |
| X103 a or b | N | C | —C(=O)N(H)—CH$_2$—C(=O)OH |
| X104 a or b | N | C | —CH$_2$—C(=O)N(H)—CH$_2$—C(=O)OH |
| X105 a or b | N | C | —(CH$_2$)$_2$—C(=O)N(H)—CH$_2$—C(=O)OH |
| X106 a or b | N | C | —(CH$_2$)$_3$—C(=O)N(H)—CH$_2$—C(=O)OH |
| X107 a or b | N | C | —(CH$_2$)$_4$—C(=O)N(H)—CH$_2$—C(=O)OH |
| X108 a or b | N | C | —C(=O)N(H)—(CH$_2$)$_2$—C(=O)OH |
| X109 a or b | N | C | —CH$_2$—C(=O)N(H)—(CH$_2$)$_2$—C(=O)OH |
| X110 a or b | N | C | —(CH$_2$)$_2$—C(=O)N(H)—(CH$_2$)$_2$—C(=O)OH |
| X111 a or b | N | C | —(CH$_2$)$_3$—C(=O)N(H)—(CH$_2$)$_2$—C(=O)OH |
| X112 a or b | N | C | —(CH$_2$)$_4$—C(=O)N(H)—(CH$_2$)$_2$—C(=O)OH |
| X113 a or b | N | C | —C(=O)N(H)—(CH$_2$)$_3$—C(=O)OH |
| X114 a or b | N | C | —CH$_2$—C(=O)N(H)—(CH$_2$)$_3$—C(=O)OH |
| X115 a or b | N | C | —(CH$_2$)$_2$—C(=O)N(H)—(CH$_2$)$_3$—C(=O)OH |
| X116 a or b | N | C | —(CH$_2$)$_3$—C(=O)N(H)—(CH$_2$)$_3$—C(=O)OH |
| X117 a or b | N | C | —(CH$_2$)$_4$—C(=O)N(H)—(CH$_2$)$_3$—C(=O)OH |
| X118 a or b | N | C | —C(=O)N(H)—CH$_2$—C(=O)O—CH$_3$ |
| X119 a or b | N | C | —CH$_2$—C(=O)N(H)—CH$_2$—C(=O)O—CH$_3$ |
| X120 a or b | N | C | —(CH$_2$)$_2$—C(=O)N(H)—CH$_2$—C(=O)O—CH$_3$ |
| X121 a or b | N | C | —(CH$_2$)$_3$—C(=O)N(H)—CH$_2$—C(=O)O—CH$_3$ |
| X122 a or b | N | C | —(CH$_2$)$_4$—C(=O)N(H)—CH$_2$—C(=O)O—CH$_3$ |
| X123 a or b | N | C | —C(=O)N(H)—(CH$_2$)$_2$—C(=O)O—CH$_3$ |
| X124 a or b | N | C | —CH$_2$—C(=O)N(H)—(CH$_2$)$_2$—C(=O)O—CH$_3$ |
| X125 a or b | N | C | —(CH$_2$)$_2$—C(=O)N(H)—(CH$_2$)$_2$—C(=O)O—CH$_3$ |
| X126 a or b | N | C | —(CH$_2$)$_3$—C(=O)N(H)—(CH$_2$)$_2$—C(=O)O—CH$_3$ |
| X127 a or b | N | C | —(CH$_2$)$_4$—C(=O)N(H)—(CH$_2$)$_2$—C(=O)O—CH$_3$ |
| X128 a or b | N | C | —C(=O)N(H)—(CH$_2$)$_3$—C(=O)O—CH$_3$ |
| X129 a or b | N | C | —CH$_2$—C(=O)N(H)—(CH$_2$)$_3$—C(=O)O—CH$_3$ |
| X130 a or b | N | C | —(CH$_2$)$_2$—C(=O)N(H)—(CH$_2$)$_3$—C(=O)O—CH$_3$ |

TABLE 4-continued

| Compound | U$^1$ | U$^2$ | R$^3$ (for a series) or R$^4$ (for b series) |
| --- | --- | --- | --- |
| X131 a or b | N | C | —(CH$_2$)$_3$—C(=O)N(H)—(CH$_2$)$_3$—C(=O)O—CH$_3$ |
| X132 a or b | N | C | —(CH$_2$)$_4$—C(=O)N(H)—(CH$_2$)$_3$—C(=O)O—CH$_3$ |
| X133 a or b | N | C | —C(=O)N(H)—CH$_2$—C(=O)O—CH$_2$—CH$_3$ |
| X134 a or b | N | C | —CH$_2$—C(=O)N(H)—CH$_2$—C(=O)O—CH$_2$—CH$_3$ |
| X135 a or b | N | C | —(CH$_2$)$_2$—C(=O)N(H)—CH$_2$—C(=O)O—CH$_2$—CH$_3$ |
| X136 a or b | N | C | —(CH$_2$)$_3$—C(=O)N(H)—CH$_2$—C(=O)O—CH$_2$—CH$_3$ |
| X137 a or b | N | C | —(CH$_2$)$_4$—C(=O)N(H)—CH$_2$—C(=O)O—CH$_2$—CH$_3$ |
| X138 a or b | N | C | —C(=O)N(H)—(CH$_2$)$_2$—C(=O)O—CH$_2$—CH$_3$ |
| X139 a or b | N | C | —CH$_2$—C(=O)N(H)—(CH$_2$)$_2$—C(=O)O—CH$_2$—CH$_3$ |
| X140 a or b | N | C | —(CH$_2$)$_2$—C(=O)N(H)—(CH$_2$)$_2$—C(=O)O—CH$_2$—CH$_3$ |
| X141 a or b | N | C | —(CH$_2$)$_3$—C(=O)N(H)—(CH$_2$)$_2$—C(=O)O—CH$_2$—CH$_3$ |
| X142 a or b | N | C | —(CH$_2$)$_4$—C(=O)N(H)—(CH$_2$)$_2$—C(=O)O—CH$_2$—CH$_3$ |
| X143 a or b | N | C | —C(=O)N(H)—(CH$_2$)$_3$—C(=O)O—CH$_2$—CH$_3$ |
| X144 a or b | N | C | —CH$_2$—C(=O)N(H)—(CH$_2$)$_3$—C(=O)O—CH$_2$—CH$_3$ |
| X145 a or b | N | C | —(CH$_2$)$_2$—C(=O)N(H)—(CH$_2$)$_3$—C(=O)O—CH$_2$—CH$_3$ |
| X146 a or b | N | C | —(CH$_2$)$_3$—C(=O)N(H)—(CH$_2$)$_3$—C(=O)O—CH$_2$—CH$_3$ |
| X147 a or b | N | C | —(CH$_2$)$_4$—C(=O)N(H)—(CH$_2$)$_3$—C(=O)O—CH$_2$—CH$_3$ |
| X148 a or b | N | C | —C(=O)N(CH$_3$)$_2$ |
| X149 a or b | N | C | —CH$_2$—C(=O)N(CH$_3$)$_2$ |
| X150 a or b | N | C | —(CH$_2$)$_2$—C(=O)N(CH$_3$)$_2$ |
| X151 a or b | N | C | —(CH$_2$)$_3$—C(=O)N(CH$_3$)$_2$ |
| X152 a or b | N | C | —(CH$_2$)$_4$—C(=O)N(CH$_3$)$_2$ |
| X153 a or b | C | N | H |
| X154 a or b | C | N | —C(=O)OH |
| X155 a or b | C | N | —CH$_2$—C(=O)OH |
| X156 a or b | C | N | —(CH$_2$)$_2$—C(=O)OH |
| X157 a or b | C | N | —(CH$_2$)$_3$—C(=O)OH |
| X158 a or b | C | N | —(CH$_2$)$_4$—C(=O)OH |
| X159 a or b | C | N | —C(=O)O—CH$_3$ |
| X160 a or b | C | N | —CH$_2$—C(=O)O—CH$_3$ |
| X161 a or b | C | N | —(CH$_2$)$_2$—C(=O)O—CH$_3$ |
| X162 a or b | C | N | —(CH$_2$)$_3$—C(=O)O—CH$_3$ |
| X163 a or b | C | N | —(CH$_2$)$_4$—C(=O)O—CH$_3$ |
| X164 a or b | C | N | —C(=O)O—CH$_2$—CH$_3$ |
| X165 a or b | C | N | —CH$_2$—C(=O)O—CH$_2$—CH$_3$ |
| X166 a or b | C | N | —(CH$_2$)$_2$—C(=O)O—CH$_2$—CH$_3$ |
| X167 a or b | C | N | —(CH$_2$)$_3$—C(=O)O—CH$_2$—CH$_3$ |
| X168 a or b | C | N | —(CH$_2$)$_4$—C(=O)O—CH$_2$—CH$_3$ |
| X169 a or b | C | N | —C(=O)NH$_2$ |
| X170 a or b | C | N | —CH$_2$—C(=O)NH$_2$ |
| X171 a or b | C | N | —(CH$_2$)$_2$—C(=O)NH$_2$ |
| X172 a or b | C | N | —(CH$_2$)$_3$—C(=O)NH$_2$ |
| X173 a or b | C | N | —(CH$_2$)$_4$—C(=O)NH$_2$ |
| X174 a or b | C | N | —C(=O)N(H)—CH$_3$ |
| X175 a or b | C | N | —CH$_2$—C(=O)N(H)—CH$_3$ |
| X176 a or b | C | N | —(CH$_2$)$_2$—C(=O)N(H)—CH$_3$ |
| X177 a or b | C | N | —(CH$_2$)$_3$—C(=O)N(H)—CH$_3$ |
| X178 a or b | C | N | —(CH$_2$)$_4$—C(=O)N(H)—CH$_3$ |
| X179 a or b | C | N | —C(=O)N(H)—CH$_2$—C(=O)OH |
| X180 a or b | C | N | —CH$_2$—C(=O)N(H)—CH$_2$—C(=O)OH |
| X181 a or b | C | N | —(CH$_2$)$_2$—C(=O)N(H)—CH$_2$—C(=O)OH |
| X182 a or b | C | N | —(CH$_2$)$_3$—C(=O)N(H)—CH$_2$—C(=O)OH |
| X183 a or b | C | N | —(CH$_2$)$_4$—C(=O)N(H)—CH$_2$—C(=O)OH |
| X184 a or b | C | N | —C(=O)N(H)—(CH$_2$)$_2$—C(=O)OH |
| X185 a or b | C | N | —CH$_2$—C(=O)N(H)—(CH$_2$)$_2$—C(=O)OH |
| X186 a or b | C | N | —(CH$_2$)$_2$—C(=O)N(H)—(CH$_2$)$_2$—C(=O)OH |
| X187 a or b | C | N | —(CH$_2$)$_3$—C(=O)N(H)—(CH$_2$)$_2$—C(=O)OH |
| X188 a or b | C | N | —(CH$_2$)$_4$—C(=O)N(H)—(CH$_2$)$_2$—C(=O)OH |
| X189 a or b | C | N | —C(=O)N(H)—(CH$_2$)$_3$—C(=O)OH |
| X190 a or b | C | N | —CH$_2$—C(=O)N(H)—(CH$_2$)$_3$—C(=O)OH |
| X191 a or b | C | N | —(CH$_2$)$_2$—C(=O)N(H)—(CH$_2$)$_3$—C(=O)OH |
| X192 a or b | C | N | —(CH$_2$)$_3$—C(=O)N(H)—(CH$_2$)$_3$—C(=O)OH |
| X193 a or b | C | N | —(CH$_2$)$_4$—C(=O)N(H)—(CH$_2$)$_3$—C(=O)OH |
| X194 a or b | C | N | —C(=O)N(H)—CH$_2$—C(=O)O—CH$_3$ |
| X195 a or b | C | N | —CH$_2$—C(=O)N(H)—CH$_2$—C(=O)O—CH$_3$ |
| X196 a or b | C | N | —(CH$_2$)$_2$—C(=O)N(H)—CH$_2$—C(=O)O—CH$_3$ |
| X197 a or b | C | N | —(CH$_2$)$_3$—C(=O)N(H)—CH$_2$—C(=O)O—CH$_3$ |
| X198 a or b | C | N | —(CH$_2$)$_4$—C(=O)N(H)—CH$_2$—C(=O)O—CH$_3$ |
| X199 a or b | C | N | —C(=O)N(H)—(CH$_2$)$_2$—C(=O)O—CH$_3$ |
| X200 a or b | C | N | —CH$_2$—C(=O)N(H)—(CH$_2$)$_2$—C(=O)O—CH$_3$ |
| X201 a or b | C | N | —(CH$_2$)$_2$—C(=O)N(H)—(CH$_2$)$_2$—C(=O)O—CH$_3$ |
| X202 a or b | C | N | —(CH$_2$)$_3$—C(=O)N(H)—(CH$_2$)$_2$—C(=O)O—CH$_3$ |
| X203 a or b | C | N | —(CH$_2$)$_4$—C(=O)N(H)—(CH$_2$)$_2$—C(=O)O—CH$_3$ |
| X204 a or b | C | N | —C(=O)N(H)—(CH$_2$)$_3$—C(=O)O—CH$_3$ |
| X205 a or b | C | N | —CH$_2$—C(=O)N(H)—(CH$_2$)$_3$—C(=O)O—CH$_3$ |
| X206 a or b | C | N | —(CH$_2$)$_2$—C(=O)N(H)—(CH$_2$)$_3$—C(=O)O—CH$_3$ |
| X207 a or b | C | N | —(CH$_2$)$_3$—C(=O)N(H)—(CH$_2$)$_3$—C(=O)O—CH$_3$ |
| X208 a or b | C | N | —(CH$_2$)$_4$—C(=O)N(H)—(CH$_2$)$_3$—C(=O)O—CH$_3$ |

TABLE 4-continued

| Compound | $U^1$ | $U^2$ | $R^3$ (for a series) or $R^4$ (for b series) |
|---|---|---|---|
| X209 a or b | C | N | —C(=O)N(H)—CH$_2$—C(=O)O—CH$_2$—CH$_3$ |
| X210 a or b | C | N | —CH$_2$—C(=O)N(H)—CH$_2$—C(=O)O—CH$_2$—CH$_3$ |
| X211 a or b | C | N | —(CH$_2$)$_2$—C(=O)N(H)—CH$_2$—C(=O)O—CH$_2$—CH$_3$ |
| X212 a or b | C | N | —(CH$_2$)$_3$—C(=O)N(H)—CH$_2$—C(=O)O—CH$_2$—CH$_3$ |
| X213 a or b | C | N | —(CH$_2$)$_4$—C(=O)N(H)—CH$_2$—C(=O)O—CH$_2$—CH$_3$ |
| X214 a or b | C | N | —C(=O)N(H)—(CH$_2$)$_2$—C(=O)O—CH$_2$—CH3 |
| X215 a or b | C | N | —CH$_2$—C(=O)N(H)—(CH$_2$)$_2$—C(=O)O—CH$_2$—CH$_3$ |
| X216 a or b | C | N | —(CH$_2$)$_2$—C(=O)N(H)—(CH$_2$)$_2$—C(=O)O—CH$_2$—CH$_3$ |
| X217 a or b | C | N | —(CH$_2$)$_3$—C(=O)N(H)—(CH$_2$)$_2$—C(=O)O—CH$_2$—CH$_3$ |
| X218 a or b | C | N | —(CH$_2$)$_4$—C(=O)N(H)—(CH$_2$)$_2$—C(=O)O—CH$_2$—CH$_3$ |
| X219 a or b | C | N | —C(=O)N(H)—(CH$_2$)$_3$—C(=O)O—CH$_2$—CH$_3$ |
| X220 a or b | C | N | —CH$_2$—C(=O)N(H)—(CH$_2$)$_3$—C(=O)O—CH$_2$—CH$_3$ |
| X221 a or b | C | N | —(CH$_2$)$_2$—C(=O)N(H)—(CH$_2$)$_3$—C(=O)O—CH$_2$—CH$_3$ |
| X222 a or b | C | N | —(CH$_2$)$_3$—C(=O)N(H)—(CH$_2$)$_3$—C(=O)O—CH$_2$—CH$_3$ |
| X223 a or b | C | N | —(CH$_2$)$_4$—C(=O)N(H)—(CH$_2$)$_3$—C(=O)O—CH$_2$—CH$_3$ |
| X224 a or b | C | N | —C(=O)N(CH$_3$)$_2$ |
| X225 a or b | C | N | —CH$_2$—C(=O)N(CH$_3$)$_2$ |
| X226 a or b | C | N | —(CH$_2$)$_2$—C(=O)N(CH$_3$)$_2$ |
| X227 a or b | C | N | —(CH$_2$)$_3$—C(=O)N(CH$_3$)$_2$ |
| X228 a or b | C | N | —(CH$_2$)$_4$—C(=O)N(CH$_3$)$_2$ |

4.4 Definitions

As used in connection with the Quinazolin-4(3H)-one-Type Piperidine Compounds disclosed herein, the terms used herein have the following meanings:

"—($C_1$-$C_{10}$)alkyl" means a straight chain or branched non-cyclic hydrocarbon having 1, 2, 3, 4, 5, 6, 7, 8, 9, or 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —($C_1$-$C_8$)alkyl groups, such as methyl, ethyl or propyl, replace one or both hydrogens in a —CH$_2$— group of a straight chain alkyl. A branched non-cyclic hydrocarbon means that one or more straight chain —($C_1$-$C_{10}$)alkyl groups, such as methyl, ethyl or propyl, replace one or both hydrogens in a —CH$_2$— group of a straight chain non-cyclic hydrocarbon. Representative branched —($C_1$-$C_{10}$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—($C_1$-$C_{10}$)alkyl-" means a straight chain or branched non-cyclic hydrocarbon moiety having 1, 2, 3, 4, 5, 6, 7, 8, 9, or 10 carbon atoms where two hydrogen atoms on the same or a different carbon atom of the moiety are each figuratively removed and replaced by a bond to one of the two adjoining groups. Representative —($C_1$-$C_{10}$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, n-deca-1,1-diyl, n-deca-1,2-diyl, n-deca-1,3-diyl, n-deca-1,4-diyl, n-deca-1,5-diyl, n-deca-1,6-diyl, n-deca-1,7-diyl, n-deca-1,8-diyl, n-deca-1,9-diyl, n-deca-1,10-diyl, and the like.

"—($C_1$-$C_6$)alkyl" means a straight chain or branched non-cyclic hydrocarbon having 1, 2, 3, 4, 5, or 6 carbon atoms. Representative straight chain —($C_1$-$C_6$)alkyls include -methyl, -ethyl, -n-propyl, -n-butyl, -n-pentyl, and -n-hexyl. Representative branched —($C_1$-$C_6$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl, and 3,3-dimethylbutyl.

"—($C_1$-$C_6$)alkyl-" means a straight chain or branched non-cyclic hydrocarbon moiety having 1, 2, 3, 4, 5, or 6 carbon atoms where two hydrogen atoms on the same or a different carbon atom of the moiety are each figuratively removed and replaced by a bond to one of the two adjoining groups. Representative —($C_1$-$C_6$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, and the like.

"—($C_1$-$C_4$)alkyl" means a straight chain or branched non-cyclic hydrocarbon having 1, 2, 3, or 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

"—($C_1$-$C_4$)alkyl-" means a straight chain or branched non-cyclic hydrocarbon moiety having 1, 2, 3, or 4 carbon atoms where two hydrogen atoms on the same or a different carbon atom of the moiety are each figuratively removed and replaced by a bond to one of the two adjoining groups. Representative —($C_1$-$C_4$)alkyl- moieties include meth-1,1-diyl, eth-1,1-diyl, eth-1,2-diyl, n-prop-1,1-diyl, n-prop-1,2-diyl, n-prop-1,3-diyl, n-but-1,2-diyl, n-but-1,3-diyl, n-but-1,4-diyl, and the like.

"—($C_1$-$C_3$)alkyl" means a straight chain or branched non-cyclic hydrocarbon having 1, 2, or 3 carbon atoms. Representative straight chain —($C_1$-$C_3$)alkyls include -methyl, -ethyl, -n-propyl. Representative branched —($C_1$-$C_3$)alkyls include -iso-propyl.

"—($C_1$-$C_3$)alkyl-" means a straight chain or branched non-cyclic hydrocarbon moiety having 1, 2, or 3 carbon atoms where two hydrogen atoms on the same or a different carbon atom of the moiety are each figuratively removed and replaced by a bond to one of the two adjoining groups.

Representative —$(C_1-C_3)$alkyl- moieties include meth-1,1-diyl, eth-1,1-diyl, eth-1,2-diyl, n-prop-1,1-diyl, n-prop-1,2-diyl, n-prop-1,3-diyl, and the like.

"—$(C_1-C_2)$alkyl" means a straight chain non-cyclic hydrocarbon having 1 or 2 carbon atoms. Representative —$(C_1-C_2)$alkyls include -methyl and -ethyl.

"—$(C_1-C_2)$alkyl-" means a straight chain non-cyclic hydrocarbon moiety having 1 or 2 carbon atoms where two hydrogen atoms on the same or a different carbon atom of the moiety are each figuratively removed and replaced by a bond to one of the two adjoining groups. Representative —$(C_1-C_2)$alkyl- moieties include meth-1,-diyl, eth-1,1-diyl, and eth-1,2-diyl.

"—$(C_2-C_{10})$alkenyl" means a straight chain or branched non-cyclic hydrocarbon having 2, 3, 4, 5, 6, 7, 8, 9, or 10 carbon atoms and including at least one carbon-carbon double bond. A branched alkenyl means that one or more straight chain —$(C_1-C_5)$alkyl groups, such as methyl, ethyl or propyl, replace one or both hydrogens in a —$CH_2$— or —$CH$= group of a straight chain alkenyl. Representative straight chain and branched $(C_2-C_{10})$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

"—$(C_2-C_{10})$alkenyl-" means a straight chain or branched non-cyclic hydrocarbon moiety having 2, 3, 4, 5, 6, 7, 8, 9, or 10 carbon atoms and including at least one carbon-carbon double bond where two hydrogen atoms on the same or a different carbon atom of the moiety are each figuratively removed and replaced by a bond to one of the two adjoining groups. Representative —$(C_2-C_{10})$alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—$(C_2-C_6)$alkenyl" means a straight chain or branched non-cyclic hydrocarbon having 2, 3, 4, 5, or 6 carbon atoms and including at least one carbon-carbon double bond. Representative straight chain and branched $(C_2-C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, and the like.

"—$(C_2-C_6)$alkenyl-" means a straight chain or branched non-cyclic hydrocarbon moiety having 2, 3, 4, 5, or 6 carbon atoms and including at least one carbon-carbon double bond where two hydrogen atoms on the same or a different carbon atom of the moiety are each figuratively removed and replaced by a bond to one of the two adjoining groups. Representative —$(C_2-C_6)$alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—$(C_2-C_3)$alkenyl" means a straight chain non-cyclic hydrocarbon having 2 or 3 carbon atoms and including at least one carbon-carbon double bond. Representative $(C_2-C_3)$alkenyls include -vinyl, -allyl, and 1-prop-1-enyl.

"—$(C_2-C_3)$alkenyl-" means a straight chain or branched non-cyclic hydrocarbon moiety having 2 or 3 carbon atoms and including at least one carbon-carbon double bond where two hydrogen atoms on the same or a different carbon atom of the moiety are each figuratively removed and replaced by a bond to one of the two adjoining groups. Representative —$(C_2-C_3)$alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, and prop-2-en-1,3-diyl.

"—$(C_2-C_{10})$alkynyl" means a straight chain or branched non-cyclic hydrocarbon having 2, 3, 4, 5, 6, 7, 8, 9, or 10 carbon atoms and including at least one carbon-carbon triple bond. A branched alkynyl means that one or more straight chain —$(C_1-C_8)$alkyl groups, such as methyl, ethyl or propyl, replace one or both hydrogens in a —$CH_2$— group of a straight chain alkynyl. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—$(C_2-C_6)$alkynyl" means a straight chain or branched non-cyclic hydrocarbon having 2, 3, 4, 5, or 6 carbon atoms and including at least one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_1-C_6)$alkoxy" means a straight chain or branched non-cyclic hydrocarbon having one or more ether groups and 1, 2, 3, 4, 5, or 6 carbon atoms. Representative straight chain and branched $(C_1-C_6)$alkoxys include -methoxy, -ethoxy, -methoxymethyl, -2-methoxyethyl, -5-methoxypentyl, -3-ethoxybutyl, (methoxymethoxy)methyl-, 1-(methoxy)-1-methoxyethyl-, trimethoxymethyl-, 2-((methoxy)methoxy)-2-methylpropyl-, 3-(1,1,1-trimethoxypropane), (methoxy)trimethoxymethyl-, (2,2,2-trimethoxyethoxy)-, and the like.

"—$(C_1-C_4)$alkoxy" means a straight chain or branched non-cyclic hydrocarbon having one or more ether groups and 1, 2, 3, or 4 carbon atoms. Representative straight chain and branched $(C_1-C_4)$alkoxys include -methoxy, -ethoxy, -methoxymethyl, -2-methoxyethyl, (methoxymethoxy)methyl-, 1-(methoxy)-1-methoxyethyl-, trimethoxymethyl-, and the like.

"—$(C_3-C_{14})$cycloalkyl" means a saturated monocyclic hydrocarbon having 3, 4, 5, 6, 7, 8, 9, 10, 11, 12, 13, or 14 carbon atoms. Representative $(C_3-C_{14})$cycloalkyls are -cyclopropyl, -cyclobutyl, -cyclopentyl, -cyclohexyl, -cycloheptyl, -cyclooctyl, -cyclononyl, -cyclodecyl, cycloundecyl, -cyclododecyl, and -cyclotetradecyl.

"—$(C_3-C_{12})$cycloalkyl" means a saturated monocyclic hydrocarbon having 3, 4, 5, 6, 7, 8, 9, 10, 11, or 12 carbon atoms. Representative $(C_3-C_{12})$Cycloalkyls are -cyclopropyl, -cyclobutyl, -cyclopentyl, -cyclohexyl, -cycloheptyl, -cyclooctyl, -cyclononyl, -cyclodecyl, -cycloundecyl, and -cyclododecyl.

"—$(C_6-C_{12})$cycloalkyl" means a saturated monocyclic hydrocarbon having 6, 7, 8, 9, 10, 11, or 12 carbon atoms. Representative $(C_6-C_{12})$cycloalkyls are -cyclohexyl, -cycloheptyl, -cyclooctyl, -cyclononyl, -cyclodecyl, -cycloundecyl, and -cyclododecyl.

"—$(C_4-C_8)$cycloalkyl" or "4- to 8-member cycloalkyl ring" means a saturated monocyclic hydrocarbon having 4, 5, 6, 7, or 8 carbon atoms. Representative —$(C_4-C_8)$cycloalkyls are -cyclobutyl, -cyclopentyl, -cyclohexyl, -cycloheptyl, and -cyclooctyl.

"—$(C_3-C_8)$cycloalkyl" means a saturated monocyclic hydrocarbon having 3, 4, 5, 6, 7, or 8 carbon atoms.

Representative $(C_3-C_8)$cycloalkyls include -cyclopropyl, -cyclobutyl, -cyclopentyl, -cyclohexyl, -cycloheptyl, and -cyclooctyl.

"—$(C_3-C_7)$cycloalkyl" means a saturated monocyclic hydrocarbon having 3, 4, 5, 6, or 7 carbon atoms. Representative $(C_3-C_7)$cycloalkyls include cyclopropyl, -cyclobutyl, -cyclopentyl, -cyclohexyl, and -cycloheptyl.

"—$(C_6-C_{14})$bicycloalkyl" means a bicyclic hydrocarbon ring system having 6, 7, 8, 9, 10, 11, 12, 13, or 14 carbon atoms and at least one saturated cyclic alkyl ring. In one embodiment, the —$(C_6-C_{14})$bicycloalkyl has one saturated cyclic alkyl ring. In another embodiment, the —$(C_6-C_{14})$bicycloalkyl has two saturated cyclic alkyl rings. Representative —$(C_6-C_{14})$bicycloalkyls include -indanyl, -norbornyl, -1,2,3,4-tetrahydronaphthyl, -5,6,7,8-tetrahydronaphthyl, -perhydronaphthyl, -bicyclo[2.2.1]hexyl, bicyclo[2.2.1.]heptyl, -bicyclo[2.2.2]octyl, -bicyclo[3.3.1]heptyl, -bicyclo[3.2.1]octyl, -bicyclo[3.3.1]nonyl, -bicyclo[3.3.2]decyl, -bicyclo[3.3.3]undecyl, -bicyclo[4.2.2]decyl, -bicyclo[4.3.2]undecyl, -bicyclo[4.3.1]decyl, and the like.

"—$(C_8-C_{20})$tricycloalkyl" means a tri-cyclic hydrocarbon ring system having 8, 9, 10, 11, 12, 13, 14, 15, 16, 17, 18, 19, or 20 carbon atoms and at least one saturated cyclic alkyl ring; thus, one of the rings can comprise, e.g., benzo. In one embodiment, the —$(C_8-C_{20})$tricycloalkyl has one saturated cyclic alkyl ring. In another embodiment, the —$(C_8-C_{20})$tricycloalkyl has two saturated cyclic alkyl rings. In another embodiment, the —$(C_8-C_{20})$tricycloalkyl has three saturated cyclic alkyl rings. Representative —$(C_8-C_{20})$tricycloalkyls include -pyrenyl, -adamantyl, -noradamantyl, -1,2,3,4-tetrahydroanthracenyl, -1,2,3,4,4a,9,9a,10-octahydroanthracenyl, -perhydroanthracenyl, -aceanthrenyl, -1,2,3,4-tetrahydropenanthrenyl, -5,6,7,8-tetrahydrophenanthrenyl, -1,2,3,4,4a,9,10,10a-octahydrophenanthrenyl, -perhydrophenanthrenyl, -tetradecahydro-1H-cyclohepta[a]naphthyl, -tetradecahydro-1H-cycloocta[e]indenyl, -tetradecahydro-1H-cyclohepta[e]azulenyl, -hexadecahydrocycloocta[b]naphthyl, -hexadecahydrocyclohepta[a]heptalenyl, -tricyclo-pentadecanyl, -tricyclo-octadecanyl, -tricyclo-nonadecanyl, -tricyclo-icosanyl, -2,3-benzobicyclo[2.2.2]octanyl, -6,7-benzobicyclo[3.2.1]octanyl, -9,10-benzobicyclo[3.3.2]decanyl, -2,3,4,4a,9,9a-hexahydro-1H-fluorenyl, -1,2,3,4,4a,8b-hexahydrobiphenylenyl, and the like.

"—$(C_5-C_{14})$cycloalkenyl" means a cyclic non-aromatic hydrocarbon having at least one carbon-carbon double bond in the cyclic system and 5, 6, 7, 8, 9, 10, 11, 12, 13, or 14 carbon atoms.

Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, -cyclododecadienyl, and the like.

"—$(C_5-C_8)$cycloalkenyl" means a cyclic non-aromatic hydrocarbon having at least one carbon-carbon double bond in the cyclic system and 5, 6, 7, or 8 carbon atoms. Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—$(C_7-C_{14})$bicycloalkenyl" means a bicyclic hydrocarbon ring system having at least one carbon-carbon double bond in each ring and 7, 8, 9, 10, 11, 12, 13, or 14 carbon atoms. Representative —$(C_7-C_{14})$bicycloalkenyls include -bicyclo[3.2.0]hept-2-enyl, -indenyl, -pentalenyl, -naphthyl, -azulenyl, -heptalenyl, -1,2,7,8-tetrahydronaphthyl, -norbornenyl, and the like.

"—$(C_8-C_{20})$tricycloalkenyl" means a tricyclic hydrocarbon ring system having at least one carbon-carbon double bond in each ring and 8, 9, 10, 11, 12, 13, 14, 15, 16, 17, 18, 19, or 20 carbon atoms. Representative —$(C_8-C_{20})$tricycloalkenyls include -anthracenyl, -phenanthrenyl, -phenalenyl, -acenaphthyl, -as-indacenyl, -s-indacenyl, -2,3,6,7,8,9,10,11-octahydro-1H-cycloocta[e]indenyl, 2,3,4,7,8,9,10,11-octahydro-1H-cyclohepta[a]naphthyl, -8,9,10,11-tetrahydro-7H-cyclohepta[a]naphthyl, -2,3,4,5,6,7,8,9,10,11,12,13-dodecahydro-1H-cyclohepta[a]heptalenyl, -1,2,3,4,5,6,7,8,9,10,11,12,13,14-tetradecahydro-dicyclohepta[a,c]cyclooctenyl, -2,3,4,5,6,7,8,9,10,11,12,13-dodecahydro-1H-dibenzo[a,d]cyclononenyl, and the like.

"-(3- to 7-membered)heterocycle" or "-(3- to 7-membered)heterocyclo" means a 3- to 7-membered monocyclic heterocyclic ring, i.e., a monocyclic ring comprising at least one heteroatom, which is either saturated, unsaturated non-aromatic or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring, i.e., a monocyclic ring comprising at least one heteroatom, which is either saturated, unsaturated non-aromatic or aromatic. A 5-membered heterocycle can contain 1, 2, 3, or 4 heteroatoms and a 6-membered heterocycle can contain 1, 2, 3, or 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(7- to 10-membered)bicycloheterocycle" or "-(7- to 10-membered)bicycloheterocyclo" means a 7- to 10-membered bicyclic, heterocyclic ring, each ring of which is independently either saturated, unsaturated non-aromatic or aromatic, i.e., where at least one ring comprises at least one heteroatom. A -(7- to 10-membered)bicycloheterocycle contains 1, 2, 3, or 4 heteroatoms independently selected from nitrogen, which can be quaternized; oxygen; and sulfur, including sulfoxide and sulfone. The -(7- to 10-membered) bicycloheterocycle can be attached via a nitrogen or carbon atom. Representative -(7- to 10-membered)bicycloheterocycles include -quinolinyl, -isoquinolinyl, -2,3-dihydrobenzofuranyl, -1,3-dihydroisobenzofuranyl, -benzo[d][1,3]dioxolyl, -2,3-dihydrobenzo[b]thiophenyl, -1,3-dihydrobenzo[c]thiophenyl, -benzo[d][,3]dithiolyl, -chromonyl, -chromanyl, -2,3-dihydrobenzo[b][1,4]dioxinyl, -thiochromonyl, -thiochromanyl, -2,3-dihydrobenzo[b][1,4]dithiinyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -indolinyl, -isoindolinyl, -1,2,3,4-tetrahydroquinolinyl, -1,2,3,4-tetrahydroisoquinolinyl, and the like.

"—$(C_3-C_{12})$cycloalkoxy" means a saturated monocyclic hydrocarbon having 3, 4, 5, 6, 7, 8, 9, 10, 11, or 12 carbon atoms where at least one of the carbon atoms is replaced by an oxygen atom. Representative $(C_3-C_{12})$cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclodecanyl, -1,7-dioxacyclodecanyl, and -1,5,9-trioxacyclododecanyl.

"—$(C_3-C_7)$cycloalkoxy" means a saturated monocyclic hydrocarbon having 3, 4, 5, 6, or 7 carbon atoms where at least one of the carbon atoms is replaced by an oxygen atom. Representative $(C_3-C_7)$cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—$(C_{14})$aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, i.e., a monocyclic aromatic ring comprising at least one heteroatom independently selected from nitrogen, oxygen, and sulfur or a bicyclic aromatic ring where at least one ring comprises at least one heteroatom independently selected from nitrogen, oxygen, and sulfur. In one embodiment, a monocyclic -(5- to 10-membered)heteroaryl comprises at least two heteroatoms independently selected from nitrogen, oxygen, and sulfur. In another embodiment, a bicyclic -(5- to 10-membered)heteroaryl comprises at least two heteroatoms, present in the same or in different rings, each heteroatom being independently selected from nitrogen, oxygen, and sulfur. In another embodiment, one of the -(5- to 10-membered)heteroaryl's rings contain at least one carbon atom. In another embodiment, both of the bicyclic -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members, i.e., a monocyclic aromatic ring comprising at least one heteroatom independently selected from nitrogen, oxygen, and sulfur. In one embodiment, the -(5- or 6-membered)heteroaryl ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—$CH_2(halo)$" means a methyl group where one of the hydrogens of the methyl group has been replaced with a halogen. Representative —$CH_2(halo)$ groups include —$CH_2F$, —$CH_2Cl$, —$CH_2Br$, and —$CH_2I$.

"—$CH(halo)_2$" means a methyl group where two of the hydrogens of the methyl group have each been independently replaced with a halogen. Representative —$CH(halo)_2$ groups include —$CHF_2$, —$CHCl_2$, —$CHBr_2$, —$CHBrCl$, —$CHClI$, and —$CHI_2$.

"—$C(halo)_3$" means a methyl group where each of the hydrogens of the methyl group has been independently replaced with a halogen. Representative —$C(halo)_3$ groups include —$CF_3$, —$CCl_3$, —$CBr_3$, —$Cl_3$, —$CF_2Br$, —$CF_2Cl$, —$CCl_2F$, and —$CFClBr$.

"—Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

"$(C_2-C_6)$bridge" as used herein means a hydrocarbon chain containing 2 to 6 carbon atoms joining two atoms of the piperidine ring of Formula (I) to form a fused bicyclic ring system. For example, compounds of the disclosure can comprise a $(C_2-C_6)$bridge joining positions 2 and 6 of the piperidine ring (A-B can together form a $(C_2-C_6)$bridge). Example compounds of the disclosure include those with an unsubstituted $(C_2)$bridge, —$CH_2$—$CH_2$—, joining positions 2 and 6 of the piperidine ring (A-B can together form a $(C_2)$bridge); an unsubstituted $(C_3)$bridge, —$CH_2$—$CH_2$—$CH_2$—, joining positions 2 and 6 of the piperidine ring (A-B can together form a $(C_3)$bridge); an unsubstituted $(C_4)$ bridge, —$CH_2$—$CH_2$—$CH_2$—$CH_2$—, joining positions 2 and 6 of the piperidine ring (A-B can together form a $(C_4)$bridge); an unsubstituted $(C_5)$bridge, —$CH_2$—$CH_2$—$CH_2$—$CH_2$—$CH_2$—, joining positions 2 and 6 of the piperidine ring (A-B can together form a $(C_5)$bridge); or an unsubstituted $(C_6)$bridge, —$CH_2$—$CH_2$—$CH_2$—$CH_2$—$CH_2$—$CH_2$—, joining positions 2 and 6 of the piperidine ring (A-B can together form a $(C_6)$bridge). Examples of compounds where A-B can together form a $(C_2-C_6)$bridge include compounds comprising the following ring systems: 8-aza-bicyclo[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane. Examples of a $(C_2-C_6)$bridge which contains —HC=CH— within the $(C_2-C_6)$bridge include —HC=CH—, —$CH_2$—HC=CH—, —HC=CH—$CH_2$—, —$CH_2$—HC=CH—$CH_2$—, and the like. Examples of a $(C_2-C_6)$bridge which contains —O— within the $(C_2-C_6)$bridge include —$CH_2$—O—$CH_2$— (containing 2 carbon atoms), —$CH_2$—O—$CH_2$—$CH_2$— and —$CH_2$—$CH_2$—O—$CH_2$— (each containing 3 carbon atoms), —$CH_2$—$CH_2$—O—$CH_2$—$CH_2$—, —$CH_2$—O—$CH_2$—$CH_2$—$CH_2$— and —$CH_2$—$CH_2$—$CH_2$—O—$CH_2$— (each containing 4 carbon atoms), and the like.

"4- to 7-membered $(C_2-C_6)$ring" as used herein means a heterocycling ring having 4, 5, 6, or 7 atoms, wherein the number of atoms in the ring includes the nitrogen atom, and wherein 1 or 2 of the ring carbon atoms is optionally and independently replaced by —O—, —S—, or —$N(R^7)$—. Preferably, the 4- to 7-membered $(C_2-C_6)$ring is a 4- to 7-membered $(C_3-C_6)$ring meaning a heterocycling ring having 4, 5, 6, or 7 atoms, wherein the number of atoms in the ring includes the nitrogen atom, and wherein 1 or 2 of the ring carbon atoms is optionally and independently replaced by —O—, —S—, or —N(R⁷)—.

"4- to 8-membered (C₂-C₇)ring" as used herein means a heterocycling ring having 4, 5, 6, 7, or 8 atoms, wherein the number of atoms in the ring includes the nitrogen atom, which ring is unsubstituted or substituted with 1, 2, 3, or 4 independently selected R⁵ groups, and wherein 1 or 2 of the ring carbon atoms is optionally and independently replaced by —O—, —S—, or —N(R⁷)—. Preferably, the 4- to 8-membered (C₂-C₇)ring is a 4- to 8-membered (C₃-C₇)ring meaning a heterocycling ring having 4, 5, 6, 7, or 8 atoms, wherein the number of atoms in the ring includes the nitrogen atom, which ring is unsubstituted or substituted with 1, 2, 3, or 4 independently selected R⁵ groups, and wherein 1 or 2 of the ring carbon atoms is optionally and independently replaced by —O—, —S—, or —N(R⁷)—.

The terms "benzo," "benzo group," and the like, when used in connection with the Q ring, mean

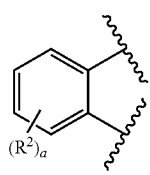

wherein R², and a are defined above for the Quinazolin-4(3H)-one-Type Piperidine Compounds.

The terms "pyridyl," "pyridino," "pyridino group," and the like, when used in connection with the Q ring, mean

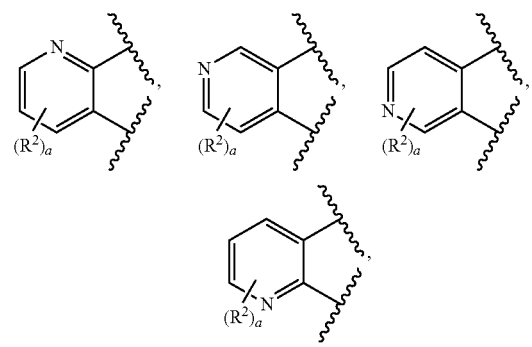

wherein R², and a are defined above for the Quinazolin-4(3H)-one-Type Piperidine Compounds. In the above pyridyl structures, the upper portion of the ring—e.g., the part including the pyridyl nitrogen atom in the first structure—is on the same side of the compound of Formula (I) as the nitrogen directly bonded to R³. Similar spatial relationships hold for the other Q ring embodiments described below.

The position of the pyridyl nitrogen in the Q ring may be expressed in relation to the nitrogen directly bonded to R³ using the following numbering or atoms:

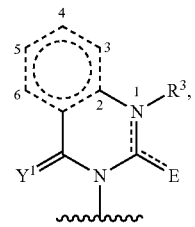

wherein the nitrogen atom, the substitution of the pryridyl and the lower part of Formula I are not shown, and the above structure should not be construed restrictive, but rather illustrative for the atom numbering only.

In one embodiment, the optionally-substituted pyridyl Q ring is

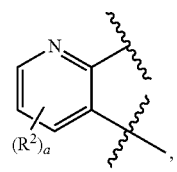

i.e., the pyridyl nitrogen in the Q ring is in a 1,3-relationship with the nitrogen directly bonded to R³. In another embodiment, the optionally-substituted pyridyl Q ring is

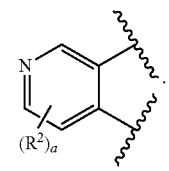

i.e., the pyridyl nitrogen in the Q ring is in a 1,4-relationship with the nitrogen directly bonded to R³.

The position of the pyridyl nitrogen in the Q ring may be expressed in relation to the carbon atom double bonded to Y¹ using the following numbering or atoms:

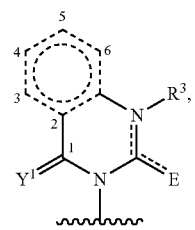

wherein the nitrogen atom, the substitution of the pryridyl and the lower part of Formula I are not shown, and the above structure should not be construed restrictive, but rather illustrative for the atom numbering only.

In another embodiment, the optionally-substituted pyridyl Q ring is

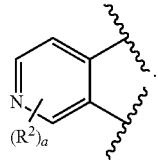

i.e., wherein the pyridyl nitrogen in the Q ring is in a 1,4-relationship with the carbon atom double bonded to $Y^1$. In another embodiment, the optionally-substituted-pyridyl Q ring is

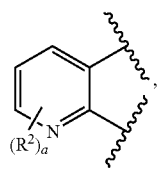

i.e., wherein the pyridyl nitrogen in the Q ring is in a 1,3-relationship with the carbon atom double bonded to $Y^1$.

The terms "pyrimidyl," "pyrimidino", "pyrimidino group," and the like, when used in connection with the optionally-substituted Q ring, mean

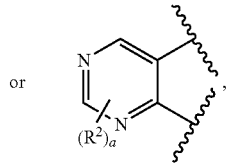

wherein $R^2$ and a are defined above for the Quinazolin-4(3H)-one-Type Piperidine Compounds. In one embodiment, the optionally-substituted pyrimidino Q ring is

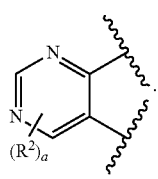

In another embodiment, the optionally-substituted pyrimidino Q ring is

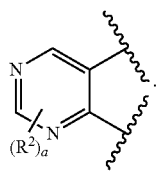

The terms "pyrazinyl," "pyrazino", "pyrazino group," and the like, when used in connection with the optionally-substituted Q ring, mean

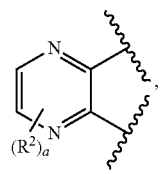

wherein $R^2$ and a are defined above for the Quinazolin-4(3H)-one-Type Piperidine Compounds.

The terms "pyridazinyl," "pyridazino", "pyridazino group," and the like, when used in connection with the optionally-substituted Q ring, mean

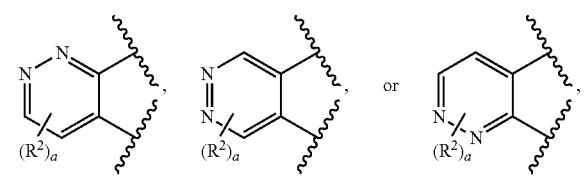

wherein $R^2$ and a are defined above for the Quinazolin-4(3H)-one-Type Piperidine Compounds. In one embodiment, the optionally-substituted pyridazino Q ring is

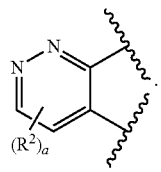

In another embodiment, the optionally-substituted pyridazino Q ring is

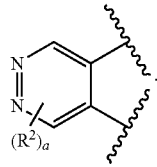

In another embodiment, the optionally-substituted pyridazino Q ring is

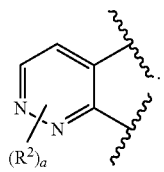

The terms "pyrrolidinyl", "pyrrolino", "pyrrolino group," and the like, when used in connection with the optionally-substituted Q ring, mean

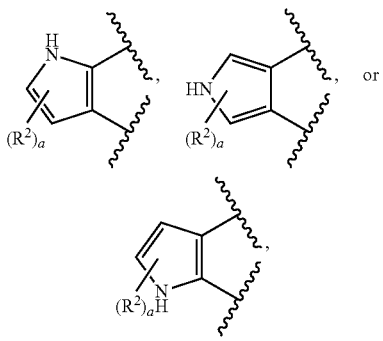

wherein R² and a are defined above for the Quinazolin-4(3H)-one-Type Piperidine Compounds. In one embodiment, the optionally-substituted pyrrolino Q ring is

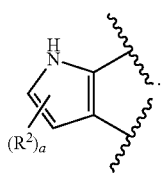

In another embodiment, the optionally-substituted pyrrolino Q ring is

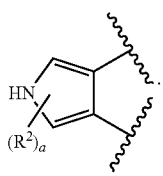

In another embodiment, the optionally-substituted pyrrolino Q ring is

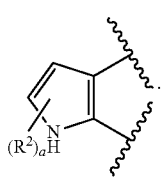

The terms "imidazolyl," "imidazolino", "imidazolino group," and the like, when used in connection with the optionally-substituted Q ring, mean

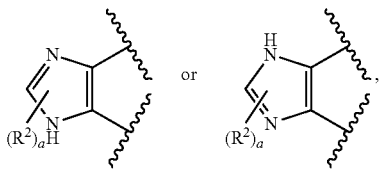

wherein R² and a are defined above for the Quinazolin-4(3H)-one-Type Piperidine Compounds. In one embodiment, the optionally-substituted imidazolino Q ring is

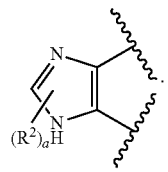

In another embodiment, the optionally-substituted imidazolino Q ring is

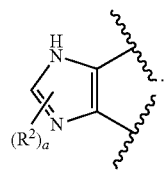

The terms "pyrazolyl," "pyrazolino," "pyrazolino group," and the like, when used in connection with the optionally-substituted Q ring, mean

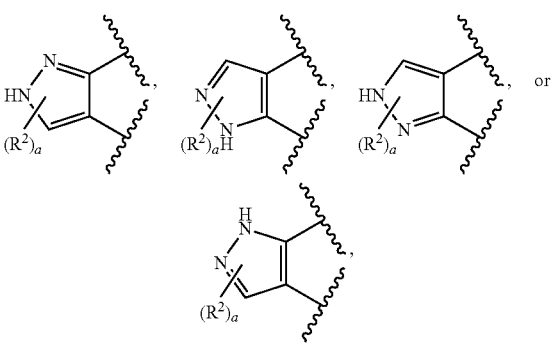

wherein R₂ and a are defined above for the Quinazolin-4(3H)-one-Type Piperidine Compounds. In one embodiment, the optionally-substituted pyrazolino Q ring is

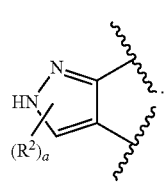

In another embodiment, the optionally-substituted pyrazolino Q ring is

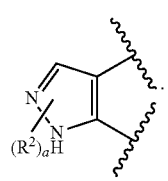

In another embodiment, the optionally-substituted pyrazolino Q ring is

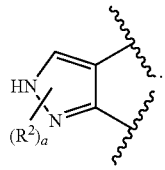

In another embodiment, the optionally-substituted pyrazolino Q ring is

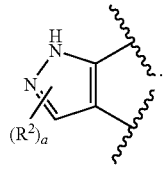

The terms "triazolyl," "triazolino", "triazolino group," and the like, when used in connection with the optionally-substituted Q ring, mean

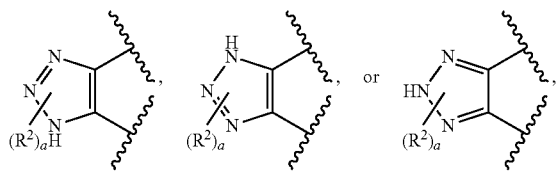

wherein $R^2$ and a are defined above for the Quinazolin-4(3H)-one-Type Piperidine Compounds. In one embodiment, the optionally-substituted triazolino Q ring is

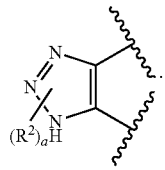

In another embodiment, the optionally-substituted triazolino Q ring is

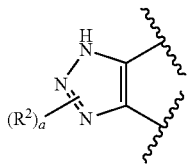

In another embodiment, the optionally-substituted triazolino Q ring is

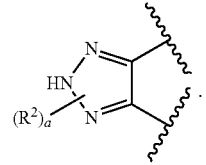

The terms "furyl," "furano," "furano group," and the like, when used in connection with the optionally-substituted Q ring, mean

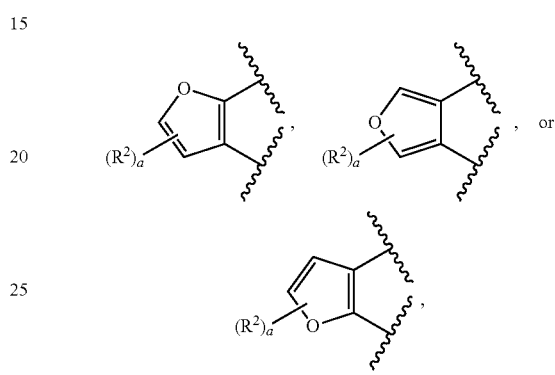

wherein $R^2$ and a are defined above for the Quinazolin-4(3H)-one-Type Piperidine Compounds. In one embodiment, the optionally-substituted furano Q ring is

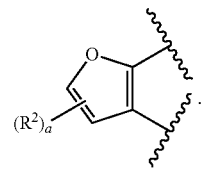

In another embodiment, the optionally-substituted furano Q ring is

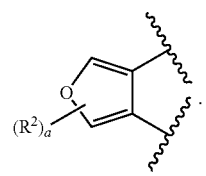

In another embodiment, the optionally-substituted furano Q ring is

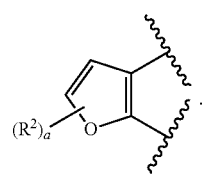

The terms "oxazolyl," "oxazolino," "oxazolino group" and the like, when used in connection with the optionally-substituted Qing, mean

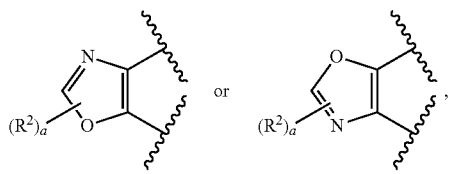

wherein R² and a are defined above for the Quinazolin-4 (3H)-one-Type Piperidine Compounds. In one embodiment, the optionally-substituted oxazolino Q ring is

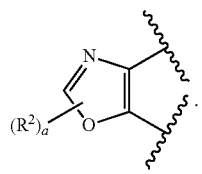

In another embodiment, the optionally-substituted oxazolino Q ring is

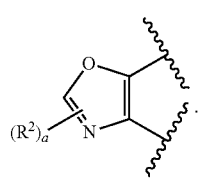

The terms "isoxazolyl," "isoxazolino," "isoxazolino group," and the like, when used in connection with the optionally-substituted Q ring, mean

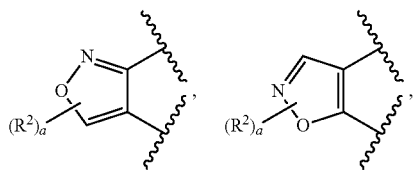

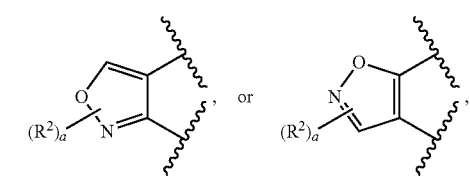

wherein R and a are defined above for the Quinazolin-4 (3H)-one-Type Piperidine Compounds. In one embodiment, the optionally-substituted isoxazolino Q ring is

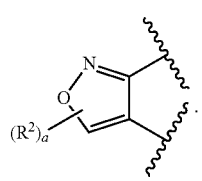

In another embodiment, the optionally-substituted isoxazolino Q ring is

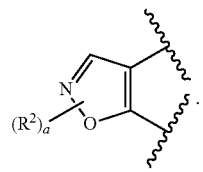

In another embodiment, the optionally-substituted isoxazolino Q ring is

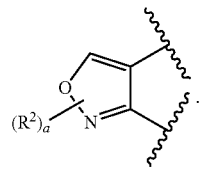

In another embodiment, the optionally-substituted isoxazolino Q ring is

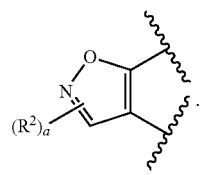

The terms "oxadiazolyl," "oxadiazolino," "oxadiazolino group," and the like, when used in connection with the optionally-substituted Q ring, mean

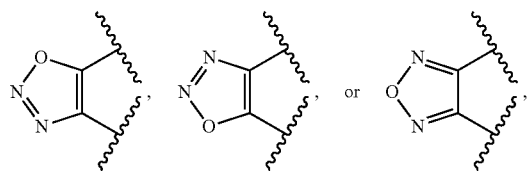

wherein a is 0 and therefore R² is absent. In one embodiment, the oxadiazolino Q ring is

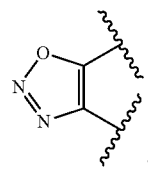

In another embodiment, the oxadiazolino Q ring is

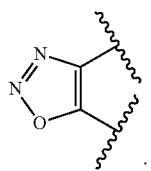 [SMILES: *c1nnoc1*]

In another embodiment, the oxadiazolino Q ring is

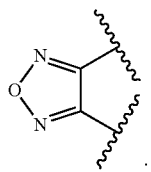

The terms "thienyl," "thiopheno," "thiopheno group," and the like, when used in connection with the optionally-substituted Q ring, mean

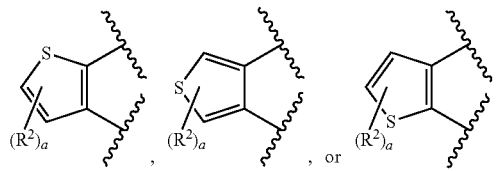

, or , wherein $R^2$ and a are defined above for the Quinazolin-4 (3H)-one-Type Piperidine Compounds. In one embodiment, the optionally-substituted thiopheno Q ring is

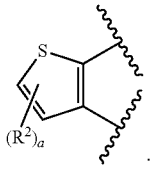

In another embodiment, the optionally-substituted thiopheno Q ring is

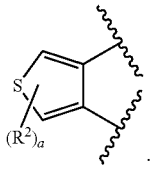

In another embodiment, the optionally-substituted thiopheno Q ring is

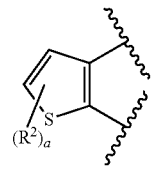

The terms "thiazolyl," "thiazolino," "thiazolino group," and the like, when used in connection with the optionally-substituted Q ring, mean

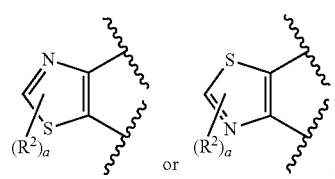

or , wherein $R^2$ and a are defined above for the Quinazolin-4 (3H)-one-Type Piperidine Compounds. In one embodiment, the optionally-substituted thiazolino Q ring is

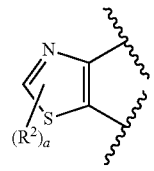

In another embodiment, the optionally-substituted thiazolino Q ring is

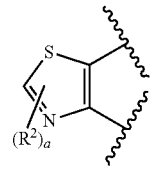

The terms "isothiazolyl," "isothiazolino," "isothiazolino group," and the like, when used in connection with the optionally-substituted Q ring, mean

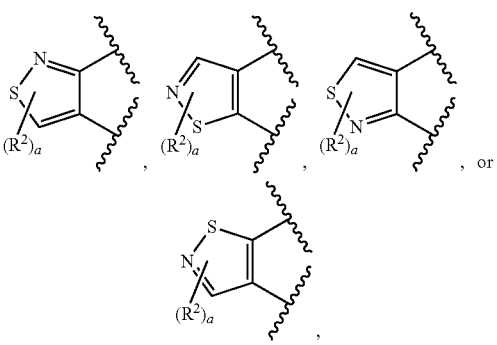

wherein R² and a are defined above for the Quinazolin-4 (3H)-one-Type Piperidine Compounds. In one embodiment, the optionally-substituted isothiazolino Q ring is

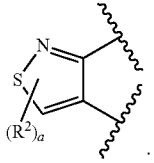

In another embodiment, the optionally-substituted isothiazolino Q ring is

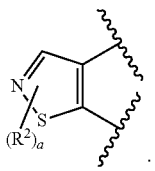

In another embodiment, the optionally-substituted isothiazolino Q ring is

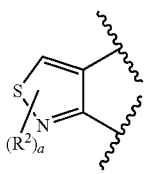

In another embodiment, the optionally-substituted isothiazolino Q ring is

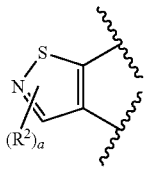

The terms "thiadiazolyl," "thiadiazolino," "thiadiazolino group," and the like, when used in connection with the optionally-substituted Q ring, means

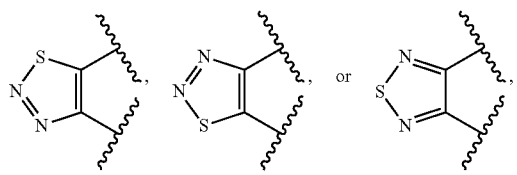

wherein a is 0 and therefore R² is absent. In one embodiment, the optionally-substituted thiadiazolino Q ring is

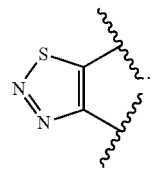 [SMILES: *c1nnsc1*]

In another embodiment, the optionally-substituted thiadiazolino Q ring is

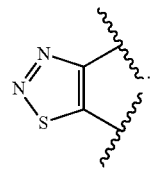

In another embodiment, the optionally-substituted thiadiazolino Q ring is

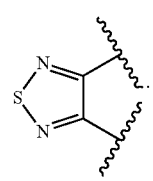 [SMILES: *c1nsnc1*]

In one embodiment, the term "optionally substituted bicyclo[3.3.1]nonyl" and the like when used in connection with the optionally-substituted R¹ group is understood to refer to one of the structures below:

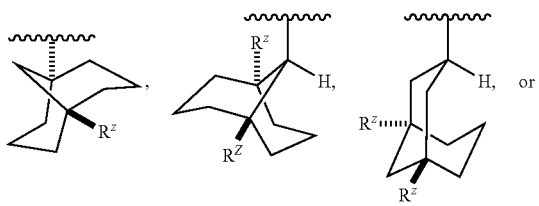

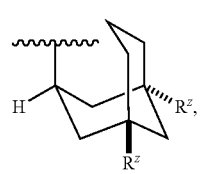

wherein $R^z$ is as defined above for the Quinazolin-4(3H)-one-Type Piperidine Compounds; and where in one or more embodiments, the optionally substituted R¹ group comprises one or more of the above-recited optionally substituted bicycle[3.3.1]nonyl structures.

In one embodiment, the term "optionally substituted —($C_6$-$C_{14}$)bicycloalkyl" means

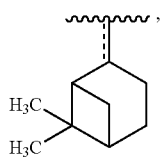

wherein --- denotes a double bond or a single bond at that position. When --- denotes a double bond, then the group above is understood to appear as follows

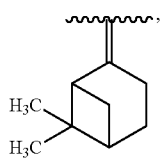

and when --- denotes a single bond, then the optionally substituted —($C_6$-$C_{14}$)bicycloalkyl group above is understood to appear as follows

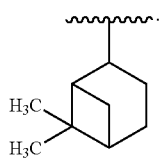

The term "tetrazolyl" and "tetrazolyl group" mean

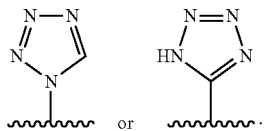

In one embodiment, the tetrazolyl group is

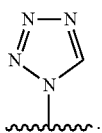

In another embodiment, the tetrazolyl group is

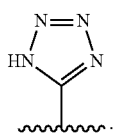

When a first group is "substituted with one or more" second groups, one or more hydrogen atoms of the first group are replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with two second groups. In another embodiment, a first group is substituted with two second groups and each second group is identical. In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

In one embodiment, the Quinazolin-4(3H)-one-Type Piperidine Compound of the present disclosure is in the form of a pharmaceutically acceptable salt, solvate, radiolabeled form, stereoisomer, enantiomer, diastereomer, racemic mixture, or tautomer thereof.

The term "pharmaceutically acceptable salt", as used herein, is any pharmaceutically acceptable salt that can be prepared from a Quinazolin-4(3H)-one-Type Piperidine Compound including a salt formed from an acid and a basic functional group, such as a nitrogen group, of a Quinazolin-4(3H)-one-Type Piperidine Compound, i.e., an "acid addition salt." Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. For example, for a Quinazolin-4(3H)-one-Type Piperidine Compound, a chloride salt can be formed by reacting the compound with HCl to provide the hydrochloride of the Quinazolin-4(3H)-one-Type Piperidine Compound. The term "pharmaceutically acceptable salt" also includes a salt prepared from a Quinazolin-4(3H)-one-Type Piperidine Compound having an acidic functional group, such as a carboxylic acid functional group, and a pharmaceutically acceptable inorganic or organic base, i.e., a "base addition salt." Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxyl-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxytert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, apara-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of a Quinazolin-4(3H)-one-Type Piperidine Compound and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of a Quinazolin-4(3H)-one-Type Piperidine Compound and 0.5 equivalents of fumaric acid. One skilled in the art will recognize that, e.g., acid addition salts, of a Quinazolin-4(3H)-one-Type Piperidine Compound can be prepared by reaction of the compounds with the appropriate acid by a variety of known methods.

In certain embodiments, the pharmaceutically acceptable salt includes two or more salt groups, such as two halide salt groups, and/or a combination of salt types, such as a chloride salt group and a bromide salt group. For example, in some embodiments, the pharmaceutically acceptable salt includes both a base addition salt group and an acid addition salt group. In certain embodiments, the pharmaceutically acceptable salt is a zwitterion.

In certain embodiments, the Quinazolin-4(3H)-one-Type Piperidine Compound is in the form of an anhydrate. The term "anhydrate" as used herein, is any crystalline form of a Quinazolin-4(3H)-one-Type Piperidine Compound in which water molecules are a non-integral part of the crystal. An anhydrate of a Quinazolin-4(3H)-one-Type Piperidine Compound can be prepared, for example, by crystallization from a solvent substantially free of water. In one embodiment, the Quinazolin-4(3H)-one-Type Piperidine Compound is present as an anhydrate, i.e., as a free base where the crystal lattice is substantially free of water molecules and any water molecules present are present as "surface water" (e.g., loosely bound to the crystal's surface) as would be discernable and distinguishable to those in the art by, e.g., thermogravimetric analysis (TGA) and/or differential scanning calorimetry (DSC), from water molecules that are an integral part of the crystal (e.g., a hydrate). An anhydrate of a Quinazolin-4(3H)-one-Type Piperidine Compound has less than about 0.2 mole water in one embodiment, less than about 0.15 mole water in another embodiment, less than about 0.12 mole water in another embodiment, less than about 0.1 mole water in another embodiment, less than about 0.085 mole water in another embodiment, less than about 0.075 mole water in another embodiment, less than about 0.06 mole water in another embodiment, less than about 0.057 mole water in another embodiment, less than about 0.05 mole water in another embodiment, less than about 0.03 mole water in another embodiment, less than about 0.025 mole water in another embodiment, less than about 0.02 mole water in another embodiment, less than about 0.01 mole water in another embodiment, less than about 0.005 mole water in another embodiment, and less than about 0.001 mole water in another embodiment, each said embodiment taking into account the presence of surface water and each said embodiment being per 1 mole of a Quinazolin-4(3H)-one-Type Piperidine Compound.

In some embodiments, the Quinazolin-4(3H)-one-Type Piperidine Compound includes all solvates thereof. "Solvates" are known in the art and are considered in view of this disclosure to be a combination, physical association and/or solvation of a Quinazolin-4(3H)-one-Type Piperidine Compound with a solvent molecule. This physical association can involve varying degrees of ionic and covalent bonding, including hydrogen bonding. When the solvate is of the stoichiometric type, there is a fixed ratio of the solvent molecule to Quinazolin-4(3H)-one-Type Piperidine Compound, e.g., a disolvate, monosolvate or hemisolvate when the solvent molecule:Quinazolin-4(3H)-one-Type Piperidine Compound molecule molar ratio is 2:1, 1:1 or 1:2, respectively. In other embodiments, the solvate is of the nonstoichiometric type. For example, the Quinazolin-4(3H)-one-Type Piperidine Compound crystal can contain solvent molecules in the structural voids, e.g., channels, of the crystal lattice. In certain instances, the solvate can be isolated, for example when one or more solvent molecules are incorporated into the crystal lattice of a crystalline solid. Thus, "solvate", as used herein, encompasses both solution-phase and isolatable solvates. A Quinazolin-4(3H)-one-Type Piperidine Compound can be present as a solvated form with a pharmaceutically acceptable solvent, such as water, methanol, ethanol, and the like, and it is intended that the disclosure include both solvated and unsolvated Quinazolin-4(3H)-one-Type Piperidine Compound forms. As "hydrate" relates to a particular subgroup of solvates, i.e., where the solvent molecule is water, hydrates are included within the solvates of the disclosure. In one embodiment, the Quinazolin-4(3H)-one-Type Piperidine Compound is present as a monohydrate, i.e., as a free base where the water:Quinazolin-4(3H)-one-Type Piperidine Compound molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.*, 93(3): 601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. Sci. Tech.*, 5(1):Article 12 (2004), and Bingham et al., "Over one hundred solvates of sulfathiazole," *Chem. Comm.*, pp. 603-604 (2001). In one embodiment, a non-limiting, process involves dissolving the Quinazolin-4(3H)-one-Type Piperidine Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

In addition, one or more hydrogen, carbon or other atoms of a Quinazolin-4(3H)-one-Type Piperidine Compound can be replaced by a radioactive isotope of the hydrogen, carbon or other atoms. Such a "radiolabeled", "radiolabeled form", and the like of a Quinazolin-4(3H)-one-Type Piperidine Compound, each of which is encompassed by the present disclosure, may be useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Quinazolin-4(3H)-one-Type Piperidine Compound include isotopes of hydrogen, carbon, nitrogen, oxygen, phosphorous, sulfur, fluorine, chlorine, bromine, and iodine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{9}F$, $^{36}Cl$, $^{37}Cl$, $^{76}Br$, $^{77}Br$, $^{81}Br$, $^{123}I$, $^{124}I$, $^{125}I$, and $^{131}I$, respectively. In one embodiment, a radiolabeled Quinazolin-4(3H)-one-Type Piperidine Compound contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Quinazolin-4(3H)-one-Type Piperidine Compound contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Quinazolin-4(3H)-one-Type Piperidine Compound contains 1 radioactive isotope which is selected from hydrogen, carbon, nitrogen, oxygen, phosphorous, sulfur, fluorine, chlorine, bromine, and iodine. In another embodiment, a radiolabeled Quinazolin-4(3H)-one-Type Piperidine Compound contains 1, 2, 3, 4, or more radioactive isotopes, each of which is independently selected from $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Quinazolin-4(3H)-one-Type Piperidine Compound contains 1 or 2 radioactive isotopes, each of which is independently selected from $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Quinazolin-4(3H)-one-Type Piperidine Compound contains 1 radioactive isotope which is selected from $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Quinazolin-4(3H)-one-Type Piperidine Compound contains 1, 2, 3, 4, or more radioactive isotopes, each of which is independently selected from $^{2}H$, $^{3}H$, $^{13}C$, $^{14}C$, $^{15}N$, $^{18}O$, $^{32}P$, and $^{125}I$. In another embodiment, a radiolabeled Quinazolin-4(3H)-one-Type Piperidine Compound contains 1 or 2 radioactive isotopes, each of which is independently selected from $^{3}H$, $^{14}C$, $^{15}N$, $^{18}O$, $^{32}P$, and $^{125}I$. In another embodiment, a radiolabeled Quinazolin-4(3H)-one-Type Piperidine Compound contains 1 radioactive isotope which is selected from $^{3}H$, $^{14}C$, $^{15}N$, $^{18}O$, $^{32}P$, and $^{125}I$.

Radiolabeled compounds of the disclosure can be prepared by methods known in the art. For example, tritiated Quinazolin-4(3H)-one-Type Piperidine Compounds can be prepared by introducing tritium into the particular Quinazolin-4(3H)-one-Type Piperidine Compound, for example, by catalytic dehalogenation with tritium. This method can include reacting a suitably halogen-substituted precursor of a Quinazolin-4(3H)-one-Type Piperidine Compound with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," *Isotopes in the Physical and Biomedical Sciences, Vol.* 1, *Labeled Compounds (Part A)*, E. Buncel et al, eds., Chapter 6, pp. 155-192 (1987). $^{14}C$-labeled compounds can be prepared by employing starting materials having a $^{14}C$ carbon. Compounds containing piperazine isotopcially enriched with $^{13}C$ and/or $^{15}N$ can be prepared as described in, e.g., FIG. 5A and the associated description, of U.S. Pat. No. 7,355,045 B2. Radiolabeled compounds containing $^{18}F$ at the 6-position of an aniline ring can be prepared as described in column 27 of U.S. Pat. No. 6,562,319 B2.

A Quinazolin-4(3H)-one-Type Piperidine Compound can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. When a Quinazolin-4(3H)-one-Type Piperidine Compound contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., lactam-lactim, urea-isourea, ketone-enol, amide-imidic acid, enamine-imine, amine-imine, and enamine-enimine tautomers, are intended to be encompassed by the disclosure as well.

As used herein, the terms "stereoisomer," "stereoisomeric form," and the like are general terms for all isomers of individual molecules that differ only in the orientation of their atoms in space. It includes enantiomers and isomers of compounds with more than one chiral center that are not mirror images of one another ("diastereomers").

The terms "stereogenic center," "asymmetric center," and "chiral center" refer to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Quinazolin-4(3H)-one-Type Piperidine Compound can be obtained by known techniques such as chiral chromatography or formation of diastereomeric salts from an optically active acid or base.

Optical purity can be stated in terms of enantiomeric excess (% ee). Diastereomeric purity can be stated in terms of diastereomeric excess (% de). Enantiomeric excess and diastereomeric excess are determined by the appropriate formula below:

$$\% \ ee = \left[\frac{\text{major enantiomer(mol)} - \text{minor enantiomer(mol)}}{\text{major enantiomer(mol)} + \text{minor enantiomer(mol)}}\right] \times 100\%$$

$$\% \ de = \left[\frac{\text{major diastereomer(mol)} - \text{minor diastereomers(mol)}}{\text{major diastereomer(mol)} + \text{minor diastereomers(mol)}}\right] \times 100\%.$$

The term "MeOH" means methanol, i.e., methyl alcohol. The term "EtOH" means ethanol, i.e., ethyl alcohol. The term "Et$_2$O" means diethyl ether, i.e., ethoxyethane. The term "THF" means tetrahydrofuran. The term "DMF" means N,N-dimethylformamide. The term "DCM" means methylene chloride, i.e., dichloromethane or CH$_2$Cl$_2$. The term "DCE" means 1,2-dichloroethane. The term "EtOAc" means ethyl acetate. The term "MeCN" means acetonitrile. The term "DMSO" means dimethylsulfoxide, i.e., methylsulfinylmethane. The term "NMP" means N-methylpyrrolidinone, i.e., 1-methylpyrrolidin-2-one. The term "DMA" means N,N-dimethylacetamide. The term "MTBE" means tert-butyl methyl ether, i.e., 2-methoxy-2-methylpropane. The term "AcOH" means acetic acid. The term "TFA" means 2,2,2-trifluoroacetic acid. The term "TEA" means triethylamine. The term "DIEA" or "DIPEA" means N,N-di-iso-propylethylamine or N-ethyl-N-iso-propylpropan-2- amine. The term "TMSBr" means trimethylsilyl bromide, i.e., bromotrimethylsilane. The term "TMSCl" means trimethylsilyl chloride or $(CH_3)_3SiCl$.

The term "Bn" means benzyl, i.e.:

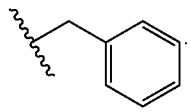

The term "BOC" means tert-butyloxycarbonyl, i.e.:

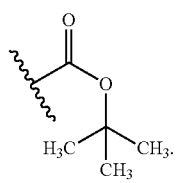

The term "mesylate" means:

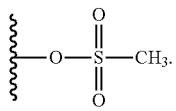

The term "tosylate" means:

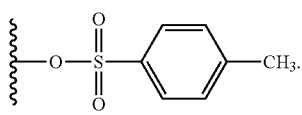 [SMILES: *OS(=O)(=O)c1ccc(C)cc1]

The term "IBD" means inflammatory-bowel disease. The term "IBS" means irritable-bowel syndrome. The term "ALS" means amyotrophic lateral sclerosis.

The term "effective amount," when used in connection with a Quinazolin-4(3H)-one-Type Piperidine Compound, means an amount effective for: (a) treating or preventing a Condition or symptom thereof; (b) detectably inhibiting ORL-1 receptor function in a cell; or (c) detectably activating ORL-1 receptor function in a cell.

The term "effective amount," when used in connection with a second therapeutic agent, means an amount for providing the therapeutic effect of the second therapeutic agent.

The terms "modulate," "modulating," and the like as used herein with respect to the ORL-1 receptor mean the mediation of a pharmacodynamic response (e.g., analgesia) in an animal from (i) inhibiting the receptor, (ii) activating the receptor, or (iii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist." As used herein, a compound that binds to a receptor and is only partly effective as an agonist is defined as a "partial agonist." As used herein, a compound that binds to a receptor but produces no regulatory effect, but rather blocks binding of another agent to the receptor is defined as an "antagonist." (See Ross et al., "Pharmacodynamics: Mechanisms of Drug Action and the Relationship Between Drug Concentration and Effect," in Goodman & Gilman's The Pharmacological Basis of Therapeutics pp. 31-43 (Goodman et al., eds., $10^{th}$ Ed., McGraw-Hill, New York 2001)).

The terms "treatment of," "treating," and the like include the amelioration or cessation of a Condition or a symptom thereof. In one embodiment, treating includes inhibiting, for example, decreasing the overall frequency of episodes of a Condition or a symptom thereof.

The terms "prevention of," "preventing," and the like include the avoidance of the onset of a Condition or a symptom thereof.

A "disorder" includes, but is not limited to, the Conditions defined herein.

In the event of doubt as to the agreement of a depicted chemical structure and a chemical name, the depicted chemical structure governs.

It is appreciated that various features of the present disclosure which are, for clarity, described in the context of separate embodiments, can also be provided in combination in a single embodiment unless otherwise specifically herein excluded. Conversely, various features of the present disclosure which are, for brevity, described in the context of a single embodiment, can also be provided separately and/or in any suitable subcombination unless otherwise specifically herein excluded.

4.5 Methods for Making Quinazolin-4(3H)-One-Type Piperidine Compounds

Quinazolin-4(3H)-one-Type Piperidine Compounds can be made in view of the present disclosure, for example, including the following illustrative methods shown in the Schemes below, and in combination with conventional organic synthesis techniques. In the below Schemes, $R^1$, $R^2$, $R^3$, $R^4$, Q, $Y^1$, $Y^2$, Z, A, B, E, a and any other variables are defined above; L is a leaving group, such as a halogen leaving group (for example, chloro, bromo, or iodo), a hydroxyl group, an alkoxy group, or the like; LA is a Lewis acid, such as a silicon-based Lewis acid (such as a trialkyl-silyl-halide or triflate, for example, TMS-Cl), a transition metal Lewis acid (such as aluminum or titanium halides or alkoxides), or a boron-based Lewis acid (such as boron trifluroride diethyletherate); PG is a protecting group, such as those described in "Protective Groups in Organic Synthesis," $4^{th}$ Ed. by Greene and Wuts (New York: Wiley & Sons, Inc., 2006); and R' and R", independently, are carbon groups (such as —$(C_1-C_6,)$alkyl, benzyl, etc.). For simplicity, in the following Schemes, the exemplary Q ring is benzo which is sometimes unsubstituted with $R^2$; however, the schemes are also applicable to substituted benzo and any of the (5- or 6-membered) heteroaryl Q rings, whether unsubstituted or optionally substituted.

4.5.1 Scheme A—Preparation of Intermediate Diamine A7

In some embodiments, preparation of Quinazolin-4(3H)-one-Type Piperidine Compounds proceeds through use of intermediate diamines of structure A7. In certain embodiments, preparation of A7 proceeds according to Scheme A:

Scheme A

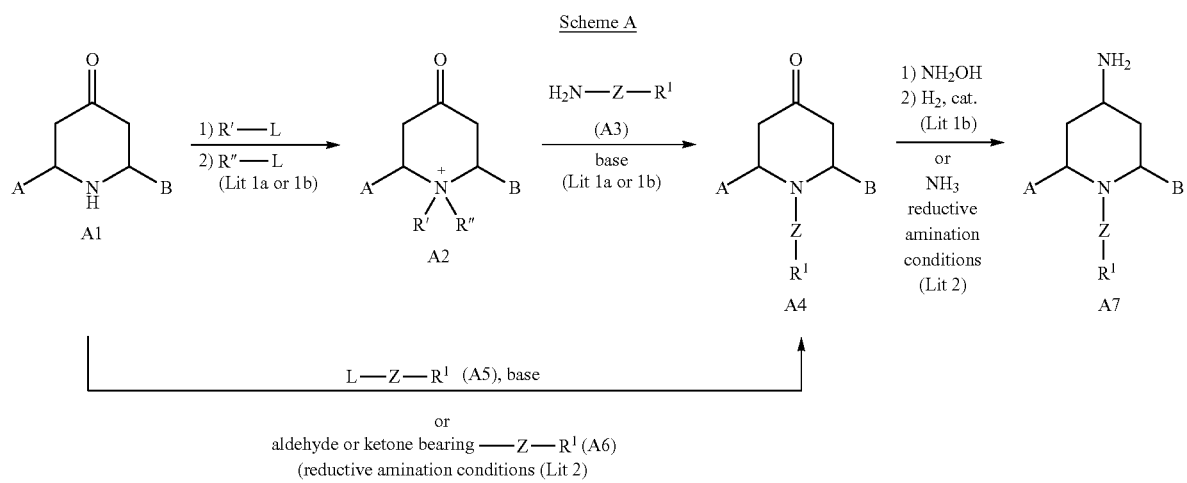

As depicted in Scheme A, in some embodiments, compounds of structure A1 are subject to two displacement reactions resulting in double alkylation of A1 to afford A2 (counter anion not pictured), for example, according to Lit 1a (Tortolani et al., "A Convenient Synthesis to N-Aryl-Substituted 4-Piperidones," *Org. Lett.* 1:1261-1262 (1999)) and/or Lit 1b (International PCT Publication No. WO 2005/075459 of Euro-Celtique S.A.). Subsequently, in certain embodiments, A2 is treated with A3, an amine bearing the —Z—R¹ group, to afford substituted amine A4, for example, according to Lit 1a and/or Lit 1b. In other embodiments, A4 is prepared by displacement reaction between A1 and A5, an electrophile bearing the —Z—R¹ group, under basic conditions, for example, according to Lit 2 (U.S. Pat. No. 6,635,653 by Goehring et al.). In an alternate embodiment, amine A1 is subjected to reductive amination conditions with A6, an appropriate aldehyde or ketone bearing the —Z—R¹ group, to afford amine A4, for example, according to Lit 2.

Regardless of its preparation, in some embodiments, A4 can be subjected to reductive amination conditions with hydroxyl amine followed by hydrogenation with hydrogen and the appropriate catalyst (such as a noble metal catalyst, such as a palladium catalyst) to afford intermediate diamine A7, for example, according to Lit 1b. In other embodiments, A4 is subjected to reductive amination conditions with ammonia or an equivalent reagent to afford intermediate diamine A7, for example, according to Lit 2. Compounds of structure A1 are commercially available or can be synthesized by routine methods in the art.

4.5.2 Scheme B—Preparation of Intermediate Arylamine B3 from Intermediate Diamine A7

In some embodiments, preparation of Quinazolin-4(3H)-one-Type Piperidine Compounds proceeds through use of intermediate arylamines of structure B3. In certain embodiments, preparation of B3 proceeds via intermediate diamine A7 according to Scheme B:

Scheme B

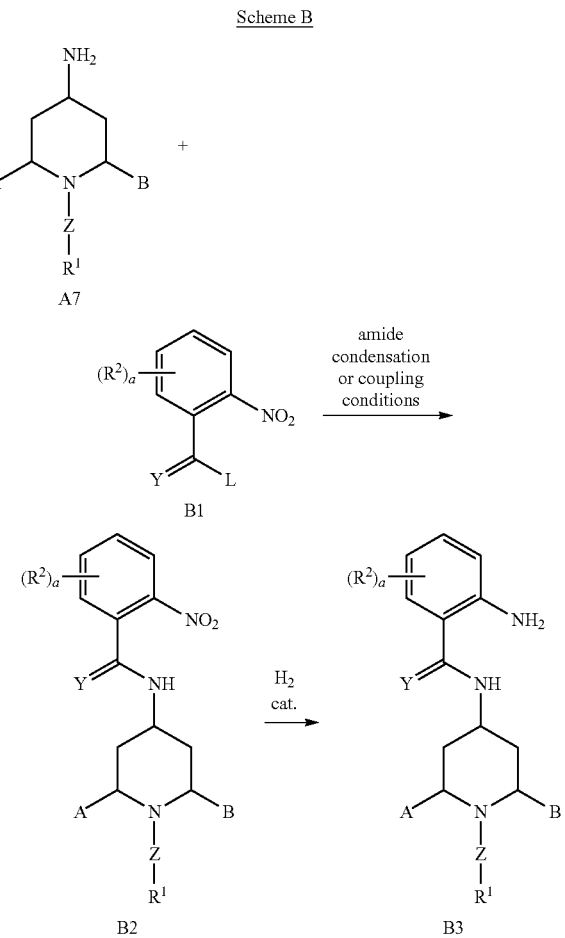

As depicted in Scheme B, in some embodiments, intermediate diamines of structure A7 are coupled with activated arylcarbonyls or thiocarbonyls of structure B1 to afford coupling products B2. In certain embodiments, subsequent reduction of the nitro group of B2 affords intermediate arylamine B3. Alternatively, the activated arylcarbonyl or thiocarbonyl B1 may possess a protected amine in place of the nitro group (not pictured), and this amine can be deprotected following coupling with A7 to afford intermediate arylamine B3.

4.5.3 Scheme C—Preparation of Quinazolin-4(3H)-One-Type Piperidine Compounds from Intermediate Arylamine B3

In some embodiments, preparation of Quinazolin-4(3H)-one-Type Piperidine Compounds proceeds through use of intermediate arylamines of structure B3 according to Scheme C:

C2 and C3 is a displacement reaction. In other embodiments, the reaction between C2 and C3 is an amide coupling or condensation reaction.

In other embodiments, intermediate arylamines of structure B3 are reacted with C5, a singly activated carbonyl or thiocarbonyl bearing the —$R^4$ group (such as esters or acid halides), to yield amide coupling or condensation product C6. In some embodiments, C6 can undergo internal condensation in the presence of a Lewis acid or heat to afford condensation product C7, which is a compound according to

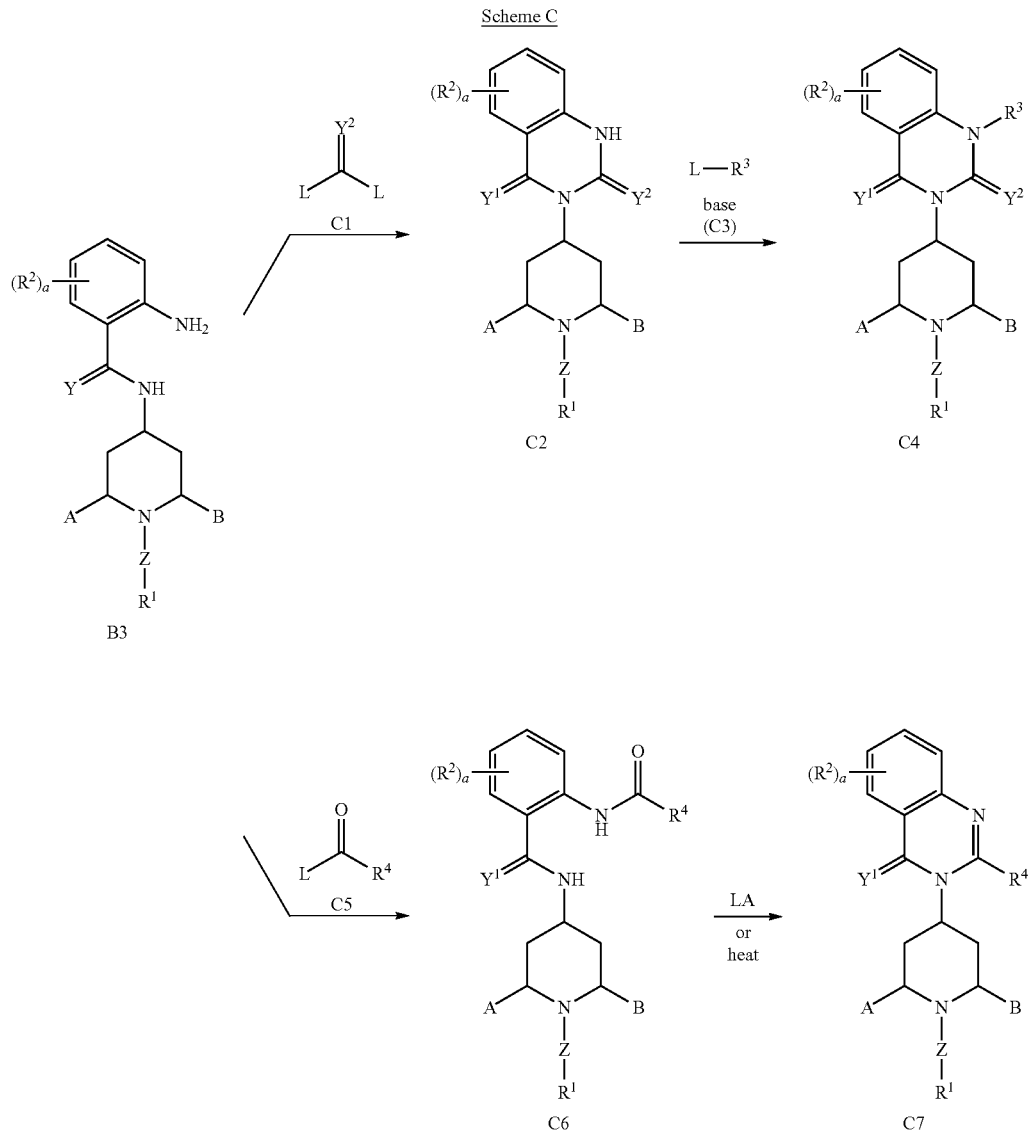

As depicted in Scheme C, in some embodiments, intermediate arylamines of structure B3 are reacted with C1, a doubly activated carbonyl or thiocarbonyl (such as phosgene, thiophosgene, diphosgene, or triphosgene), often at elevated temperatures to afford condensation product C2. In certain embodiments, the amide proton of C2 is subsequently deprotonated with strong base followed by reaction with C3, an electrophile bearing the —$R^3$ group, to afford C4, which is a compound according to Formula (I), wherein the --- connected to E denotes a double bond, $R^1$ is present, and E is $Y^1$. In certain embodiments, the reaction between Formula (I), wherein the --- connected to $N(R^3)$ denotes a double bond, $R^3$ is absent, and E is $R^4$.

4.5.4 Scheme D—Preparation of Quinazolin-4(3H)-One-Type Piperidine Compounds Via Late Stage Installation of the —Z—$R^1$ Group In alternate embodiments, preparation of Quinazolin-4(3H)-one-Type Piperidine Compounds involves installation of the —Z—$R^1$ group at a later stage of the synthesis according to Scheme D:

Scheme D

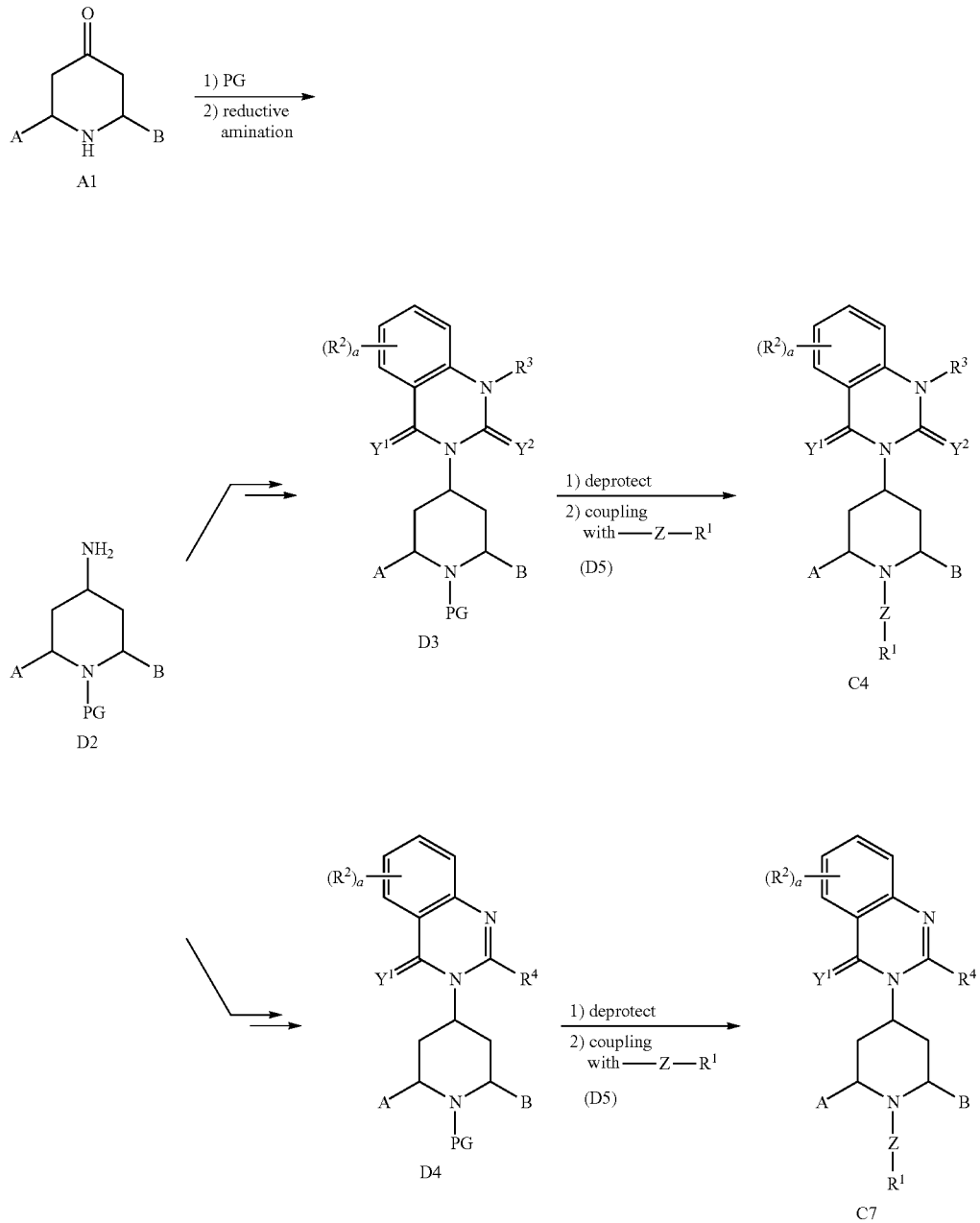

As depicted in Scheme D, in some embodiments, amines with structure A1 are initially protected to afford amine-protected compounds D1 (not pictured). For example, in some embodiments, the amino group of D1 is protected by a benzyl group (which can be removed later by hydrogenation) or by a carbonyl group (which can be removed later by amide hydrolysis). In certain embodiments, the carbonyl of amine-protected compounds D1 is converted to an amine under similar conditions to that noted above for A4 (e.g., Lit 1b or 2) to afford mono-protected diamines D2. In certain embodiments, D2 is then processed through several steps analogously to B3 in Scheme C to afford protected amines D3 or D4. In some embodiments, either D3 or D4 is then deprotected, followed by coupling with D5, a reagent bearing the —Z—$R^1$ group, for example, under conditions similar to those noted above for preparing A4 (e.g., Lit 1a, 1b, and 2), to afford either coupling product C4, which is a compound according to Formula (I), wherein the --- connected to E denotes a double bond, $R^1$ is present, and E is $Y^2$, or coupling product C7, which is a compound according to Formula (I), wherein the --- connected to $N(R^3)$ denotes a double bond, $R^3$ is absent, and E is $R^4$.

4.5.5 Scheme E—Preparation of Quinazolin-4(3H)-One-Type Piperidine Compounds Via Late Stage Installation of the —$R^4$ Group In alternate embodiments, preparation of Quinazolin-4 (3H)-one-Type Piperidine Compounds involves installation of the —$R^4$ group at a later stage of the synthesis according to Scheme E:

Scheme E

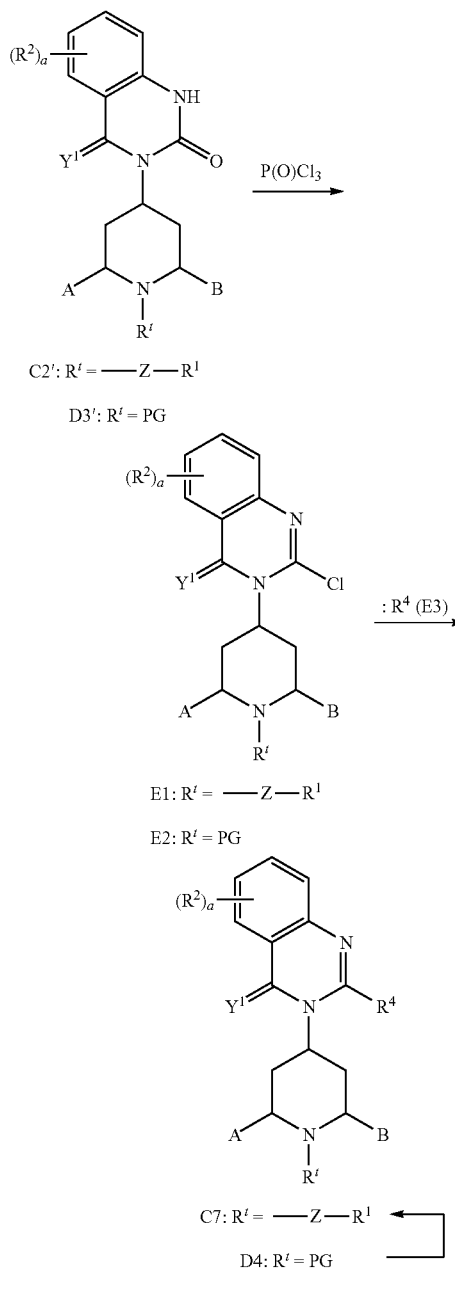

As depicted in Scheme E, in some embodiments, amines with structure C2' (which is analogous to C2, wherein $Y^2$ is O, and may be prepared in similar fashion as C2), are reacted with phosphoryl chloride or an equivalent halogenating agent (such as thionyl chloride, phosphorus trichloride, or phosphorus pentachloride; see Dudash et al., "Synthesis and evaluation of 3-anilino-quinoxalinones as glycogen phosphorylase inhibitors," *Bioorg. Med. Chem. Lett.*, 15(21): 4790-4793 (2005); Pizey, "Thionyl Chloride," Ch. 4 in *Synthetic Reagents*, John Wiley & Sons, New York, Vol. 1, pp. 321-357 (1974)) to afford chlorinated compounds E1. Similarly, in some embodiments, protected amines with structure D3' (which is analogous to D3, wherein $Y^2$ is O and $R^3$ is H, and may be prepared in similar fashion as D3) are reacted with phosphoryl chloride or an equivalent halogenating agent (such as thionyl chloride, phosphorus trichloride, or phosphorus pentachloride) to afford chlorinated compounds E2. Alternatively, other known reagents can be reacted with C2' or D3' to afford compounds analogous to E1 or E2 but bearing a different leaving group at the carbon bearing the chloro group. In certain embodiments, E1 (or analogous compounds with different leaving groups at the chloro-position) is reacted with E3, a nucleophilic reagent bearing the —$R^4$ group, to afford C7, which is a compound according to Formula (I), wherein the --- connected to $N(R^3)$ denotes a double bond, $R^3$ is absent, and E is $R^4$.

Similarly, in certain embodiments, E2 (or analogous compounds with different leaving groups at the chloro-position) are reacted with E3, a nucleophilic reagent bearing the —$R^4$ group, to afford protected amines with structure D4, which may be deprotected, as described above, followed by coupling with D5, a reagent bearing the —Z—$R^1$ group, to afford coupling product C7. In some embodiments, he nucleophilic component of E3 can be a heteroatom nucleophile (such as a free amine, hydroxyl, or deprotonated versions thereof) or a carbon nucleophile (such as a metallocarbon species, e.g., a Grignard reagent or organocopper reagent). In some embodiments, the nucleophilic component of E3 is a free amine group (such as the N-terminal amine group of an amino acid chain or of an amino acid side chain), and the coupling reaction is optionally carried out in the presence of a base (such as an amine base, such as triethylamine).

In other embodiments not depicted here, chloro compounds E1 or E2 or other similar compounds with different leaving groups, such as other halogens, can undergo a transition metal-catalyzed coupling reaction with E3 at the carbon bearing the leaving group. For example, in some embodiments, the coupling reaction is a palladium-, nickel-, or copper-catalyzed coupling reaction with an organotin (Stille coupling), organozinc (Negishi coupling), organoboron (Suzuki coupling), or organomagnesium (Kumada coupling) embodiment of E3.

4.5.6 Scheme F—Alternate Method for Preparing Mono-Protected Diamine D2

In alternate embodiments, preparation of mono-protected diamines of structure D2 proceeds according to Scheme F:

Scheme F

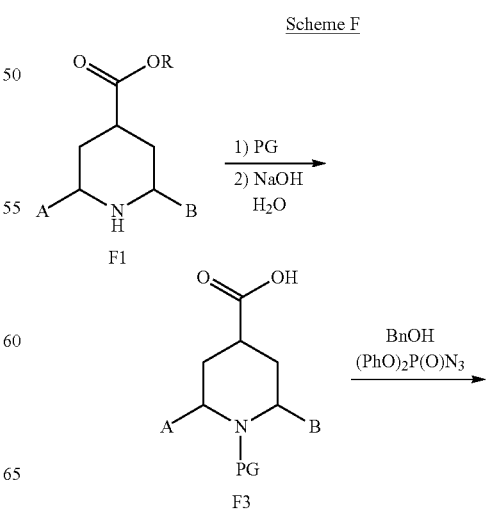

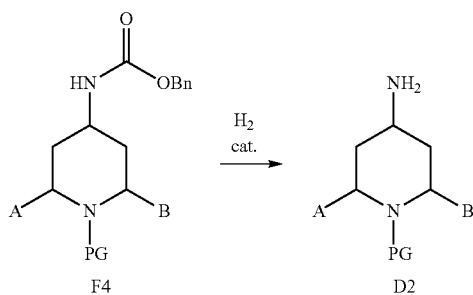

4.5.7 Scheme G—Methods for Diastereoselectively Preparing Intermediates in the Diastereoselective Synthesis of Quinazolin-4(3H)-One-Type Piperidine Compounds In some embodiments, Quinazolin-4(3H)-one-Type Piperidine Compounds are prepared diastereoselectively, i.e., yielding products with an excess of one or more diastereomers, such as endo or exo diastereomers of the piperidine ring. In certain embodiments, diastereoselective preparation of Quinazolin-4(3H)-one-Type Piperidine Compounds proceeds from diastereoselective preparation of intermediates, such as according to Scheme G:

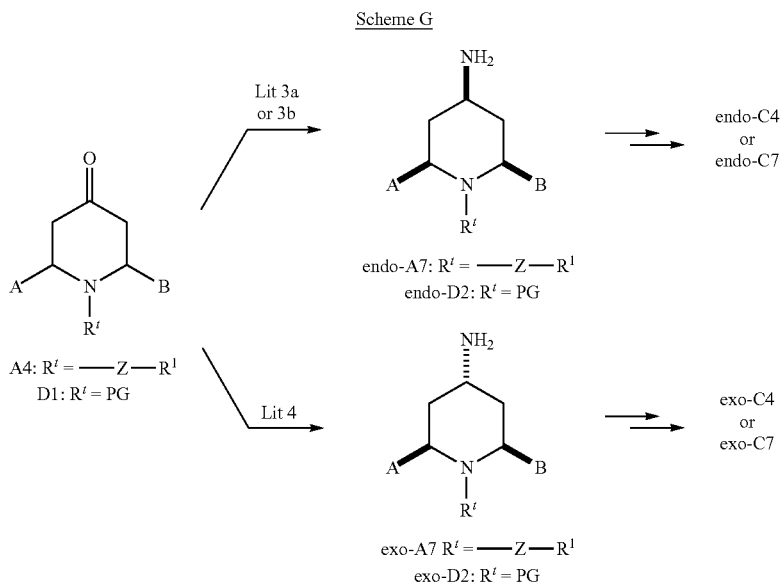

As depicted in Scheme F, in some embodiments, amines of structure F1 are protected to yield protected amines F2 (not pictured) followed by hydrolysis of the ester of F2 by a hydroxide source (such as aqueous sodium hydroxide, potassium hydroxide, lithium hydroxide, barium hydroxide, etc.) to afford the free acid compounds F3. In certain embodiments, the free acid compounds F3 are then treated with diphenyl phosphorazidate (or an equivalent reagent) and benzyl alcohol under Curtius rearrangement conditions to afford carbamates with structure F4. In some embodiments, subsequent hydrogenation of F4 with hydrogen and a suitable catalyst affords mono-protected diamines of structure D2, which can then be processed as described above to prepare Quinazolin-4(3H)-one-Type Piperidine Compounds. Compounds of structure F1 (wherein R is H, a carbon group, such as —($C_1$-$C_6$)alkyl, benzyl, etc.) are commercially available or can be made by routine methods in the art.

As depicted in Scheme G, in some embodiments, amines of structure A4 or amine-protected compounds of structure D1 (which is prepared from A1 according to Scheme D) can be subject to reductive amination according to Lit 3a (U.S. Patent Application Publication 2010/0216726) (e.g., by conversion to an oxime using aqueous hydroxylamine in an acidic solvent, such as acetic acid, followed by reduction by hydrogenation using a noble metal catalyst, such as platinum oxide, in a solvent, such as acetic acid) to afford the endo diastereomers of A7 or D2, respectively.

Alternatively, in some embodiments, amines of structure A4 or amine-protected compounds of structure D1 can be subject to reductive amination according to Lit 3b (Berdini et al., "A Modified Palladium Catalyzed Reductive Amination Procedure," *Tetrahedron*, 58:5669-5674 (2002)) (e.g., by treatment with ammonium formate and a noble metal catalyst, such as, palladium on carbon, in a solvent, such as ethanol or methanol) to afford the endo diastereomers of A7 or D2, respectively.

In other embodiments, amines of structure A4 or amine-protected compounds of structure D1 can be converted to the exo diastereomers of A7 or D2, respectively, according to the procedures of Lit 4 (Lewin et al., "Molecular Features Associated with Polyamine Modulation of NMDA Receptors," *J. Med. Chem.* 41:988-995 (1998)) (e.g., by reaction with aqueous hydroxylamine in a solvent, such as hexanes, to form an intermediate hydroxylamine, which can be converted to its oxime by dehydration in a solvent with a high boiling point, such as toluene, under Dean-stark conditions, followed by reduction of the oxime intermediate using a reductive metal, such as, sodium in propanol).

In these embodiments, the methods may produce, depending on the starting compound and the reagents selected, endo-A7, endo-D2, exo-A7, or exo-D2 with a percent diastereomeric excess (% de) of at least about 90%. In another embodiment, the endo-A7, endo-D2, exo-A7, or exo-D2 produced has a % de of at least about 95%. In another embodiment, the endo-A7, endo-D2, exo-A7, or exo-D2 produced has a % de of at least about 97%. In another embodiment, the endo-A7, endo-D2, exo-A7, or exo-D2 produced has a % de of at least about 98%. In another embodiment, the endo-A7, endo-D2, exo-A7, or exo-D2 produced has a % de of at least about 99%. In another embodiment, the endo-A7, endo-D2, exo-A7, or exo-D2 produced has a % de of greater than 99% (e.g., 99.1% to 99.9% or higher). In some embodiments, the above endo and exo diastereomers will have different spatial shapes and/or polarities and may be separable by chromatographic methods. As a result, if a given reaction produced a mixture of endo and exo diastereomers, in certain embodiments, routine chromatographic methods can be used to isolate either diastereomer or to prepare a diastereomeric mixture further enriched in a particular diastereomer. This mixture can then be iteratively purified to afford product mixtures increasingly enriched in a particular diastereomer.

In certain embodiments, endo-A7 or endo-D2 prepared according to Scheme G can be further processed to afford compounds endo-C4 or endo-C7, according to the procedures outlined in Schemes C, D, and E. Similarly, in some embodiments, the exo-A7 or exo-D2 prepared according to Scheme G can be further processed to afford compounds exo-C4 or exo-C7, according to the procedures outlined in Schemes C, D, and E. It is understood that the final C4 or C7 product, which are Quinazolin-4(3H)-one-Type Piperidine Compounds, will typically inherit the diastereoisomerism of the precursor compounds A7 or D2, although subsequent enrichment in one of the diastereomers is possible based on purification steps following each reaction. As noted above, the above endo and exo diastereomers may be separated and isolated using routine chromatographic methods. If a diastereomeric mixture resulting from a reaction is not separable or is only partially separable, the diastereomers may be separated after subsequent reactions that result in diastereomers that are more separable. As a result, diastereomers with the % de values noted above may be obtained.

4.5.8 Scheme H—Method for Preparing Selected Bicyclic Intermediates Corresponding to the —Z—R¹ Group of Quinazolin-4(3H)-One-Type Piperidine Compounds In certain embodiments, preparation of intermediates bearing the —Z—R¹ Group of Quinazolin-4(3H)-one-Type Piperidine Compounds proceeds according to Scheme H:

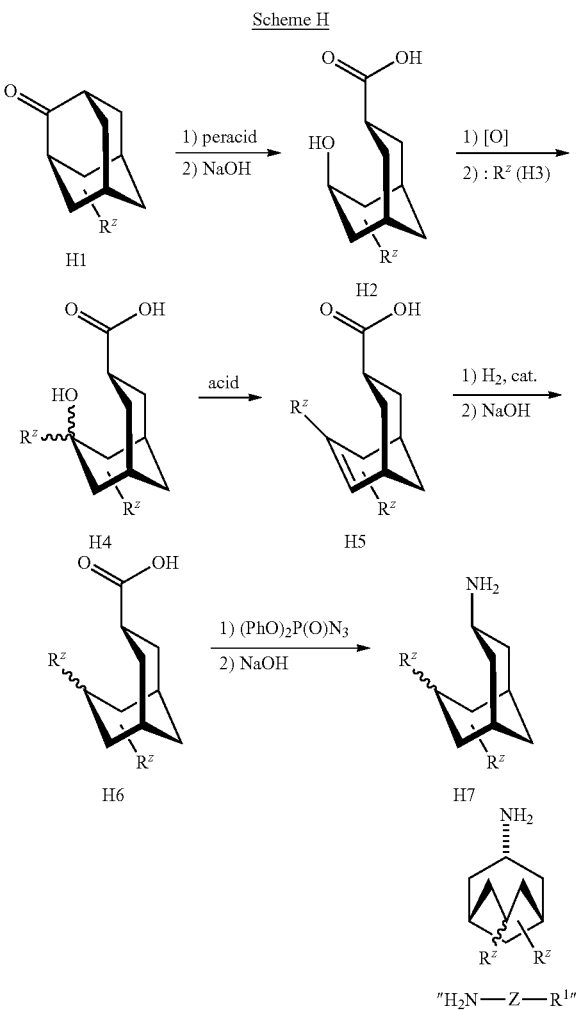

As depicted in Scheme H, commercially available 2-adamantanones H1, optionally substituted with one or more independently selected $R^z$ groups, can undergo Baeyer-Villiger oxidation to afford a lactone (not pictured). Suitable conditions include, for example, use of trifluoroacetic acid as solvent and a peracid, such sodium percarbonate, at from about 20° C. to about 30° C. In some embodiments, the lactone is then hydrolyzed to the corresponding hydroxycarboxylic acid H2, for example, by reaction with sodium hydroxide in a solvent, such as MeOH or water, under reflux. During hydrolysis, the stereochemistry of the carboxyl group may epimerize from endo, relative to the bridge bearing the hydroxyl group, to exo.

In certain embodiments, the hydroxyl group of H2 can be oxidized to give a ketone (not pictured), which may then be reacted with H3, a nucleophilic reagent bearing an independently selected $R^z$ group, to afford addition product H4. In some embodiments, H4 may be dehydrated, for example, using an acid (such as methanesulfonic acid, tosic acid, trifluoroacetic acid, hydrochloric acid, sulfuric acid, etc.) in a solvent (such as toluene) by azeotropic drying, to afford the olefin H5.

In some embodiments, the olefin of H5 can be reduced with hydrogen and a catalyst, such as a noble metal catalyst (for example, palladium on carbon in a mixed solvent system, such as MeOH and EtOAc) to provide the saturated acid H6. In certain embodiments, the face of the double bond in H5 that is hydrogenated is governed by sterics and may afford H6 with the R$^z$ group of the double bond cis to the bridge bearing the carboxyl group (i.e., "up" in Scheme H). In other embodiments, the face of the double bond in H5 that is hydrogenated is directed by the carboxyl group (for example, by chelation of the catalyst), and may afford H6 with the R$^z$ group of the double bond trans to the bridge bearing the carboxyl group (i.e., "down" in Scheme H). In some embodiments wherein an alcoholic solvent is used for the hydrogenation, reduction of H5 may afford a mixture of the saturated acid H6 and the corresponding alcoholic ester (for example, the methyl ester of H6 if MeOH is used as solvent). In certain of such embodiments, the ester in the mixture can be hydrolyzed to the acid H6 by treating the mixture with a hydroxide source (such as sodium hydroxide, potassium hydroxide, lithium hydroxide, barium hydroxide, etc) in aqueous systems.

In some embodiments, H6 can then be converted to an isocyanate (not pictured) using diphenyl phosphorazidate, i.e., diphenylphosphoryl azide or DPPA (or an equivalent reagent) and a base (such as triethylamine in a solvent, such as toluene) in a Curtius-type reaction. In certain embodiments, the isocyanate can then be hydrolyzed to exo-amine H7, for example, using sodium hydroxide, potassium hydroxide, lithium hydroxide, barium hydroxide, etc in aqueous THF or another aprotic water miscible solvent. Amine H7 is one embodiment of A3 from Scheme A and which is used in preparing Quinazolin-4(3H)-one-Type Piperidine Compounds according to the above Schemes.

In alternate embodiments, hydroxycarboxylic acid H2 is directly dehydrated to give H5 wherein the R$^z$ group in the middle of the bridge is —H. In some embodiments, H5 is then processed to H7 as described above.

4.5.9 Scheme J—Alternate Method for Preparing Selected Bicyclic Intermediates Corresponding to the —Z—R$^1$ Group of Quinazolin-4(3H)-One-Type Piperidine Compounds In certain embodiments, preparation of intermediates bearing the —Z—R$^1$ Group of Quinazolin-4(3H)-one-Type Piperidine Compounds proceeds according to Scheme J:

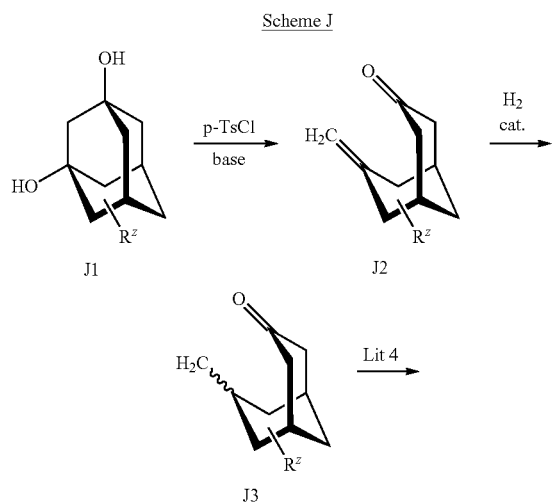

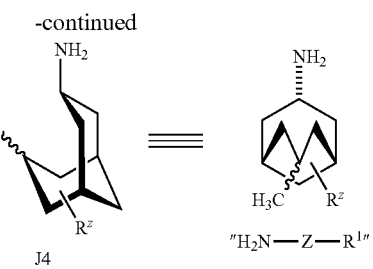

As depicted in Scheme J, in some embodiments, commercially available 1,3-dihydroxyadamantanes J1, optionally substituted with one or more independently selected R$^z$ groups, can be treated in the presence of a base with a reagent that converts a hydroxyl group into a leaving group to afford elimination product J2. Suitable conditions include, for example, exposure of J1 to p-toluenesulfonyl chloride in pyridine at a temperature of about 70° C. for from about 2 h to about 6 h. In certain embodiments, olefin J2 can subsequently be hydrogenated to saturated compound J3 using hydrogen and a catalyst, such as a noble metal catalyst (for example, palladium on carbon or platinum oxide in a non-polar solvent, such as cyclohexane). In certain embodiments, the face of the double bond in J2 that is hydrogenated is governed by sterics and may afford J3 with the resulting methyl group cis to the bridge bearing the carbonyl group (i.e., "up" in Scheme J). In other embodiments, the face of the double bond in J2 that is hydrogenated is directed by the carbonyl group (for example, by chelation of the catalyst), and may afford J3 with the resulting methyl group trans to the bridge bearing the carbonyl group (i.e., "down" in Scheme J). In some embodiments, J3 can be converted to the exo-amine J4 by conditions noted above in Lit 4 (for example, by formation of an oxime from J3 by reaction with hydroxylamine in acetic acid at a temperature from about 25° C. to about 40° C., followed by subsequent reduction with sodium metal in iso-propanol and in a solvent, such as toluene, at a temperature of about 100° C.). Amine J4 is one embodiment of the compound H$_2$N—Z—R$^1$ (A3) used in Scheme A in preparing Quinazolin-4(3H)-one-Type Piperidine Compounds according to the above Schemes.

4.5.10 Scheme K—Second Alternate Method for Preparing Selected Bicyclic Intermediates Corresponding to the —Z—R$^1$ Group of Quinazolin-4(3H)-One-Type Piperidine Compounds In certain embodiments, preparation of intermediates bearing the —Z—R$^1$ Group of Quinazolin-4(3H)-one-Type Piperidine Compounds proceeds according to Scheme K:

Scheme K

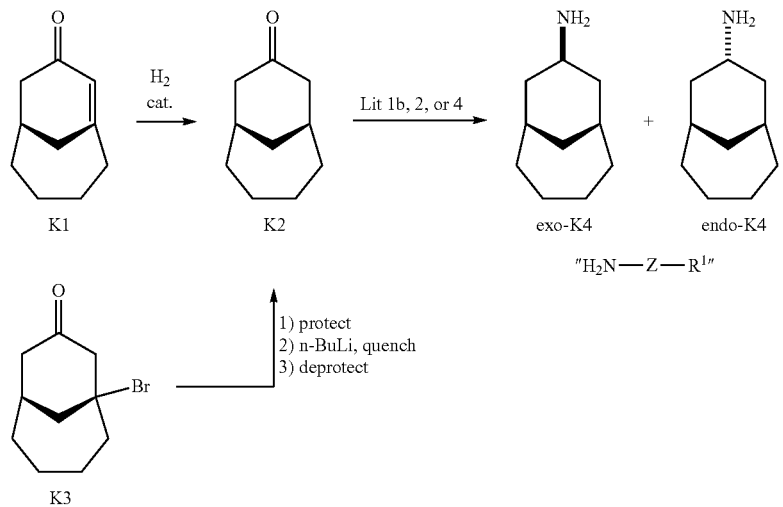

As depicted in Scheme K, in some embodiments, α,β-unsaturated ketone K1 is hydrogenated to saturated ketone K2 using hydrogen and a catalyst, such as a noble metal catalyst (for example, palladium on carbon or platinum oxide in a non-polar solvent, such as cyclohexane or toluene, or in a polar solvent, such as ethanol). In other embodiments, K2 is prepared from bromo-ketone K3 by the sequence of (1) protection of the carbonyl group, (2) debromination with n-butyl lithium or another alkyl lithium reagent capable of halogen-lithium exchange, followed by quenching with water, and (3) deprotection of the carbonyl group. Starting ketones K1, (R)-bicyclo[4.3.1]dec-6-en-8-one, as well as K3, (1S,6S)-1-bromobicyclo[4.3.1]decan-8-one, can be prepared by methods known to the art, e.g., as described in House et al., *J. Org. Chem.* 44:2819-2824 (1979) and House et al., *J. Org. Chem.* 45:1800-1806 (1980).

Saturated ketone K2 can then be converted to one or both of the corresponding exo or endo bicyclic amines exo-K4 and endo-K4 ((1R,6S)-bicyclo[4.3.1]decan-8-amine) through literature methods, such as reductive amination methods discussed in Scheme A (Lit 1b and 2), Scheme G (Lit 3a, 3b, and 4), and in Scheme J (Lit 4). In certain embodiments, exo-K4 or endo-K4 are prepared selectively, for example, in one or more of the diastereomeric ratios described in Scheme G for A7 and D2. In other embodiments, exo-K4 and endo-K4 are prepared as a mixture with substantial amounts of each, but are routinely separable because the two compounds are diastereomers with different physical properties. In specific embodiments, exo-K4 is prepared selectively using the procedure of Lit 4 in Scheme J (for example, by formation of an oxime from K2 by reaction with hydroxylamine in acetic acid at a temperature from about 25° C. to about 40° C., followed by subsequent reduction with sodium metal in iso-propanol and in a solvent, such as toluene, at a temperature of about 100° C.), which, as noted for Scheme J, preferentially results in preparation of the exo-amine. Bicyclic amines exo-K4 and endo-K4 are embodiments of the compound $H_2N-Z-R^1$ (A3) used in Scheme A in preparing Quinazolin-4(3H)-one-Type Piperidine Compounds according to the above Schemes.

4.6 Therapeutic Uses of Quinazolin-4(3H)-One-Type Piperidine Compounds

In accordance with the disclosure, the Quinazolin-4(3H)-one-Type Piperidine Compounds are administered to an animal in need of treatment or prevention of a Condition.

In one embodiment, an effective amount of a Quinazolin-4(3H)-one-Type Piperidine Compound can be used to treat or prevent any condition treatable or preventable by inhibiting the activity of the ORL-1 receptor. Examples of Conditions that are treatable or preventable by inhibiting the activity of the ORL-1 receptor include, but are not limited to: pain (CNS effect), memory disorders, obesity, constipation, depression, dementia, Parkinsonism, a sleep disorder, a metabolic disorder, a renal disorder, and a cardiovascular disorder.

In another embodiment, an effective amount of a Quinazolin-4(3H)-one-Type Piperidine Compound can be used to treat or prevent any condition treatable or preventable by activating the ORL-1 receptor. Examples of Conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, and drug abuse.

The Quinazolin-4(3H)-one-Type Piperidine Compounds can be used to treat or prevent acute or chronic pain. Examples of pain that can be treated or prevented using a Quinazolin-4(3H)-one-Type Piperidine Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Quinazolin-4(3H)-one-Type Piperidine Compounds can also be used to treat or prevent pain associated with inflammation or with an inflammatory disease in an animal. Such pain can arise where there is an inflammation of the body tissue, which can be a local inflammatory response or a systemic inflammation. For example, a Quinazolin-4(3H)-one-Type Piperidine Compound can be used to treat or prevent pain associated with inflammatory diseases including, but not limited to, organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. A Quinazolin-4(3H)-one-Type Piperidine Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Quinazolin-4(3H)-one-Type Piperidine Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue.

The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Quinazolin-4(3H)-one-Type Piperidine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Quinazolin-4(3H)-one-Type Piperidine Compounds can be used to treat or prevent a sleep disorder including, but not limited to, insomnia, hypersomnia, sleep deprivation, sleep apnea, dysomnia, delayed sleep phase syndrome (DSPS), advanced sleep phase syndrome (ASPS), non-24-hour sleep-wake syndrome (e.g., circadian rhythm sleep disorder), situational circadian rhythm sleep disorders (e.g., jet lag, shift work sleep disorders), hypopnea, irregular sleep wake rhythm, nightmares, night terror, parasomnia, restless leg syndrome (RLS), nocturnal mycolonus/periodic limb movement disorder (PLMD), rapid eye movement (REM) sleep disorder, somnambulism/sleep walking, somniloquy/sleep talking, and somniphobia. For example, U.S. Pat. No. 8,003,669 discloses a class of ORL-1 agonists said to be therapeutic agents for circadian rhythm sleep disorder and Miyakawa et al. disclose that administration of the ORL-1 receptor agonist known as W-212393 induces phase advance of locomotor activity circadian rhythm in mice ("ORL1 receptor-mediated down-regulation of mPER2 in the suprachiasmatic nucleus accelerates re-entrainment of the circadian clock following a shift in the environmental light/dark cycle," *Neuropharmacol.* 52:1055-1064 (2007)).

Metabolic disorders can be caused by an abnormal metabolic process and can be acquired, e.g., failure of a metabolically important organ such as the liver or disease of an endocrine organ, or congenital, e.g., an inherited enzyme abnormality. A congenital metabolic disorder can be caused by a defect in a single gene; some of the more well-known inborn metabolic errors include sickle cell anemia, hypothyroidism, Tay-Sachs disease, phenylketonuria, and cystic fibrosis. The Quinazolin-4(3H)-one-Type Piperidine Compounds can be used to treat or prevent a metabolic disorder including, but not limited to, anorexia nervosa, bulimia, and obesity. For example, U.S. Pat. No. 7,241,770 discloses a class of hydronopol derivative ORL-1 agonists said to be therapeutic agents for metabolic disorders.

A renal disorder may be acute or chronic. An acute renal disorder can be caused by impaired blood flow to the kidneys due to, e.g., blood loss, heart attack, or liver failure; kidney damage due to, e.g., blood clots, hemolytic uremic syndrome, or vasculitis; or urine blockage due to, e.g., bladder cancer, an enlarged prostate, or kidney stones. A chronic renal disorder can be caused by, e.g., diabetes mellitus, hypertension, or polycystic kidney disease. The Quinazolin-4(3H)-one-Type Piperidine Compounds can be used to treat or prevent a renal disorder including, but not limited to, those renal disorders characterized by the syndrome of inappropriate antidiuretic hormone secretion (SIADH) or by imbalances of water retention and/or water excretion or salt excretion. For example, U.S. Pat. No. 6,869,960 discloses a class of spiropiperidine ORL-1 ligands said to be therapeutic agents for renal disorders.

Cardiovascular disorders represent the leading cause of death in the United States, responsible for about 27% of yearly deaths. Cardiovascular disorders can be caused by tobacco use, alcohol abuse, obesity, diabetes mellitus, high cholesterol, high blood pressure, and other factors. The Quinazolin-4(3H)-one-Type Piperidine Compounds can be used to treat or prevent a cardiovascular disorder including, but not limited to, myocardial infarction, arrhythmias, bradycardia, hypertension, hypotension, thrombosis, anemia, arteriosclerosis, and angina pectoris. For example, U.S. Pat. No. 7,241,770 discloses a class of hydronopol derivative ORL-1 agonists said to be therapeutic agents for cardiovascular disorders.

According to the disclosure, some of the Quinazolin-4 (3H)-one-Type Piperidine Compounds are agonists at the ORL-1 receptor, some of the Quinazolin-4(3H)-one-Type Piperidine Compounds are partial agonists at the ORL-1 receptor, and some of the Quinazolin-4(3H)-one-Type Piperidine Compounds are antagonists at the ORL-1 receptor. In another embodiment, a Quinazolin-4(3H)-one-Type Piperidine Compound is an agonist at the ORL-1 receptor and an agonist at a μ, κ and/or δ opioid receptor, particularly at a μ opioid receptor. In another embodiment, a Quinazolin-4(3H)-one-Type Piperidine Compound is a partial agonist at the ORL-1 receptor and an agonist at μ, κ and/or δ opioid receptor, particularly at a μ opioid receptor. In another embodiment, a Quinazolin-4(3H)-one-Type Piperidine Compound is an antagonist at the ORL-1 receptor and an agonist at a μ, κ and/or δ opioid receptor, particularly at a μ opioid receptor. In another embodiment, a Quinazolin-4 (3H)-one-Type Piperidine Compound is an agonist at the ORL-1 receptor and an antagonist at a μ, κ and/or δ opioid receptor, particularly at a μ opioid receptor. In another embodiment, a Quinazolin-4(3H)-one-Type Piperidine Compound is a partial agonist at the ORL-1 receptor and an antagonist at a μ, κ and/or δ opioid receptor, particularly at a μ opioid receptor. In another embodiment, a Quinazolin-4(3H)-one-Type Piperidine Compound is an antagonist at the ORL-1 receptor and an antagonist at a μ, κ and/or δ opioid receptor, particularly at a μ opioid receptor.

The disclosure also provides methods for inhibiting ORL-1 receptor function in a cell, comprising contacting a cell capable of expressing the ORL-1 receptor with an amount of a Quinazolin-4(3H)-one-Type Piperidine Compound effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of a Quinazolin-4(3H)-one-Type Piperidine Compound. In one embodiment, the method is useful for treating or preventing pain in an animal in need of such treatment or prevention. In another embodiment, the method is useful for treating or preventing a memory disorder, obesity, constipation, depression, dementia, Parkinsonism, a sleep disorder, a metabolic disorder, a renal disorder, or a cardiovascular disorder in an animal in need of such treatment or prevention.

The present disclosure also relates to methods for activating ORL-1 receptor function in a cell, comprising contacting a cell capable of expressing the ORL-1 receptor with an amount of a Quinazolin-4(3H)-one-Type Piperidine Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of a Quinazolin-4(3H)-one-Type Piperidine Compound. In one embodiment, the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S]GTPγS Binding Assays," *TIPS* 24(2):87-90 (2003); and Lazareno, "Measurement of Agonist-stimulated [$^{35}$S]GTPγS Binding to Cell Membranes," *Methods in Molecular Biology* 106:231-245 (1999).

4.7 Therapeutic/Prophylactic Administration and Compositions

Due to their activity, the Quinazolin-4(3H)-one-Type Piperidine Compounds are advantageously useful in human and veterinary medicine. As described above, the Quinazolin-4 (3H)-one-Type Piperidine Compounds are useful for treating or preventing a Condition in an animal in need thereof. The Quinazolin-4(3H)-one-Type Piperidine Compounds of the disclosure can be administered to any animal requiring modulation of the opioid and/or ORL-1 receptors.

When administered to an animal, a Quinazolin-4(3H)-one-Type Piperidine Compound can be administered as a component of a composition that comprises a pharmaceutically acceptable carrier or excipient. The compositions, which comprise a Quinazolin-4(3H)-one-Type Piperidine Compound, can be administered orally. A Quinazolin-4(3H)-one-Type Piperidine Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Quinazolin-4(3H)-one-Type Piperidine Compound.

Methods of administration include, but are not limited to, intradermal, intramuscular, intraperitoneal, parenteral, intravenous, subcutaneous, intranasal, epidural, oral, sublingual, intracerebral, intravaginal, transdermal (e.g., via a patch), rectal, by inhalation, transmucosal, or topical, particularly to the ears, nose, eyes, or skin. The method of administration is left to the discretion of the practitioner. In some instances, administration will result in the release of a Quinazolin-4 (3H)-one-Type Piperidine Compound into the bloodstream. In other instances, administration will result in only local release of a Quinazolin-4(3H)-one-Type Piperidine Compound.

In specific embodiments, it can be desirable to administer a Quinazolin-4(3H)-one-Type Piperidine Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Quinazolin-4(3H)-one-Type Piperidine Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Quinazolin-4(3H)-one-Type Piperidine Compound can be formulated as a suppository, with traditional binders and excipients such as triglycerides.

When a Quinazolin-4(3H)-one-Type Piperidine Compound is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A Quinazolin-4(3H)-one-Type Piperidine Compound can also be in the form of a powder for reconstitution as an injectable formulation.

In another embodiment, a Quinazolin-4(3H)-one-Type Piperidine Compound can be delivered in a vesicle, in particular a liposome (see Langer, "New Methods of Drug Delivery," *Science* 249:1527-1533 (1990); and Treat et al., "Liposome Encapsulated Doxorubicin Preliminary Results of Phase I and Phase II Trials," pp. 317-327 and 353-365 in *Liposomes in the Therapy of Ilnfectious Disease and Cancer* (1989)).

In yet another embodiment, a Quinazolin-4(3H)-one-Type Piperidine Compound can be delivered in a controlled-release system or sustained-release system (see, e.g., Goodson, "Dental Applications," in *Medical Applications of Controlled Release, Vol. 2, Applications and Evaluation*, Langer and Wise, eds., CRC Press, Chapter 6, pp. 115-138 (1984), hereafter "Goodson"). Other controlled- or sustained-release systems discussed in the review by Langer, *Science* 249: 1527-1533 (1990) can be used. In one embodiment, a pump can be used (Langer, *Science* 249:1527-1533 (1990); Sefton, "Implantable Pumps," in *CRC Crit. Rev. Biomed. Eng.* 14(3):201-240 (1987); Buchwald et al., "Long-term, Continuous Intravenous Heparin Administration by an Implantable Infusion Pump in Ambulatory Patients with Recurrent Venous Thrombosis," *Surgery* 88:507-516 (1980); and Saudek et al., "A Preliminary Trial of the Programmable Implantable Medication System for Insulin Delivery," *New Engl. J. Med.* 321:574-579 (1989)). In another embodiment, polymeric materials can be used (see Goodson; Smolen et al., "Drug Product Design and Performance," *Controlled Drug Bioavailability Vol.* 1, John Wiley & Sons, New York (1984); Langer et al., "Chemical and Physical Structure of Polymers as Carriers for Controlled Release of Bioactive Agents: A Review," *J. Macromol. Sci. Rev. Macromol. Chem.* C23(1):61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356 (1989); and Howard et al., "Intracerebral drug delivery in rats with lesion-induced memory deficits," *J. Neurosurg.* 71:105-112 (1989)). In yet another embodiment, a controlled- or sustained-release system can be placed in proximity of a target of a Quinazolin-4(3H)-one-Type Piperidine Compound, e.g., the spinal column, brain, or gastrointestinal tract, thus requiring only a fraction of the systemic dose.

In certain embodiments, compositions of the disclosure further comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Quinazolin-4(3H)-one-Type Piperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, EtOH, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, DC, 1986), incorporated herein by reference.

In certain embodiments, compositions of the disclosure take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described by Radebough et al., "Preformulation," pp. 1447-1676 in *Remington's Pharmaceutical Sciences Vol.* 2

(Gennaro, ed., 19th Ed., Mack Publishing, Easton, Pa., 1995), incorporated herein by reference.

In one embodiment, the Quinazolin-4(3H)-one-Type Piperidine Compounds are formulated in accordance with routine procedures as a composition adapted for oral administration to human beings. A Quinazolin-4(3H)-one-Type Piperidine Compound to be orally delivered can be in the form of tablets, capsules, gelcaps, caplets, lozenges, aqueous or oily solutions, suspensions, granules, powders, emulsions, syrups, or elixirs, for example. When a Quinazolin-4(3H)-one-Type Piperidine Compound is incorporated into oral tablets, such tablets can be compressed, tablet triturates, enteric-coated, sugar-coated, film-coated, multiply compressed, or multiply layered. Techniques and compositions for making solid oral dosage forms are described in *Pharmaceutical Dosage Forms: Tablets* (Lieberman et al., eds., 2nd Ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., 16th Ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., 2nd Ed., Marcel Dekker, Inc., 1996 & 1998).

When a Quinazolin-4(3H)-one-Type Piperidine Compound is to be injected parenterally, it can be, e.g., in the form of an isotonic sterile solution. Alternatively, when a Quinazolin-4(3H)-one-Type Piperidine Compound is to be inhaled, it can be formulated into a dry aerosol or can be formulated into an aqueous or partially aqueous solution.

An orally administered Quinazolin-4(3H)-one-Type Piperidine Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Quinazolin-4(3H)-one-Type Piperidine Compounds can be formulated for intravenous administration. In certain embodiments, compositions for intravenous administration comprise sterile isotonic aqueous buffer. Where necessary, the compositions can also include a solubilizing agent. A Quinazolin-4(3H)-one-Type Piperidine Compound for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Quinazolin-4(3H)-one-Type Piperidine Compound is to be administered by infusion, it can be dispensed, for example, with an infusion bottle containing sterile pharmaceutical grade water or saline. When a Quinazolin-4(3H)-one-Type Piperidine Compound is administered by injection, an ampule of sterile water for injection or saline can be provided so that the ingredients can be mixed prior to administration.

A Quinazolin-4(3H)-one-Type Piperidine Compound can be administered by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Quinazolin-4(3H)-one-Type Piperidine Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Quinazolin-4(3H)-one-Type Piperidine Compound, and can thus reduce the occurrence of adverse side effects.

Controlled- or sustained-release compositions can initially release an amount of a Quinazolin-4(3H)-one-Type Piperidine Compound that promptly produces the desired therapeutic or prophylactic effect, and gradually and continually release other amounts of the Quinazolin-4(3H)-one-Type Piperidine Compound to maintain this level of therapeutic or prophylactic effect over an extended period of time. To maintain a constant level of the Quinazolin-4(3H)-one-Type Piperidine Compound in the body, the Quinazolin-4(3H)-one-Type Piperidine Compound can be released from the dosage form at a rate that will replace the amount of Quinazolin-4(3H)-one-Type Piperidine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Quinazolin-4(3H)-one-Type Piperidine Compound that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are, in certain embodiments, from about 0.01 mg/kg of body weight to about 2500 mg/kg of body weight of the animal per day or from about 0.01 mg/kg of body weight to about 1000 mg/kg of body weight of the animal per day. In another embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Quinazolin-4 (3H)-one-Type Piperidine Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one Quinazolin-4(3H)-one-Type Piperidine Compound is administered, the effective dosage amounts correspond to the total amount administered.

Where a cell capable of expressing the ORL-1 receptor, the μ-opioid receptor, the κ-opioid receptor and/or the δ-opioid receptor is contacted with a Quinazolin-4(3H)-one-Type Piperidine Compound in vitro, the amount effective for inhibiting or activating that receptor function in a cell will, in certain embodiments, range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Quinazolin-4(3H)-one-Type Piperidine Compound will be from about 0.01 μL to about 1 mL. In another embodiment, the volume of solution or suspension will be about 200 μL.

A Quinazolin-4(3H)-one-Type Piperidine Compound has a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

In certain embodiments, a Quinazolin-4(3H)-one-Type Piperidine Compound has a Ki (nM) of about 300 or less for binding to ORL-1 receptors. In one embodiment, a Quinazolin-4(3H)-one-Type Piperidine Compound has a $K_i$ (nM) of about 100 or less. In another embodiment, a Quinazolin-4(3H)-one-Type Piperidine Compound has a $K_i$ (nM) of about 35 or less. In another embodiment, a Quinazolin-4(3H)-one-Type Piperidine Compound has a $K_i$ (nM) of about 20 or less. In another embodiment, a Quinazolin-4(3H)-one-Type Piperidine Compound has a $K_i$ (nM) of about 15 or less. In another embodiment, a Quinazolin-4(3H)-one-Type Piperidine Compound has a $K_i$ (nM) of about 10 or less. In another embodiment, a Quinazolin-4(3H)-one-Type Piperidine Compound has a $K_i$ (nM) of about 4 or less. In another embodiment, a Quinazolin-4(3H)-one-Type Piperidine Compound has a $K_i$ (nM) of about 1 or less. In another embodiment, a Quinazolin-4(3H)-one-Type Piperidine Compound has a $K_i$ (nM) of about 0.4 or less. In another embodiment, a Quinazolin-4(3H)-one-Type Piperidine Compound has a $K_i$ (nM) of about 0.1 or less.

ORL-1 GTP $EC_{50}$ is the concentration of a compound providing 50% of the maximal response for the compound at an ORL-1 receptor. In one embodiment, a Quinazolin-4(3H)-one-Type Piperidine Compound has an ORL-1 GTP $EC_{50}$ (nM) of about 5000 or less to stimulate ORL-1 receptor function. In another embodiment, a Quinazolin-4(3H)-one-Type Piperidine Compound has an ORL-1 GTP $EC_{50}$ (nM) of about 1000 or less. In another embodiment, a Quinazolin-4(3H)-one-Type Piperidine Compound has an ORL-1 GTP $EC_{50}$ (nM) of about 100 or less. In another embodiment, a Quinazolin-4(3H)-one-Type Piperidine Compound has an ORL-1 GTP $EC_{50}$ (nM) of about 80 or less. In another embodiment, a Quinazolin-4(3H)-one-Type Piperidine Compound has an ORL-1 GTP $EC_{50}$ (nM) of about 50 or less. In another embodiment, a Quinazolin-4(3H)-one-Type Piperidine Compound has an ORL-1 GTP $EC_{50}$ (nM) of about 35 or less. In another embodiment, a Quinazolin-4(3H)-one-Type Piperidine Compound has an ORL-1 GTP $EC_{50}$ (nM) of about 15 or less. In another embodiment, a Quinazolin-4(3H)-one-Type Piperidine Compound has an ORL-1 GTP $EC_{50}$ (nM) of about 10 or less. In another embodiment, a Quinazolin-4(3H)-one-Type Piperidine Compound has an ORL-1 GTP $EC_{50}$ (nM) of about 4 or less. In another embodiment, a Quinazolin-4(3H)-one-Type Piperidine Compound has an ORL-1 GTP $EC_{50}$ (nM) of about 1 or less. In another embodiment, a Quinazolin-4(3H)-one-Type Piperidine Compound has an ORL-1 GTP $EC_{50}$ (nM) of about 0.4 or less. In another embodiment, a Quinazolin-4(3H)-one-Type Piperidine Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In certain embodiments, a Quinazolin-4(3H)-one-Type Piperidine Compound acting as an agonist has an ORL-1 GTP Emax (%) of about 50% or greater. In one embodiment, agonist Quinazolin-4(3H)-one-Type Piperidine Compounds has an ORL-1 GTP Emax (%) of about 75% or greater. In another embodiment, an agonist Quinazolin-4(3H)-one-Type Piperidine Compound has an ORL-1 GTP Emax (%) of about 85% or greater. In another embodiment, an agonist Quinazolin-4(3H)-one-Type Piperidine Compound has an ORL-1 GTP Emax (%) of about 95% or greater. In another embodiment, an agonist Quinazolin-4(3H)-one-Type Piperidine Compound has an ORL-1 GTP Emax (%) of about 100% or greater. In certain embodiments, a Quinazolin-4(3H)-one-Type Piperidine Compound acting as a partial agonist has an ORL-1 GTP Emax (%) of less than about 10%. In one embodiment, a partial agonist Quinazolin-4(3H)-one-Type Piperidine Compound has an ORL-1 GTP Emax (%) of less than about 20%. In another embodiment, a partial agonist Quinazolin-4(3H)-one-Type Piperidine Compound has an ORL-1 GTP Emax (%) of less than about 30%. In another embodiment, a partial agonist Quinazolin-4(3H)-one-Type Piperidine Compound has an ORL-1 GTP Emax (%) of less than about 40%. In another embodiment, a partial agonist Quinazolin-4(3H)-one-Type Piperidine Compound has an ORL-1 GTP Emax (%) of less than about 50%.

In certain embodiments, a Quinazolin-4(3H)-one-Type Piperidine Compound has a binding affinity ($K_i$) for the human μ-opioid receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

In certain embodiments, a Quinazolin-4(3H)-one-Type Piperidine Compound has a $K_i$ (nM) for the human μ-opioid receptor of about 3000 or less for binding to a human μ-opioid receptor, or about 1000 or less, or about 650 or less, or about 525 or less, or about 250 or less, or about 100 or less, or about 10 or less, or about 1 or less. In one embodiment, a Quinazolin-4(3H)-one-Type Piperidine Compound has substantially no activity.

μ GTP $EC_{50}$ is the concentration of a compound providing 50% of the maximal response for the compound at a human μ-opioid receptor. In certain embodiments, a Quinazolin-4(3H)-one-Type Piperidine Compound has a μ GTP $EC_{50}$ (nM) of about 20,000 or less to stimulate human μ-opioid receptor function, or about 10,000 or less. In other embodiments, a Quinazolin-4(3H)-one-Type Piperidine Compound has a μ GTP $EC_{50}$ (nM) of about 5000 or less to stimulate human μ-opioid receptor function, or about 4100 or less, or about 3100 or less, or about 2000 or less, or about 1000 or less, or about 100 or less, or about 10 or less, or about 1 or less, or about 0.4 or less.

μ GTP Emax (%) is the maximal effect elicited by a compound relative to the effect elicited by DAMGO, a standard μ agonist. In certain embodiments, a Quinazolin-4(3H)-one-Type Piperidine Compound has a μ GTP Emax (%) of about 10% or greater, or about 20% or greater, or about 50% or greater, or about 65% or greater, or about 75% or greater, or about 88% or greater. In other embodiments, a Quinazolin-4(3H)-one-Type Piperidine Compound has a μ GTP Emax (%) of about 10% or less, or about 5% or less, or about 2% or less.

In one embodiment, a Quinazolin-4(3H)-one-Type Piperidine Compound has a $K_i$ (nM) of about 20,000 or less for binding to a human κ-opioid receptor. In another embodiment, a Quinazolin-4(3H)-one-Type Piperidine Compound has substantially no activity. In certain embodiments, a Quinazolin-4(3H)-one-Type Piperidine Compound that binds to the human κ-opioid receptor has a $K_i$ (nM) of about 10,000 or less, or about 5000 or less, or about 1000 or less, or about 500 or less, or about 300 or less, or about 100 or less, or about 50 or less, or about 20 or less, or about 15 or less.

κ GTP $EC_{50}$ is the concentration of a compound providing 50% of the maximal response for the compound at a human κ-opioid receptor. In certain embodiments, a Quinazolin-4(3H)-one-Type Piperidine Compound has a κ GTP $EC_{50}$ (nM) of about 20,000 or less to stimulate human κ-opioid receptor function, or about 10,000 or less, or about 5000 or less, or about 2000 or less, or about 1500 or less, or about 800 or less, or about 500 or less, or about 300 or less, or about 100 or less, or about 50 or less, or about 25 or less.

κ GTP Emax (%) is the maximal effect elicited by a compound relative to the effect elicited by U69,593. In certain embodiments, a Quinazolin-4(3H)-one-Type Piperidine Compound has a κ GTP Emax (%) of about 10% or greater, or about 15% or greater, or about 30% or greater, or about 40% or greater, or about 45% or greater, or about 75% or greater, or about 90% or greater. In other embodiments, a Quinazolin-4(3H)-one-Type Piperidine Compound has a κ GTP Emax (%) of about 10% or less, or about 5% or less, or about 2% or less.

In one embodiment, a Quinazolin-4(3H)-one-Type Piperidine Compound has a $K_i$ (nM) of about 20,000 or less for binding to a human δ-opioid receptor. In another embodiment, a Quinazolin-4(3H)-one-Type Piperidine Compound has substantially no activity. In other embodiments, a Quinazolin-4(3H)-one-Type Piperidine Compound that binds to the human δ-opioid receptor has a $K_i$ (nM) of about 10,000 or less, or about 9000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less.

δ GTP $EC_{50}$ is the concentration of a compound providing 50% of the maximal response for the compound at a human δ-opioid receptor. In certain embodiments, a Quinazolin-4(3H)-one-Type Piperidine Compound has a δ GTP $EC_{50}$ (nM) of about 20,000 or less to stimulate human δ-opioid receptor function, or about 10,000 or less, or about 1000 or less, or about 100 or less, or about 90 or less, or about 50 or less, or about 25 or less or less.

δ GTP Emax (%) is the maximal effect elicited by a compound relative to the effect elicited by met-enkephalin. In certain embodiments, a Quinazolin-4(3H)-one-Type Piperidine Compound has a δ GTP Emax (%) of about 10% or greater, or about 30% or greater, or about 50% or greater, or about 75% or greater, or about 90% or greater, or about 100% or greater. In other embodiments, a Quinazolin-4(3H)-one-Type Piperidine Compound has a δ GTP Emax (%) of about 10% or less, or about 5% or less, or about 2% or less.

The Quinazolin-4(3H)-one-Type Piperidine Compounds can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal a Quinazolin-4(3H)-one-Type Piperidine Compound (i.e., a first therapeutic agent) and a second therapeutic agent. In one embodiment, the second therapeutic agent is administered in an effective amount.

An effective amount of the second therapeutic agent will be known to those skilled the art depending on the agent.

However, it is well within the skilled artisan's purview to determine the second therapeutic agent's optimal effective-amount range. A Quinazolin-4(3H)-one-Type Piperidine Compound and the second therapeutic agent combined can act either additively or synergistically to treat the same Condition, or they may act independently of each other such that the Quinazolin-4(3H)-one-Type Piperidine Compound treats or prevents a first Condition and the second therapeutic agent treats or prevents a second disorder, which can be the same as the first Condition or another disorder. In one embodiment, where a second therapeutic agent is administered to an animal for treatment of a Condition (e.g., pain), the minimal effective amount of the Quinazolin-4(3H)-one-Type Piperidine Compound will be less than its minimal effective amount would be where the second therapeutic agent is not administered. In this embodiment, the Quinazolin-4(3H)-one-Type Piperidine Compound and the second therapeutic agent can act synergistically to treat or prevent a Condition. In one embodiment, a Quinazolin-4(3H)-one-Type Piperidine Compound is administered concurrently with a second therapeutic agent as a single composition comprising an effective amount of a Quinazolin-4(3H)-one-Type Piperidine Compound and an effective amount of the second therapeutic agent. Alternatively, a composition comprising an effective amount of a Quinazolin-4(3H)-one-Type Piperidine Compound and a second composition comprising an effective amount of the second therapeutic agent are concurrently administered. In another embodiment, an effective amount of a Quinazolin-4(3H)-one-Type Piperidine Compound is administered prior or subsequent to administration of an effective amount of the second therapeutic agent. In this embodiment, the Quinazolin-4(3H)-one-Type Piperidine Compound is administered while the second therapeutic agent exerts its therapeutic effect, or the second therapeutic agent is administered while the Quinazolin-4(3H)-one-Type Piperidine Compound exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., eds., 9th Ed., McGraw-Hill, New York 1996), and Hanson, "Analgesic, Antipyretic and Anti-Inflammatory Drugs," pp. 1196-1221 in *Remington: The Science and Practice of Pharmacy Vol. II* (Gennaro, ed., 19th Ed., Mack Publishing, Easton, Pa., 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, a sleep disorder, a metabolic disorder, a renal disorder, a cardiovascular disorder and/or treating, preventing or inhibiting vomiting include those that are known in the art and can be selected by those skilled in the art.

A composition of the disclosure can be prepared by a method comprising admixing a Quinazolin-4(3H)-one-Type Piperidine Compound or a pharmaceutically acceptable salt or solvate thereof with a pharmaceutically acceptable carrier or excipient. Admixing can be accomplished using methods known for admixing a compound and a pharmaceutically acceptable carrier or excipient. In one embodiment, the Quinazolin-4(3H)-one-Type Piperidine Compound is present in the composition in an effective amount.

4.8 Kits

The disclosure further provides kits that can simplify the handling and administration of a Quinazolin-4(3H)-one-Type Piperidine Compound to an animal.

A typical kit of the disclosure comprises a unit dosage form of a Quinazolin-4(3H)-one-Type Piperidine Compound. In one embodiment, the unit dosage form comprises a first container, which can be sterile, containing an effective amount of a Quinazolin-4(3H)-one-Type Piperidine Compound and a pharmaceutically acceptable carrier or excipient. The kit can further comprise a label or printed instructions instructing the use of the Quinazolin-4(3H)-one-Type Piperidine Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Quinazolin-4(3H)-one-Type Piperidine Compound, an effective amount of a second therapeutic agent and a pharmaceutically acceptable carrier or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

5. EXAMPLES

The following Examples are set forth to assist in understanding the claimed invention and should not be construed as specifically limiting. Variations of the claimed invention that would be within the purview of those skilled in the art, including the substitution of equivalents now known or later developed, as well as changes in formulation or changes in experimental design, are considered to fall within the scope of the claimed invention.

Certain Examples below relate to the synthesis of illustrative Quinazolin-4(3H)-one-Type Piperidine Compounds.

Example 1: Synthesis of ethyl 3-((1R,1'R,3R,3'R, 5S,5'S)-9'-aza[3,9'-bi(bicyclo[3.3.1]nonan)]-3'-yl)-4-oxo-3,4-dihydroquinazoline-2-carboxylate (8) (Compound D12b)

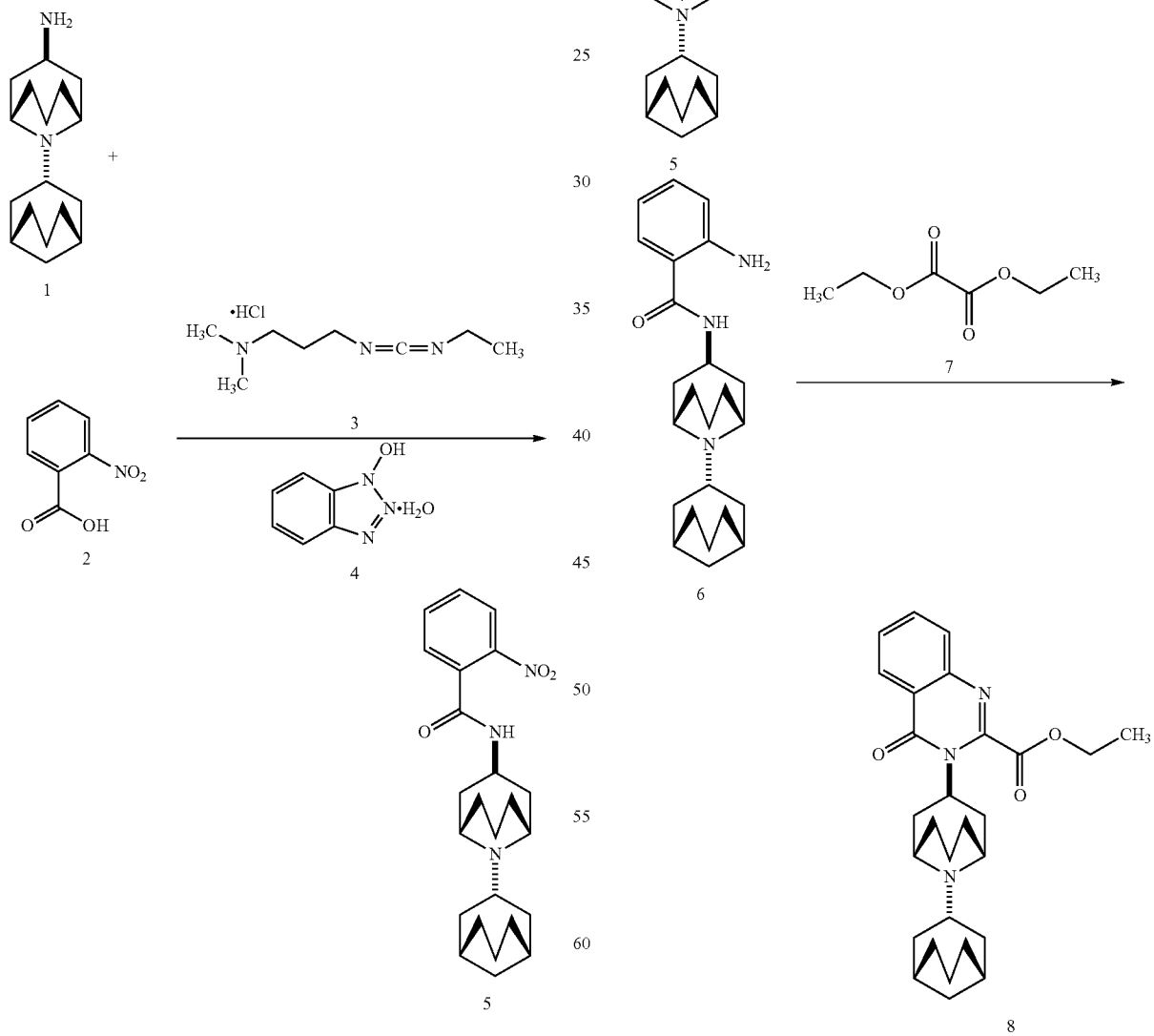

To a solution of 2-nitrobenzoic acid (2) (2.0 g, 11.98 mmol) and (1R,1'R,3r,3'R,5S,5'S)-9'-aza[3,9'-bi(bicyclo [3.3.1]nonan)]-3'-amine (1) (3.0 g, 11.41 mmol) in DMF (100 ml), EDC (3) (3.4 g, 17.78 mmol) and HOBT (4) (2.4 g, 17.78 mmol) were added. The solution was stirred at room temperature overnight. LC/MS indicated product formation, then the reaction mixture was concentrated and dissolved in H$_2$O (100 ml). The crude was extracted from DCM (100 ml), and the organic solvent dried with anhydrous Na$_2$SO$_4$. The filtrate was concentrated and purified by ISCO column chromatography first using 10% to 50% EtOAc/Hex to remove impurities and then by eluting with 5% MeOH/DCM to give 5.

To a solution of N-((1R,1'R,3r,3'R,5S,5'S)-[3,9'-bi(9'-azabicyclo[3.3.1]nonan)]-3'-yl)-2-nitrobenzamide (5) (3 g, 7.28 mmol) of in MeOH (100 ml), was added 10% Pd—C (2.0 g, 23.6 mmol). The solution was subjected to Parr hydrogenation at 55 psi overnight. After completion, the mixture was filtered through Celite and washed with MeOH several times and evaporated to provide white solid product of N-((1R,1'R,3r,3'R,5S,5'S)-[3,9'-bi(9'-azabicyclo[3.3.1]nonan)]-3'-yl)-2-aminobenzamide (6).

In a sealed tube, N-((1R,1'R,3r,3'R,5S,5'S)-[3,9'-bi(9'-azabicyclo[3.3.1]nonan)]-3'-yl)-2-aminobenzamide (6) (1 g, 2.07 mmol) and diethyloaxalate (7) (20 ml) were added together and stirred at 185-187° C. overnight. The reaction mixture was cooled down to room temperature and allowed to dry overnight under vacuum (Geneva-Vac). The crude product was purified by ISCO column chromatography using 20% to 60% EtOAc/Hex to give the desired product of ethyl 3-((1R,1'R,3R,3'R,5S,5'S)-9'-aza[3,9'-bi(bicyclo[3.3.1]nonan)]-3'-yl)-4-oxo-3,4-dihydroquinazoline-2-carboxylate (8) (Compound D12b) as brownish solid.

Example 2: Synthesis of 3-((1R,1'R,3R,3'R,5S,5'S)-[3,9'-bi(9'-azabicyclo[3.3.1]nonan)]-3'-yl)-4-oxo-3,4-dihydroquinazoline-2-carboxylic acid (9) (Compound D2b)

mixture was evaporated and the crude was dissolved in $H_2O$ (3 ml), then acidified by 2N HCl to pH 4. Chloroform was added to the solution and the crude was extracted. The organic solvent was evaporated and crude product was purified by ISCO column chromatography using 5% to 15% MeOH/DCM to give the desired product 3-((1R,1'R,3R,3'R,5S,5'S)-[3,9'-bi(9'-azabicyclo[3.3.1]nonan)]-3'-yl)-4-oxo-3,4-dihydroquinazoline-2-carboxylic acid (9) (Compound D2b).

9 (Compound D2b): $^1$H NMR (CDCl$_3$) δ: 11:17-11:28 (br, 1H), 8:05-8:19 (d, J=9.21 Hz, 1H), 7:51-7:66 (m, 1H), 7:36-7:48 (d, J=8.77 Hz, 1H), 7:25-7:36 (t, J=7.24 Hz, 1H), 5:49-5:67 (br, 1H), 3:95-4:16 (br, 3H), 2:74-3:02 (m, 4H), 2:13-2:44 (br, 5H), 1:43-2:01 (br, 5H), 1:29-1:76 (br, 9H) ppm; MS: (m/e): 435.6 (M+1).

Example 3: Synthesis of ethyl 2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1(2H)-yl)acetate (8) (Compound D12b)

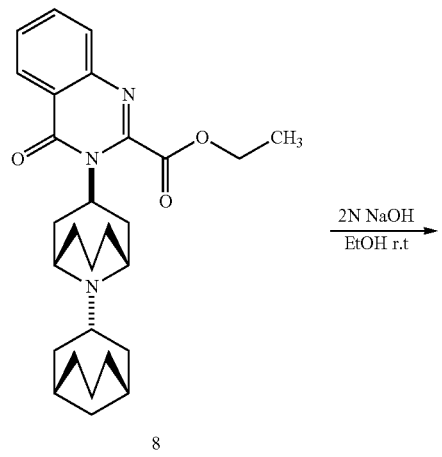

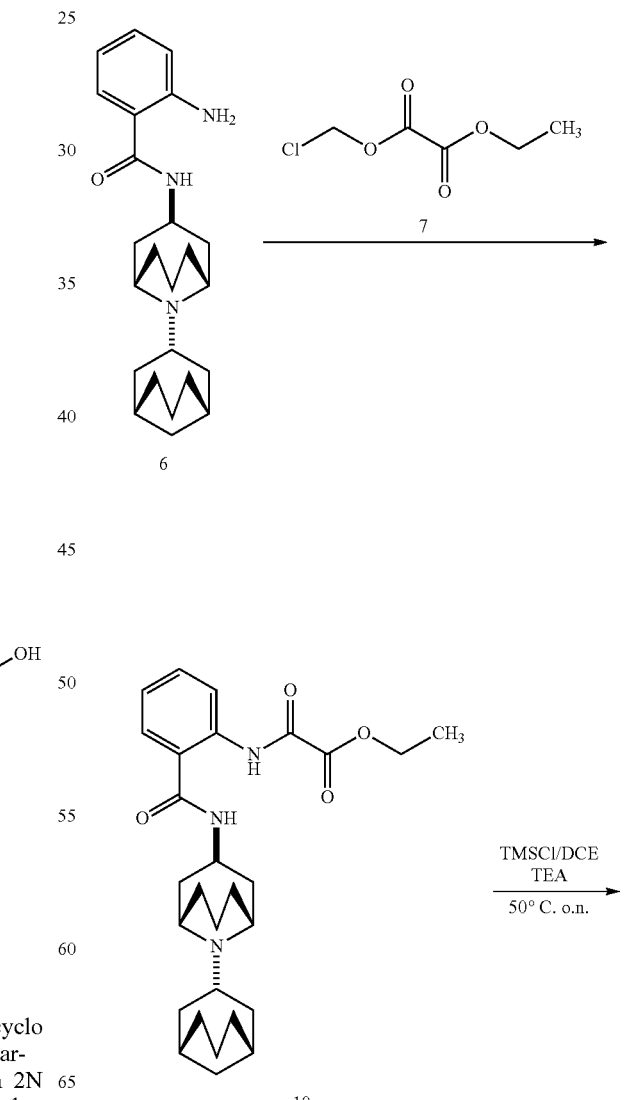

Ethyl 3-((1R,1'R,3R,3'R,5S,5'S)-9'-aza[3,9'-bi(bicyclo[3.3.1]nonan)]-3'-yl)-4-oxo-3,4-dihydroquinazoline-2-carboxylate (8) (300 mg, 0.61 mmol) was dissolved in 2N NaOH (1 ml) and EtOH (4 ml). The mixture was stirred at room temperature for 1 hr. After reaction was completed, the -continued

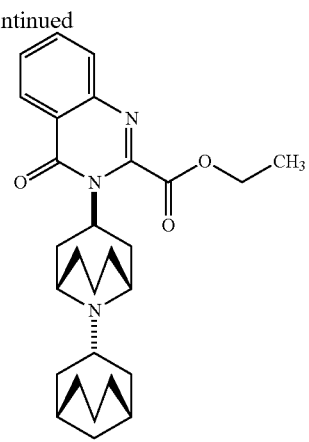

8

In a round bottom flask, N-((1R,1'R,3r,3'R,5S,5'S)-[3,9'-bi(9'-azabicyclo[3.3.1]nonan)]-3'-yl)-2-aminobenzamide (6) (0.5 g, 1.31 mmol) and ethyl chlorooxalate (7) (15 ml) was added together and stirred at room temperature overnight. LC/MS indicated formation of the monoester. The mixture was put under vacuum (Geneva-Vac) and evaporated overnight. The crude product was purified by ISCO column chromatography using 20% to 60% EtOAc/Hex to give ethyl 2-((2-((1R,1'R,3r,3'R,5S,5'S)-[3,9'-bi(9'-azabicyclo[3.3.1]nonan)]-3'-ylcarbamoyl)phenyl)amino)-2-oxoacetate (10).

To a solution of ethyl 2-((2-((1R,1'R,3r,3'R,5S,5'S)-[3,9'-bi(9'-azabicyclo[3.3.1]nonan)]-3'-ylcarbamoyl)phenyl)amino)-2-oxoacetate (10) (241 mg, 0.5 mmol) in DCE (15 ml) were added TMSCl and TEA, and the mixture stirred at 50° C. in a sealed vial overnight. After the mixture was cooled, EtOAc was added and washed successively with 1M aq. HCl, sat. NaHCO$_3$, and brine. The organic layer was extracted and dried with Mg$_2$SO$_4$. The filtrate was evaporated and purified by ISCO column chromatography using 5% to 10% MeOH/DCM to give ethyl 3-((1R,1'R,3R,3'R,5S,5'S)-9'-aza[3,9'-bi(bicyclo[3.3.1]nonan)]-3'-yl)-4-oxo-3,4-dihydroquinazoline-2-carboxylate (8) (Compound D12b) as a white solid.

8 (Compound D12b): $^1$H NMR (CDCl$_3$) δ: 8:11-8:23 (d, J=8.9 Hz, 1H), 7:537:67 (m, 2H), 7:33-7:45 (t, J=8.1 Hz, 1H), 4:34-4:35 (m, 2H), 4:15-4:31 (br, 1H), 3:19-3:42 (br, 3H), 2:18-2:35 (m, 2H), 1:93-2:05 (br, 4H), 1:73-1:91 (br, 2H), 1:61-1:75 (br, 8H), 1:41-1:59 (br, 7H), 1:24-1:42 (br, 4H) ppm; MS: (m/e): 464.2 (M+1).

Example 4: Synthesis of 3-((1R,1'R,3r,3'R,5S,5'S)-[3,9'-bi(9'-azabicyclo[3.3.1]nonan)]-3'-yl)quinazoline-2,4(1H,3H)-dione (12) (Compound D1a)

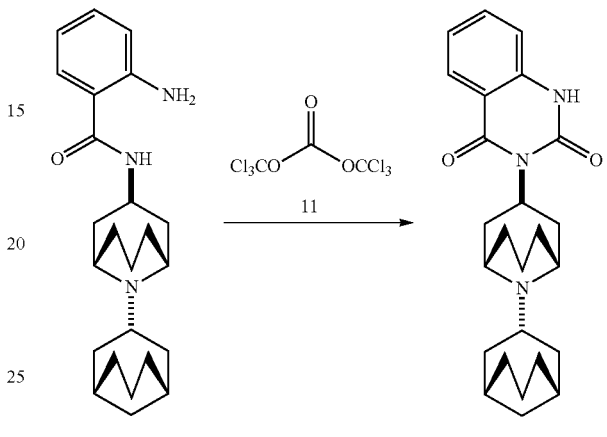

In a sealed tube, N-((1R,1'R,3r,3'R,5S,5'S)-[3,9'-bi(9'-azabicyclo[3.3.1]nonan)]-3'-yl)-2-aminobenzamide (6) (1 g, 2.62 mmol) was dissolved in THF (40 ml). Triphosgene (11) (4 g, 13.10 mmol) was added to the reaction mixture, and the solution was stirred at 65° C. for 1 h. LC/MS indicated product formation. The reaction mixture was cooled down to room temperature, and EtOAc was added to the mixture followed by washing with NaHCO$_3$. The organic solvent was extracted, and the majority of the product remained in the aqueous layer as a precipitated solid. The aqueous layer was filtered and dried on high vacuum overnight to give the desire product 3-((1R,1'R,3r,3'R,5S,5'S)-[3,9'-bi(9'-azabicyclo[3.3.1]nonan)]-3'-yl)quinazoline-2,4(1H,3H)-dione (12) (Compound D1a) as a white solid.

12 (Compound D1a): $^1$H NMR (CD$_3$OD) δ 7:88-7:98 (d, J=10:1 Hz, 1H), 7:49-7:59 (m, 1H), 7:10-7:18 m, 1H), 6:97-7:10 (m, 1H), 5:59-5:75 (br, 1H), 3:97-4:26 (br, 3H), 2:79-2:91 (br, 1H), 2:50-2:71 (br, 1H), 1:65:-2:39 (br, 16H), 1:47-2:63 (br, 7H), ppm; MS: (m/e): 408.4 (M+1).

Example 5: Synthesis of ethyl 2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1(2H)-yl)acetate (14) (Compound D13a)

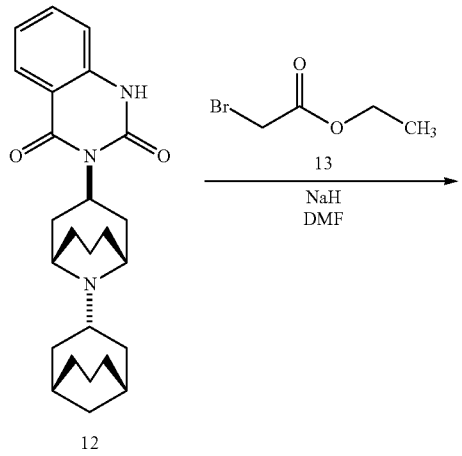

12

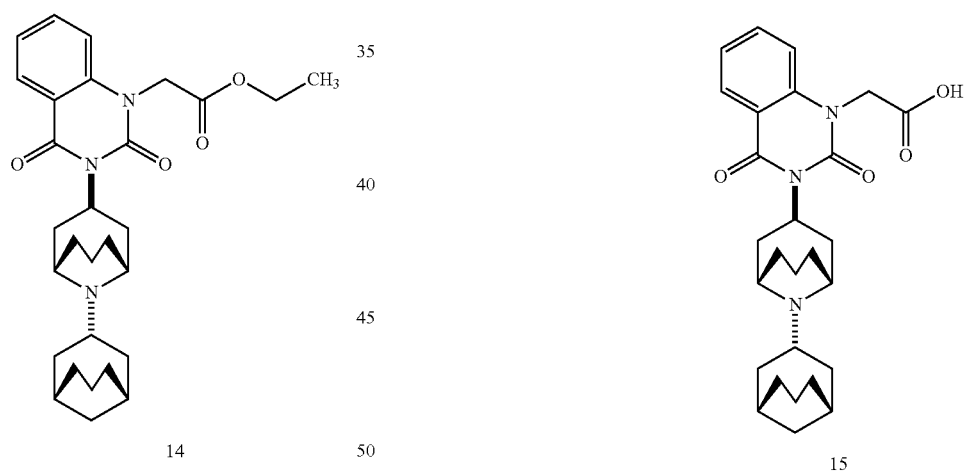

14

Example 6: Synthesis of 2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1(2H)-yl)acetic acid (15) (Compound D3a)

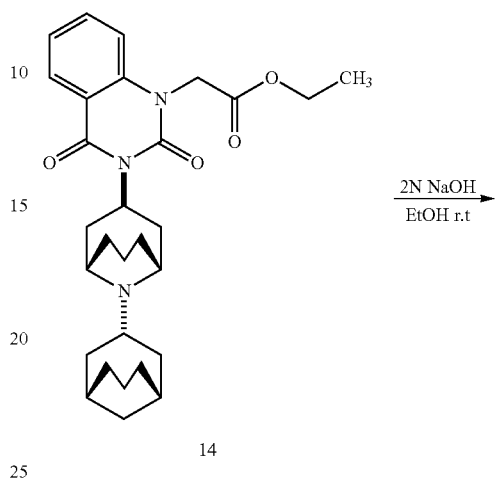

14

15

To a suspension of NaH (19 mg) in DMF (10 ml), was added, 3-((1R,1'R,3r,3'R,5S,5'S)-[3,9'-bi(9'-azabicyclo[3.3.1]nonan)]-3'-yl)quinazoline-2,4(1H,3H)-dione (12). The mixture was stirred at 0° C. for 0.5 h before the addition of ethyl 2-bromoacetate (13) (0.52 ml). The mixture was stirred at room temperature overnight. Formation of 14 was confirmed by LC/MS. The mixture of 14 was evaporated to dryness, and the crude was dissolved in DCM and then washed with H₂O. The organic solvent was dried with Na₂SO₄ and the filtrate was evaporated. The crude was purified by ISCO column chromatography using 30 to 50% EtOAc/Hex to obtain the desired ester product ethyl 2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1(2H)-yl)acetate (14) (Compound D13a)

14 (Compound D13a): MS: (m/e): 494.4 (M+1).

The ester 14 was hydrolyzed with 2N NaOH (1.0 ml) in EtOH (4.0 ml) and stirred at room temperature for 1 hr. The mixture was evaporated and crude was dissolved in H₂O, and then neutralized with 2N HCl to pH 4. The mixture was dissolved in chloroform and the solvent was extracted. The evaporated crude product was purified by ISCO column chromatography using 5% to 15% MeOH/DCM to give the desire product 2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1(2H)-yl)acetic acid (15) (Compound D3a).

15 (Compound D3a): $^1$H NMR (CD$_3$OD) δ 8:00-8:16 (d, J=8.1 Hz, 1H), 7:52-7:77 (m, 1H), 7:04-7:32 (m, 2H), 5:55-5:86 (br, 1H), 4:01-4:38 (br, 3H), 2:74-2:91 (br, 2H), 2:43-2:66 (br, 1H), 1:95-2:42 (br, 8H), 1:43-1:91 (br, 15H), ppm; MS: (m/e): 466.2 (M+1).

Example 7: Synthesis of methyl 2-(2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1 (2H)-yl)acetamido)acetate (17) (Compound D43a)

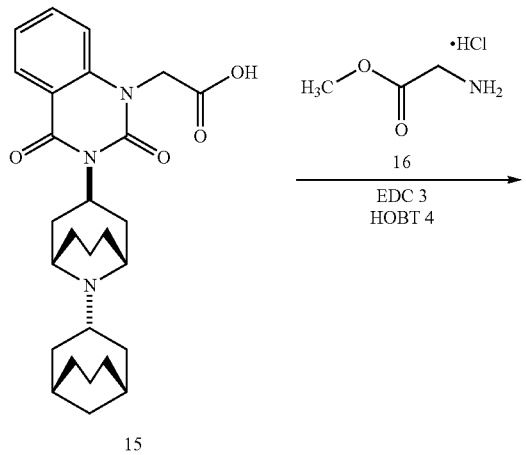

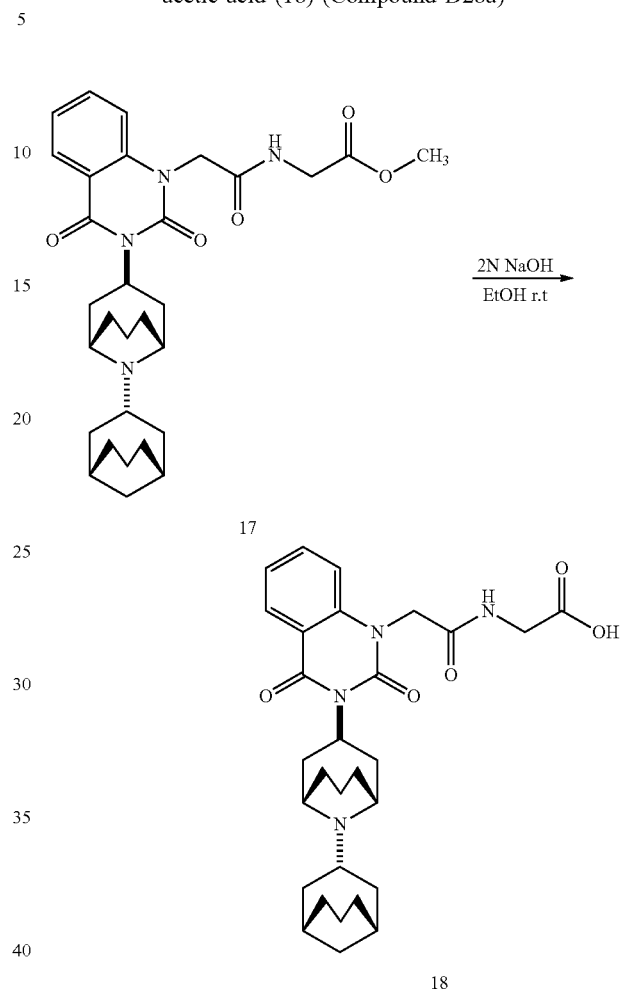

Example 8: Synthesis of 2-(2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1(2H)-yl)acetamido)acetic acid (18) (Compound D28a)

2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1(2H)-yl)acetic acid (15) (0.82 g, 0.176 mmol) was dissolved in THF (20 ml). To the mixture was added glycine methyl ester hydrochloride (16) (0.027 g, 0.211 mmol), EDC (3) (0.051 g, 0.264 mmol), and HOBT (4) (0.040 g, 0.264 mmol), and the reaction stirred at room temperature for 4 hrs and monitored by LC/MS. The resulting mixture was concentrated and the crude was dissolved with EtOAc and brine. The organic layer was dried with Na$_2$SO$_4$ and concentrated and purified by ISCO column chromatography using 5% MeOH/DCM to give methyl 2-(2-(3-((1R,1'R,3r,3'R,5S,5'S)-[3,9'-bi(9'-azabicyclo[3.3.1]nonan)]-3'-yl)-2,4-dioxo-3,4-dihydroquinazolin-1 (2H)-yl)acetamido)acetate (17) (Compound D43a).

17 (Compound D43a): MS: (m/e): 537.6 (M+1).

Methyl 2-(2-(3-((1R,1'R,3r,3'R,5S,5'S)-[3,9'-bi(9'-azabicyclo[3.3.1]nonan)]-3'-yl)-2,4-dioxo-3,4-dihydroquinazolin-(2H)-yl)acetamido)acetate (17) (150 mg, 0.280 mmol) was dissolved in EtOH (6 ml) and 2N NaOH (1.5 ml), and the reaction mixture was stirred at room temperature for 1 hr. The mixture was concentrated and the crude was dissolved with H$_2$O, and then adjusted to pH~2 to 4 with 3N HCl. The solution was extracted with chloroform, and the organic layer was dried with Na$_2$SO$_4$. The filtrate was evaporated and crude was purified by ISCO column chromatography using 5 to 20% MeOH/DCM to provide the desired product 2-(2-(3-((1R,1'R,3r,3'R,5S,5'S)-[3,9'-bi(9'-azabicyclo[3.3.1] nonan)]-3'-yl)-2,4-dioxo-3,4-dihydroquinazolin-1 (2H)-yl) acetamido)acetic acid (18) (Compound D28a).

18 (Compound D28a): $^1$H NMR (CD$_3$OD) δ 7:88-8:20 (d, J=9.21 Hz, H), 7:45-7:76 (t, J=7.02 Hz 1H), 6:96-7:35 (m, 2H), 5:52-5:-82 (br, 1H), 4:83-4:91 (br, 2H), 3:96-4:28 (br, 3H), 3:82-3:93 (br, 1H), 2:76-2:91 (br, 1H), 2:43-2:71 (br, 1H), 2:17-2:38 (br, 2H), 1:82-2:18 (br, 6H), 1:29-1:85 (br, 16H), ppm; MS: (m/e): 523.2 (M+1).

Example 9: Synthesis of ethyl 2-(3-((1R,3R,5S)-9-((1R,6S,8r)-bicyclo[4.3.1]decan-8-yl)-9-azabicyclo[3.3.1]nonan-3-yl)-2,4-dioxo-3,4-dihydroquinazolin-1(2H)-yl)acetate (20) (Compound J13a)

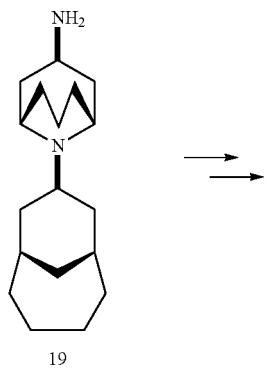

Ethyl 2-(3-((1R,3R,5S)-9-((1R,6S,8r)-bicyclo[4.3.1]decan-8-yl)-9-azabicyclo[3.3.1]nonan-3-yl)-2,4-dioxo-3,4-dihydroquinazolin-1(2H)-yl)acetate (20) was prepared from amine 19 in similar fashion as 14 was prepared from 1 above.

20 (Compound J13a): MS: (m/e): 508.4 (M+1).

Example 10: Synthesis of 2-(3-((1R,3R,5S)-9-((1R,6S,8r)-bicyclo[4.3.1]decan-8-yl)-9-azabicyclo[3.3.1]nonan-3-yl)-2,4-dioxo-3,4-dihydroquinazolin-1(2H)-yl)acetic acid (21) (Compound J3a)

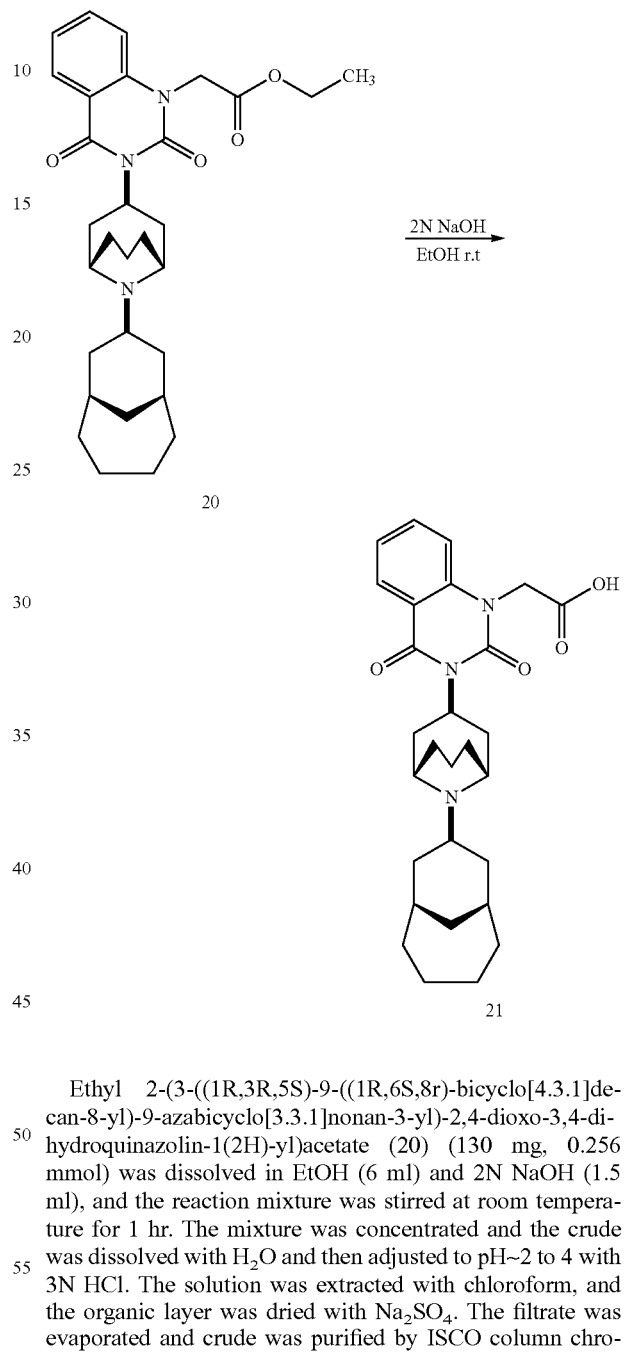

Ethyl 2-(3-((1R,3R,5S)-9-((1R,6S,8r)-bicyclo[4.3.1]decan-8-yl)-9-azabicyclo[3.3.1]nonan-3-yl)-2,4-dioxo-3,4-dihydroquinazolin-1(2H)-yl)acetate (20) (130 mg, 0.256 mmol) was dissolved in EtOH (6 ml) and 2N NaOH (1.5 ml), and the reaction mixture was stirred at room temperature for 1 hr. The mixture was concentrated and the crude was dissolved with H$_2$O and then adjusted to pH~2 to 4 with 3N HCl. The solution was extracted with chloroform, and the organic layer was dried with Na$_2$SO$_4$. The filtrate was evaporated and crude was purified by ISCO column chromatography using 5 to 20% MeOH/DCM to yield 2-(3-((1R,3R,5S)-9-((1R,6S,8r)-bicyclo[4.3.1]decan-8-yl)-9-azabicyclo[3.3.1]nonan-3-yl)-2,4-dioxo-3,4-dihydroquinazolin-1(2H)-yl)acetic acid (21) (Compound J3a).

21 (Compound J3a): $^1$H NMR (CD$_3$OD) δ 8:09-8:26 (d, J=Hz, 1H), 7:65-7:78 (t, 1H), 7:16-7:35 (m, 2H), 5:68-5:93 (br, 1H), 4:76-4:86 (br, 2H), 4:19-4:30 (br, 2H), 3:63-3:98 (br, 1H), 2:69-3:05 (br, 2H), 2:34-2:57 (br, 4H), 1:99-2:28 (br, 4H), 1:52-2:00 (br, 16H), ppm; MS: (m/e): 480.3 (M+1).

Example 11: Synthesis of ethyl 2-(3-((1R,1'R,3r,3'R,5S,5'S)-7-ethyl-[3,9'-bi(9'-azabicyclo[3.3.1]nonan)]-3'-yl)-2,4-dioxo-3,4-dihydroquinazolin-1(2H)-yl)acetate (23) (Compound D469a)

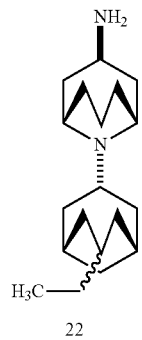

22

→ →

Example 12: Synthesis of 2-(3-((1R,1'R,3r,3'R,5S,5'S)-7-ethyl-[3,9'-bi(9'-azabicyclo[3.3.1]nonan)]-3'-yl)-2,4-dioxo-3,4-dihydroquinazolin-1(2H)-yl)acetic acid (24) (Compound D459a)

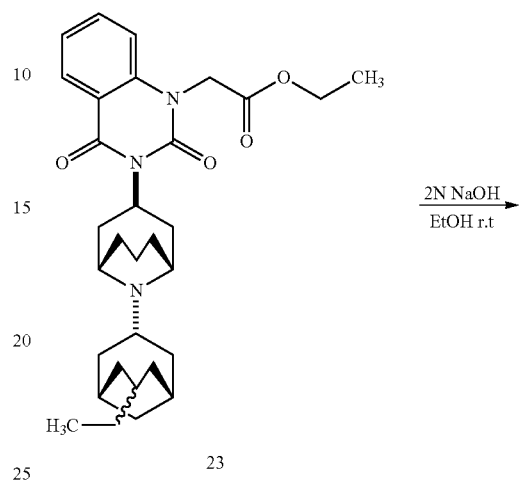

23

$\xrightarrow{\text{2N NaOH}}_{\text{EtOH r.t}}$

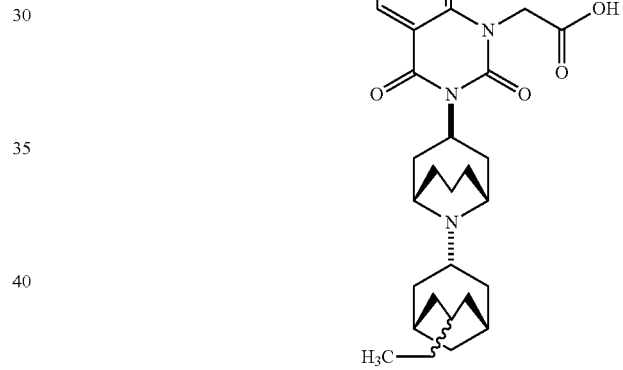

24

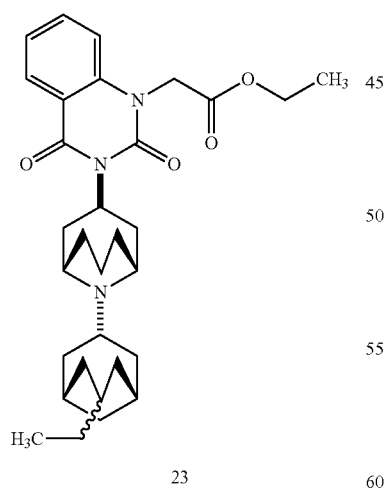

23

Ethyl 2-(3-((1R,1'R,3r,3'R,5S,5'S)-7-ethyl-[3,9'-bi(9'-azabicyclo[3.3.1]nonan)]-3'-yl)-2,4-dioxo-3,4-dihydroquinazolin-1(2H)-yl)acetate (23) was prepared from amine 22 in similar fashion as 14 was prepared from 1 above.

23 (Compound D469a): MS: (m/e): 522.2 (M+1).

Ethyl 2-(3-((1R,1'R,3r,3'R,5S,5'S)-7-ethyl-[3,9'-bi(9'-azabicyclo[3.3.1]nonan)]-3'-yl)-2,4-dioxo-3,4-dihydroquinazolin-1(2H)-yl)acetate (23) (180 mg, 0.345 mmol) was dissolved in EtOH (6 ml) and 2N NaOH (1.5 ml), and the reaction mixture was stirred at room temperature for 1 hr. The mixture was concentrated and the crude was dissolved with $H_2O$, and then adjusted to pH~2 to 4 with 3N HCl. The solution was extracted with chloroform, and the organic layer was dried with $Na_2SO_4$. The filtrate was evaporated and crude was purified by ISCO column chromatography using 5 to 20% MeOH/DCM to yield 2-(3-((1R,1'R,3r,3'R,5S,5'S)-7-ethyl-[3,9'-bi(9'-azabicyclo[3.3.1]nonan)]-3'-yl)-2,4-dioxo-3,4-dihydroquinazolin-1(2H)-yl)acetic acid (24) (Compound D459a).

24 (Compound D459a): $^1$H NMR (CD$_3$OD) δ 8:03-8:12 (d, J=7.89 Hz, 1H), 7:58-7:69 (t, J=7.45 Hz 1H), 7:11-7:26 (m, 2H), 5:57-5:80 (br, 1H), 4:79-4:86 (br, 2H), 4:02-2:15 (br, 2H), 3:47-3:83 (br, 1H), 2:54-2:92 (br, 3H), 2:17-2:39 (br, 4H), 1:88-2:16 (br, 7H), 1:68-1:87 (br, 3H), 1:43-1:63 (br, 4H), 0:58-1:10 (br, 7H), ppm; MS: (m/e): 494.2 (M+1).

Example 13: Synthesis of (1R,1'R,3r,3'R,5S,5'S)-9'-aza[3,9'-bi(bicyclo[3.3.1]nonan)]-3'-amine acetate (34), the Acetic Acid Salt of (1)

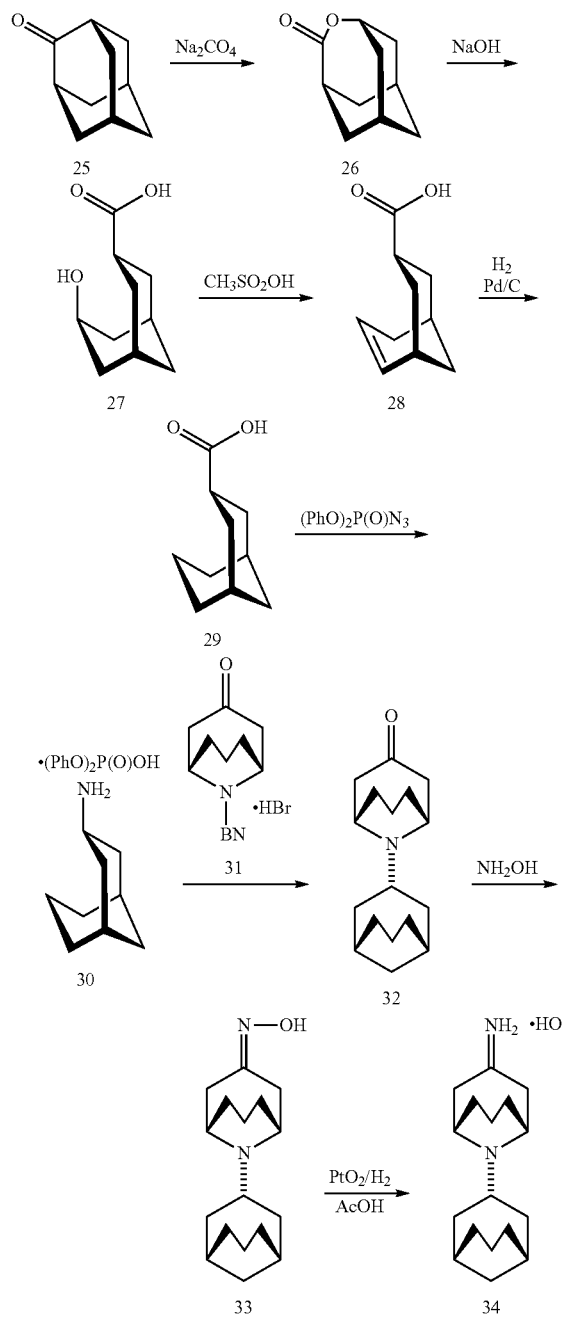

Commercially available 2-adamantanone (25) (1000 g, 6.66 mol, Sigma-Aldrich) was dissolved in TFA (3 L, Sigma-Aldrich). To this mechanically stirred mixture surrounded by a cooling bath with a temperature maintained at 20° C. was added sodium percarbonate (1254.8 g, 7.99 mol, Sigma-Aldrich) (or sodium peroxocarbonate) portion-wise over 1 h; the temperature of the reaction mixture increased to 60° C. during the addition. After 2 h additional stirring, deionized water (4 L) was added followed by four extractions with DCM (2 L for each extraction). The organic portions were combined, dried (MgSO$_4$), filtered, and evaporated under reduced pressure to provide 1180 g of (1R,3r,6s,8S)-4-oxatricyclo[4.3.1.1 3,8]undecan-5-one (26) as a white crystalline solid (yield 97%).

26: $^1$H-NMR: $\delta_H$ (ppm, 400 MHz, CDCl$_3$): 4.48 (1H, s), 3.06 (1H, m), 2.09 (2H, m), 2.00 (3H, m), 1.95 (2H, m), 1.81 (2H, m), 1.70 (2H, m); TLC (SiO$_2$) 1:1 EtOAc:hexanes: R$_f$=0.8 (visualized with molybdenum blue spray reagent).

26 (1572.7 g, 9.46 mol) was taken up in MeOH (2 L). To this was added NaOH (2270 g, 56.7 mol) in deionized water (6 L); the temperature of the mixture increased from about 25° C. to 54° C. during the addition. With stirring, the resulting reaction mixture was heated to a gentle reflux and refluxed for 36 h. After cooling to a temperature of about 25° C., the MeOH was removed by vacuum distillation at 60° C. The resulting solution was stirred and acidified with concentrated HCl to a pH of about 2.5. The white precipitate that formed was allowed to stir for 18 h at a temperature of about 25° C. then filtered under reduced pressure to provide partially dried (1R,3r,5S,7r)-7-hydroxybicyclo[3.3.1]nonane-3-carboxylic acid (27).

27: $^1$H-NMR: $\delta_H$ (ppm, 400 MHz, d6-DMSO): 11.88 (1H, s), 4.44 (1H, s), 3.73 (1H, m), 1.95 (4H, m), 1.63 (2H, m), 1.41 (3H, m), 1.22 (2H, m), 1.16 (1H, m); TLC (SiO$_2$) 2:1:0.1 EtOAc:hexanes:AcOH: R$_f$=0.3 (visualized with molybdenum blue spray reagent).

27, taken directly from the previous step, was suspended in toluene (8 L). To this was added methane sulfonic acid (367 mL, 4.73 mol, Sigma-Aldrich). With stirring, the resulting reaction mixture was heated to reflux and water removed azeotropically for 5 h. After cooling to a temperature of about 25° C., deionized water (4 L) was added with stirring. The organic layer was separated, dried (MgSO$_4$), filtered, and concentrated to provide (1R,3S,5S)-bicyclo[3.3.1]non-6-ene-3-carboxylic acid (28).

28: $^1$H-NMR: $\delta_H$ (ppm, 400 MHz, CDCl$_3$): 10.45 (1H, bs), 5.85 (1H, m), 5.70 (1H, m), 2.79 (1H, m), 2.37 (2H, m), 2.11 (1H, m), 1.81 (3H, m), 1.61 (4H, m); TLC (SiO$_2$) 1:1:0.1 EtOAc:hexanes:AcOH: R$_f$=0.8 (visualized with molybdenum blue spray reagent).

28 was taken directly from the previous step and taken up in MeOH (1 L). This was divided into six batches and to each, under a hydrogen atmosphere, was added 10% Pd/C (0.01 mol). The reaction mixtures were each hydrogenated at 50 psi until hydrogen uptake ceased (10 h to 15 h). The mixtures were combined, filtered through CELITE, and NaOH (1 kg) in deionized water (400 mL) was added. The mixture was stirred for 4 h at a temperature of about 25° C. The mixture was concentrated under reduced pressure and deionized water (4 L) was added. Concentrated HCl was added until a pH within the range of 3-4 was achieved. The white solid that formed was allowed to stir for 1 h at a temperature of about 25° C. and then was filtered under reduced pressure to provide 1.232 kg of (1R,3r,5S)-bicyclo[3.3.1]nonane-3-carboxylic acid (29) as an off-white crystalline solid (78% yield from 26).

29: $^1$H-NMR: $\delta_H$ (ppm, 400 MHz, CDCl$_3$): 9.25 (1H, bs), 3.13 (1H, m), 1.97 (4H, m), 1.80 (2H, m), 1.70 (5H, m), 1.57 (3H, m); TLC (SiO$_2$) 1:1:0.1 EtOAc:hexanes:AcOH: R$_f$=0.8 (visualized with molybdenum blue spray reagent).

29 (1108.5 g, 6.59 mol) was taken up in toluene (5 L) in a 20 L reaction vessel. To this was added TEA (1013.3 mL, 7.26 mol). The resulting mixture was stirred and heated to 75° C. under a nitrogen atmosphere. The diphenyl phosphoryl azide (DPPA) (1564 mL, 7.26 mol, Sigma-Aldrich) was diluted with toluene to 2 L total volume and added slowly via addition funnel over 1.5 h; during this addition the temperature increased by about 10° C. to 15° C. The resulting reaction mixture was allowed to stir for 3 h at 75° C. The mixture was then concentrated to a brownish-yellow oil by vacuum distillation at 90° C. The oil was cooled to 5° C. and THF (2.5 L) was added. The mixture was allowed to stir and cool to 0° C. NaOH (792 g, 19.80 mol) in deionized water (3 L) was added over 1 h keeping the temperature below 5° C. The mixture was stirred for 18 h at 5° C. The resulting mixture was then extracted twice with Et$_2$O (4 L for each extraction). To the remaining aqueous mixture at 5° C. was slowly added concentrated HCl until a pH of about 6-7 was reached; no significant change in temperature occurred during this neutralization. The resulting white precipitate was allowed to stir for 2 h at 0° C. The precipitate was then filtered under reduced pressure and dried under reduced pressure at 50° C. to provide 1.875 kg of (1R,3r,5S)-bicyclo[3.3.1]nonan-3-amine diphenyl phosphate salt (30) as a white solid (yield 73.1%).

30: $^1$H-NMR: $\delta_H$ (ppm, 400 MHz, d6-DMSO): 7.78 (2H, s), 7.22 (4H, t), 7.11 (4H, m), 6.93 (2H, t), 3.61 (1H, m), 3.31 (1H, s), 1.93 (4H, m), 1.33-1.60 (10H, m). 30 (1037.5 g, 2.67 mol) and commercially available 9-benzyl-3-oxo-9-azoniabicyclo[3.3.1]nonane bromide (31) (1000 g, 3.08 mol) were suspended in EtOH (6.2 L) and deionized water (2 L). To this stirred mixture was added potassium carbonate (390.72 g, 2.83 mol) in deionized water (800 mL). The resulting reaction mixture was stirred for 18 h at a temperature of about 25° C. The reaction mixture was then heated to reflux, about 81° C., and refluxed for 3 h. Thereafter, the mixture was allowed to cool slowly over 4 h to a temperature of about 25° C. with vigorous stirring during which time a white precipitate formed. The mixture was then cooled to 5° C. and allowed to stir for 2 h at that temperature. The white precipitate was filtered under reduced pressure, washed with deionized water (8 L), and dried under reduced pressure at 60° C. to provide 580.1 g of (1R,1'R,3r,5S,5'S)-9'-aza[3,9'-bi(bicyclo[3.3.1]nonan)]-3'-one (32) as a white crystalline solid (yield 83.1%).

32: $^1$H-NMR: $\delta_H$ (ppm, 400 MHz, CDCl$_3$): 3.69 (2H, s), 3.38 (1H, m), 2.62 (2H, m), 2.21 (2H, d), 2.12 (4H, m), 1.85 (2H, m), 1.41-1.78 (14H, m); TLC (SiO$_2$) 7:3 hexanes: EtOAc: R$_f$=0.4 (visualized with potassium iodoplatinate spray).

32 (580.1 g, 2.22 mol) and THF (4 L) were introduced into a reactor; the reactor temperature control was set to 18° C. 50% Aqueous NH$_2$OH (415 mL, 6.66 mol) was added followed by the slow addition of AcOH (381.25 mL, 6.66 mol). The temperature of the reaction mixture increased to 28° C. during the addition. The reaction mixture was stirred for 16 h at a temperature of about 25° C. then heated to a gentle reflux and refluxed for 1 h. The mixture was cooled to a temperature of about 25° C. and deionized water (4 L) and DCM (4 L) were added. With vigorous stirring, solid NaHCO$_3$ (560 g, 6.66 mol) was then slowly added over 30 min and the mixture was allowed to stir until effervescence ceased. The white precipitate that formed was filtered under reduced pressure, washed with deionized water (1 L), and dried under reduced pressure at 60° C. for 72 h to provide 432.5 g (1R,1'R,3r,5S,5'S)-9'-aza[3,9'-bi(bicyclo[3.3.1]nonan)]-3'-one oxime (33) as a white solid (yield 70.6%). The filtrate was allowed to form layers and the organic layer was separated. The aqueous layer was washed three times with DCM (2 L for each wash). The organic portions were combined, dried (MgSO$_4$), filtered, and evaporated under reduced pressure to provide a pale yellow solid. The solid was triturated with 10:1 Et$_2$O:EtOAc (1 L), stirred for 1 h, and filtered under reduced pressure to provide a residue which was dried under reduced pressure at 60° C. for 72 h to provide an additional 138.4 g of 33 as a white solid (yield 22.6%, overall yield 93.2%).

33 (570.9 g, 2.07 mol) was taken up in AcOH (3 L). This mixture, with a total dissolved volume of 3.3 L, was divided into ten 330 mL batches. Under a hydrogen atmosphere, to each batch was added platinum (IV) oxide (9.40 g, 0.041 mol) and each batch was then hydrogenated at 50 psi for 16 h to 18 h. The batches were combined and filtered through CELITE. The filter cake was washed with AcOH (500 mL). The filtrate was concentrated under reduced pressure at 70° C. to provide an oil. To the oil was added Et$_2$O (6 L). The mixture was stirred and cooled to 0° C. for 1 h. The white precipitate that formed was filtered under reduced pressure and washed with Et$_2$O (2 L) to provide 253.4 g of (1R,1'R,3r,3'R,5S,5'S)-9'-aza[3,9'-bi(bicyclo[3.3.1]nonan)]-3'-amine acetate (34) (yield 35.3%). The filtrate was evaporated under reduced pressure to provide a residue which was subjected to the same treatment with Et$_2$O. A second crop of 213.7 g of 34 was isolated (yield 32.1%). The filtrate was again evaporated under reduced pressure to provide 201.1 g of 34 (yield 25.4%, overall yield 92.8%).

34: $^1$H-NMR: $\delta_H$ (ppm, 400 MHz, CD$_3$OD): 3.63 (3H, m), 3.42 (1H, m), 2.36 (2H, m), 2.01 (5H, m), 1.89 (5H, m), 1.39-1.78 (13H, m), 1.12 (2H, m).

34 is the acetic acid salt of 1 and can be converted to 1 by neutralization with base, such as dilute aqueous NaOH. Amine 1 can then be processed as in Example 1 and/or A7 in Scheme B to prepare Quinazolin-4(3H)-one-Type Piperidine Compounds.

Example 14: Synthesis of (1R,1'R,3r,3'R,5S,5'S,7S)-7-methyl-9'-aza[3,9'-bi(bicyclo[3.3.1]nonan)]-3'-amine acetate (42)

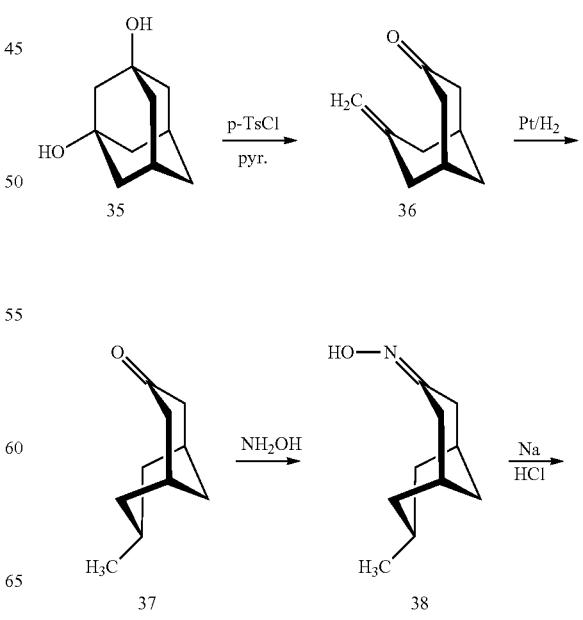

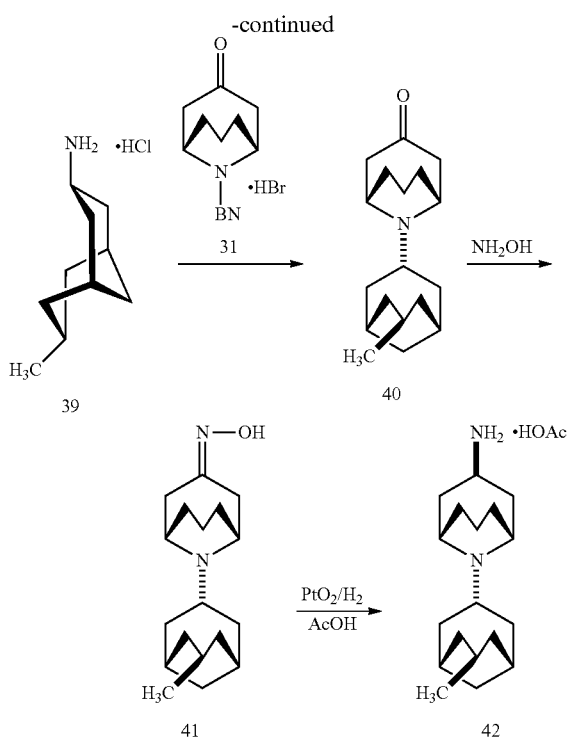

Commercially available 2-adamantanediol (35), (500 g, 2.97 mol, Sigma-Aldrich), p-tosyl chloride (624 g, 3.27 mol, Sigma-Aldrich), and pyridine (1.5 L) were combined and stirred under an argon atmosphere. The reaction mixture was heated to a temperature in the range of 68-71° C. and remained at that temperature for 2.5 h. The reaction mixture was cooled to a temperature of about 25° C. and poured into saturated brine (6 L). The resulting mixture was extracted three times with MTBE (4 L for each extraction). The organic portions were combined, dried (MgSO$_4$), filtered, and concentrated onto 1 kg silica gel (pre-treated with hexanes:TEA). The adsorbed material was chromatographed on 1.5 kg silica eluted sequentially with 1:10 EtOAc: hexanes (5 L) then 2:10 EtOAc:hexanes (5 L). All product fractions were combined and evaporated under reduced pressure to provide a residue. The residue was suspended in deionized water (2 L), stirred for 10 min, and filtered under reduced pressure to remove any excess reactants. The remaining solids were taken up in MTBE (2 L), dried (MgSO$_4$), filtered, and evaporated under reduced pressure to provide 301 g of (1R,5S)-7-methylenebicyclo[3.3.1]nonan-3-one (36) as a white crystalline solid (yield 67%).

36: $^1$H-NMR: $\delta_H$ (ppm, 400 MHz, CDCl$_3$): 4.79 (2H, s), 2.51 (8H, m), 2.29 (2H, m), 1.94 (2H, m), 1.60 (1H, m); TLC (SiO$_2$) 1:10 EtOAc:hexanes: R$_f$=0.25 (visualized with KMnO$_4$ spray reagent).

36 (250 g, 1.66 mol) was divided into five equal batches. Under a hydrogen atmosphere, the first batch was hydrogenated over platinum black (5 g, Sigma-Aldrich) at 50 psi in dry 99:1 cyclohexane:EtOAc (200 mL) for 2 h. The reaction mixture was decanted and the remaining catalyst washed with cyclohexane until no product remained as determined by TLC. The reaction flask was then recharged with the next batch of 36, cyclohexane (200 mL), and hydrogen and the reaction mixture was hydrogenated at 50 psi for 2 h. This procedure was repeated until all batches were reacted. All filtrates were combined, filtered through CELITE, and concentrated at a temperature of about 25° C. to provide 7-methylbicyclo[3.3.1]nonan-3-one (37) as a colorless oil.

37: $^1$H-NMR: $\delta_H$ (ppm, 400 MHz, CDCl$_3$): 2.42 (4H, m), 2.26 (2H, m), 1.98-2.00 (3H, m), 1.65 (1H, m), 1.54 (1H, m), 0.80 (1H, m); TLC (SiO$_2$) 2:10 EtOAc:hexanes: R$_f$=0.30 (visualized with KMnO$_4$ spray reagent).

37 was taken directly from the previous step and taken up in AcOH (1 L). To this was added 50% aqueous NH$_2$OH (100 mL, Sigma-Aldrich). With stirring, the reaction mixture was heated to a gentle reflux and refluxed for 1 h. The mixture was cooled to a temperature of about 25° C. and slowly poured into 2.5M Na$_2$CO$_3$ aqueous solution (5 L) with stirring. Thereafter, the mixture was stirred vigorously for 1 h. Deionized water (1 L) was added and the mixture was stirred for another 0.5 h. The precipitate that formed was collected by filtering under reduced pressure and washed with deionized water (2 L). The residue was taken up in DCM (1 L), dried (MgSO$_4$), filtered, and evaporated under reduced pressure to provide 231.5 g of 7-methylbicyclo [3.3.1]nonan-3-one oxime (38) as a white fluffy solid (85% yield from 36).

38: $^1$H-NMR: $\delta_H$ (ppm, 400 MHz, CDCl$_3$): 3.21 (1H, d), 2.05-2.41 (4H, m), 1.73-2.11 (4H, m), 1.51-1.73 (2H, m), 1.33 (1H, d), 0.82 (4H, m), 0.63 (1H, t).

To a three neck 5 L round bottom flask equipped with an overhead stirrer, 1 L pressure equalizing dropping funnel, and temperature probe was added toluene (about 3 L) and Na metal (67.17 g, 2.8 mol, Sigma-Aldrich). Under an argon atmosphere, the mixture was heated to a gentle reflux until the Na metal became molten. A solution of a portion of 38 (66.66 g, 0.40 mol) in dry isopropyl alcohol (230 mL) was then added dropwise via the dropping funnel over 1.5 h. With stirring, the resulting reaction mixture was heated to reflux and refluxed for 16 h. After cooling to a temperature of about 25° C., the following materials were added in sequential order: EtOH (164 mL) dropwise over 15 min, 1:1 EtOH:H$_2$O (164 mL) dropwise over 15 min, and water (500 mL) dropwise over 30 min. The resulting mixture was stirred for 2 h.

The mixture was poured into a 6 L separatory funnel and the organic layer was separated. The aqueous portion was extracted three times with Et$_2$O (1 L for each extraction).

The process just described was repeated twice more with 66.66 g batches of 38 being used each time. All organic portions were combined, dried (MgSO$_4$), and filtered into a 6 L Erlenmeyer flask. To the mixture was added 2M HCl in Et$_2$O (1.5 L, 2.5 eq). The mixture was allowed to stir and cool in an ice:MeOH bath for 1 h. The solids that formed were filtered under reduced pressure and dried under reduced pressure at 50° C. for 18 h to provide 100.01 g of (3s,7s)-7-methylbicyclo[3.3.1]nonan-3-amine hydrochloride (39) as a white crystalline solid. The filtrate was evaporated under reduced pressure to provide a residue which was triturated with Et$_2$O (2 L). The solids that remained were filtered and washed with Et$_2$O (2 L) to provide 87.1 g of a second crop of 39 after drying (overall yield 39%).

39: $^1$H-NMR: $\delta_H$ (ppm, 400 MHz, CDCl$_3$): 8.28 (3H, bs), 3.55 (1H, m), 2.25 (2H, m), 1.81-2.09 (4H, m), 1.85 (1H, m), 1.61 (3H, m) 1.08 (1H, d), 0.70-0.88 (5H, m).

39 (87.1 g, 0.463 mol), commercially available 9-benzyl-3-oxo-9-azoniabicyclo[3.3.1]nonane bromide (31) (165.20 g, 0.509 mol, Sigma-Aldrich), potassium carbonate (67.83 g, 0.491 mol), EtOH (1.07 L), and water (346 mL) were combined. The resulting reaction mixture was stirred for about 16 h at a temperature of about 25° C. The reaction mixture was then heated to reflux and refluxed for 3 h.

Thereafter, the mixture was cooled to a temperature of about 25° C. then further cooled to 5° C. in an ice/MeOH bath and allowed to stir for 30 min at that temperature. The solids that formed were filtered under reduced pressure, washed with deionized water, and dried under reduced pressure to provide 102.1 g of (1R,3r,5S,7s)-7-methyl-9'-aza[3,9'-bi(bicyclo[3.3.1]nonan)]-3'-one (40) as an off-white crystalline solid (yield 80%).

40: $^1$H-NMR: $\delta_H$ (ppm, 400 MHz, CDCl$_3$): 3.68 (2H, m), 3.05 (1H, m), 2.61 (2H, m), 2.25 (4H, m), 1.98 (1H, m), 1.85 (4H, m), 1.49-1.78 (7H, m), 1.25 (2H, m), 1.07 (1H, d), 0.86 (3H, d), 0.78 (2H, t).

40 (67 g, 0.243 mol), THF (500 mL), and AcOH (41.78 mL, 0.730 mol) were combined. To this mixture was added 50% aqueous NH$_2$OH (45 mL, 0.730 mol). With stirring, the resulting reaction mixture was heated to reflux and refluxed for 1 h. The mixture was cooled to a temperature of about 25° C. and deionized water was added (500 mL). Potassium carbonate (100 g, 0.730 mol) in deionized water (500 mL) was then added in one portion. The resulting mixture was stirred and cooled in an ice bath for 1 h. The solids that formed were filtered under reduced pressure and dried under reduced pressure at 60° C. to provide (1R,3r,5S,7s)-7-methyl-9'-aza[3,9'-bi(bicyclo[3.3.1]nonan)]-3'-one oxime (41) (yield >99%).

41: $^1$H-NMR: $\delta_H$ (ppm, 400 MHz, CD$_3$OD): 3.76 (1H, m), 3.45 (2H, m), 3.18 (1H, m), 3.02 (1H, m), 2.62 (1H, m), 2.27 (4H, m), 1.78-2.08 (7H, m), 1.67 (1H, m), 1.58 (2H, m), 1.46 (1H, m), 1.22 (2H, t), 1.09 (1H, d), 0.85 (5H, m).

41 (70.01 g, 0.241 mol) was taken up in AcOH (400 mL). This mixture was divided into two batches. Under a hydrogen atmosphere, to each batch was added platinum (IV) oxide (5.98 g, 0.2 eq, Sigma-Aldrich) and each batch was then hydrogenated at 50 psi for 16 h to 18 h. The batches were combined and filtered through CELITE. The filter cake was washed with AcOH (500 mL). The filtrate was concentrated under reduced pressure at 70° C. to provide an oil. To the oil was added MTBE (6 L). The mixture was stirred and cooled to 0° C. for 1 h. The white precipitate that formed was filtered under reduced pressure, washed with Et$_2$O (2 L), and dried under reduced pressure to provide 76.2 g of (1R,1'R,3r,3'R,5S,5'S,7S)-7-methyl-9'-aza[3,9'-bi(bicyclo[3.3.1]nonan)]-3'-amine acetate (42) as a white solid (yield 94%).

42: $^1$H-NMR: $\delta_H$ (ppm, 400 MHz, CD$_3$OD): 3.73 (2H, m), 3.55 (1H, m), 2.46 (2H, m), 2.24 (2H, m), 1.75-2.12 (11H, m), 1.45-1.75 (4H, m), 1.28 (4H, m), 1.06 (1H, d), 0.89 (3H, d), 0.80 (2H, t); LC/MS (t$_r$=1.689 min): m/z=277.3 [M+H]+ (Calc: 276.5).

42 can then be processed similar to 1 in Example 1 and/or A7 in Scheme B to prepare Quinazolin-4(3H)-one-Type Piperidine Compounds.

Example 15: Synthesis of (1R,3R,5S)-9-((1R,6S,8s)-bicyclo[4.3.1]decan-8-yl)-9-azabicyclo[3.3.1]nonan-3-amine acetate (19)

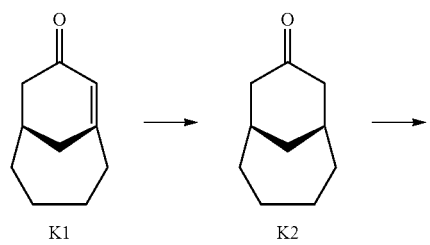

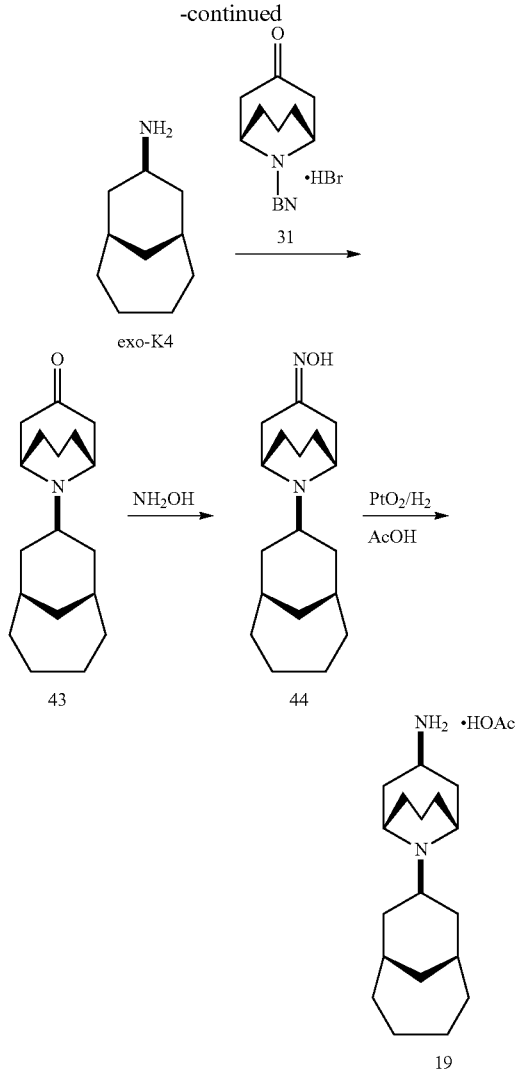

K1, K2, and exo-K4 were prepared as discussed in Scheme K.

K1: MS: m/z=151.4 [M+H]+.
K2: MS: m/z=153.4 [M+H]+.
exo-K4: MS: m/z=154.4 [M+H]+.

Diamine 19 was prepared from exo-K4 by compling with commercially available 31 followed by two-step reductive amination with hydroxylamine and hydrogen in the presence of platinum catalyst, e.g., analogously to the conversion of 30 to 34 in Example 13 or the conversion of 39 to 42 in Example 14.

(1R,5S)-9-((1R,6S,8s)-bicyclo[4.3.1]decan-8-yl)-9-azabicyclo[3.3.1]nonan-3-one, 43: $^1$H-NMR: $\delta_H$ (ppm, CD$_3$OD): 3.76 (br, 2H), 3.45 (m, 1H), 3.13 (m, 1H), 2.70 (m, 2H), 2.38-2.20 (m, 4H), 1.99-1.76 (m, 9H), 1.75-1.34 (m, 10H); MS: m/z=276.4 [M+H]+.

(1R,5S)-9-((1R,6S,8s)-bicyclo[4.3.1]decan-8-yl)-9-azabicyclo[3.3.1]nonan-3-one oxime, 44: $^1$H-NMR: $\delta_H$ (ppm, CDCl$_3$): 8.29 (br, 1H), 3.52 (br, 2H), 3.03 (m, 2H), 2.63 (m, 1H), 2.27 (m, 4H), 1.95-1.26 (m, 20H); MS: m/z=291.4 [M+H]+.

(1R,3R,5S)-9-((1 R,6S,8s)-bicyclo[4.3.1]decan-8-yl)-9-azabicyclo[3.3.1]nonan-3-amine acetate, 19: $^1$H-NMR: $\delta_H$ (ppm, CD$_3$OD): 3.49 (m, 2H), 3.20 (m, 1H), 3.05 (m, 1H), 2.27 (m, 4H), 2.04 (m, 1H), 1.91 (s, 3H), 1.81 (m, 7H), 1.71-1.42 (m, 8H), 1.31-1.15 (m, 6H); MS: m/z=277.4 [M+H]+.

19 can then be processed similar to 1 in Example 1 and/or A7 in Scheme B to prepare Quinazolin-4(3H)-one-Type Piperidine Compounds.

Example 16: In vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/mL. Protein concentrations were determined using the BioRad protein assay reagent with bovine serum albumen as a standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 μg membrane protein in a final volume of 500 μL binding buffer (10 mM $MgCl_2$, 1 mM EDTA, 5% DMSO, 50 mM HEPES, pH 7.4). Non-specific binding was determined 20 in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma-Aldrich). Harvesting was performed using a 96-well tissue harvester (Packard) followed by three filtration washes with 500 μL ice-cold binding buffer. Filter plates were subsequently dried at 50° C. for 2-3 hours. Fifty μL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data: A Quinazolin-4(3H)-one-Type Piperidine Compound has a binding affinity ($K_i$) for the human ORL-1 receptor of about 1000 nM or less in one embodiment, or about 500 nM or less in another embodiment. In certain embodiments, a Quinazolin-4(3H)-one-Type Piperidine Compound has a $K_i$ (nM) of about 300 or less for binding to ORL-1 receptors. In one embodiment, a Quinazolin-4(3H)-one-Type Piperidine Compound has a $K_i$ (nM) of about 100 or less. In another embodiment, a Quinazolin-4(3H)-one-Type Piperidine Compound has a $K_i$ (nM) of about 35 or less. In another embodiment, a Quinazolin-4(3H)-one-Type Piperidine Compound has a $K_i$ (nM) of about 20 or less. In another embodiment, a Quinazolin-4(3H)-one-Type Piperidine Compound has a $K_i$ (nM) of about 15 or less. In another embodiment, a Quinazolin-4(3H)-one-Type Piperidine Compound has a $K_i$ (nM) of about 10 or less. In another embodiment, a Quinazolin-4(3H)-one-Type Piperidine Compound has a $K_i$ (nM) of about 4 or less. In another embodiment, a Quinazolin-4(3H)-one-Type Piperidine Compound has a $K_i$ (nM) of about 1 or less. In another embodiment, a Quinazolin-4(3H)-one-Type Piperidine Compound has a $K_i$ (nM) of about 0.4 or less. In another embodiment, a Quinazolin-4(3H)-one-Type Piperidine Compound has a $K_i$ (nM) of about 0.1 or less.

Example 17: In vitro ORL-1 Receptor Functional Assay

ORL-1 Receptor [$^{35}$S]GTPγS Binding Assay Procedures: Membranes from recombinant HEK-293 cells expressing the human opioid receptor-like (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 μg/μL ORL-1 membrane protein, 10 μg/mL saponin, 3 μM GDP and 0.20 nM [35S]GTPγS to binding buffer (100 mM NaCl, 10 mM $MgCl_2$, 20 mM HEPES, pH 7.4) on ice. The prepared membrane solution (190 μL/well) was transferred to 96-shallow well polypropylene plates containing 10 μL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 2-3 hours. Fifty μL/well scintillation cocktail (BetaScint; Wallac) was added and plates were counted in Packard Top-Count for 1 min/well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. In one embodiment, a Quinazolin-4(3H)-one-Type Piperidine Compound has an ORL-1 GTP $EC_{50}$ (nM) of about 5000 or less to stimulate ORL-1 receptor function. In another embodiment, a Quinazolin-4(3H)-one-Type Piperidine Compound has an ORL-1 GTP $EC_{50}$ (nM) of about 1000 or less. In another embodiment, a Quinazolin-4(3H)-one-Type Piperidine Compound has an ORL-1 GTP $EC_{50}$ (nM) of about 100 or less. In another embodiment, a Quinazolin-4(3H)-one-Type Piperidine Compound has an ORL-1 GTP $EC_{50}$ (nM) of about 80 or less. In another embodiment, a Quinazolin-4(3H)-one-Type Piperidine Compound has an ORL-1 GTP $EC_{50}$ (nM) of about 50 or less. In another embodiment, a Quinazolin-4(3H)-one-Type Piperidine Compound has an ORL-1 GTP $EC_{50}$ (nM) of about 35 or less. In another embodiment, a Quinazolin-4(3H)-one-Type Piperidine Compound has an ORL-1 GTP $EC_{50}$ (nM) of about 15 or less. In another embodiment, a Quinazolin-4(3H)-one-Type Piperidine Compound has an ORL-1 GTP $EC_{50}$ (nM) of about 10 or less. In another embodiment, a Quinazolin-4(3H)-one-Type Piperidine Compound has an ORL-1 GTP $EC_{50}$ (nM) of about 4 or less.

In another embodiment, a Quinazolin-4(3H)-one-Type Piperidine Compound has an ORL-1 GTP $EC_{50}$ (nM) of about 1 or less. In another embodiment, a Quinazolin-4(3H)-one-Type Piperidine Compound has an ORL-1 GTP $EC_{50}$ (nM) of about 0.4 or less. In another embodiment, a Quinazolin-4(3H)-one-Type Piperidine Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In one embodiment, a Quinazolin-4(3H)-one-Type Piperidine Compound has an ORL-1 GTP Emax (%) of about 50% or greater. In another embodiment, a Quinazolin-4(3H)-one-Type Piperidine Compound has an ORL-1 GTP Emax (%) of about 75% or greater. In another embodiment, a Quinazolin-4(3H)-one-Type Piperidine Compound has an ORL-1 GTP Emax (%) of about 85% or greater. In another embodiment, a Quinazolin-4(3H)-one-Type Piperidine Compound has an ORL-1 GTP Emax (%) of about 95% or greater. In another embodiment, a Quinazolin-4(3H)-one-Type Piperidine Compound has an ORL-1 GTP Emax (%) of about 100% or greater. In another embodiment, a Quinazolin-4(3H)-one-Type Piperidine Compound has an ORL-1 GTP Emax (%) of about 110% or greater. In certain embodiments, a Quinazolin-4(3H)-one-Type Piperidine Compound acting as a partial agonist has an ORL-1 GTP Emax (%) of less than about 10%. In one embodiment, partial agonist Quinazolin-4(3H)-one-Type Piperidine Compounds has an ORL-1 GTP Emax (%) of less than about 20%. In another embodiment, partial agonist Quinazolin-4(3H)-one-Type Piperidine Compounds has an ORL-1 GTP Emax (%) of less than about 30%. In another embodiment, partial agonist Quinazolin-4(3H)-one-Type Piperidine Compounds has an ORL-1 GTP Emax (%) of less than about 40%. In another embodiment, partial agonist Quinazolin-4(3H)-one-Type Piperidine Compounds has an ORL-1 GTP Emax (%) of less than about 50%. In some embodiments, a Quinazolin-4(3H)-one-Type Piperidine Compound acting as an antagonist has an ORL-1 GTP Emax (%) of less than about 5%, for example, less than about 2%, such as around 1%.

Example 18: In vitro Mu-opioid Receptor Binding Assays

µ-Opioid Receptor Binding Assay Procedures: Radioligand binding assays are conducted using freshly thawed membranes expressing human µ-receptors (Perkin Elmer, Shelton, Conn.). Radioligand dose-displacement binding assays for human µ-opioid receptors use 0.2 nM[$^{3}$H]-diprenorphine (NEN, Boston, Mass.), with 5-20 mg membrane protein/well in a final volume of 500 µL binding buffer (10 mM $MgCl_2$, 1 mM EDTA, 5% DMSO, 50 mM HEPES, pH 7.4). Reactions are carried out in the absence or presence of increasing concentrations of unlabeled naloxone. All reactions are conducted in 96-deep well polypropylene plates for 1-2 hr at about 25° C. Binding reactions are terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed by performing three filtration washes with 500 µL of ice-cold binding buffer. Filter plates are subsequently dried at 50° C. for 2-3 hours. BetaScint scintillation cocktail (Wallac, Turku, Finland) is added (50 µL/well), and plates are counted using a Packard Top-Count for 1 min/well. The data are analyzed using the one-site competition curve fitting functions in GraphPad PRISM v. 3.0 (San Diego, Calif.), or an in-house function for one-site competition curve-fitting.

µ-Opioid Receptor Binding Data: In certain embodiments, a Quinazolin-4(3H)-one-Type Piperidine Compound has a $K_i$ (nM) of about 3000 or less for binding to µ-opioid receptors, or about 1000 or less, or about 650 or less, or about 525 or less, or about 250 or less, or about 100 or less, or about 10 or less, or about 1 or less, or about 0.1 or less.

Example 19: In vitro Mu-Opioid Receptor Functional Assays

µ-Opioid Receptor Functional Assay Procedures: [$^{35}$S] GTPγS functional assays are conducted using freshly thawed membranes expressing human µ-receptors. Assay reactions are prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 L/well) is transferred to 96-shallow well polypropylene plates containing 10 µL of 20× concentrated stock solutions of the agonist DAMGO ([D-Ala2, N-methyl-Phe4 Gly-ol5]-enkephalin) prepared in DMSO. Plates are incubated for 30 min at about 25° C. with shaking. Reactions are terminated by rapid filtration onto 96-well Unifilter GF/B filter plates (Packard, Meriden, Conn.) using a 96-well tissue harvester (Brandel, Gaithersburg, Md.) followed by three filtration washes with 2001 µL of ice-cold wash buffer (10 mM $NaH_2PO_4$, 10 mM $Na_2HPO_4$, pH 7.4). Filter plates are subsequently dried at 50° C. for 2-3 hr. BetaScint scintillation cocktail (Wallac, Turku, Finland) is added (50 µL/well) and plates are counted using a Packard Top-Count for 1 min/well. Data are analyzed using the sigmoidal dose-response curve fitting functions in GraphPad PRISM v. 3.0, or an in-house function for non-linear, sigmoidal dose-response curve-fitting.

µ-Opioid Receptor Functional Data: µ GTP $EC_{50}$ is the concentration of a compound providing 50% of the maximal response for the compound at a µ-opioid receptor. In certain embodiments, a Quinazolin-4(3H)-one-Type Piperidine Compound has a µ GTP $EC_{50}$ (nM) of about 5000 or less, or about 4100 or less, or about 3100 or less, or about 2000 or less, or about 1000 or less, or about 100 or less, or about 10 or less, or about 1 or less, or about 0.4 or less, or about 0.1 or less.

µ GTP Emax (%) is the maximal effect elicited by a compound relative to the effect elicited by DAMGO, a standard µ agonist. In certain embodiments, a Quinazolin-4(3H)-one-Type Piperidine Compound has a µ GTP Emax (%) of about 10% or greater, or about 20% or greater, or about 50% or greater, or about 65% or greater, or about 75% or greater, or about 88% or greater, or about 100% or greater. In other embodiments, a Quinazolin-4(3H)-one-Type Piperidine Compound has a µ GTP Emax (%) of about 10% or less, or about 5% or less, or about 2% or less.

Example 20: In vitro Kappa-opioid Receptor Binding Assays

κ-Opioid Receptor Binding Assay Procedures: Membranes from recombinant HEK-293 cells expressing the human kappa opioid receptor (kappa) (cloned in house) are prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/mL.

Protein concentrations are determined using the BioRad protein assay reagent with bovine serum albumen as a standard. Aliquots of kappa receptor membranes are stored at −80° C.

Radioligand dose displacement assays use 0.4-0.8 nM [$^1$H]-U69,593 (NEN; 40 Ci/mmole) with 10-20 μg membrane protein (recombinant kappa opioid receptor expressed in HEK 293 cells; in-house prep) in a final volume of 200 μL binding buffer (5% DMSO, 50 mM Trizma base, pH 7.4). Non-specific binding is determined in the presence of 10 μM unlabeled naloxone or U69,593. All reactions are performed in 96-well polypropylene plates for 1 h at a temperature of about 25° C. Binding reactions are determined by rapid filtration onto 96-well Unifilter GF/C filter plates (Packard) presoaked in 0.5% polyethylenimine (Sigma-Aldrich). Harvesting is performed using a 96-well tissue harvester (Packard) followed by five filtration washes with 200 μL ice-cold binding buffer. Filter plates are subsequently dried at 50° C. for 1-2 hours. Fifty μL/well scintillation cocktail (MicroScint20, Packard) is added and plates counted in a Packard Top-Count for 1 min/well.

κ-Opioid Receptor Binding Data: In one embodiment, a Quinazolin-4(3H)-one-Type Piperidine Compound has substantially no activity at a κ-opioid receptor. In certain embodiments, a Quinazolin-4(3H)-one-Type Piperidine Compound has a $K_i$ (nM) of about 20,000 or less, or about 10,000 or less, or about 5000 or less, or about 500 or less, or about 300 or less, or about 100 or less, or about 50 or less, or about 20 or less, or about 15 or less, or about 10 or less.

Example 21: In vitro Kappa-Opioid Receptor Functional Assays

κ-Opioid Receptor Functional Assay Procedures: Functional [$^{13}$S]GTPyS binding assays are conducted as follows. Kappa opioid receptor membrane solution is prepared by sequentially adding final concentrations of 0.026 μg/μL kappa membrane protein (in-house), 10 μg/mL saponin, 3 μM GDP and 0.20 nM [$^{35}$S]GTPyS to binding buffer (100 mM NaCl, 10 mM MgCl$_2$, 20 mM HEPES, pH 7.4) on ice. The prepared membrane solution (190 μL/well) is transferred to 96-shallow well polypropylene plates containing 10 μL of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Packard) using a 96-well tissue harvester (Packard) and followed by three filtration washes with 200 μL ice-cold binding buffer (10 mM NaH$_2$PO$_4$, 10 mM Na$_2$HPO$_4$, pH 7.4). Filter plates are subsequently dried at 50° C. for 2-3 hours. Fifty μL/well scintillation cocktail (MicroScint20, Packard) is added and plates counted in a Packard Top-Count for 1 min/well.

κ-Opioid Receptor Functional Data: κ GTP EC$_{50}$ is the concentration of a compound providing 50% of the maximal response for the compound at a κ-opioid receptor. In certain embodiments, a Quinazolin-4(3H)-one-Type Piperidine Compound has a κ GTP EC$_{50}$ (nM) of about 20,000 or less, or about 10,000 or less, or about 5000 or less, or about 2000 or less, or about 1500 or less, or about 800 or less, or about 500 or less, or about 300 or less, or about 100 or less, or about 50 or less, or about 10 or less.

κ GTP Emax (%) is the maximal effect elicited by a compound relative to the effect elicited by U69,593. In certain embodiments, a Quinazolin-4(3H)-one-Type Piperidine Compound has a κ GTP Emax (%) of about 10% or greater, or about 15% or greater, or about 30% or greater, or about 40% or greater, or about 45% or greater, or about 75% or greater, or about 90% or greater, or about 100% or greater. In other embodiments, a Quinazolin-4(3H)-one-Type Piperidine Compound has a κ GTP Emax (%) of about 10% or less, or about 5% or less, or about 2% or less.

Example 22: In vitro Delta-opioid Receptor Binding Assays

δ-Opioid Receptor Binding Assay Procedures: Radioligand dose-displacement assays use 0.2 nM [$^3$H]-Naltrindole (NEN; 33.0 Ci/mmole) with 10-20 μg membrane protein (recombinant delta opioid receptor expressed in CHO-K1 cells; Perkin Elmer) in a final volume of 500 μL binding buffer (5 mM MgCl$_2$, 5% DMSO, 50 mM Trizma base, pH 7.4). Non-specific binding is determined in the presence of 25 μM unlabeled naloxone. All reactions are performed in 96-deep well polypropylene plates for 1 h at a temperature of about 25° C. Binding reactions are determined by rapid filtration onto 96-well Unifilter GF/C filter plates (Packard) presoaked in 0.5% polyethylenimine (Sigma-Aldrich). Harvesting is performed using a 96-well tissue harvester (Packard) followed by five filtration washes with 500 μL ice-cold binding buffer. Filter plates are subsequently dried at 50° C. for 1-2 hours. Fifty μL/well scintillation cocktail (MicroScint20, Packard) is added and plates counted in a Packard Top-Count for 1 min/well.

δ-Opioid Receptor Binding Data: In one embodiment, a Quinazolin-4(3H)-one-Type Piperidine Compound has substantially no activity at a δ-opioid receptor. In certain embodiments, a Quinazolin-4(3H)-one-Type Piperidine Compound has a $K_i$ (nM) of about 20,000 or less, or about 10,000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less, or about 10 or less.

Example 23: In vitro Delta-Opioid Receptor Functional Assays

δ-Opioid Receptor Functional Assay Procedures: Functional [$^{35}$S]GTPyS binding assays are conducted as follows using membranes expressing human δ-opioid receptors. Delta opioid receptor membrane solution is prepared by sequentially adding final concentrations of 0.026 μg/L delta membrane protein (Perkin Elmer), 10 μg/mL saponin, 3 μM GDP and 0.20 nM [$^{35}$S]GTPyS to binding buffer (100 mM NaCl, 10 mM MgCl$_2$, 20 mM HEPES, pH 7.4) on ice. The prepared membrane solution (190 L/well) is transferred to 96-shallow well polypropylene plates containing 10 L of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Packard) using a 96-well tissue harvester (Packard) and followed by three filtration washes with 200 μL ice-cold binding buffer (10 mM NaH$_2$PO$_4$, 10 mM Na$_2$HPO$_4$, pH 7.4). Filter plates are subsequently dried at 50° C. for 1-2 hours. Fifty μL/well scintillation cocktail (MicroScint20, Packard) is added and plates counted in a Packard Top-count for 1 min/well.

δ-Opioid Receptor Functional Data: δ GTP EC$_{50}$ is the concentration of a compound providing 50% of the maximal response for the compound at a δ receptor. In certain embodiments, a Quinazolin-4(3H)-one-Type Piperidine Compound has a δ GTP EC$_{50}$ (nM) of about 20,000 or less, or about 10,000 or less, or about 100 or less, or about 1000 or less, or about 90 or less, or about 50 or less, or about 25 or less, or about 10 or less.

δ GTP Emax (%) is the maximal effect elicited by a compound relative to the effect elicited by met-enkephalin. In certain embodiments, a Quinazolin-4(3H)-one-Type Piperidine Compound has a δ GTP Emax (%) of about 10% or greater, or about 30% or greater, or about 50% or greater, or about 75% or greater, or about 90% or greater, or about 100% or greater, or about 110% or greater. In other embodiments, a Quinazolin-4(3H)-one-Type Piperidine Compound has a δ GTP Emax (%) of about 10% or less, or about 5% or less, or about 2% or less.

Example 24: Cytochrome P450 1A2, 2C9, 2D6, and 3A4

Cytochrome P450 1A2 (CYP1A2), 2C9 (CYP2C9), 2D6 (CYP2D6), and 3A4 (CYP3A4) are enzymes of the cytochrome P450 super family known to be involved in metabolizing and eliminating many drugs, e.g., orally-administered opiates, particularly at lower concentrations. Quinazolin-4(3H)-one-Type Piperidine Compounds were tested for the extent to which they inhibited production of reference metabolites for these enzymes.

For example, using commercially available pooled human hepatic microsome and employing, as an indicator, the O-demethylation of dextromethorphan ((4bR,8aS,9R)-3-methoxy-11-methyl-6,7,8,8a,9,10-hexahydro-5H-9,4b-(epiminoethano)phenanthrene) as a typical substrate metabolism reaction for human CYP2D6, Quinazolin-4(3H)-one-Type Piperidine Compounds were tested for the extent to which they inhibited reference metabolite production by CYP2D6. The reaction conditions were as follows: 5 μmol/L dextromethorphan substrate, 15 minute reaction time, 37° C. reaction temperature, 0.2 mg protein/mL pooled human hepatic microsome enzyme, and Quinazolin-4(3H)-one-Type Piperidine Compound concentrations of 1, 5, 10, and 20 μmol/L (four concentrations for each compound). Similar reactions were performed for the other CYP enzymes.

The substrate, human hepatic microsome, or a Quinazolin-4(3H)-one-Type Piperidine Compound in 50 mmol/L HEPES buffer as a reaction solution was added to a 96-well plate at the concentrations as described above, cofactor NADPH was added to initiate metabolism reactions as a marker and, after incubation at 37° C. for 15 minutes, a 1:1 MeOH:MeCN (vol:vol) solution was added to stop the reaction. Following centrifugation at 3000 rpm for 15 minutes, the amount of dextrorphan ((4bR,8aS,9R)-11-methyl-6,7,8,8a,9,10-hexahydro-5H-9,4b-(epiminoethano)phenanthren-3-ol, the CYP2D6 metabolite) present was determined quantitatively by LC/MS/MS.

As a control, addition of only DMSO (a solvent for Quinazolin-4(3H)-one-Type Piperidine Compounds) to a reaction system was adopted (i.e., 100% metabolite production). At each concentration of a Quinazolin-4(3H)-one-Type Piperidine Compound added, the activity (%) was calculated from the amount of dextrorphan present. The IC$_{50}$ was determined by reverse presumption by a logistic model using a concentration and an inhibition rate.

A "low" value of CYP1A2, CYP2C9, CYP2D6, or CYP3A4 IC$_{50}$, e.g., about 1 μM or less, is an indicator that undesirable drug-drug interactions are possible. In contrast, a "high" value of CYP1A2, CYP2C9, CYP2D6, or CYP3A4 IC$_{50}$, e.g., about 17-20 μM or greater, is an indicator of the absence of undesirable drug-drug interactions.

In certain embodiments, a Quinazolin-4(3H)-one-Type Piperidine Compound has a CYP1A2, CYP2C9, CYP2D6, or CYP3A4 IC$_{50}$ of about 15 1M or greater, or of about 16 μM or greater, or of about 17 μM or greater, or of about 17.5 μM or greater, or of about 18 μM or greater, or of about 18.5 μM or greater, or of about 19 μM or greater, or of about 20 μM or greater.

Example 25: Efficacy of Receptor Binding and Activity Response

The following Tables provide, for several Quinazolin-4 (3H)-one-Type Piperidine Compounds, results on the efficacy of binding and activity response to the ORL-1 receptor, and CYP1A2, CYP2C9, CYP2D6, and CYP3A4 response.

In Table 5, binding efficacy to the ORL-1 receptor was determined by the procedure in Example 10. Activity response to the ORL-1 receptor was determined by the procedure in Example 11. Also in Table 5, Cytochrome P450 (i.e., CYP1A2, CYP2C9, CYP2D6, and CYP3A4) response, in the form of IC$_{50}$, was determined by the procedure in Example 18.

TABLE 5

Efficacy of Receptor Binding, Activity Response, and Cytochrome P450 Response of Selected Quinazolin-4(3H)-one-Type Piperidine Compounds

| Ref. No. | Compound | ORL-1 K$_i$* | GTPγS EC$_{50}$ | E$_{max}$ | Cytochrome P450° |
|---|---|---|---|---|---|
| 12 (D1a) | | 4.98 ± 0.43 | >20 | 1.33 ± 0.33 | CYP1A2: >20<br>CYP2C9: >20<br>CYP2D6: 8.9<br>CYP3A4: >20 |
| 9 (D2b) | | 8.86 ± 2.14 | >20 | 1 ± 0 | CYP1A2: >20<br>CYP2C9: >20<br>CYP2D6: 2.6<br>CYP3A4: >20 |
| 15 (D3a) | | 46.13 ± 2.02 | >20 | — | CYP1A2: >20<br>CYP2C9: >20<br>CYP2D6: >20<br>CYP3A4: >20 |

TABLE 5-continued

Efficacy of Receptor Binding, Activity Response, and Cytochrome P450 Response of Selected Quinazolin-4(3H)-one-Type Piperidine Compounds

| Ref. No. | Compound | ORL-1 $K_i$* | GTPγS $EC_{50}$ | $E_{max}$ | Cytochrome P450° |
|---|---|---|---|---|---|
| 21 (J3a) | | 72.71 ± 14.24 | >20 | — | CYP1A2: 5.5<br>CYP2C9: >20<br>CYP2D6: >20<br>CYP3A4: 2.3 |
| 18 (D28a) | | 133.52 ± 53.38 | >20 | 1 ± 0 | CYP1A2: >20<br>CYP2C9: >20<br>CYP2D6: 1.6<br>CYP3A4: >20 |
| 24 (D459a) | | 228.61 ± 59.29 | >20 | — | CYP1A2: >20<br>CYP2C9: >20<br>CYP2D6: 18.7<br>CYP3A4: 5.8 |

TABLE 5-continued

Efficacy of Receptor Binding, Activity Response, and Cytochrome P450 Response of Selected Quinazolin-4(3H)-one-Type Piperidine Compounds

| | | ORL-1 | | | |
|---|---|---|---|---|---|
| | | | GTPγS | | Cytochrome |
| Ref. No. | Compound | $K_i$* | $EC_{50}$ | $E_{max}$ | P450° |
| 8 (D12b) | [structure: quinazolin-4(3H)-one with ethyl ester and bicyclic piperidine substituents] | 252.38 ± 81.74 | — | — | CYP1A2: >20<br>CYP2C9: >20<br>CYP2D6: 9.7<br>CYP3A4: 6.5 |

*$K_i$ [Average ± Std Deviation] (nM)
^GTPγS ($EC_{50}$: μM, $E_{max}$: %) [mean ± SEM]
°$IC_{50}$ (μM)

Example 26: In Vivo Assays for Prevention or Treatment of Pain

Test Animals: Each experiment uses rats weighing between 200-260 g at the start of the experiment. The rats are group-housed and have free access to food and water at all times, except prior to oral administration of a Quinazolin-4(3H)-one-Type Piperidine Compound when food is removed for 16 hours before dosing. A control group acts as a comparison to rats treated with a Quinazolin-4(3H)-one-Type Piperidine Compound. The control group is administered the carrier for the Quinazolin-4(3H)-one-Type Piperidine Compound. The volume of carrier administered to the control group is the same as the volume of carrier and Quinazolin-4(3H)-one-Type Piperidine Compound administered to the test group.

Acute Pain: To assess the actions of a Quinazolin-4(3H)-one-Type Piperidine Compound for the treatment or prevention of acute pain, the rat tail flick test is used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Quinazolin-4(3H)-one-Type Piperidine Compound. Data are expressed as tail flick latency(s) and the percentage of the maximal possible effect (% MPE), i.e., 20 seconds, is calculated as follows:

$$\% \ MPE = \frac{[(\text{post administration latency}) - (\text{pre-administration latency})]}{(20 \ s \ \text{pre-administration latency})} \times 100$$

The rat tail flick test is described in D'Amour et al., "A Method for Determining Loss of Pain Sensation," *J. Pharmacol. Exp. Ther.* 72:74-79 (1941).

Inflammatory Pain: To assess the actions of a Quinazolin-4(3H)-one-Type Piperidine Compound for the treatment or prevention of inflammatory pain, the Freund's complete adjuvant ("FCA") model of inflammatory pain is used. FCA-induced inflammation of the rat hind paw is associated with the development of persistent inflammatory mechanical hyperalgesia and provides reliable prediction of the antihyperalgesic action of clinically useful analgesic drugs (Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990)). The left hind paw of each animal is administered a 50 μL intraplantar injection of 50% FCA. 24 hour post injection, the animal is assessed for response to noxious mechanical stimuli by determining the PWT, as described below. Rats are then administered a single injection of 1, 3, 10 or 30 mg/kg of either a Quinazolin-4(3H)-one-Type Piperidine Compound; 30 mg/kg of a control selected from Celebrex, indomethacin, and naproxen; or carrier. Responses to noxious mechanical stimuli are then determined 1, 3, 5 and 24 hours post administration. Percentage reversal of hyperalgesia for each animal is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Quinazolin-4(3H)-one-Type Piperidine Compound for the treatment or prevention of neuropathic pain, either the Seltzer model or the Chung model is used.

In the Seltzer model, the partial sciatic nerve ligation model of neuropathic pain is used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. The wound area is then dusted with antibiotic powder. Sham treatment involved an identical surgical procedure except that the sciatic nerve is not manipulated or ligated.

Following surgery, animals are weighed and placed on a warm pad until they recovered from anesthesia. Animals are then returned to their home cages until behavioral testing began. The animal is assessed for response to noxious mechanical stimuli by determining PWT for the rear paw of the animal, as described below, prior to surgery (baseline), then immediately prior to and 1, 3, and 5 hours after oral drug-in-vehicle administration (for day 1). Thus, the 24 hour time point is the start of the next day when drug-in-vehicle was again orally administered (24 hours after the prior administration). On days 4 and 7, PWT response is determined 1, 3, and 5 hours thereafter. Percentage reversal of neuropathic hyperalgesia at each of the specified times after administration is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Additionally, 10 mg/kg of pregabalin (Kemprotec, Ltd., Middlesbrough, UK), an anticonvulsant accepted for relief of particular neuropathic pain, in vehicle and the vehicle alone (0.5% weight/volume methylcellulose (400 cP, Wako Pure Chemical Industries, Ltd.)/aqueous solution) are orally administered as controls. Eight rats that underwent partial ligation of the left sciatic nerve are used for each treatment group except for pregabalin, where six rats are treated. Dunnett's test is conducted for the % reversal; values with $p<0.05$ are considered to be statistically significant.

Additionally, as a control the rats undergo sham surgery in which an identical surgical procedure is followed with regard to the right thigh but the sciatic nerve is neither manipulated nor ligated.

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Quinazolin-4(3H)-one-Type Piperidine Compound for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay is used to assess mechanical hyperalgesia. For this assay, hind paw withdrawal thresholds (PWT) to a noxious mechanical stimulus are determined using an analgesymeter (Model 37215, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," *Pharmacol. Biochem. Behavior* 31:451-455 (1988). The maximum weight that can be applied to the hind paw is set at 250 g and the end point is taken as complete withdrawal of the paw. PWT is determined once for each rat at each time point and either only the affected (ipsilateral) paw is tested, or both the ipsilateral and contralateral (non-injured) paw are tested.

Response to Thermal Stimuli as an Assessment of Thermal Hyperalgesia: The plantar test is used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

6. EQUIVALENTS

The claimed invention is not to be limited in scope by the specific embodiments disclosed in the Examples, which are intended as illustrations of a few aspects of the claimed invention. Embodiments that are functionally equivalent to those described herein are within the scope of the claimed invention. Indeed, various modifications of the claimed invention, in addition to those shown and described herein, may become apparent to those skilled in the art and are intended to fall within the scope of the following claims.

The entire disclosures of all publications and documents cited herein are expressly incorporated herein by reference for all purposes.

The invention claimed is:

1. A compound of Formula (Ia'):

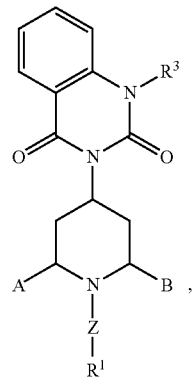

(Ia')

or a pharmaceutically acceptable salt or solvate thereof, wherein

A and B together form a $(C_2-C_6)$bridge, wherein the 6-membered, nitrogen-containing ring that is fused to the benzene ring is in the endo- or exo-configuration with respect to the A-B bridge;

$R^3$ is H, $-(CH_2)_dC(=Y)YT$, or $-(CH_2)_dC(=Y)N(T)_2$,

Y, each independently, is O or S;

Z is a direct bond;

$R^1$ is $-(C_3-C_{14})$cycloalkyl or $-(C_6-C_{14})$bicycloalkyl, each of which is unsubstituted or substituted with $R^5$;

each T is independently selected from
  —H, or $-(C_1-C_{10})$alkyl, unsubstituted or substituted with 1, or 2 independently selected $R^5$ groups each $R^5$ is independently $-(C_1-C_6)$alkyl;

each $R^7$ is independently —H, or $-(C_1-C_6)$alkyl;

each d is an integer independently selected from 0, 1, 2, 3, 4, 5, and 6.

2. The compound of claim 1, wherein $R^3$ is $-(CH_2)_dC(=Y)YT$ or $-(CH_2)_dC(=Y)N(T)_2$.

3. The compound of claim 1, wherein $R^3$ is $-(CH_2)_dC(=Y)YT$, wherein Y is O for each occurrence and d is 1 or 2, and T is —H or unsubstituted $-(C_1-C_6)$alkyl.

4. The compound of claim 1, wherein $R^3$ is $-(CH_2)_dC(=Y)N(T)_2$, wherein Y is O, d is 1 or 2.

5. The compound of claim 4, wherein one T is —H, and the other occurrence of T is $-(C_1-C_6)$alkyl substituted with at least one $R^5$.

6. The compound of claim 5, wherein at least one $R^5$ in an occurrence of T of $R^3$ is $-C(=O)OR^7$.

7. The compound of claim 1, wherein $R^3$ is —H.

8. The compound of claim 1, wherein A and B together form a bridge such that the bridged-piperidine is:

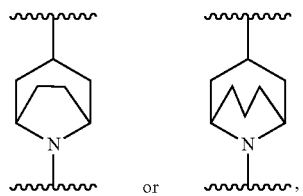 [SMILES: *C1CC2CCC(C1)N2* ; *C1CC2CCCC(C1)N2*]

wherein the piperidine nitrogen is optionally in pharmaceutically acceptable salt form.

9. The compound of claim 8, wherein the 6-membered, nitrogen-containing ring that is fused to the benzene ring is in the endo-configuration with respect to the A-B bridge.

10. The compound of claim 1, wherein $R^1$ is $-(C_6-C_{14})$bicycloalkyl, which is unsubstituted or substituted with $R^5$ wherein $R^5$ is $-OR^7$ or $=O$.

11. The compound of claim 1, wherein $-Z-R^1$ is:

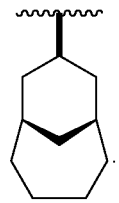

12. The compound of claim 1, wherein $-Z-R^1$ is:

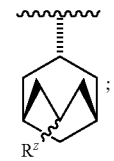

$R^z$ is —H or $-(C_1-C_6)$alkyl.

13. A compound selected from:
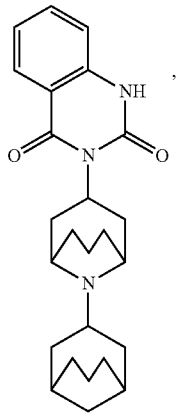 , 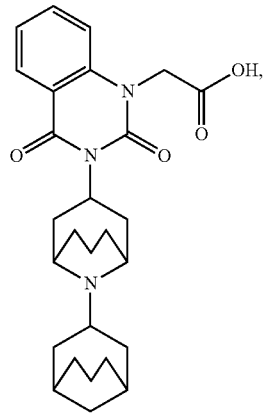
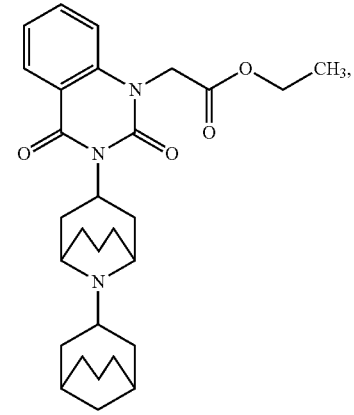
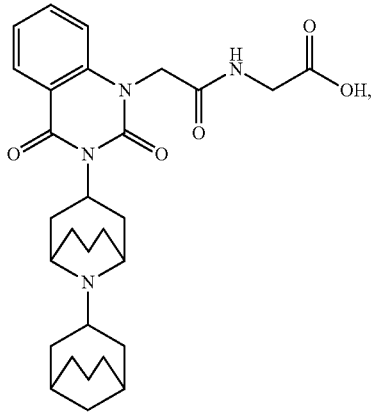
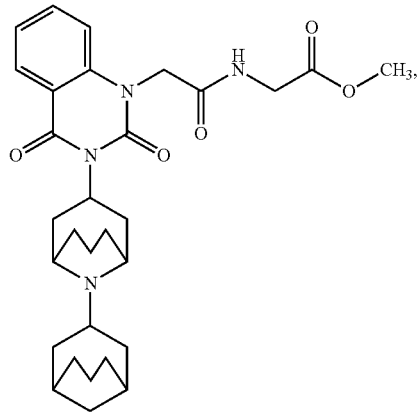
-continued
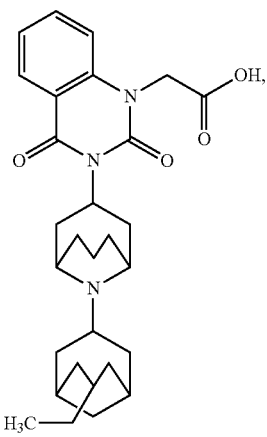
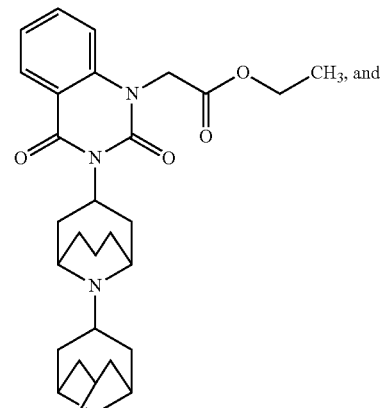
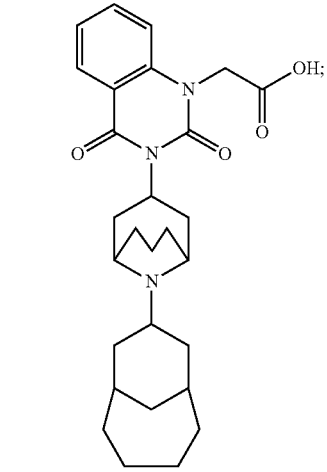 [SMILES: O=C(O)Cn1c(=O)n(C2CC3CCCC(C2)N3C2CC3CCCCC(C3)C2)c(=O)c2ccccc21]
and the pharmaceutically acceptable salts and solvates thereof.

14. The compound of claim 13 selected from:

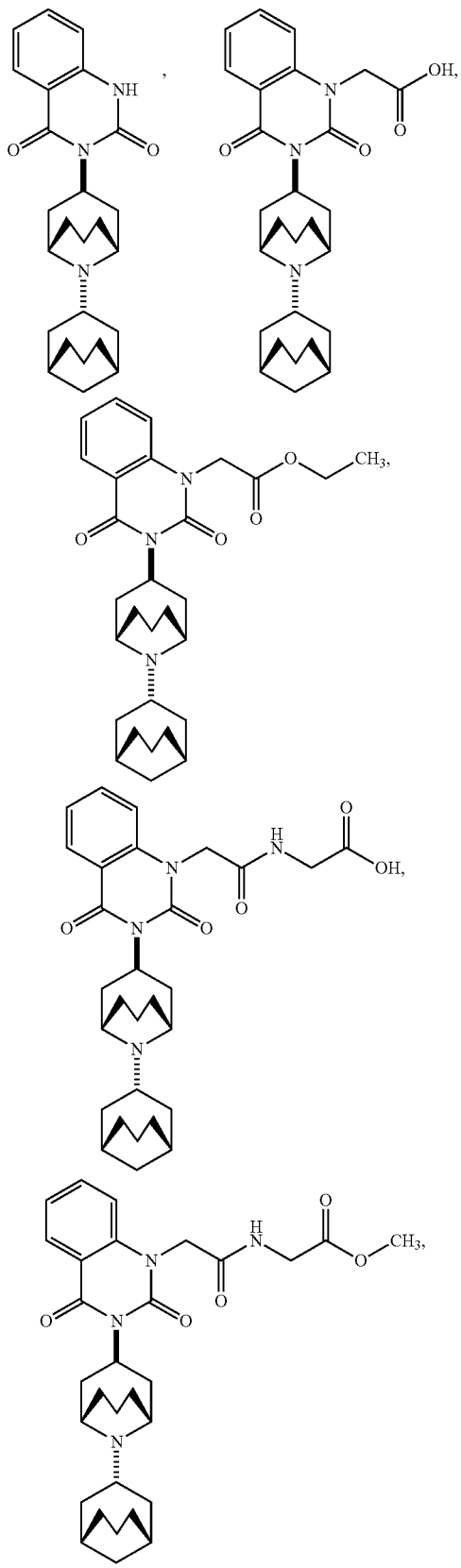

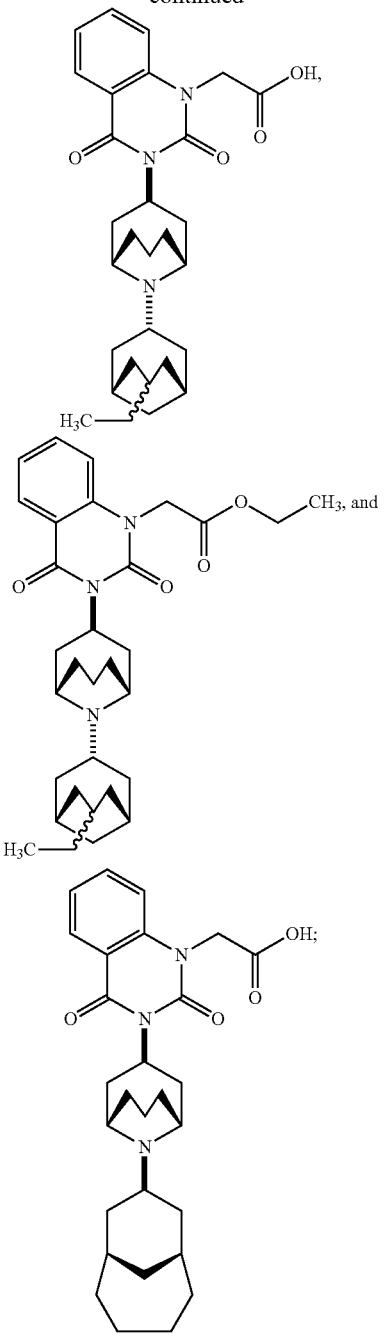

and the pharmaceutically acceptable salts and solvates thereof.

15. A composition comprising an effective amount of the compound of claim 1 and a pharmaceutically acceptable carrier or excipient.

16. A method for modulating ORL-1 receptor function in a cell, comprising contacting a cell capable of expressing the ORL-1 receptor with an effective amount of the compound of claim 1.

17. A method for treating pain in an animal, comprising administering to an animal in need thereof an effective amount of the compound of claim 1.

* * * * *